United States Patent
Konnai et al.

(10) Patent No.: US 11,312,773 B2
(45) Date of Patent: Apr. 26, 2022

(54) ANTI-PD-L1 ANTIBODY

(71) Applicants: Fuso Pharmaceutical Industries, Ltd., Osaka (JP); National University Corporation Hokkaido University, Hokkaido (JP)

(72) Inventors: Satoru Konnai, Hokkaido (JP); Kazuhiko Ohashi, Hokkaido (JP); Shiro Murata, Hokkaido (JP); Tomohiro Okagawa, Hokkaido (JP); Asami Nishimori, Hokkaido (JP); Naoya Maekawa, Hokkaido (JP); Yasuhiko Suzuki, Hokkaido (JP); Chie Nakajima, Hokkaido (JP)

(73) Assignees: Fuso Pharmaceutical Industries, Ltd., Osaka (JP); National University Corporation Hokkaido University, Sapporoshi (JP)

( * ) Notice: Subject to any disclaimer, the term of this patent is extended or adjusted under 35 U.S.C. 154(b) by 492 days.

(21) Appl. No.: 16/325,040

(22) PCT Filed: Aug. 10, 2017

(86) PCT No.: PCT/JP2017/029055
§ 371 (c)(1),
(2) Date: Feb. 12, 2019

(87) PCT Pub. No.: WO2018/034225
PCT Pub. Date: Feb. 22, 2018

(65) Prior Publication Data
US 2021/0277124 A1 Sep. 9, 2021

(30) Foreign Application Priority Data

Aug. 15, 2016 (JP) .............................. JP2016-159088
Aug. 15, 2016 (JP) .............................. JP2016-159089
Mar. 27, 2017 (JP) .............................. JP2017-061454
Jun. 5, 2017 (JP) .............................. JP2017-110723

(51) Int. Cl.
*A61K 39/395* (2006.01)
*C07K 16/28* (2006.01)

(52) U.S. Cl.
CPC ...... *C07K 16/2827* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS 5,852,183 A 12/1998 Maeda et al.
2015/0376264 A1 12/2015 Wang et al.

FOREIGN PATENT DOCUMENTS

| EA | 19344 B1 | 3/2014 | | |
|---|---|---|---|---|
| EP | 0419858 A1 | * | 4/1991 | ........... C07K 16/462 |
| JP | 03201986 A | | 9/1991 | |
| JP | 0440894 A | | 2/1992 | |
| JP | 2015509091 A | | 3/2015 | |
| JP | 2015521461 A | | 7/2015 | |
| WO | WO-2013106489 A1 | * | 7/2013 | .............. A61P 35/00 |
| WO | WO-2015035173 A1 | | 3/2015 | |
| WO | WO-201509191 | | 6/2015 | |
| WO | WO-2016050721 A | * | 4/2016 | .............. A61P 35/00 |
| WO | WO-2017062253 A2 | * | 4/2017 | ......... C07K 16/2803 |

OTHER PUBLICATIONS

Maekawa et al., PLoS One. Jun. 8, 2016; 11(6):e0157176. doi: 10.1371/journal.pone.0157176. eCollection 2016. PMID: 27276060.*
Ikebuchi et al., Immunology. Aug. 2014;142(4):551-61. doi: 10.1111/imm.12243. PMID: 24405267.*
Author Guidelines for Immunology, downloaded Jun. 23, 2021 from ttps://onlinelibrary.wiley.com/page/journal/13652567/homepage/forauthors.html, 8 pages.*
Akinleye et al., J Hematol Oncol. Sep. 5, 2019;12(1):92. doi: 10.1186/s13045-019-0779-5. PMID: 31488176.*
"Russian Application No. 2019105697, Office Action dated Jul. 24, 2020", w/ English Translation, (dated Jul. 24, 2020), 11 pgs.
"Russian Application No. 2019105697, Search Report dated Jul. 24, 2020", w/ English Translation, (dated Jul. 24, 2020), 4 pgs.
Ishida, Yasumasa, et al.,"Induced expression of PD-1, a novel member of the immunoglobulin gene superfamily, upon programmed cell death". The EMBOjournal 11.11. (1992), 3887-3895.
Maekawa, Naoya, et al., "Expression of PD-L1 on canine tumor cells and enhancement of IFN-? production from tumor-infiltrating cells by PD-L1 blockade", PLoSOne 9.6, (2014), e98415.
Mingala, Claro N., et al., "Characterization of CTLA-4, PD-1 and PDL-1 of swamp and riverine type water buffaloes", Comparative immunology, microbiology and infectious diseases 34.1, (2011), 55-63.

(Continued)

*Primary Examiner* — Michael Szperka
(74) *Attorney, Agent, or Firm* — Schwegman Lundberg & Woessner, P.A.

(57) ABSTRACT

The present invention provides an anti-PD-L1 antibody capable of repeated administration even to animals other than rat. An anti-PD-L1 antibody comprising (a) a light chain comprising a light chain variable region containing CDR1 having the amino acid sequence of QSLLY-SENQKDY (SEQ ID NO: 37), CDR2 having the amino acid sequence of WAT and CDR3 having the amino acid sequence of GQYLVYPFT (SEQ ID NO: 38) and the light chain constant region of an antibody of an animal other than rat; and (b) a heavy chain comprising a heavy chain variable region containing CDR1 having the amino acid sequence of GYTFTSNF (SEQ ID NO: 39), CDR2 having the amino acid sequence of IYPEYGNT (SEQ ID NO: 40) and CDR3 having the amino acid sequence of ASEEAVISLVY (SEQ ID NO: 41) and the heavy chain constant region of an antibody of an animal other than rat. A pharmaceutical composition comprising the above anti-PD-L1 antibody as an active ingredient. A method for preparing the above anti-PD-L1 antibody is also provided.

13 Claims, 28 Drawing Sheets

Specification includes a Sequence Listing.

(56) References Cited

OTHER PUBLICATIONS

"European Application Serial No. 17841448.8, Extended European Search Report dated Dec. 5, 2019", (dated Dec. 5, 2019), 9 pgs.

Buss, Nicholas, et al., "Monoclonal antibody therapeutics: history and future", Current opinion in pharmacology 12.5, (Oct. 1, 2012), 615-622.

"International Application Serial No. PCT/JP2017/029055, International Preliminary Report on Patentability dated Feb. 28, 2019", 10 pgs.

"2013 Fiscal Year Annual Research Report Ushi no Men'eki Yokusei Juyotai no Kino Kaiseki Oyobi Nanjisei Shippei no Shinki Seigyoho eno Oyo Kenkyu", [Online], Retrieved from the Internet: <URL:<https://kaken.nii.ac.jp/ja/report/KAKENHI-PROJECT-13J01442/13J014422013jisseki/>, (Jun. 25, 2015), 2 pgs.

"2014 Fiscal Year Annual Research Report Ushi no Men'eki Yokusei Juyotai no Kino Kaiseki Oyobi Nanjisei Shippei no Shinki Seigyoho eno Oyo Kenkyu", [Online]. Retrieved from the Internet: <URL: https://kaken.nii.ac.jp/ja/report/KAKENHI-PROJECT-13J01442/13J014422014jisseki/>, (Jun. 1, 2016), 3 pgs.

"Heisei 26 Nendo Norin Suisangyo•Shokuhin Sangyo Kagaku Gijutsu Kenkyu Suishin Jigyo Hatten Yugo Stage Shinki Saitaku Kadai Ichiran", Research Project No. 26058B, [Online]. Retrieved from the Internet: <URL:http://www.affrc.maff.go.jp/docs/gaiyou/pdf/pdf/h26hatten_sinkisaitaku_itiran.pdf>, (Jul. 30, 2014), 3 pgs.

"International Application Serial No. PCT/JP2017/029055, International Search Report dated Nov. 7, 2017", (dated Nov. 7, 2017), 8 pgs.

"International Application Serial No. PCT/JP2017/029055, Written Opinion dated Nov. 7, 2017", (dated Nov. 7, 2017), 6 pgs.

Ikebuchl, Ryoyo, et al., "Influence of PD-L 1 cross-linking on cell death in PD-L 1-expressing cell lines and bovine lymphocytes", Immunology 142.4, (2014), 551-561.

"Singaporean Application Serial No. 11201901317T, Search Report dated Apr. 16, 2020", (Apr. 16, 2020), 2 pgs.

Singer, J., et al., "Generation of a canine anti-EGFR (ErbB-1) antibody for passive immunotherapy in dog cancer patients", Mol Cancer Ther., vol. 13, No. 7, (Apr. 22, 2014), 1777-1790.

"Korean Application Serial No. 10 2019 7007407, Office Action dated Jan. 4, 2022", w/English Translation, (Jan. 4, 2022), 14 pgs.

Symons, D B, et al., "Ig heavy chain precursor (B/MT.4A.17.H5.A5)—bovine", NCBI Mol. Immunol. 26 (9) [Online], Retrieved from the Internet: <URL: https://www.ncbi.nlm.nih.gov/protein/S22080?report=genbank&log$=prottop&blast_rank=1&RID=7245NB05013>, (1999), 2 pgs.

\* cited by examiner

Fig. 15

CDR1
CDR2
CDR3

Light chain variable region

MESQTHVLISLLSVSGTYGDIAITQSPSSVAVSVGETVTLSCKSSQSLLYSENQKDYL
                                              CDR1

GWYQQKPGQTPKPLIYWATNRHTGVPDRFTGSGSGTDFTLIISSVQAEDLADYYC
             CDR2

GQYLVYPFTFGPGTKLELK
       CDR3

Heavy chain variable region

MGWSQIILFLVAAATGVHSQVQLQQSGAELVKPGSSVKISCKASGYTFTSNFMHWV
                                              CDR1

KQQPGNGLEWIGWIYPEYGNTKYNQKFDGKATLTADKSSSTAYMQLSSLTSEDSAV
             CDR2

YFCASEEAVISLVYWGQGTLVTVSS
      CDR3

Fig. 19

Light Chain

*Italicized: Variable region sequence (Underlined boldface: CDR1, CDR2, CDR3 in this order from NH2 terminus)*

Non-italicized: Constant region sequence (bovine Ig lambda, GenBank: X62917)

*MEISQTHVLISLLLSVSGTYG*DIAITQSPSSVAVSVGETVTLSCKSSQSLLYSENQKDYLGWYQQKPGQTPKPLIYWATNRHTGVPDRFTGSGSGTDFTLTISSVQAEDLADYYCGQYLVPFTFGPGTKLELKQPKSSPSVTLFPPSTEELNGNKATLVCLISDFYPGSVTVVWKADGSTITRNVETTRASKQSNSKYAASSYLSLTSSDWKSKGSYSCEVTHEGSTVTKTVKPSECS*

Heavy Chain

*Italicized: Variable region sequence (Underlined boldface: CDR1, CDR2, CDR3 in this order from NH2 terminus)*

Non-italicized: Constant region sequence (bovine IgG1, modified from GenBank: X62916)

Doubly underlined: mutated amino acids in bovine IgG1 (CH2 domain)
(Amino acid numbers and mutations: 250 E→P, 251 L→V, 252 P→A, 253 G→deletion, 347 A→S, 348 P→S)

*MGWSQIILFLVAAATGVH*SQVQLQQSGAELVKPGSSVKISCKASGYTFTSNFMHWVKQQPGNGLEWIGWIYPEYGNTKYNQKFKDKATLTADKSSSTAYMQLSSLTSEDSAVYFCASREAVISLIYWGQGTLVTVSSASTTAPKVYPLSSCCGDKSSSTVTLGCLVSSYMPEPVTVTWNSGALKSGVHTFPAVLQSSGLYSLSSMVTVPGSTSGQTFTCNVAHPASSTKVDKAVDPTCKPSPCDCCPPPPVAGPSVFIFPPKPKDTLTISGTPEVTCVVVDVGHDDPEVKFSWFVDDVEVNTATTKPREEQFNSTYRVVSALRIQHQDWTGGKEFKCKVHNEGLPSSIVRTISRTKGPAREPQVYVLAPPQEELSKSTVSLTCMVTSFYPDYIAVEWQRNGQPESEDKYGTTPPQLDADSSYFLYSKLRVDRNSWQEGDTYTCVVMHEALHNHYTQKSTSKSAGK*

SEQUENCE LISTING

```
<160> NUMBER OF SEQ ID NOS: 138

<210> SEQ ID NO 1
<211> LENGTH: 133
<212> TYPE: PRT
<213> ORGANISM: Rattus norvegicus

<400> SEQUENCE: 1

Met Glu Ser Gln Thr His Val Leu Ile Ser Leu Leu Leu Ser Val Ser
1               5                   10                  15

Gly Thr Tyr Gly Asp Ile Ala Ile Thr Gln Ser Pro Ser Ser Val Ala
            20                  25                  30

Val Ser Val Gly Glu Thr Val Thr Leu Ser Cys Lys Ser Ser Gln Ser
        35                  40                  45

Leu Leu Tyr Ser Glu Asn Gln Lys Asp Tyr Leu Gly Trp Tyr Gln Gln
    50                  55                  60

Lys Pro Gly Gln Thr Pro Lys Pro Leu Ile Tyr Trp Ala Thr Asn Arg
65                  70                  75                  80

His Thr Gly Val Pro Asp Arg Phe Thr Gly Ser Gly Ser Gly Thr Asp
                85                  90                  95

Phe Thr Leu Ile Ile Ser Ser Val Gln Ala Glu Asp Leu Ala Asp Tyr
            100                 105                 110

Tyr Cys Gly Gln Tyr Leu Val Tyr Pro Phe Thr Phe Gly Pro Gly Thr
        115                 120                 125

Lys Leu Glu Leu Lys
    130

<210> SEQ ID NO 2
<211> LENGTH: 137
<212> TYPE: PRT
<213> ORGANISM: Rattus norvegicus
```

```
<400> SEQUENCE: 2

Met Gly Trp Ser Gln Ile Ile Leu Phe Leu Val Ala Ala Ala Thr Cys
1               5                   10                  15

Val His Ser Gln Val Gln Leu Gln Gln Ser Gly Ala Glu Leu Val Lys
            20                  25                  30

Pro Gly Ser Ser Val Lys Ile Ser Cys Lys Ala Ser Gly Tyr Thr Phe
        35                  40                  45

Thr Ser Asn Phe Met His Trp Val Lys Gln Pro Gly Asn Gly Leu
    50                  55                  60

Glu Trp Ile Gly Trp Ile Tyr Pro Glu Tyr Gly Asn Thr Lys Tyr Asn
65              70                  75                  80

Gln Lys Phe Asp Gly Lys Ala Thr Leu Thr Ala Asp Lys Ser Ser
            85                  90                  95

Thr Ala Tyr Met Gln Leu Ser Ser Leu Thr Ser Glu Asp Ser Ala Val
            100                 105                 110

Tyr Phe Cys Ala Ser Glu Glu Ala Val Ile Ser Leu Val Tyr Trp Gly
        115                 120                 125

Gln Gly Thr Leu Val Thr Val Ser Ser
    130                 135

<210> SEQ ID NO 3
<211> LENGTH: 105
<212> TYPE: PRT
<213> ORGANISM: Canis lupus

<400> SEQUENCE: 3

Gln Pro Lys Ala Ser Pro Ser Val Thr Leu Phe Pro Pro Ser Ser Glu
1               5                   10                  15

Glu Leu Gly Ala Asn Lys Ala Thr Leu Val Cys Leu Ile Ser Asp Phe
            20                  25                  30

Tyr Pro Ser Gly Val Thr Val Ala Trp Lys Ala Ser Gly Ser Pro Val
        35                  40                  45

Thr Gln Gly Val Glu Thr Thr Lys Pro Ser Lys Gln Ser Asn Asn Lys
    50                  55                  60

Tyr Ala Ala Ser Ser Tyr Leu Ser Leu Thr Pro Asp Lys Trp Lys Ser
65              70                  75                  80

His Ser Ser Phe Ser Cys Leu Val Thr His Glu Gly Ser Thr Val Glu
            85                  90                  95

Lys Lys Val Ala Pro Ala Glu Cys Ser
            100                 105

<210> SEQ ID NO 4
<211> LENGTH: 331
<212> TYPE: PRT
<213> ORGANISM: Canis lupus

<400> SEQUENCE: 4

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60
```

| | | | | | | | | | | | |
|---|---|---|---|---|---|---|---|---|---|---|---|
| Leu | Ser | Ser | Thr | Val | Thr | Val | Pro | Ser | Ser | Arg | Trp | Pro | Ser | Glu | Thr |
| 65 | | | | 70 | | | | | 75 | | | | | 80 | |

Leu Ser Ser Thr Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val Pro Lys Glu Ser Thr Cys Lys Cys Ile Ser Pro Cys Pro Val
            100                 105                 110

Pro Glu Ser Leu Gly Gly Pro Ser Val Phe Ile Phe Pro Pro Lys Pro
            115                 120                 125

Lys Asp Ile Leu Arg Ile Thr Arg Thr Pro Glu Ile Thr Cys Val Val
130                 135                 140

Leu Asp Leu Gly Arg Glu Asp Pro Glu Val Gln Ile Ser Trp Phe Val
145                 150                 155                 160

Asp Gly Lys Glu Val His Thr Ala Lys Thr Gln Pro Arg Glu Gln Gln
                165                 170                 175

Phe Asn Ser Thr Tyr Arg Val Val Ser Val Leu Pro Ile Glu His Gln
            180                 185                 190

Asp Trp Leu Thr Gly Lys Glu Phe Lys Cys Arg Val Asn His Ile Gly
            195                 200                 205

Leu Pro Ser Pro Ile Glu Arg Thr Ile Ser Lys Ala Arg Gly Gln Ala
210                 215                 220

His Gln Pro Ser Val Tyr Val Leu Pro Pro Ser Pro Lys Glu Leu Ser
225                 230                 235                 240

Ser Ser Asp Thr Val Thr Leu Thr Cys Leu Ile Lys Asp Phe Phe Pro
            245                 250                 255

Pro Glu Ile Asp Val Glu Trp Gln Ser Asn Gly Gln Pro Glu Pro Glu
            260                 265                 270

Ser Lys Tyr His Thr Thr Ala Pro Gln Leu Asp Glu Asp Gly Ser Tyr
            275                 280                 285

Phe Leu Tyr Ser Lys Leu Ser Val Asp Lys Ser Arg Trp Gln Gln Gly
            290                 295                 300

Asp Thr Phe Thr Cys Ala Val Met His Glu Ala Leu Gln Asn His Tyr
305                 310                 315                 320

Thr Asp Leu Ser Leu Ser His Ser Pro Gly Lys
                325                 330

<210> SEQ ID NO 5
<211> LENGTH: 399
<212> TYPE: DNA
<213> ORGANISM: Rattus norvegicus

<400> SEQUENCE: 5
atggaatcac agacgcatgt cctcatttcc cttctgctct cggtatctgg tacctatggg      60
gacattgcga taacccagtc tccatcctct gtggctgtgt cagtaggaga gacggtcact     120
ctgagctgca gtccagtca gagtctttta tacagtgaaa accaaaagga ctatttgggc     180
tggtaccagc agaaaccagg gcagactcct aaaccccta tctactgggc aaccaaccgg     240
cacactgggg tccctgatcg cttcacaggt agtggatccg ggacagactt cactctgatc     300
atcagcagtg tgcaggctga agacctggct gattattact gtgggcagta ccttgtctat     360
ccgttcacgt ttggacctgg gaccaagctg gaactgaaa                            399

<210> SEQ ID NO 6
<211> LENGTH: 411
<212> TYPE: DNA
<213> ORGANISM: Rattus norvegicus

```
<400> SEQUENCE: 6
atgggatgga gccagatcat cctctttctg gtggcagcag ctacatgtgt tcactcccag     60
gtacagctgc agcaatctgg ggctgaatta gtgaagcctg gtcctcagt gaaaatttcc    120 tgcaaggctt ctggctacac cttcaccagt aactttatgc actgggtaaa gcagcagcct   180
ggaaatggcc ttgagtggat tgggtggatt tatcctgaat atggtaatac taagtacaat   240
caaaagttcg atgggaaggc aacactcact gcagacaaat cctccagcac agcctatatg   300
cagctcagca gcctgacatc tgaggactct gcagtctatt tctgtgcaag tgaggaggca   360
gttatatccc ttgtttactg gggccaaggc actctggtca ctgtctcttc a            411

<210> SEQ ID NO 7
<211> LENGTH: 318
<212> TYPE: DNA
<213> ORGANISM: Canis lupus

<400> SEQUENCE: 7
cagcccaagg cctcccctc ggtcacactc ttcccgccct cctctgagga gctcggcgcc    60
aacaaggcca ccctggtgtg cctcatcagc gacttctacc ccagcggcgt gacggtggcc   120
tggaaggcaa gcggcagccc cgtcacccag ggcgtggaga ccaccaagcc ctccaagcag   180
agcaacaaca gtacgcggc cagcagctac ctgagcctga cgcctgacaa gtggaaatct   240
cacagcagct tcagctgcct ggtcacgcac gaggggagca ccgtggagaa gaaggtggcc   300
cccgcagagt gctcttag                                                 318

<210> SEQ ID NO 8
<211> LENGTH: 996
<212> TYPE: DNA
<213> ORGANISM: Canis lupus

<400> SEQUENCE: 8
gcctccacca cggccccctc ggttttccca ctggccccca gctgcgggtc cacttccggc    60
tccacggtgg ccctggcctg cctggtgtca ggctacttcc ccgagcctgt aactgtgtcc   120
tggaattccg gctccttgac cagcggtgtg cacaccttcc cgtccgtcct gcagtcctca   180
gggctctact ccctcagcag cacggtgaca gtgccctcca gcaggtggcc cagcgagacc   240
ttcacctgca acgtggtcca cccggccagc aacactaaag tagacaagcc agtgcccaaa   300
gagtccacct gcaagtgtat atccccatgc ccagtccctg aatcactggg agggccttcg   360
gtcttcatct ttcccccgaa acccaaggac atcctcagga ttacccgaac acccgagatc   420
acctgtgtgt gtttagatct gggccgtgag accctgaggt gcagatcag ctggttcgtg    480 gatggtaagg aggtgcacac agccaagacg cagcctcgtg agcagcagtt caacagcacc   540
taccgtgtgg tcagcgtcct ccccattgag caccaggact ggctcaccgg aaaggagttc   600
aagtgcagag tcaaccacat aggcctcccg tcccccatcg agaggactat ctccaaagcc   660
agagggcaag cccatcagcc cagtgtgtat gtcctgccac catccccaaa ggagttgtca   720
tccagtgaca cggtcaccct gacctgcctg atcaaagact tcttcccacc tgagattgat   780
gtggagtggc agagcaatgg acagccggag cccgagagca gtaccacac gactgcgccc    840 cagctggacg aggacgggtc ctacttcctg tacagcaagc tctctgtgga caagagccgc   900
tggcagcagg agagacacctt cacatgtgcg gtgatgcatg aagctctaca gaaccactac   960
acagatctat ccctctccca ttctccgggt aaatga                            996
```

```
<210> SEQ ID NO 9
<211> LENGTH: 238
<212> TYPE: PRT
<213> ORGANISM: Artificial Sequence
<220> FEATURE:
<223> OTHER INFORMATION: chimeric L chain

<400> SEQUENCE: 9

Met Glu Ser Gln Thr His Val Leu Ile Ser Leu Leu Ser Val Ser
1               5                   10                  15

Gly Thr Tyr Gly Asp Ile Ala Ile Thr Gln Ser Pro Ser Ser Val Ala
            20                  25                  30

Val Ser Val Gly Glu Thr Val Thr Leu Ser Cys Lys Ser Gln Ser
        35                  40                  45

Leu Leu Tyr Ser Glu Asn Gln Lys Asp Tyr Leu Gly Trp Tyr Gln Gln
        50                  55                  60

Lys Pro Gly Gln Thr Pro Lys Pro Leu Ile Tyr Trp Ala Thr Asn Arg
65                  70                  75                  80

His Thr Gly Val Pro Asp Arg Phe Thr Gly Ser Gly Ser Gly Thr Asp
                85                  90                  95

Phe Thr Leu Ile Ile Ser Ser Val Gln Ala Glu Asp Leu Ala Asp Tyr
            100                 105                 110

Tyr Cys Gly Gln Tyr Leu Val Tyr Pro Phe Thr Phe Gly Pro Gly Thr
        115                 120                 125

Lys Leu Glu Leu Lys Gln Pro Lys Ala Ser Pro Ser Val Thr Leu Phe
130                 135                 140

Pro Pro Ser Ser Glu Glu Leu Gly Ala Asn Lys Ala Thr Leu Val Cys
145                 150                 155                 160

Leu Ile Ser Asp Phe Tyr Pro Ser Gly Val Thr Val Ala Trp Lys Ala
                165                 170                 175

Ser Gly Ser Pro Val Thr Gln Gly Val Glu Thr Thr Lys Pro Ser Lys
            180                 185                 190

Gln Ser Asn Asn Lys Tyr Ala Ala Ser Ser Tyr Leu Ser Leu Thr Pro
        195                 200                 205

Asp Lys Trp Lys Ser His Ser Ser Phe Ser Cys Leu Val Thr His Glu
    210                 215                 220

Gly Ser Thr Val Glu Lys Lys Val Ala Pro Ala Glu Cys Ser
225                 230                 235

<210> SEQ ID NO 10
<211> LENGTH: 468
<212> TYPE: PRT
<213> ORGANISM: Artificial Sequence
<220> FEATURE:
<223> OTHER INFORMATION: chimeric H chain

<400> SEQUENCE: 10

Met Gly Trp Ser Gln Ile Ile Leu Phe Leu Val Ala Ala Thr Cys
1               5                   10                  15

Val His Ser Gln Val Gln Leu Gln Gln Ser Gly Ala Glu Leu Val Lys
            20                  25                  30

Pro Gly Ser Ser Val Lys Ile Ser Cys Lys Ala Ser Gly Tyr Thr Phe
        35                  40                  45

Thr Ser Asn Phe Met His Trp Val Lys Gln Gln Pro Gly Asn Gly Leu
    50                  55                  60
```

```
Glu Trp Ile Gly Trp Ile Tyr Pro Glu Tyr Gly Asn Thr Lys Tyr Asn
65                  70                  75                  80

Gln Lys Phe Asp Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Ser Glu Ala Val Ile Ser Leu Val Tyr Trp Gly
        115                 120                 125

Gln Gly Thr Leu Val Thr Val Ser Ser Ala Ser Thr Ala Pro Ser
    130                 135                 140

Val Phe Pro Leu Ala Pro Ser Cys Gly Ser Thr Ser Gly Ser Thr Val
145                 150                 155                 160

Ala Leu Ala Cys Leu Val Ser Gly Tyr Phe Pro Glu Pro Val Thr Val
                165                 170                 175

Ser Trp Asn Ser Gly Ser Leu Thr Ser Gly Val His Thr Phe Pro Ser
                180                 185                 190

Val Leu Gln Ser Ser Gly Leu Tyr Ser Leu Ser Ser Val Thr Val
    195                 200                 205

Pro Ser Ser Arg Trp Pro Ser Glu Thr Phe Thr Cys Asn Val Val His
    210                 215                 220

Pro Ala Ser Asn Thr Lys Val Asp Lys Pro Val Pro Lys Glu Ser Thr
225                 230                 235                 240

Cys Lys Cys Ile Ser Pro Cys Pro Val Pro Glu Ser Leu Gly Gly Pro
                245                 250                 255

Ser Val Phe Ile Phe Pro Pro Lys Pro Lys Asp Ile Leu Arg Ile Thr
                260                 265                 270

Arg Thr Pro Glu Ile Thr Cys Val Val Leu Asp Leu Gly Arg Glu Asp
            275                 280                 285

Pro Glu Val Gln Ile Ser Trp Phe Val Asp Gly Lys Glu Val His Thr
    290                 295                 300

Ala Lys Thr Gln Pro Arg Glu Gln Gln Phe Asn Ser Thr Tyr Arg Val
305                 310                 315                 320

Val Ser Val Leu Pro Ile Glu His Gln Asp Trp Leu Thr Gly Lys Glu
                325                 330                 335

Phe Lys Cys Arg Val Asn His Ile Gly Leu Pro Ser Pro Ile Glu Arg
                340                 345                 350

Thr Ile Ser Lys Ala Arg Gly Gln Ala His Gln Pro Ser Val Tyr Val
            355                 360                 365

Leu Pro Pro Ser Pro Lys Glu Leu Ser Ser Ser Asp Thr Val Thr Leu
    370                 375                 380

Thr Cys Leu Ile Lys Asp Phe Phe Pro Pro Glu Ile Asp Val Glu Trp
385                 390                 395                 400

Gln Ser Asn Gly Gln Pro Glu Pro Glu Ser Lys Tyr His Thr Ala
                405                 410                 415

Pro Gln Leu Asp Glu Asp Gly Ser Tyr Phe Leu Tyr Ser Lys Leu Ser
                420                 425                 430

Val Asp Lys Ser Arg Trp Gln Gln Gly Asp Thr Phe Thr Cys Ala Val
                435                 440                 445

Met His Glu Ala Leu Gln Asn His Tyr Thr Asp Leu Ser Leu Ser His
        450                 455                 460

Ser Pro Gly Lys
465
```

<210> SEQ ID NO 11
<211> LENGTH: 106
<212> TYPE: PRT
<213> ORGANISM: Homo sapiens

<400> SEQUENCE: 11

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 12
<211> LENGTH: 326
<212> TYPE: PRT
<213> ORGANISM: Homo sapiens

<400> SEQUENCE: 12

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

```
Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Val Leu Asp Ser Asp Gly Ser Phe Phe Leu Tyr Ser Arg
    275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 13
<211> LENGTH: 321
<212> TYPE: DNA
<213> ORGANISM: Homo sapiens

<400> SEQUENCE: 13
actgtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                              321

<210> SEQ ID NO 14
<211> LENGTH: 981
<212> TYPE: DNA
<213> ORGANISM: Homo sapiens

<400> SEQUENCE: 14
tccaccaagg gcccatccgt cttccccctg gcgccctgct ccaggagcac ctccgagagc    60
acagccgccc tgggctgcct ggtcaaggac tacttccccg aaccggtgac ggtgtcgtgg   120
aactcaggcg ccctgaccag cggcgtgcac accttcccgg ctgtcctaca gtcctcagga   180
ctctactccc tcagcagcgt ggtgaccgtg ccctccagca gcttgggcac gaagacctac   240
acctgcaacg tagatcacaa gcccagcaac accaaggtgg acaagagagt tgagtccaaa   300
tatggtcccc catgcccatc atgcccagca cctgagttcc tggggggacc atcagtcttc   360
ctgttccccc caaaacccaa ggacactctc atgatctccc ggacccctga ggtcacgtgc   420
gtggtggtgg acgtgagcca ggaagacccc gaggtccagt tcaactggta cgtggatggc   480
gtggaggtgc ataatgccaa gacaaagccg cgggaggagc agttcaacag cacgtaccgt   540
gtggtcagcg tcctcaccgt cctgcaccag gactggctga acggcaagga gtacaagtgc   600
aaggtctcca acaaaggcct cccgtcctcc atcgagaaaa ccatctccaa agccaaaggg   660
cagccccgag agccacaggt gtacaccctg cccccatccc aggaggagat gaccaagaac   720
caggtcagcc tgacctgcct ggtcaaaggc ttctacccca gcgacatcgc cgtggagtgg   780
gagagcaatg ggcagccgga gaacaactac aagaccacgc ctcccgtgct ggactccgac   840
ggctccttct tcctctacag caggctaacc gtggacaaga gcaggtggca ggaggggaat   900
```

| | |
|---|---|
| gtcttctcat gctccgtgat gcatgaggct ctgcacaacc actacacaca gaagagcctc | 960 |
| tccctgtctc tgggtaaatg a | 981 |

```
<210> SEQ ID NO 15
<211> LENGTH: 399
<212> TYPE: DNA
<213> ORGANISM: Artificial Sequence
<220> FEATURE:
<223> OTHER INFORMATION: codon-optimized sequence

<400> SEQUENCE: 15
```

| | |
|---|---|
| atggaatctc aaactcatgt tttgatttca ttacttctga gtgtttccgg aacctacggt | 60 |
| gatatcgcta tcactcaatc tccctcctct gttgctgtgt ctgtgggcga aaccgttacc | 120 |
| ctgtcctgca gtccagtca gtctcttctc tactccgaga atcaaaagga ctacctgggc | 180 |
| tggtaccaac agaagcccgg ccagacccca agccactga tatactgggc aaccaacagg | 240 |
| cacaccggag tgcccgacag gttcacaggc agtggatctg caccgactt taccttgatc | 300 |
| atttcaagcg tgcaggctga agatctggcc gactactact gtggtcagta tctggtgtat | 360 |
| cctttcactt cgggccagg gacaaaattg gaattgaag | 399 |

```
<210> SEQ ID NO 16
<211> LENGTH: 411
<212> TYPE: DNA
<213> ORGANISM: Artificial Sequence
<220> FEATURE:
<223> OTHER INFORMATION: codon-optimized sequence

<400> SEQUENCE: 16
```

| | |
|---|---|
| atgggttggt ctcaaattat cttgtttttg gttgctgcag ccacttgtgt tcattctcag | 60 |
| gtgcagctgc aacaaagcgg cgcagaactg gtgaaacctg gcagcagcgt gaaaatatct | 120 |
| tgtaaggcca gcggatatac tttcaccctcc aatttcatgc attgggtcaa acagcagccc | 180 |
| ggcaacggac tcgagtggat cggctggatc taccccgagt atggcaacac aaaatataac | 240 |
| caaaaatttg atggaaaggc taccctgact gccgataagt cctccagcac cgcatacatg | 300 |
| caactctcct ccctgacctc cgaggatagc gctgtctact ctgtgcttc cgaagaggct | 360 |
| gtcatatcct tggtctattg gggccaagga actctggtga ccgtctcatc t | 411 |

```
<210> SEQ ID NO 17
<211> LENGTH: 318
<212> TYPE: DNA
<213> ORGANISM: Artificial Sequence
<220> FEATURE:
<223> OTHER INFORMATION: codon-optimized sequence

<400> SEQUENCE: 17
```

| | |
|---|---|
| cagcccaaag cctctcccag cgtcaccctc ttcccacctt ccagtgagga gctgggggca | 60 |
| aacaaagcca ctttggtgtg tctcatctcc gattttttacc cctccggggt cacagtcgca | 120 |
| tggaaggcct ccgatccccc tgtgacacag ggagtggaga acaacaaaacc tagcaagcag | 180 |
| agtaacaata gtatgccgc ctcaagctat ctcagcctta ctcctgataa gtggaagtca | 240 |
| catagcagtt ttagttgcct cgtaacacat gagggttcaa ctgtggagaa aaagtagct | 300 |
| ccagctgagt gctcatga | 318 |

```
<210> SEQ ID NO 18
<211> LENGTH: 996
<212> TYPE: DNA
<213> ORGANISM: Artificial Sequence
```

<220> FEATURE:
<223> OTHER INFORMATION: codon-optimized sequence

<400> SEQUENCE: 18

```
gctagcacaa ccgctccctc cgttttcccc ctcgccccat cctgcgggtc aaccagcgga      60
tccaccgtcg ctctggcttg tctggtgtca ggatacttcc ccgagcctgt caccgtttct     120
tggaatagcg gcagccttac ttccggcgtg catacctccc ctagcgtgct tcagtcctcc     180
ggtctgtatt ccctcagctc caccgtaact gtcccaagct caaggtggcc ctctgagaca     240
tttacctgca atgtggtcca tcctgcttca ataccaaag tggacaagcc cgtcccaaaa      300
gagtctacct gcaaatgtat cagtccttgt cccgtgcccg agtctctggg cggaccctca     360
gtctttatct tcccacccaa gccaaaggac atattgcgca ttacacggac acccgaaatc     420
acctgtgttg tgttggatct cggccgggaa gatcctgagg tgcagattag ttggtttgtt     480
gatggcaagg aggtgcacac agcaaaaaca gcccagag   aacagcagtt caacagtact     540
tatagagtag tgagtgtgtt gcctatagag catcaggact ggctgacagg caaagaattc     600
aaatgtaggg ttaaccacat tggcctccct agtccaatcg agaggacaat ctctaaagcc     660
cgaggccagg ctcatcagcc ttctgtgtac gttctgcctc ctagtcctaa ggaactgtct     720
tcttcagaca cagtaacact cacttgcctg attaaggact tttttcctcc agagattgat     780
gtggaatggc agtctaacgg gcagccgag   ccagaatcta gtaccacac tactgcacca     840
cagctggatg aggatgggtc ttacttcctg tacagtaagc tgagtgtgga caagtctcga     900
tggcagcagg gggatacttt tacttgcgca gtaatgcacg aagcattgca gaaccactac     960
actgacctgt cacttagtca ctcaccaggg aagtaa                              996
```

<210> SEQ ID NO 19
<211> LENGTH: 717
<212> TYPE: DNA
<213> ORGANISM: Artificial Sequence
<220> FEATURE:
<223> OTHER INFORMATION: codon-optimized sequence

<400> SEQUENCE: 19

```
atggaatctc aaactcatgt tttgatttca ttacttctga gtgtttccgg aacctacggt      60
gatatcgcta tcactcaatc tccctcctct gttgctgtgt ctgtgggcga aaccgttacc     120
ctgtcctgca gtccagtca  gtctcttctc tactccagaa atcaaaagga ctacctgggc     180
tggtaccaac agaagcccgg ccagacccca aagccactga tatactgggc aaccaacagg     240
cacaccggag tgcccgacag gttcacaggc agtggatctg gcaccgactt taccttgatc     300
atttcaagcg tgcaggctga agatctggcc gactactact gtgtcagta  tctggtgtat     360
cctttcactt tcgggccagg gacaaaattg gaattgaagc agcccaaagc ctctcccagc     420
gtcaccctct cccaccttc  cagtgaggag ctgggggcaa acaaagccac tttggtgtgt     480
ctcatctccg attttaccc  ctccggggtc acagtcgcat ggaaggcctc cggatcccct     540
gtgacacagg gagtggagac aacaaaacct agcaagcaga taacaataa  gtatgccgcc     600
tcaagctatc tcagccttac tcctgataag tggaagtcac atagcagttt tagttgcctc     660
gtaacacatg agggttcaac tgtggagaaa aaagtagctc agctgagtg  ctcatga        717
```

<210> SEQ ID NO 20
<211> LENGTH: 1407
<212> TYPE: DNA
<213> ORGANISM: Artificial Sequence
<220> FEATURE:
<223> OTHER INFORMATION: codon-optimized sequence

<400> SEQUENCE: 20

```
atgggttggt ctcaaattat cttgtttttg gttgctgcag ccacttgtgt tcattctcag      60
gtgcagctgc aacaaagcgg cgcagaactg gtgaaacctg gcagcagcgt gaaaatatct     120
tgtaaggcca gcggatatac tttcacctcc aatttcatgc attgggtcaa acagcagccc     180
ggcaacggac tcgagtggat cggctggatc taccccgagt atggcaacac aaaatataac     240
caaaaatttg atggaaaggc taccctgact gccgataagt cctccagcac cgcatacatg     300
caactctcct ccctgacctc cgaggatagc gctgtctact tctgtgcttc cgaagaggct     360
gtcatatcct tggtctattg gggccaagga actctggtga ccgtctcatc tgctagcaca     420
accgctccct ccgttttttcc cctcgcccca tcctgcgggt caaccagcgg atccaccgtc     480
gctctggctt gtctggtgtc aggatacttc cccgagcctg tcaccgtttc ttggaatagc     540
ggcagcctta cttccggcgt gcataccttc cctagcgtgc ttcagtcctc cggtctgtat     600
tccctcagct ccaccgtaac tgtcccaagc tcaaggtggc cctctgagac atttacctgc     660
aatgtggtcc atcctgcttc aaataccaaa gtggacaagc ccgtcccaaa agagtctacc     720
tgcaaatgta tcagtccttg tcccgtgccc gagtctctgg gcggacccctc agtctttatc     780
ttcccaccca agccaaagga catattgcgc attacacgga cacccgaaat cacctgtgtt     840
gtgttggatc tcggccggga agatcctgag gtgcagatta gttggtttgt tgatggcaag     900
gaggtgcaca cagcaaaaac acagcccaga gaacagcagt tcaacagtac ttatagagta     960
gtgagtgtgt tgcctataga gcatcaggac tggctgacag gcaaagaatt caaatgtagg    1020
gttaaccaca ttggcctccc tagtccaatc gagaggacaa tctctaaagc ccgaggccag    1080
gctcatcagc cttctgtgta cgttctgcct cctagtccta aggaactgtc ttcttcagac    1140
acagtaacac tcacttgcct gattaaggac ttttttcctc agagattga tgtggaatgg    1200
cagtctaacg ggcagccaga gccagaatct aagtaccaca ctactgcacc acagctggat    1260
gaggatgggt cttacttcct gtacagtaag ctgagtgtgg acaagtctcg atggcagcag    1320
ggggatactt ttacttgcgc agtaatgcac gaagcattgc agaaccacta cactgacctg    1380
tcacttagtc actcaccagg gaagtaa                                        1407
```

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21

```
aggatggctc ctagactccc                                                  20
```

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22

```
agacgatggt ggcatactcg                                                  20
```

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
atgagaatgt ttagtgtctt                                        20

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
ttatgtctct tcaaattgta tatc                                   24

<210> SEQ ID NO 25
<211> LENGTH: 16
<212> TYPE: DNA
<213> ORGANISM: Artificial Sequence
<220> FEATURE:
<223> OTHER INFORMATION: primer

<400> SEQUENCE: 25
gttgatctgt gtgttg                                            16

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
cgggacttcc acatgagcat                                        20

<210> SEQ ID NO 27
<211> LENGTH: 17
<212> TYPE: DNA
<213> ORGANISM: Artificial Sequence
<220> FEATURE:
<223> OTHER INFORMATION: primer

<400> SEQUENCE: 27
ttttagacag aaagtga                                           17

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
gaccagctct tcttggggaa                                        20

<210> SEQ ID NO 29
<211> LENGTH: 29
<212> TYPE: DNA
<213> ORGANISM: Artificial Sequence
<220> FEATURE:
<223> OTHER INFORMATION: primer

<400> SEQUENCE: 29
ccgctcgaga tggggagccg gcgggggcc                                    29

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
cgcggatcct gaggggccac aggccgggtc                                   30

<210> SEQ ID NO 31
<211> LENGTH: 26
<212> TYPE: DNA
<213> ORGANISM: Artificial Sequence
<220> FEATURE:
<223> OTHER INFORMATION: primer

<400> SEQUENCE: 31
gaagatctat gagaatgttt agtgtc                                       26

<210> SEQ ID NO 32
<211> LENGTH: 28
<212> TYPE: DNA
<213> ORGANISM: Artificial Sequence
<220> FEATURE:
<223> OTHER INFORMATION: primer

<400> SEQUENCE: 32
ggaattctgt ctcttcaaat tgtatatc                                     28

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
cgcggctagc atggggagcc ggcgggggcc                                   30

<210> SEQ ID NO 34
<211> LENGTH: 30
<212> TYPE: DNA
<213> ORGANISM: Artificial Sequence
<220> FEATURE:
<223> OTHER INFORMATION: primer

<400> SEQUENCE: 34
cgcggatatc cagcccctgc aactggccgc                                   30

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
cgcggctagc atgagaatgt ttagtgtctt                                   30

-continued

```
<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
cgcggatatc agtcctctca cttgctggaa                                     30

<210> SEQ ID NO 37
<211> LENGTH: 12
<212> TYPE: PRT
<213> ORGANISM: Rattus norvegicus

<400> SEQUENCE: 37

Gln Ser Leu Leu Tyr Ser Glu Asn Gln Lys Asp Tyr
1               5                   10

<210> SEQ ID NO 38
<211> LENGTH: 9
<212> TYPE: PRT
<213> ORGANISM: Rattus norvegicus

<400> SEQUENCE: 38

Gly Gln Tyr Leu Val Tyr Pro Phe Thr
1               5

<210> SEQ ID NO 39
<211> LENGTH: 8
<212> TYPE: PRT
<213> ORGANISM: Rattus norvegicus

<400> SEQUENCE: 39

Gly Tyr Thr Phe Thr Ser Asn Phe
1               5

<210> SEQ ID NO 40
<211> LENGTH: 8
<212> TYPE: PRT
<213> ORGANISM: Rattus norvegicus

<400> SEQUENCE: 40

Ile Tyr Pro Glu Tyr Gly Asn Thr
1               5

<210> SEQ ID NO 41
<211> LENGTH: 11
<212> TYPE: PRT
<213> ORGANISM: Rattus norvegicus

<400> SEQUENCE: 41

Ala Ser Glu Glu Ala Val Ile Ser Leu Val Tyr
1               5                   10

<210> SEQ ID NO 42
<211> LENGTH: 331
<212> TYPE: PRT
<213> ORGANISM: Ovis aries

<400> SEQUENCE: 42

Ala Ser Thr Thr Pro Pro Lys Val Tyr Pro Leu Thr Ser Cys Cys Gly
1               5                   10                  15

Asp Thr Ser Ser Ser Ile Val Thr Leu Gly Cys Leu Val Ser Ser Tyr
            20                  25                  30
```

```
Met Pro Glu Pro Val Thr Val Thr Trp Asn Ser Gly Ala Leu Thr Ser
         35                  40                  45
Gly Val His Thr Phe Pro Ala Ile Leu Gln Ser Gly Leu Tyr Ser
 50                  55                  60
Leu Ser Ser Val Val Thr Val Pro Ala Ser Thr Ser Gly Ala Gln Thr
 65                  70                  75                  80
Phe Ile Cys Asn Val Ala His Pro Ala Ser Ser Thr Lys Val Asp Lys
                 85                  90                  95
Arg Val Glu Pro Gly Cys Pro Asp Pro Cys Lys His Cys Arg Cys Pro
                100                 105                 110
Pro Pro Glu Leu Pro Gly Gly Pro Ser Val Phe Ile Phe Pro Pro Lys
            115                 120                 125
Pro Lys Asp Thr Leu Thr Ile Ser Gly Thr Pro Glu Val Thr Cys Val
130                 135                 140
Val Val Asp Val Gly Gln Asp Asp Pro Glu Val Gln Phe Ser Trp Phe
145                 150                 155                 160
Val Asp Asn Val Glu Val Arg Thr Ala Arg Thr Lys Pro Arg Glu Glu
                165                 170                 175
Gln Phe Asn Ser Thr Phe Arg Val Val Ser Ala Leu Pro Ile Gln His
            180                 185                 190
Gln Asp Trp Thr Gly Gly Lys Glu Phe Lys Cys Lys Val His Asn Glu
            195                 200                 205
Ala Leu Pro Ala Pro Ile Val Arg Thr Ile Ser Arg Thr Lys Gly Gln
        210                 215                 220
Ala Arg Glu Pro Gln Val Tyr Val Leu Ala Pro Pro Gln Glu Glu Leu
225                 230                 235                 240
Ser Lys Ser Thr Leu Ser Val Thr Cys Leu Val Thr Gly Phe Tyr Pro
                245                 250                 255
Asp Tyr Ile Ala Val Glu Trp Gln Lys Asn Gly Gln Pro Glu Ser Glu
            260                 265                 270
Asp Lys Tyr Gly Thr Thr Thr Ser Gln Leu Asp Ala Asp Gly Ser Tyr
        275                 280                 285
Phe Leu Tyr Ser Arg Leu Arg Val Asp Lys Asn Ser Trp Gln Glu Gly
290                 295                 300
Asp Thr Tyr Ala Cys Val Val Met His Glu Ala Leu His Asn His Tyr
305                 310                 315                 320
Thr Gln Lys Ser Ile Ser Lys Pro Pro Gly Lys
                325                 330

<210> SEQ ID NO 43
<211> LENGTH: 996
<212> TYPE: DNA
<213> ORGANISM: Ovis aries

<400> SEQUENCE: 43
gcctcaacaa cacccccgaa agtctaccct ctgacttctt gctgcgggga cacgtccagc      60
tccatcgtga ccctgggctg cctggtctcc agctatatgc ccgagccggt gaccgtgacc     120
tggaactctg gtgccctgac cagcggcgtg cacaccttcc cggccatcct gcagtcctcc     180
gggctctact ctctcagcag cgtggtgacc gtgccggcca gcacctcagg agcccagacc     240
ttcatctgca acgtagccca cccggccagc agcaccaagg tggacaagcg tgttgagccc     300
ggatgccccg acccatgcaa acattgccga tgcccacccc ctgagctccc cggaggaccg     360
tctgtcttca tcttcccacc gaaacccaag gacacccctta caatctctgg aacgcccgag     420
```

```
gtcacgtgtg tggtggtgga cgtgggccag gatgaccccg aggtgcagtt ctcctggttc    480
gtggacaacg tggaggtgcg cacggccagg acaaagccga gagaggagca gttcaacagc    540
accttccgcg tggtcagcgc cctgcccatc cagcaccaag actggactgg aggaaaggag    600
ttcaagtgca aggtccacaa cgaagccctc ccggccccca tcgtgaggac catctccagg    660
accaaagggc aggcccggga ccgcaggtg tacgtcctgg ccccacccca ggaagagctc    720
agcaaaagca cgctcagcgt cacctgcctg gtcaccggct tctacccaga ctacatcgcc    780
gtggagtggc agaaaaatgg gcagcctgag tcggaggaca gtacggcac gaccacatcc    840 cagctggacg ccgacggctc ctacttcctg tacagcaggc tcagggtgga caagaacagc    900
tggcaagaag gagacaccta cgcgtgtgtg gtgatgcacg aggctctgca caaccactac    960
acacagaagt cgatctctaa gcctccgggt aaatga                              996
```

<210> SEQ ID NO 44
<211> LENGTH: 329
<212> TYPE: PRT
<213> ORGANISM: Ovis aries

<400> SEQUENCE: 44

```
Ala Ser Thr Thr Ala Pro Lys Val Tyr Pro Leu Thr Ser Cys Cys Gly
1               5                   10                  15

Asp Thr Ser Ser Ser Ser Ile Val Thr Leu Gly Cys Leu Val Ser
            20                  25                  30

Ser Tyr Met Pro Glu Pro Val Thr Val Thr Trp Asn Ser Gly Ala Leu
        35                  40                  45

Thr Ser Gly Val His Thr Phe Pro Ala Ile Leu Gln Ser Ser Gly Leu
    50                  55                  60

Tyr Ser Leu Ser Ser Val Val Thr Val Pro Ala Ser Thr Ser Gly Ala
65                  70                  75                  80

Gln Thr Phe Ile Cys Asn Val Ala His Pro Ala Ser Ser Ala Lys Val
                85                  90                  95

Asp Lys Arg Val Gly Ile Ser Ser Asp Tyr Ser Lys Cys Ser Lys Pro
            100                 105                 110

Pro Cys Val Ser Arg Pro Ser Val Phe Ile Phe Pro Pro Lys Pro Lys
        115                 120                 125

Asp Ser Leu Met Ile Thr Gly Thr Pro Glu Val Thr Cys Val Val Val
    130                 135                 140

Asp Val Gly Gln Gly Asp Pro Glu Val Gln Phe Ser Trp Phe Val Asp
145                 150                 155                 160

Asn Val Glu Val Arg Thr Ala Arg Thr Lys Pro Arg Glu Glu Gln Phe
                165                 170                 175

Asn Ser Thr Phe Arg Val Val Ser Ala Leu Pro Ile Gln His Asp His
            180                 185                 190

Trp Thr Gly Gly Lys Glu Phe Lys Cys Lys Val His Ser Lys Gly Leu
        195                 200                 205

Pro Ala Pro Ile Val Arg Thr Ile Ser Arg Ala Lys Gly Gln Ala Arg
    210                 215                 220

Glu Pro Gln Val Tyr Val Leu Ala Pro Gln Glu Glu Leu Ser Lys
225                 230                 235                 240

Ser Thr Leu Ser Val Thr Cys Leu Val Thr Gly Phe Tyr Pro Asp Tyr
                245                 250                 255

Ile Ala Val Glu Trp Gln Arg Ala Arg Gln Pro Glu Ser Glu Asp Lys
            260                 265                 270
```

Tyr Gly Thr Thr Thr Ser Gln Leu Asp Ala Asp Gly Ser Tyr Phe Leu
            275                 280                 285

Tyr Ser Arg Leu Arg Val Asp Lys Ser Ser Trp Gln Arg Gly Asp Thr
    290                 295                 300

Tyr Ala Cys Val Val Met His Glu Ala Leu His Asn His Tyr Thr Gln
305                 310                 315                 320

Lys Ser Ile Ser Lys Pro Pro Gly Lys
                325

<210> SEQ ID NO 45
<211> LENGTH: 990
<212> TYPE: DNA
<213> ORGANISM: Ovis aries

<400> SEQUENCE: 45

| | | |
|---|---|---|
| gcctccacca cagccccgaa agtctaccct ctgacttctt gctgcgggga cacgtccagc | 60 |
| tccagctcca tcgtgaccct gggctgcctg gtctccagct atatgcccga gccggtgacc | 120 |
| gtgacctgga actctggtgc cctgaccagc ggcgtgcaca ccttcccggc catcctgcag | 180 |
| tcctccgggc tctactctct cagcagcgtg gtgaccgtgc cggccagcac ctcaggagcc | 240 |
| cagaccttca tctgcaacgt agcccacccg gccagcagcg ccaaggtgga caagcgtgtt | 300 |
| gggatctcca gtgactactc caagtgttct aaaccgcctt gcgtgagccg accgtctgtc | 360 |
| ttcatcttcc ccccgaaacc caaggacagc ctcatgatca caggaacgcc cgaggtcacg | 420 |
| tgtgtggtgg tggacgtggg ccagggtgac cccgaggtgc agttctcctg gttcgtggac | 480 |
| aacgtggagg tgcgcacggc caggacaaag ccgagagagg agcagttcaa cagcaccttc | 540 |
| cgcgtggtca gcgccctgcc catccagcac gaccactgga ctggaggaaa ggagttcaag | 600 |
| tgcaaggtcc acagcaaagg cctcccggcc ccatcgtga ggaccatctc cagggccaaa | 660 |
| gggcaggccc gggagccgca ggtgtacgtc ctggccccac cccaggaaga gctcagcaaa | 720 |
| agcacgctca gcgtcacctg cctggtcacc ggcttctacc cagactacat cgccgtggag | 780 |
| tggcagagag cgcggcagcc tgagtcggag acaagtacg gcacgaccac atcccagctg | 840 |
| gacgccgacg gctcctactt cctgtacagc aggctcaggg tggacaagag cagctggcaa | 900 |
| agaggagaca cctacgcgtg tgtggtgatg cacgaggctc tgcacaacca ctacacacag | 960 |
| aagtcgatct ctaagcctcc gggtaaatga | 990 |

<210> SEQ ID NO 46
<211> LENGTH: 102
<212> TYPE: PRT
<213> ORGANISM: Ovis aries

<400> SEQUENCE: 46

Pro Ser Val Phe Leu Phe Lys Pro Ser Glu Glu Gln Leu Arg Thr Gly
1               5                   10                  15

Thr Val Ser Val Val Cys Leu Val Asn Asp Phe Tyr Pro Lys Asp Ile
            20                  25                  30

Asn Val Lys Val Lys Val Asp Gly Val Thr Gln Asn Ser Asn Phe Gln
            35                  40                  45

Asn Ser Phe Thr Asp Gln Asp Ser Lys Lys Ser Thr Tyr Ser Leu Ser
        50                  55                  60

Ser Thr Leu Thr Leu Ser Ser Ser Glu Tyr Gln Ser His Asn Ala Tyr
65              70                  75                  80

Ala Cys Glu Val Ser His Lys Ser Leu Pro Thr Ala Leu Val Lys Ser
                85                  90                  95

Phe Asn Lys Asn Glu Cys
            100

<210> SEQ ID NO 47
<211> LENGTH: 309
<212> TYPE: DNA
<213> ORGANISM: Ovis aries

<400> SEQUENCE: 47
ccatccgtct tcctcttcaa accatctgag gaacagctga ggaccggaac tgtctctgtc      60
gtgtgcttgg tgaatgattt ctaccccaaa gatatcaatg tcaaggtgaa agtggatggg     120
gttacccaga acagcaactt ccagaacagc ttcacagacc aggacagcaa gaaaagcacc     180
tacagcctca gcagcaccct gacactgtcc agctcagagt accagagcca taacgcctat     240
gcgtgtgagg tcagccacaa gagcctgccc accgccctcg tcaagagctt caataagaat     300
gaatgttag                                                            309

<210> SEQ ID NO 48
<211> LENGTH: 106
<212> TYPE: PRT
<213> ORGANISM: Ovis aries

<400> SEQUENCE: 48

Gly Gln Pro Lys Ser Ala Pro Ser Val Thr Leu Phe Pro Pro Ser Thr
1               5                   10                  15

Glu Glu Leu Ser Thr Asn Lys Ala Thr Val Val Cys Leu Ile Asn Asp
                20                  25                  30

Phe Tyr Pro Gly Ser Val Asn Val Val Trp Lys Ala Asp Gly Ser Thr
            35                  40                  45

Ile Asn Gln Asn Val Lys Thr Thr Gln Ala Ser Lys Gln Ser Asn Ser
        50                  55                  60

Lys Tyr Ala Ala Ser Ser Tyr Leu Thr Leu Thr Gly Ser Glu Trp Lys
65                  70                  75                  80

Ser Lys Ser Ser Tyr Thr Cys Glu Val Thr His Glu Gly Ser Thr Val
                85                  90                  95

Thr Lys Thr Val Lys Pro Ser Glu Cys Ser
            100                 105

<210> SEQ ID NO 49
<211> LENGTH: 321
<212> TYPE: DNA
<213> ORGANISM: Ovis aries

<400> SEQUENCE: 49
ggtcagccca agtccgcacc ctcggtcacc ctgttcccgc cttccacgga ggagctcagt      60
accaacaagg ccaccgtggt gtgtctcatc aacgacttct acccgggtag cgtgaacgtg     120
gtctggaagg cagatggcag caccatcaat cagaacgtga agaccaccca ggcctccaaa     180
cagagcaaca gcaagtacgc ggccagcagc tacctgaccc tgacgggcag cgagtggaag     240
tctaagagca gttacacctg cgaggtcacg cacgagggga gcaccgtgac gaagacagtg     300
aagccctcag agtgttctta g                                              321

```
<210> SEQ ID NO 50
<211> LENGTH: 328
<212> TYPE: PRT
<213> ORGANISM: Sus scrofa

<400> SEQUENCE: 50

Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Met Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Lys Val Asp Lys
                85                  90                  95

Arg Val Gly Thr Lys Thr Lys Pro Pro Cys Pro Ile Cys Pro Gly Cys
            100                 105                 110

Glu Val Ala Gly Pro Ser Val Phe Ile Phe Pro Pro Lys Pro Lys Asp
        115                 120                 125

Thr Leu Met Ile Ser Gln Thr Pro Glu Val Thr Cys Val Val Val Asp
    130                 135                 140

Val Ser Lys Glu His Ala Glu Val Gln Phe Ser Trp Tyr Val Asp Gly
145                 150                 155                 160

Val Glu Val His Thr Ala Glu Thr Arg Pro Lys Glu Gln Phe Asn
                165                 170                 175

Ser Thr Tyr Arg Val Val Ser Val Leu Pro Ile Gln His Gln Asp Trp
            180                 185                 190

Leu Lys Gly Lys Glu Phe Lys Cys Lys Val Asn Asn Val Asp Leu Pro
        195                 200                 205

Ala Pro Ile Thr Arg Thr Ile Ser Lys Ala Ile Gly Gln Ser Arg Glu
    210                 215                 220

Pro Gln Val Tyr Thr Leu Pro Pro Ala Glu Glu Leu Ser Arg Ser
225                 230                 235                 240

Lys Val Thr Val Thr Cys Leu Val Ile Gly Phe Tyr Pro Pro Asp Ile
                245                 250                 255

His Val Glu Trp Lys Ser Asn Gly Gln Pro Glu Pro Glu Gly Asn Tyr
            260                 265                 270

Arg Thr Thr Pro Pro Gln Gln Asp Val Asp Gly Thr Phe Phe Leu Tyr
        275                 280                 285

Ser Lys Leu Ala Val Asp Lys Ala Arg Trp Asp His Gly Glu Thr Phe
    290                 295                 300

Glu Cys Ala Val Met His Glu Ala Leu His Asn His Tyr Thr Gln Lys
305                 310                 315                 320

Ser Ile Ser Lys Thr Gln Gly Lys
                325

<210> SEQ ID NO 51
<211> LENGTH: 987
<212> TYPE: DNA
<213> ORGANISM: Sus scrofa
```

<400> SEQUENCE: 51

```
gcccccaaga cggccccatc ggtctaccct ctggcccct gcggcaggga cacgtctggc        60
cctaacgtgg ccttgggctg cctggcctca agctacttcc ccgagccagt gaccatgacc      120
tggaactcgg gcgccctgac cagtggcgtg cataccttcc catccgtcct gcagccgtca      180
gggctctact ccctcagcag catggtgacc gtgccggcca gcagcctgtc cagcaagagc      240
tacacctgca atgtcaacca cccggccacc accaccaagg tggacaagcg tgttggaaca      300
aagaccaaac caccatgtcc catatgccca ggctgtgaag tggccgggcc ctcggtcttc      360
atcttccctc caaaacccaa ggacacccte atgatctccc agaccccga ggtcacgtgc       420
gtggtggtgg acgtcagcaa ggagcacgcc gaggtccagt tctcctggta cgtggacggc      480
gtagaggtgc acacggccga gacgagacca aaggaggagc agttcaacag cacctaccgt      540
gtggtcagcg tcctgcccat ccagcaccag gactggctga aggggaagga gttcaagtgc      600
aaggtcaaca acgtagacct cccagccccc atcacgagga ccatctccaa ggctataggg      660
cagagccggg agccgcaggt gtacaccctg cccccacccg ccgaggagct gtccaggagc      720
aaagtcaccg taacctgcct ggtcattggc ttctacccac ctgacatcca tgttgagtgg      780
aagagcaacg acagccgga gccagagggc aattaccgca ccaccccgcc ccagcaggac      840
gtggacggga ccttcttcct gtacagcaag ctcgcggtgg acaaggcaag atgggaccat      900
ggagaaacat ttgagtgtgc ggtgatgcac gaggctctgc acaaccacta cacccagaag      960
tccatctcca agactcaggg taaatga                                          987
```

<210> SEQ ID NO 52
<211> LENGTH: 328
<212> TYPE: PRT
<213> ORGANISM: Sus scrofa

<400> SEQUENCE: 52

```
Ala Pro Lys Thr Ala Pro Ser Val Tyr Pro Leu Ala Pro Cys Gly Arg
1               5                   10                  15

Asp Val Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Ile His Gln Pro Gln Thr Cys Pro Ile Cys Pro Gly Cys
            100                 105                 110

Glu Val Ala Gly Pro Ser Val Phe Ile Phe Pro Pro Lys Pro Lys Asp
        115                 120                 125

Thr Leu Met Ile Ser Gln Thr Pro Glu Val Thr Cys Val Val Val Asp
    130                 135                 140

Val Ser Lys Glu His Ala Glu Val Gln Phe Ser Trp Tyr Val Asp Gly
145                 150                 155                 160

Val Glu Val His Thr Ala Glu Thr Arg Pro Lys Glu Glu Gln Phe Asn
                165                 170                 175

Ser Thr Tyr Arg Val Val Ser Val Leu Pro Ile Gln His Gln Asp Trp
            180                 185                 190
```

Leu Lys Gly Lys Glu Phe Lys Cys Lys Val Asn Asn Val Asp Leu Pro
        195                 200                 205

Ala Pro Ile Thr Arg Thr Ile Ser Lys Ala Ile Gly Gln Ser Arg Glu
210                 215                 220

Pro Gln Val Tyr Thr Leu Pro Pro Ala Glu Glu Leu Ser Arg Ser
225                 230                 235                 240

Lys Val Thr Leu Thr Cys Leu Val Ile Gly Phe Tyr Pro Pro Asp Ile
                245                 250                 255

His Val Glu Trp Lys Ser Asn Gly Gln Pro Glu Pro Glu Asn Thr Tyr
            260                 265                 270

Arg Thr Thr Pro Pro Gln Gln Asp Val Asp Gly Thr Phe Phe Leu Tyr
        275                 280                 285

Ser Lys Leu Ala Val Asp Lys Ala Arg Trp Asp His Gly Asp Lys Phe
    290                 295                 300

Glu Cys Ala Val Met His Glu Ala Leu His Asn His Tyr Thr Gln Lys
305                 310                 315                 320

Ser Ile Ser Lys Thr Gln Gly Lys
                325

<210> SEQ ID NO 53
<211> LENGTH: 987
<212> TYPE: DNA
<213> ORGANISM: Sus scrofa

<400> SEQUENCE: 53
gcccccaaga cggcccccatc ggtctaccct ctggcccccct gcggcaggga cgtgtctggc    60
cctaacgtgg ccttgggctg cctggcctca agctacttcc ccgagccagt gaccgtgacc   120
tggaactcgg gcgccctgac cagtggcgtg cacaccttcc catccgtcct gcagccgtca   180
gggctctact ccctcagcag catggtgacc gtgccggcca gcagcctgtc cagcaagagc   240
tacacctgca atgtcaacca cccggccacc accaccaagg tggacaagcg tgttggaata   300
caccagccgc aaacatgtcc catatgccca ggctgtgaag tggccgggcc ctcggtcttc   360
atcttccctc caaaacccaa ggacaccctc atgatctccc agaccccga ggtcacgtgc   420 gtggtggtgg acgtcagcaa ggagcacgcc gaggtccagt tctcctggta cgtggacggc   480
gtagaggtgc acacggccga gacgagacca aggaggagc agttcaacag cacctaccgt   540
gtggtcagcg tcctgcccat ccagcaccag gactggctga aggggaagga gttcaagtgc   600
aaggtcaaca acgtagacct cccagccccc atcacgagga ccatctccaa ggctataggg   660
cagagccggg agccgcaggt gtacaccctg cccccacccg ccgaggagct gtccaggagc   720
aaagtcacgc taacctgcct ggtcattggc ttctacccac ctgacatcca tgttgagtgg   780
aagagcaacg gacagccgga gccagagaac atataccgca ccaccccgcc cagcaggac   840 gtggacggga ccttcttcct gtacagcaaa ctcgcggtgg acaaggcaag atgggaccat   900
ggagacaaat ttgagtgtgc ggtgatgcac gaggctctgc acaaccacta cacccagaag   960
tccatctcca agactcaggg taaatga                                       987

<210> SEQ ID NO 54
<211> LENGTH: 328
<212> TYPE: PRT
<213> ORGANISM: Sus scrofa

<400> SEQUENCE: 54

```
Ala Pro Lys Thr Ala Pro Ser Val Tyr Pro Leu Ala Pro Cys Ser Arg
1               5                   10                  15
Asp Thr Ser Gly Pro Asn Val Ala Leu Gly Cys Leu Ala Ser Ser Tyr
            20                  25                  30
Phe Pro Glu Pro Val Thr Val Thr Trp Asn Ser Gly Ala Leu Ser Ser
        35                  40                  45
Gly Val His Thr Phe Pro Ser Val Leu Gln Pro Ser Gly Leu Tyr Ser
    50                  55                  60
Leu Ser Ser Met Val Thr Val Pro Ala Ser Ser Leu Ser Ser Lys Ser
65                  70                  75                  80
Tyr Thr Cys Asn Val Asn His Pro Ala Thr Thr Lys Val Asp Lys
                85                  90                  95
Arg Val Gly Thr Lys Thr Lys Pro Pro Cys Pro Ile Cys Pro Ala Cys
            100                 105                 110
Glu Ser Pro Gly Pro Ser Val Phe Ile Phe Pro Pro Lys Pro Lys Asp
        115                 120                 125
Thr Leu Met Ile Ser Arg Thr Pro Gln Val Thr Cys Val Val Val Asp
    130                 135                 140
Val Ser Gln Glu Asn Pro Glu Val Gln Phe Ser Trp Tyr Val Asp Gly
145                 150                 155                 160
Val Glu Val His Thr Ala Gln Thr Arg Pro Lys Glu Glu Gln Phe Asn
                165                 170                 175
Ser Thr Tyr Arg Val Val Ser Val Leu Pro Ile Gln His Gln Asp Trp
            180                 185                 190
Leu Asn Gly Lys Glu Phe Lys Cys Lys Val Asn Asn Lys Asp Leu Pro
        195                 200                 205
Ala Pro Ile Thr Arg Ile Ile Ser Lys Ala Lys Gly Gln Thr Arg Glu
    210                 215                 220
Pro Gln Val Tyr Thr Leu Pro Pro His Ala Glu Glu Leu Ser Arg Ser
225                 230                 235                 240
Lys Val Ser Ile Thr Cys Leu Val Ile Gly Phe Tyr Pro Pro Asp Ile
                245                 250                 255
Asp Val Glu Trp Gln Arg Asn Gly Gln Pro Glu Pro Glu Gly Asn Tyr
            260                 265                 270
Arg Thr Thr Pro Pro Gln Gln Asp Val Asp Gly Thr Tyr Phe Leu Tyr
        275                 280                 285
Ser Lys Phe Ser Val Asp Lys Ala Ser Trp Gln Gly Gly Ile Phe
    290                 295                 300
Gln Cys Ala Val Met His Glu Ala Leu His Asn His Tyr Thr Gln Lys
305                 310                 315                 320
Ser Ile Ser Lys Thr Pro Gly Lys
                325
```

<210> SEQ ID NO 55
<211> LENGTH: 987
<212> TYPE: DNA
<213> ORGANISM: Sus scrofa

<400> SEQUENCE: 55

```
gcccccaaga cggccccatc ggtctaccct ctggcccct gcagcaggga cacgtctggc      60
cctaacgtgg ccttgggctg cctggcctca agctacttcc ccgagccagt gaccgtgacc    120
tggaactcgg gcgccctgtc cagtggcgtg catacctcc catccgtcct gcagccgtca     180
```

```
gggctctact ccctcagcag catggtgacc gtgccggcca gcagcctgtc cagcaagagc      240
tacacctgca atgtcaacca cccggccacc accaccaagg tggacaagcg tgttggaaca      300
aagaccaaac caccatgtcc catatgccca gcctgtgaat caccagggcc ctcggtcttc      360
atcttccctc caaacccaa ggacaccctc atgatctccc ggacacccca ggtcacgtgc       420
gtggtggttg atgtgagcca ggagaacccg gaggtccagt tctcctggta cgtggacggc      480
gtagaggtgc acacggccca gacgaggcca aggaggagc agttcaacag cacctaccgc       540
gtggtcagcg tcctacccat ccagcaccag gactggctga acgggaagga gttcaagtgc      600
aaggtcaaca acaaagacct cccagccccc atcacaagga tcatctccaa ggccaaaggg      660
cagacccggg agccgcaggt gtacaccctg cccccacacg ccgaggagct gtccaggagc      720
aaagtcagca taacctgcct ggtcattggc ttctacccac ctgacatcga tgtcgagtgg      780
caaagaaacg gacagccgga gccagagggc aattaccgca ccaccccgcc ccagcaggac      840
gtggacggga cctacttcct gtacagcaag ttctcggtgg acaaggccag ctggcagggt      900
ggaggcatat tccagtgtgc ggtgatgcac gaggctctgc acaaccacta cacccagaag      960
tctatctcca agactccggg taaatga                                          987
```

<210> SEQ ID NO 56
<211> LENGTH: 328
<212> TYPE: PRT
<213> ORGANISM: Sus scrofa

<400> SEQUENCE: 56

```
Ala Pro Lys Thr Ala Pro Leu Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Thr Lys Thr Lys Pro Pro Cys Pro Ile Cys Pro Ala Cys
            100                 105                 110

Glu Ser Pro Gly Pro Ser Val Phe Ile Phe Pro Pro Lys Pro Lys Asp
        115                 120                 125

Thr Leu Met Ile Ser Arg Thr Pro Gln Val Thr Cys Val Val Val Asp
    130                 135                 140

Val Ser Gln Glu Asn Pro Glu Val Gln Phe Ser Trp Tyr Val Asp Gly
145                 150                 155                 160

Val Glu Val His Thr Ala Gln Thr Arg Pro Lys Glu Glu Gln Phe Asn
                165                 170                 175

Ser Thr Tyr Arg Val Val Ser Val Leu Pro Ile Gln His Gln Asp Trp
            180                 185                 190

Leu Asn Gly Lys Glu Phe Lys Cys Lys Val Asn Asn Lys Asp Leu Pro
        195                 200                 205

Ala Pro Ile Thr Arg Ile Ile Ser Lys Ala Lys Gly Gln Thr Arg Glu
    210                 215                 220
```

```
Pro Gln Val Tyr Thr Leu Pro Pro His Ala Glu Glu Leu Ser Arg Ser
225                 230                 235                 240

Lys Val Ser Ile Thr Cys Leu Val Ile Gly Phe Tyr Pro Pro Asp Ile
            245                 250                 255

Asp Val Glu Trp Gln Arg Asn Gly Gln Pro Glu Pro Glu Gly Asn Tyr
        260                 265                 270

Arg Thr Thr Pro Pro Gln Gln Asp Val Asp Gly Thr Tyr Phe Leu Tyr
            275                 280                 285

Ser Lys Phe Ser Val Asp Lys Ala Ser Trp Gln Gly Gly Ile Phe
        290                 295                 300

Gln Cys Ala Val Met His Glu Ala Leu His Asn His Tyr Thr Gln Lys
305                 310                 315                 320

Ser Ile Ser Lys Thr Pro Gly Lys
                325

<210> SEQ ID NO 57
<211> LENGTH: 987
<212> TYPE: DNA
<213> ORGANISM: Sus scrofa

<400> SEQUENCE: 57
gcccccaaga cggcccatt  ggtctaccct ctggcccct  gcggcaggga cacgtctggc     60
cctaacgtgg ccttgggctg cctggcctca agctacttcc ccgagccagt gaccgtgacc    120
tggaactcgg gcgccctgac cagtggcgtg cataccttcc catccgtcct gcagccgtca    180
gggctctact ccctcagcag catggtgacc gtgccggcca gcagcctgtc agcaagagc    240 tacacctgca atgtcaacca cccggccacc accaccaagg tggacaagcg tgttggaaca    300
aagaccaaac caccatgtcc catatgccca gcctgtgaat cgccagggcc ctcggtcttc    360
atcttccctc caaaacccaa ggacaccctc atgatctccc ggacacccca ggtcacgtgc    420
gtggtagttg atgtgagcca ggagaacccg gaggtccagt tctcctggta cgtggacggc    480
gtagaggtgc acacggccca gacgaggcca aggaggagc  agttcaacag cacctaccgc    540
gtggtcagcg tcctgcccat ccagcaccag gactggctga acgggaagga gttcaagtgc    600
aaggtcaaca acaaagacct cccagccccc atcacaagga tcatctccaa ggccaaaggg    660
cagacccggg agccgcaggt gtacaccctg cccccacacg ccgaggagct gtccaggagc    720
aaagtcagca taacctgcct ggtcattggc ttctacccac ctgacatcga tgtcgagtgg    780
caaagaaacg gacagccgga gccagagggc aattaccgca ccacccccgcc ccagcaggac    840 gtggacggga cctacttcct gtacagcaag ttctcggtgg acaaggccag ctggcagggt    900
ggaggcatat tccagtgtgc ggtgatgcac gaggctctgc acaaccacta cacccagaag    960
tctatctcca agactccggg taaatga                                        987

<210> SEQ ID NO 58
<211> LENGTH: 333
<212> TYPE: PRT
<213> ORGANISM: Sus scrofa

<400> SEQUENCE: 58

Ala Tyr Asn Thr Ala Pro Ser Val Tyr Pro Leu Ala Pro Cys Gly Arg
1               5                   10                  15

Asp Val Ser Asp His Asn Val Ala Leu Gly Cys Leu Val Ser Ser Tyr
            20                  25                  30

Phe Pro Glu Pro Val Thr Val Thr Trp Asn Ser Gly Ala Leu Ser Arg
        35                  40                  45
```

```
Val Val His Thr Phe Pro Ser Val Leu Gln Pro Ser Gly Leu Tyr Ser
     50                  55                  60
Leu Ser Ser Met Val Ile Val Ala Ala Ser Ser Leu Ser Thr Leu Ser
 65                  70                  75                  80
Tyr Thr Cys Asn Val Tyr His Pro Ala Thr Asn Thr Lys Val Asp Lys
                 85                  90                  95
Arg Val Asp Ile Glu Pro Pro Thr Pro Ile Cys Pro Glu Ile Cys Ser
            100                 105                 110
Cys Pro Ala Ala Glu Val Leu Gly Ala Pro Ser Val Phe Leu Phe Pro
        115                 120                 125
Pro Lys Pro Lys Asp Ile Leu Met Ile Ser Arg Thr Pro Lys Val Thr
    130                 135                 140
Cys Val Val Val Asp Val Ser Gln Glu Glu Ala Glu Val Gln Phe Ser
145                 150                 155                 160
Trp Tyr Val Asp Gly Val Gln Leu Tyr Thr Ala Gln Thr Arg Pro Met
                165                 170                 175
Glu Glu Gln Phe Asn Ser Thr Tyr Arg Val Val Ser Val Leu Pro Ile
            180                 185                 190
Gln His Gln Asp Trp Leu Lys Gly Lys Glu Phe Lys Cys Lys Val Asn
        195                 200                 205
Asn Lys Asp Leu Leu Ser Pro Ile Thr Arg Thr Ile Ser Lys Ala Thr
    210                 215                 220
Gly Pro Ser Arg Val Pro Gln Val Tyr Thr Leu Pro Pro Ala Trp Glu
225                 230                 235                 240
Glu Leu Ser Lys Ser Lys Val Ser Ile Thr Cys Leu Val Thr Gly Phe
                245                 250                 255
Tyr Pro Pro Asp Ile Asp Val Glu Trp Gln Ser Asn Gly Gln Gln Glu
            260                 265                 270
Pro Glu Gly Asn Tyr Arg Thr Thr Pro Pro Gln Gln Asp Val Asp Gly
        275                 280                 285
Thr Tyr Phe Leu Tyr Ser Lys Leu Ala Val Asp Lys Val Arg Trp Gln
    290                 295                 300
Arg Gly Asp Leu Phe Gln Cys Ala Val Met His Glu Ala Leu His Asn
305                 310                 315                 320
His Tyr Thr Gln Lys Ser Ile Ser Lys Thr Gln Gly Lys
                325                 330

<210> SEQ ID NO 59
<211> LENGTH: 1002
<212> TYPE: DNA
<213> ORGANISM: Sus scrofa

<400> SEQUENCE: 59
gcctacaaca cagctccatc ggtctaccct ctggccccct gtggcaggga cgtgtctgat      60
cataacgtgg ccttgggctg ccttgtctca agctacttcc ccgagccagt gaccgtgacc     120
tggaactcgg gtgccctgtc cagagtcgtg cataccttcc catccgtcct gcagccgtca     180
gggctctact ccctcagcag catggtgatc gtggcggcca gcagcctgtc caccctgagc     240
tacacgtgca acgtctacca cccggccacc aacaccaagg tggacaagcg tgttgacatc     300 gaaccccca cacccatctg tccgaaattt gctcatgcc agctgcaga ggtcctggga      360 gcaccgtcgg tcttcctctt ccctccaaaa cccaaggaca tcctcatgat ctcccggaca     420
cccaaggtca cgtgcgtggt ggtggacgtg agccaggagg aggctgaagt ccagttctcc     480
tggtacgtgg acggcgtaca gttgtacacg gcccagacga ggccaatgga ggagcagttc     540
```

```
aacagcacct accgcgtggt cagcgtcctg cccatccagc accaggactg gctgaagggg    600
aaggagttca agtgcaaggt caacaacaaa gacctccttt cccccatcac gaggaccatc    660
tccaaggcta cagggccgag ccgggtgccg caggtgtaca ccctgccccc agcctgggaa    720
gagctgtcca agagcaaagt cagcataacc tgcctggtca ctggcttcta cccacctgac    780
atcgatgtcg agtggcagag caacggacaa caagagccag agggcaatta ccgcaccacc    840 ccgcccagc aggacgtgga tgggacctac ttcctgtaca gcaagctcgc ggtggacaag    900
gtcaggtggc agcgtggaga cctattccag tgtgcggtga tgcacgaggc tctgcacaac    960
cactacaccc agaagtccat ctccaagact cagggtaaat ga                     1002
```

<210> SEQ ID NO 60
<211> LENGTH: 277
<212> TYPE: PRT
<213> ORGANISM: Sus scrofa

<400> SEQUENCE: 60

```
Thr Phe Pro Ser Val Leu Gln Pro Ser Gly Leu Tyr Ser Leu Ser Ser
1               5                   10                  15

Met Val Thr Val Pro Ala Ser Ser Leu Ser Ser Lys Ser Tyr Thr Cys
            20                  25                  30

Asn Val Asn His Pro Ala Thr Thr Lys Val Asp Lys Arg Val Gly
        35                  40                  45

Thr Lys Thr Lys Pro Pro Cys Pro Ile Cys Pro Ala Cys Glu Gly Pro
    50                  55                  60

Gly Pro Ser Ala Phe Ile Phe Pro Pro Lys Pro Lys Asp Thr Leu Met
65                  70                  75                  80

Ile Ser Arg Thr Pro Lys Val Thr Cys Val Val Val Asp Val Ser Gln
                85                  90                  95

Glu Asn Pro Glu Val Gln Phe Ser Trp Tyr Val Asp Gly Val Glu Val
            100                 105                 110

His Thr Ala Gln Thr Arg Pro Lys Glu Glu Gln Phe Asn Ser Thr Tyr
        115                 120                 125

Arg Val Val Ser Val Leu Pro Ile Gln His Gln Asp Trp Leu Asn Gly
    130                 135                 140

Lys Glu Phe Lys Cys Lys Val Asn Asn Lys Asp Leu Pro Ala Pro Ile
145                 150                 155                 160

Thr Arg Ile Ile Ser Lys Ala Lys Gly Gln Thr Arg Glu Pro Gln Val
                165                 170                 175

Tyr Thr Leu Pro Pro Pro Thr Glu Glu Leu Ser Arg Ser Lys Val Thr
            180                 185                 190

Leu Thr Cys Leu Val Thr Gly Phe Tyr Pro Pro Asp Ile Asp Val Glu
        195                 200                 205

Trp Gln Arg Asn Gly Gln Pro Glu Pro Glu Gly Asn Tyr Arg Thr Thr
    210                 215                 220

Pro Pro Gln Gln Asp Val Asp Gly Thr Tyr Phe Leu Tyr Ser Lys Leu
225                 230                 235                 240

Ala Val Asp Lys Ala Ser Trp Gln Arg Gly Asp Thr Phe Gln Cys Ala
                245                 250                 255

Val Met His Glu Ala Leu His Asn His Tyr Thr Gln Lys Ser Ile Phe
            260                 265                 270

Lys Thr Pro Gly Lys
        275
```

<210> SEQ ID NO 61
<211> LENGTH: 834
<212> TYPE: DNA
<213> ORGANISM: Sus scrofa

<400> SEQUENCE: 61

```
accttcccat ccgtcctgca gccgtcaggg ctctactccc tcagcagcat ggtgaccgtg      60
ccggccagca gcctgtccag caagagctac acctgcaatg tcaaccaccc ggccaccacc     120
accaaggtgg acaagcgtgt tggaacaaag accaaaccac catgtcccat atgcccagcc     180
tgtgaagggc ccggggccctc ggccttcatc ttccctccaa aacccaagga caccctcatg    240
atctcccgga cccccaaggt cacgtgcgtg gtggtagatg tgagccagga gaacccggag     300
gtccagttct cctggtacgt ggacggcgta gaggtgcaca cggcccagac gaggccaaag     360
gaggagcagt tcaacagcac ctaccgcgtg gtcagcgtcc tgcccatcca gcaccaggac     420
tggctgaacg gaaggagtt caagtgcaag gtcaacaaca aagacctccc agccccatc       480
acaaggatca tctccaaggc caaagggcag acccgggagc cgcaggtgta caccctgccc     540
ccacccaccg aggagctgtc caggagcaaa gtcacgctaa cctgcctggt cactggcttc     600
tacccacctg acatcgatgt cgagtggcaa agaaacggac agccggagcc agagggcaat     660
taccgcacca ccccgccccca gcaggacgtg gacgggacct acttcctgta cagcaagctc     720
gcggtggaca aggccagctg gcagcgtgga gacacattcc agtgtgcggt gatgcacgag     780
gctctgcaca accactacac ccagaagtcc atcttcaaga ctccgggtaa atga           834
```

<210> SEQ ID NO 62
<211> LENGTH: 318
<212> TYPE: PRT
<213> ORGANISM: Sus scrofa

<400> SEQUENCE: 62

```
Ala Pro Lys Thr Ala Pro Ser Val Tyr Pro Leu Ala Pro Cys Gly Arg
1               5                   10                  15

Asp Val Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Lys Ser
65                  70                  75                  80

Tyr Thr Cys Asn Val Asn His Pro Ala Thr Thr Lys Val Asp Lys
                85                  90                  95

Arg Val Gly Ile His Gln Pro Gln Thr Cys Pro Ile Cys Pro Ala Cys
            100                 105                 110

Glu Gly Pro Gly Pro Ser Ala Phe Ile Phe Pro Pro Lys Pro Lys Asp
        115                 120                 125

Thr Leu Met Ile Ser Arg Thr Pro Lys Val Thr Cys Val Val Val Asp
    130                 135                 140

Val Ser Gln Glu Asn Pro Glu Val Gln Phe Ser Trp Tyr Val Asp Gly
145                 150                 155                 160

Val Glu Val His Thr Ala Gln Thr Arg Pro Lys Glu Glu Gln Phe Asn
                165                 170                 175

Ser Thr Tyr Arg Val Val Ser Val Leu Leu Ile Gln His Gln Asp Trp
            180                 185                 190
```

```
Leu Asn Gly Lys Glu Phe Lys Cys Lys Val Asn Asn Lys Asp Leu Pro
        195                 200                 205

Ala Pro Ile Thr Arg Ile Ile Ser Lys Ala Lys Gly Gln Thr Arg Glu
    210                 215                 220

Pro Gln Val Tyr Thr Leu Pro Pro Thr Glu Glu Leu Ser Arg Ser
225                 230                 235                 240

Lys Val Thr Leu Thr Cys Leu Val Thr Gly Phe Tyr Pro Pro Asp Ile
                245                 250                 255

Asp Val Glu Trp Gln Arg Asn Gly Gln Pro Glu Pro Glu Gly Asn Tyr
                260                 265                 270

Arg Thr Thr Pro Pro Gln Gln Asp Val Asp Gly Thr Tyr Phe Leu Tyr
            275                 280                 285

Ser Lys Leu Ala Val Asp Lys Ala Ser Trp Gln Arg Gly Asp Thr Phe
        290                 295                 300

Gln Cys Ala Val Met His Glu Ala Leu His Asn His Tyr Thr
305                 310                 315
```

```
<210> SEQ ID NO 63
<211> LENGTH: 955
<212> TYPE: DNA
<213> ORGANISM: Sus scrofa

<400> SEQUENCE: 63
gcccccaaga cggcccccatc ggtctaccct ctggccccct gcggcaggga cgtgtctggc     60
cctaacgtgg ccttgggctg cctggcctca agctacttcc ccgagccagt gaccgtgacc    120
tggaactcgg gcgccctgac cagtggcgtg cacaccttcc catccgtcct gcagccgtca    180
gggctctact ccctcagcag catggtgacc gtgccggcca gcagcctgtc cagcaagagc    240
tacacctgca atgtcaacca cccggccacc accaccaagg tggacaagcg tgttggaata    300
caccagccgc aaacatgtcc catatgccca gcctgtgaag ggcccgggcc ctcggccttc    360
atcttccctc caaaacccaa ggacaccctc atgatctccc ggacccccaa ggtcacgtgc    420
gtggtggttg atgtgagcca ggagaacccg gaggtccagt tctcctggta cgtggacggc    480
gtagaggtgc acacggccca gacgaggcca aggaggagc agttcaacag cacctaccgc    540
gtggtcagcg tcctgctcat ccagcaccag gactggctga acgggaagga gttcaagtgc    600
aaggtcaaca caaagacct cccagccccc atcacaagga tcatctccaa ggccaaaggg    660
cagacccggg agccgcaggt gtacaccctg cccccacccca tcgaggagct gtccaggagc    720
aaagtcacgc taacctgcct ggtcactggc ttctacccac ctgacatcga tgtcgagtgg    780
caaagaaacg gacagccgga gccagagggc aattaccgca ccaccccgcc ccagcaggac    840
gtggacggga cctacttcct gtacagcaag ctcgcggtgg acaaggccag ctggcagcgt    900
ggagacacat tccagtgtgc ggtgatgcac gaggctctgc acaaccacta caccc         955
```

```
<210> SEQ ID NO 64
<211> LENGTH: 323
<212> TYPE: PRT
<213> ORGANISM: Sus scrofa

<400> SEQUENCE: 64

Ala Pro Lys Thr Ala Pro Ser Val Tyr Pro Leu Ala Pro Cys Ser Arg
1               5                   10                  15

Asp Thr Ser Gly Pro Asn Val Ala Leu Gly Cys Leu Val Ser Ser Tyr
                20                  25                  30
```

Phe Pro Glu Pro Val Thr Val Thr Trp Asn Ser Gly Ala Leu Thr Ser
 35                  40                  45

Gly Val His Thr Phe Pro Ser Val Leu Gln Pro Ser Gly Leu Tyr Ser
 50                  55                  60

Leu Ser Ser Met Val Thr Val Pro Ala His Ser Leu Ser Ser Lys Arg
65                  70                  75                  80

Tyr Thr Cys Asn Val Asn His Pro Ala Thr Lys Thr Lys Val Asp Leu
                 85                  90                  95

Cys Val Gly Arg Pro Cys Pro Ile Cys Pro Gly Cys Glu Val Ala Gly
            100                 105                 110

Pro Ser Val Phe Ile Phe Pro Pro Lys Pro Lys Asp Ile Leu Met Ile
        115                 120                 125

Ser Arg Thr Pro Glu Val Thr Cys Val Val Val Asp Val Ser Lys Glu
130                 135                 140

His Ala Glu Val Gln Phe Ser Trp Tyr Val Asp Gly Glu Glu Val His
145                 150                 155                 160

Thr Ala Glu Thr Arg Pro Lys Glu Glu Gln Phe Asn Ser Thr Tyr Arg
                165                 170                 175

Val Val Ser Val Leu Pro Ile Gln His Glu Asp Trp Leu Lys Gly Lys
            180                 185                 190

Glu Phe Glu Cys Lys Val Asn Asn Glu Asp Leu Pro Gly Pro Ile Thr
        195                 200                 205

Arg Thr Ile Ser Lys Ala Lys Gly Val Val Arg Ser Pro Glu Val Tyr
210                 215                 220

Thr Leu Pro Pro Pro Ala Glu Glu Leu Ser Lys Ser Ile Val Thr Leu
225                 230                 235                 240

Thr Cys Leu Val Lys Ser Ile Phe Pro Phe Ile His Val Glu Trp Lys
                245                 250                 255

Ile Asn Gly Lys Pro Glu Pro Glu Asn Ala Tyr Arg Thr Thr Pro Pro
            260                 265                 270

Gln Glu Asp Glu Asp Arg Thr Tyr Phe Leu Tyr Ser Lys Leu Ala Val
        275                 280                 285

Asp Lys Ala Arg Trp Asp His Gly Glu Thr Phe Glu Cys Ala Val Met
290                 295                 300

His Glu Ala Leu His Asn His Tyr Thr Gln Lys Ser Ile Ser Lys Thr
305                 310                 315                 320

Gln Gly Lys

<210> SEQ ID NO 65
<211> LENGTH: 975
<212> TYPE: DNA
<213> ORGANISM: Sus scrofa
<220> FEATURE:
<221> NAME/KEY: misc_feature
<222> LOCATION: (748)..(748)
<223> OTHER INFORMATION: n is a, c, g, or t

<400> SEQUENCE: 65
gcccccaaga cggccccatc ggtctaccct ctggcccct gcagcaggga cacgtctggc      60
cctaacgtgg ccttgggctg cctggtctca agctacttcc ccgagccagt gaccgtgacc    120
tggaactcgg gcgccctgac cagtggcgtg cacaccttcc catccgtcct gcagccgtca    180
gggctctact ccctcagcag catggtgacc gtgccggccc acagcttgtc cagcaagcgc    240
tatacgtgca atgtcaacca cccagccacc aaaaccaagg tggacctgtg tgttggacga    300
ccatgtccca tgcccagg ctgtgaagtg gccgggccct cggtcttcat cttccctcca    360

-continued

```
aaacccaagg acatcctcat gatctcccgg accccgagg tcacgtgcgt ggtggtggac    420
gtcagcaagg agcacgccga ggtccagttc tcctggtacg tggacggcga agaggtgcac    480
acggccgaga cgaggccaaa ggaggagcag ttcaacagca cctaccgcgt ggtcagcgtc    540
ctgcccatcc agcacgagga ctggctgaag gggaaggagt tcgagtgcaa ggtcaacaac    600
gaagacctcc caggcccat cacgaggacc atctccaagg ccaaggggt ggtacggagc      660 ccggaggtgt acaccctgcc cccacccgcc gaggagctgt ccaagagcat agtcacgcta    720
acctgcctgg tcaaaagcat cttcccgnct ttcatccatg ttgagtggaa aatcaacgga    780
aaaccagagc cagagaacgc atatcgcacc accccgcctc aggaggacga ggacaggacc    840
tacttcctgt acagcaagct cgcggtggac aaggcaagat gggaccatgg agaaacattt    900
gagtgtgcgg tgatgcacga ggctctgcac aaccactaca cccagaagtc catctccaag    960
actcagggta aatga                                                    975
```

<210> SEQ ID NO 66
<211> LENGTH: 317
<212> TYPE: PRT
<213> ORGANISM: Sus scrofa

<400> SEQUENCE: 66

```
Ala Tyr Asn Thr Ala Pro Ser Val Tyr Pro Leu Ala Pro Cys Gly Arg
1               5                   10                  15

Asp Val Ser Asp His Asn Val Ala Leu Gly Cys Leu Val Ser Ser Tyr
            20                  25                  30

Phe Pro Glu Pro Val Thr Val Thr Trp Asn Trp Gly Ala Gln Thr Ser
        35                  40                  45

Gly Val His Thr Phe Pro Ser Val Leu Gln Pro Ser Gly Leu Tyr Ser
    50                  55                  60

Leu Ser Ser Thr Val Thr Val Pro Ala His Ser Leu Ser Ser Lys Cys
65                  70                  75                  80

Phe Thr Cys Asn Val Asn His Pro Ala Thr Thr Thr Lys Val Asp Leu
                85                  90                  95

Cys Val Gly Lys Lys Thr Lys Pro Arg Cys Pro Ile Cys Pro Gly Cys
            100                 105                 110

Glu Val Ala Gly Pro Ser Val Phe Ile Phe Pro Pro Lys Pro Lys Asp
        115                 120                 125

Ile Leu Met Ile Ser Arg Thr Pro Glu Val Thr Cys Val Val Val Asp
    130                 135                 140

Val Ser Lys Glu His Ala Glu Val Gln Phe Ser Trp Tyr Val Asp Gly
145                 150                 155                 160

Glu Glu Val His Thr Ala Glu Thr Arg Pro Lys Glu Glu Gln Phe Asn
                165                 170                 175

Ser Thr Tyr Arg Val Val Ser Val Leu Pro Ile Gln His Glu Asp Trp
            180                 185                 190

Leu Lys Gly Lys Glu Phe Glu Cys Lys Val Asn Asn Glu Asp Leu Pro
        195                 200                 205

Gly Pro Ile Thr Arg Thr Ile Ser Lys Ala Lys Gly Val Val Arg Ser
    210                 215                 220

Pro Glu Val Tyr Thr Leu Pro Pro Ala Glu Glu Leu Ser Lys Ser
225                 230                 235                 240

Ile Val Thr Leu Thr Cys Leu Val Lys Ser Phe Phe Pro Pro Phe Ile
                245                 250                 255
```

His Val Glu Trp Lys Ile Asn Gly Lys Pro Glu Pro Glu Asn Ala Tyr
                260                 265                 270

Arg Thr Thr Pro Pro Gln Glu Asp Glu Asp Gly Thr Tyr Phe Leu Tyr
            275                 280                 285

Ser Lys Phe Ser Val Glu Lys Phe Arg Trp His Ser Gly Gly Ile His
        290                 295                 300

Cys Ala Val Met His Glu Ala Leu His Asn His Tyr Thr
305                 310                 315

<210> SEQ ID NO 67
<211> LENGTH: 952
<212> TYPE: DNA
<213> ORGANISM: Sus scrofa

<400> SEQUENCE: 67

| | | | | | |
|---|---|---|---|---|---|
| gcctacaaca | cagctccatc | ggtctaccct | ctggccccct | gtggcaggga | cgtgtctgat | 60 |
| cataacgtgg | ccttgggctg | cctggtctca | agctacttcc | ccgagccagt | gaccgtgacc | 120 |
| tggaactggg | gcgcccagac | cagtggcgtg | cacaccttcc | catccgtcct | gcagccgtca | 180 |
| gggctctact | ccctcagcag | cacggtgacc | gtgccggccc | acagcttgtc | cagcaagtgc | 240 |
| ttcacgtgca | atgtcaacca | cccggccacc | accaccaagg | tggacctgtg | tgttggaaaa | 300 |
| aagaccaagc | ctcgatgtcc | catatgccca | ggctgtgaag | tggccgggcc | ctcggtcttc | 360 |
| atcttccctc | caaaacccaa | ggacatcctc | atgatctccc | ggacccccga | ggtcacgtgc | 420 |
| gtggtggtgg | acgtcagcaa | ggagcacgcc | gaggtccagt | tcctcctggta | cgtggacggc | 480 |
| gaagaggtgc | acacggccga | gacgagacca | aggaggagc | agttcaacag | cacttaccgc | 540 |
| gtggtcagcg | tcctgcccat | ccagcacgag | gactggctga | aggggaagga | gttcgagtgc | 600 |
| aaggtcaaca | acgaagacct | cccaggcccc | atcacgagga | ccatctccaa | ggccaaaggg | 660 |
| gtggtacgga | gcccggaggt | gtacaccctg | cccccacccg | ccgaggagct | gtccaagagc | 720 |
| atagtcacgc | taacctgcct | ggtcaaaagc | ttcttcccgc | ctttcatcca | tgttgagtgg | 780 |
| aaaatcaacg | gaaaaccaga | gccagagaac | gcataccgca | ccaccccgcc | ccaggaggac | 840 |
| gaggacggga | cctacttcct | gtacagcaag | ttctcggtgg | aaaagttcag | gtggcacagt | 900 |
| ggaggcatcc | actgtgcggt | gatgcacgag | gctctgcaca | accactacac | cc | 952 |

<210> SEQ ID NO 68
<211> LENGTH: 314
<212> TYPE: PRT
<213> ORGANISM: Sus scrofa

<400> SEQUENCE: 68

Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Leu Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Leu
                85                  90                  95

```
Cys Val Gly Arg Pro Cys Pro Ile Cys Pro Ala Cys Glu Gly Pro Gly
            100                 105                 110

Pro Ser Val Phe Ile Phe Pro Lys Pro Lys Asp Thr Leu Met Ile
        115                 120                 125

Ser Arg Thr Pro Gln Val Thr Cys Val Val Asp Val Ser Gln Glu
130                 135                 140

Asn Pro Glu Val Gln Phe Ser Trp Tyr Val Asp Gly Val Glu Val His
145                 150                 155                 160

Thr Ala Gln Thr Arg Pro Lys Glu Ala Gln Phe Asn Ser Thr Tyr Arg
                165                 170                 175

Val Val Ser Val Leu Pro Ile Gln His Glu Asp Trp Leu Lys Gly Lys
            180                 185                 190

Glu Phe Glu Cys Lys Val Asn Asn Lys Asp Leu Pro Ala Pro Ile Thr
        195                 200                 205

Arg Ile Ile Ser Lys Ala Lys Gly Pro Ser Arg Glu Pro Gln Val Tyr
    210                 215                 220

Thr Leu Ser Pro Ser Ala Glu Glu Leu Ser Arg Ser Lys Val Ser Ile
225                 230                 235                 240

Thr Cys Leu Val Thr Gly Phe Tyr Pro Pro Asp Ile Asp Val Glu Trp
                245                 250                 255

Lys Ser Asn Gly Gln Pro Glu Pro Glu Gly Asn Tyr Arg Thr Thr Pro
                260                 265                 270

Pro Gln Gln Asp Val Asp Gly Thr Tyr Phe Leu Tyr Ser Lys Leu Ala
                275                 280                 285

Val Asp Lys Ala Ser Trp Gln Arg Gly Asp Pro Phe Gln Cys Ala Val
        290                 295                 300

Met His Glu Ala Leu His Asn His Tyr Thr
305                 310

<210> SEQ ID NO 69
<211> LENGTH: 943
<212> TYPE: DNA
<213> ORGANISM: Sus scrofa

<400> SEQUENCE: 69
gcccccaaga cggccccatc ggtctaccct ctggccccct gcggcaggga cacgtctggc      60
cctaacgtgg ccttgggctg cctggcctca agctacttcc ccgagccagt gaccctgacc     120
tggaactcgg gcgccctgac cagtggcgtg cataccttcc catccgtcct gcagccgtca     180
gggctctact ccctcagcag catggtgacc gtgccggcca gcagcctgtc cagcaagagc     240
tacacctgca atgtcaacca cccggccacc accaccaagg tggacctgtg tgttggacga     300
ccatgtccca tgcccagc tgtgaaggg cccgggccct cggtcttcat cttccctcca     360
aaacccaagg acaccctcat gatctcccgg acacccagg tcacgtgcgt ggtggtagat     420
gtgagccagg aaaacccgga ggtccagttc tcctggtatg tggacggtgt agaggtgcac     480
acggcccaga cgaggccaaa ggaggcgcag ttcaacagca cctaccgtgt ggtcagcgtc     540
ctgcccatcc agcacgagga ctggctgaag gggaaggagt tcgagtgcaa ggtcaacaac     600
aaagacctcc cagcccccat cacaaggatc atctccaagg ccaagggcc gagccgggag     660 ccgcaggtgt acaccctgtc ccatccgcc gaggagctgt ccaggagcaa agtcagcata     720
acctgcctgg tcactggctt ctacccacct gacatcgatg tcgagtggaa gagcaacgga     780
cagccggagc cagagggcaa ttaccgcacc accccgcccc agcaggacgt ggacgggacc     840
```

```
tacttcctgt acagcaagct cgcggtggac aaggccagct ggcagcgtgg agacccattc    900
cagtgtgcgg tgatgcacga ggctctgcac aaccactaca ccc                      943
```

<210> SEQ ID NO 70
<211> LENGTH: 320
<212> TYPE: PRT
<213> ORGANISM: Sus scrofa

<400> SEQUENCE: 70

```
Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Thr Val Thr Val Pro Ala Arg Ser Ser Arg Lys Cys
65              70                  75                  80

Phe Thr Cys Asn Val Asn His Pro Ala Thr Thr Thr Lys Val Asp Leu
                85                  90                  95

Cys Val Gly Arg Pro Cys Pro Ile Cys Pro Ala Cys Glu Gly Asn Gly
            100                 105                 110

Pro Ser Val Phe Ile Phe Pro Pro Lys Pro Lys Asp Thr Leu Met Ile
        115                 120                 125

Ser Arg Thr Pro Glu Val Thr Cys Val Val Val Asp Val Ser Gln Glu
    130                 135                 140

Asn Pro Glu Val Gln Phe Ser Trp Tyr Val Asp Gly Glu Glu Val His
145                 150                 155                 160

Thr Ala Glu Thr Arg Pro Lys Glu Glu Gln Phe Asn Ser Thr Tyr Arg
                165                 170                 175

Val Val Ser Val Leu Pro Ile Gln His Gln Asp Trp Leu Lys Gly Lys
            180                 185                 190

Glu Phe Glu Cys Lys Val Asn Asn Lys Asp Leu Pro Ala Pro Ile Thr
        195                 200                 205

Arg Ile Ile Ser Lys Ala Lys Gly Pro Ser Arg Glu Pro Gln Val Tyr
    210                 215                 220

Thr Leu Ser Pro Ser Ala Glu Glu Leu Ser Arg Ser Lys Val Ser Ile
225                 230                 235                 240

Thr Cys Leu Val Thr Gly Phe Tyr Pro Pro Asp Ile Asp Val Glu Trp
                245                 250                 255

Lys Ser Asn Gly Gln Pro Glu Pro Glu Gly Asn Tyr Arg Ser Thr Pro
            260                 265                 270

Pro Gln Glu Asp Glu Asp Gly Thr Tyr Phe Leu Tyr Ser Lys Leu Ala
        275                 280                 285

Val Asp Lys Ala Arg Leu Gln Ser Gly Gly Ile His Cys Ala Val Met
    290                 295                 300

His Glu Ala Leu His Asn His Tyr Thr Gln Lys Ser Ile Ser Lys Thr
305                 310                 315                 320
```

<210> SEQ ID NO 71
<211> LENGTH: 960
<212> TYPE: DNA
<213> ORGANISM: Sus scrofa

<400> SEQUENCE: 71

```
gcccccaaga cggcccccatc ggtctaccct ctggccccct gcggcaggga cacgtctggc    60
cctaacgtgg ccttgggctg cctggcctca agctacttcc ccgagccagt gaccgtgacc   120
tggaactcgg gcgccctgac cagtggcgtg cacaccttcc catccgtcct gcagccgtca   180
gggctctact ccctcagcag cacggtgacc gtgccggcca ggagctcgtc cagaaagtgc   240
ttcacgtgca atgtcaacca cccggccacc accaccaagg tggacctgtg tgttggacga   300
ccatgtccca tatgcccagc ctgtgaaggg aacgggccct cggtcttcat cttccctcca   360
aaacccaagg acaccctcat gatctcccgg accccgaggag tcacgtgcgt ggtggtagat   420
gtgagccagg aaaacccgga ggtccagttc tcctggtacg tggacggcga agaggtgcac   480
acggccgaga cgaggccaaa ggaggagcag ttcaacagca cctaccgtgt ggtcagcgtc   540
ctgcccatcc agcaccagga ctggctgaag ggaaaggagt tcgagtgcaa ggtcaacaac   600
aaagacctcc cagcccccat acaaggatc atctccaagg ccaaagggcc gagccgggag   660
ccgcaggtgt acaccctgtc ccatccgcc gaggagctgt ccaggagcaa agtcagcata   720
acctgcctgg tcactggctt ctacccacct gacatcgatg tcgagtggaa gagcaacgga   780
cagccggagc cagagggcaa ttaccgctcc accccgcccc aggaggacga ggacgggacc   840
tacttcctgt acagcaaact cgcggtggac aaggcgaggt tgcagagtgg aggcatccac   900
tgtgcggtga tgcacgaggc tctgcacaac cactacaccc agaagtccat ctccaagact   960
```

<210> SEQ ID NO 72
<211> LENGTH: 266
<212> TYPE: PRT
<213> ORGANISM: Bubalus bubalis

<400> SEQUENCE: 72

```
Ser Gly Val His Thr Phe Pro Ala Val Leu Gln Ser Ser Gly Leu Tyr
  1               5                  10                  15

Ser Leu Ser Ser Thr Val Thr Ala Pro Ala Ser Ala Thr Lys Ser Gln
             20                  25                  30

Thr Phe Thr Cys Asn Val Ala His Pro Ala Ser Ser Thr Lys Val Asp
         35                  40                  45

Lys Ala Val Val Pro Pro Cys Arg Pro Lys Pro Cys Asp Cys Cys Pro
     50                  55                  60

Pro Pro Glu Leu Pro Gly Gly Pro Ser Val Phe Ile Phe Pro Pro Lys
 65                  70                  75                  80

Pro Lys Asp Thr Leu Thr Ile Ser Gly Thr Pro Glu Val Thr Cys Val
                 85                  90                  95

Val Val Asp Val Gly His Asp Asp Pro Glu Val Lys Phe Ser Trp Phe
            100                 105                 110

Val Asp Asp Val Glu Val Asn Thr Ala Arg Thr Lys Pro Arg Glu Glu
        115                 120                 125

Gln Phe Asn Ser Thr Tyr Arg Val Val Ser Ala Leu Pro Ile Gln His
    130                 135                 140

Asn Asp Trp Thr Gly Gly Lys Glu Phe Lys Cys Lys Val Tyr Asn Glu
145                 150                 155                 160

Gly Leu Pro Ala Pro Ile Val Arg Thr Ile Ser Arg Thr Lys Gly Gln
                165                 170                 175

Ala Arg Glu Pro Gln Val Tyr Val Leu Ala Pro Pro Gln Asp Glu Leu
            180                 185                 190
```

```
Ser Lys Ser Thr Val Ser Ile Thr Cys Met Val Thr Gly Phe Tyr Pro
        195                 200                 205
Asp Tyr Ile Ala Val Glu Trp Gln Lys Asp Gly Gln Pro Glu Ser Glu
    210                 215                 220
Asp Lys Tyr Gly Thr Thr Pro Pro Gln Leu Asp Ser Asp Gly Ser Tyr
225                 230                 235                 240
Phe Leu Tyr Ser Arg Leu Arg Val Asn Lys Asn Ser Trp Gln Glu Gly
            245                 250                 255
Gly Ala Tyr Thr Cys Val Val Met His Glu
        260                 265

<210> SEQ ID NO 73
<211> LENGTH: 801
<212> TYPE: DNA
<213> ORGANISM: Bubalus bubalis

<400> SEQUENCE: 73
gagcggcgtg cacaccttcc cggccgtcct tcagtcctcc gggctctact ctctcagcag      60
cacggtgacc gcgcccgcca gcgccacaaa aagccagacc ttcacctgca acgtagccca     120
cccggccagc agcaccaagg tggacaaggc tgttgttccc ccatgcagac cgaaaccctg     180
tgattgctgc ccacccctg agctccccgg aggaccctct gtcttcatct tcccaccaaa      240
acccaaggac accctcacaa tctctggaac tcctgaggtc acgtgtgtgg tggtggacgt     300
gggccacgat gaccccgagg tgaagttctc ctggttcgtg gacgatgtgg aggtaaacac     360
agccaggacg aagccaagag aggagcagtt caacagcacc taccgcgtgg tcagcgccct     420
gcccatccag cacaacgact ggactggagg aaaggagttc aagtgcaagg tctacaatga     480
aggcctccca gcccccatcg tgaggaccat ctccaggacc aaagggcagg cccgggagcc     540
gcaggtgtac gtcctggccc cacccccagga cgagctcagc aaaagcacgg tcagcatcac     600
ttgcatggtc actggcttct acccagacta catcgccgta gagtggcaga agatgggca      660
gcctgagtca gaggacaaat atggcacgac cccgccccag ctggacagcg atggctccta     720
cttcctgtac agcaggctca gggtgaacaa gaacagctgg caagaaggag gcgcctacac     780
gtgtgtagtg atgcatgagg c                                               801

<210> SEQ ID NO 74
<211> LENGTH: 309
<212> TYPE: PRT
<213> ORGANISM: Bulalus bubalis

<400> SEQUENCE: 74

Ala Ser Ile Thr Ala Pro Lys Val Tyr Pro Leu Thr Ser Cys Arg Gly
1               5                   10                  15
Glu Thr Ser Ser Ser Thr Val Thr Leu Gly Cys Leu Val Ser Ser Tyr
            20                  25                  30
Met Pro Glu Pro Val Thr Val Thr Trp Asn Ser Gly Ala Leu Lys Ser
        35                  40                  45
Gly Val His Thr Phe Pro Ala Val Leu Gln Ser Ser Gly Leu Tyr Ser
    50                  55                  60
Leu Ser Ser Thr Val Thr Ala Pro Ala Ser Ala Thr Lys Ser Gln Thr
65                  70                  75                  80
Phe Thr Cys Asn Val Ala His Pro Ala Ser Ser Thr Lys Val Asp Thr
            85                  90                  95
Ala Val Gly Phe Ser Ser Asp Cys Cys Lys Phe Pro Lys Pro Cys Val
            100                 105                 110
```

```
Arg Gly Pro Ser Val Phe Ile Phe Pro Pro Lys Pro Lys Asp Thr Leu
            115                 120                 125
Met Ile Thr Gly Asn Pro Glu Val Thr Cys Val Val Asp Val Gly
        130                 135                 140
Arg Asp Asn Pro Glu Val Gln Phe Ser Trp Phe Val Gly Asp Val Glu
145                 150                 155                 160
Val His Thr Gly Arg Ser Lys Pro Arg Glu Glu Gln Phe Asn Ser Thr
                165                 170                 175
Tyr Arg Val Val Ser Thr Leu Pro Ile Gln His Asn Asp Trp Thr Gly
                180                 185                 190
Gly Lys Glu Phe Lys Cys Lys Val Asn Asn Lys Gly Leu Pro Ala Pro
            195                 200                 205
Ile Val Arg Thr Ile Ser Arg Thr Lys Gly Gln Ala Arg Glu Pro Gln
            210                 215                 220
Val Tyr Val Leu Ala Pro Pro Gln Glu Glu Leu Ser Lys Ser Thr Val
225                 230                 235                 240
Ser Val Thr Cys Met Val Thr Gly Phe Tyr Pro Asp Tyr Ile Ala Val
                245                 250                 255
Glu Trp His Arg Asp Arg Gln Ala Glu Ser Glu Asp Lys Tyr Arg Thr
            260                 265                 270
Thr Pro Pro Gln Leu Asp Ser Asp Gly Ser Tyr Phe Leu Tyr Ser Arg
            275                 280                 285
Leu Lys Val Asn Lys Asn Ser Trp Gln Glu Gly Gly Ala Tyr Thr Cys
            290                 295                 300
Val Val Met His Glu
305

<210> SEQ ID NO 75
<211> LENGTH: 929
<212> TYPE: DNA
<213> ORGANISM: Bubalus bubalis

<400> SEQUENCE: 75
gcctccatca cagccccgaa agtctaccct ctgacttctt gccgcgggga aacgtccagc      60
tccaccgtga ccctgggctg cctggtctcc agctacatgc ccgagccggt gaccgtgacc     120
tggaactcgg gtgccctgaa gagcggcgtg cacaccttcc cggccgtcct tcagtcctct     180
gggctctact ctctcagcag cacggtgacc gcgcccgcca gcgccacaaa agccagacc      240
ttcacctgca acgtagccca cccggccagc agcaccaagg tggacacggc tgttgggttc     300
tccagtgact gctgcaagtt tcctaagcct tgtgtgaggg gaccatctgt cttcatcttc     360
ccgccgaaac ccaaagacac cctgatgatc acaggaaatc ccgaggtcac atgtgtggtg     420
gtggacgtgg gccgggataa ccccgaggtg cagttctcct ggttcgtggg tgatgtggag     480
gtgcacacgg gcaggtcgaa gccgagagag gagcagttca acagcaccta ccgcgtggtc     540
agcaccctgc ccatccagca caatgactgg actggaggaa aggagttcaa gtgcaaggtc     600
aacaacaaag gcctcccagc ccccatcgtg aggaccatct ccaggaccaa agggcaggcc     660
cgggagccgc aggtgtacgt cctggcccca ccccaggaag agctcagcaa agcacggtc      720
agcgtcactt gcatggtcac tggcttctac ccagactaca tcgccgtaga gtggcataga     780
gaccggcagg ctgagtcgga ggacaagtac cgcacgaccc cgccccagct ggacagcgat     840
ggctcctact tcctgtacag caggctcaag gtgaacaaga acagctggca agaaggaggc     900
gcctacacgt gtgtagtgat gcatgaggc                                       929
```

```
<210> SEQ ID NO 76
<211> LENGTH: 352
<212> TYPE: PRT
<213> ORGANISM: Bubalus bubalis

<400> SEQUENCE: 76
```

| | | | | | | | | | | | | | | | |
|---|---|---|---|---|---|---|---|---|---|---|---|---|---|---|---|
| Ala | Ser | Thr | Thr | Ala | Pro | Lys | Val | Tyr | Pro | Leu | Ala | Ser | Ser | Cys | Gly |
| 1 | | | | 5 | | | | | 10 | | | | | 15 | |
| Asp | Thr | Ser | Ser | Ser | Thr | Val | Thr | Leu | Gly | Cys | Leu | Val | Ser | Ser | Tyr |
| | | | 20 | | | | | 25 | | | | | 30 | | |
| Met | Pro | Glu | Pro | Val | Thr | Val | Thr | Trp | Asn | Ser | Gly | Ala | Leu | Lys | Asn |
| | | | 35 | | | | 40 | | | | | 45 | | | |
| Gly | Val | His | Thr | Phe | Pro | Ala | Val | Arg | Gln | Ser | Ser | Gly | Leu | Tyr | Ser |
| | 50 | | | | | 55 | | | | | 60 | | | | |
| Leu | Ser | Ser | Met | Val | Thr | Met | Pro | Thr | Ser | Thr | Ala | Gly | Thr | Gln | Thr |
| 65 | | | | 70 | | | | | 75 | | | | | 80 | |
| Phe | Thr | Cys | Asn | Val | Ala | His | Pro | Ala | Ser | Ser | Thr | Lys | Val | Asp | Thr |
| | | | | 85 | | | | | 90 | | | | | 95 | |
| Ala | Val | Thr | Ala | Arg | His | Pro | Val | Pro | Lys | Thr | Pro | Glu | Thr | Pro | Ile |
| | | | 100 | | | | | 105 | | | | | 110 | | |
| His | Pro | Val | Lys | Pro | Pro | Thr | Gln | Glu | Pro | Arg | Asp | Glu | Lys | Thr | Pro |
| | | | 115 | | | | | 120 | | | | | 125 | | |
| Cys | Gln | Cys | Pro | Lys | Cys | Pro | Glu | Pro | Leu | Gly | Gly | Leu | Ser | Val | Phe |
| 130 | | | | | 135 | | | | | 140 | | | | | |
| Ile | Phe | Pro | Pro | Lys | Pro | Lys | Asp | Thr | Leu | Thr | Ile | Ser | Gly | Thr | Pro |
| 145 | | | | 150 | | | | | 155 | | | | | 160 | |
| Glu | Val | Thr | Cys | Val | Val | Val | Asp | Val | Gly | Gln | Asp | Asp | Pro | Glu | Val |
| | | | 165 | | | | | 170 | | | | | 175 | | |
| Gln | Phe | Ser | Trp | Phe | Val | Asp | Asp | Val | Glu | Val | His | Thr | Ala | Arg | Met |
| | | | 180 | | | | | 185 | | | | | 190 | | |
| Lys | Pro | Arg | Glu | Glu | Gln | Phe | Asn | Ser | Thr | Tyr | Arg | Val | Val | Ser | Ala |
| | | | 195 | | | | | 200 | | | | | 205 | | |
| Leu | Pro | Ile | Gln | His | Gln | Asp | Trp | Leu | Arg | Glu | Lys | Glu | Phe | Lys | Cys |
| | | 210 | | | | | 215 | | | | | 220 | | | |
| Lys | Val | Asn | Asn | Lys | Gly | Leu | Pro | Ala | Pro | Ile | Val | Arg | Thr | Ile | Ser |
| 225 | | | | | 230 | | | | | 235 | | | | | 240 |
| Arg | Thr | Lys | Gly | Gln | Ala | Arg | Glu | Pro | Gln | Val | Tyr | Val | Leu | Ala | Pro |
| | | | | 245 | | | | | 250 | | | | | 255 | |
| Pro | Arg | Glu | Glu | Leu | Ser | Lys | Ser | Thr | Leu | Ser | Leu | Thr | Cys | Leu | Ile |
| | | | 260 | | | | | 265 | | | | | 270 | | |
| Thr | Gly | Phe | Tyr | Pro | Glu | Glu | Val | Asp | Val | Glu | Trp | Gln | Arg | Asn | Gly |
| | | | 275 | | | | | 280 | | | | | 285 | | |
| Gln | Pro | Glu | Ser | Glu | Asp | Lys | Tyr | His | Thr | Thr | Pro | Pro | Gln | Leu | Asp |
| | | | 290 | | | | | 295 | | | | | 300 | | |
| Ala | Asp | Gly | Ser | Tyr | Phe | Leu | Tyr | Ser | Arg | Leu | Arg | Val | Asn | Arg | Ser |
| 305 | | | | | 310 | | | | | 315 | | | | | 320 |
| Ser | Trp | Gln | Glu | Gly | Asp | His | Tyr | Thr | Cys | Ala | Val | Met | His | Glu | Ala |
| | | | | 325 | | | | | 330 | | | | | 335 | |
| Leu | Arg | Asn | His | Tyr | Lys | Glu | Lys | Pro | Ile | Ser | Arg | Ser | Pro | Gly | Lys |
| | | | 340 | | | | | 345 | | | | | 350 | | |

```
<210> SEQ ID NO 77
<211> LENGTH: 1059
<212> TYPE: DNA
<213> ORGANISM: Bubalus bubalis
```

<400> SEQUENCE: 77

```
gcctccacca cagccccgaa agtctaccct ctggcatcca gctgcgggga cacgtccagc    60
tccaccgtga ccctgggctg cctggtctcc agctacatgc ccgagccggt gaccgtgacc   120
tggaactcgg gtgccctgaa gaacggcgtg cacaccttcc cggccgtccg gcagtcctcc   180
gggctctact ctctcagcag catggtgacc atgcccacca gcaccgcagg aacccagacc   240
ttcacctgca acgtagccca cccggccagc agcaccaagg tggacacggc tgtcactgca   300
aggcatccgg tcccgaagac accagagaca cctatccatc ctgtaaaacc cccaacccag   360
gagcccagag atgaaaagac accctgccag tgtcccaaat gcccagaacc tctgggagga   420
ctgtctgtct tcatcttccc accgaaaccc aaggacaccc tcacaatctc tggaacgccc   480
gaggtcacgt gtgtggtggt ggacgtgggc caggatgacc ccgaagtgca gttctcctgg   540
ttcgtggatg acgtggaggt gcacacagcc aggatgaagc aagagagga gcagttcaac   600
agcacctacc gcgtggtcag cgccctgccc atccagcacc aggactggct gcgggaaaag   660
gagttcaagt gcaaggtcaa caacaaaggc ctcccggccc ccatcgtgag gaccatctcc   720
aggaccaaag ggcaggcccg ggagccacag gtgtatgtcc tggccccacc ccgggaagag   780
ctcagcaaaa gcacgctcag cctcacctgc ctaatcaccg gcttctaccc agaagaggta   840
gacgtggagt ggcagagaaa tgggcagcct gagtcagagg acaagtacca cacgacccca   900
ccccagctgg acgctgacgg ctcctacttc ctgtacagca ggctcagggt gaacaggagc   960
agctggcagg aaggagacca ctacacgtgt gcagtgatgc atgaagcttt acggaatcac  1020
tacaaagaga agcccatctc gaggtctccg ggtaaatga                         1059
```

<210> SEQ ID NO 78
<211> LENGTH: 105
<212> TYPE: PRT
<213> ORGANISM: Bubalus bubalis

<400> SEQUENCE: 78

```
Gln Pro Lys Ser Ala Pro Ser Val Thr Leu Phe Pro Pro Ser Thr Glu
1               5                   10                  15
Glu Leu Ser Ala Asn Lys Ala Thr Leu Val Cys Leu Ile Ser Asp Phe
            20                  25                  30
Tyr Pro Gly Ser Met Thr Val Ala Arg Lys Ala Asp Gly Ser Thr Ile
        35                  40                  45
Thr Arg Asn Val Glu Thr Thr Arg Ala Ser Lys Gln Ser Asn Ser Lys
    50                  55                  60
Tyr Ala Ala Ser Ser Tyr Leu Ser Leu Thr Gly Ser Glu Trp Lys Ser
65                  70                  75                  80
Lys Gly Ser Tyr Ser Cys Glu Val Thr His Glu Gly Ser Thr Val Thr
                85                  90                  95
Lys Thr Val Lys Pro Ser Glu Cys Ser
            100                 105
```

<210> SEQ ID NO 79
<211> LENGTH: 318
<212> TYPE: DNA
<213> ORGANISM: Bubalus buballis

<400> SEQUENCE: 79

```
cagcccaagt ccgcaccctc agtcaccctg ttcccaccct ccacggagga gctcagcgcc    60
aacaaggcca ccctggtgtg tctcatcagc gacttctacc cgggtagcat gaccgtggcc   120
```

| | |
|---|---|
| aggaaggcag acggcagcac catcacccgg aacgtggaga ccacccgggc ctccaaacag | 180 |
| agcaacagca agtacgcggc cagcagctac ctgagcctga cgggcagcga gtggaaatcg | 240 |
| aaaggcagtt acagctgcga ggtcacgcac gaggggagca ccgtgacaaa gacagtgaag | 300 |
| ccctcagagt gttcttag | 318 |

<210> SEQ ID NO 80
<211> LENGTH: 229
<212> TYPE: PRT
<213> ORGANISM: Homo sapiens

<400> SEQUENCE: 80

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 81
<211> LENGTH: 690
<212> TYPE: DNA
<213> ORGANISM: Homo sapiens

<400> SEQUENCE: 81

| | |
|---|---|
| gagtccaaat atggtccccc gtgcccatca tgcccagcac ctgagttcct ggggggacca | 60 |
| tcagtcttcc tgttcccccc aaaacccaag gacactctca tgatctcccg gacccctgag | 120 |
| gtcacgtgcg tggtggtgga cgtgagccag gaagaccccg aggtccagtt caactggtac | 180 |
| gtggatggcg tggaggtgca taatgccaag acaaagccgc gggaggagca gttcaacagc | 240 |
| acgtaccgtg tggtcagcgt cctcaccgtc gtgcaccagg actggctgaa cggcaaggag | 300 |

-continued

| | |
|---|---|
| tacaagtgca aggtctccaa caaaggcctc ccgtcctcca tcgagaaaac catctccaaa | 360 |
| gccaaagggc agccccgaga gccacaggtg tacaccctgc ccccatccca ggaggagatg | 420 |
| accaagaacc aggtcagcct gacctgcctg gtcaaaggct tctaccccag cgacatcgcc | 480 |
| gtggagtggg agagcaatgg gcagccggag aacaactaca agaccacgcc tcccgtgctg | 540 |
| gactccgacg gctccttctt cctctacagc aggctaaccg tggacaagag caggtggcag | 600 |
| gagggggaatg tcttctcatg ctccgtgatg catgaggctc tgcacaacca ctacacgcag | 660 |
| aagagcctct ccctgtctct gggtaaatga | 690 |

<210> SEQ ID NO 82
<211> LENGTH: 217
<212> TYPE: PRT
<213> ORGANISM: Homo sapiens

<400> SEQUENCE: 82

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 83
<211> LENGTH: 654
<212> TYPE: DNA
<213> ORGANISM: Homo sapiens

<400> SEQUENCE: 83

| | |
|---|---|
| gcacctgagt tcctgggggg accatcagtc ttcctgttcc ccccaaaacc caaggacact | 60 |
| ctcatgatct cccggacccc tgaggtcacg tgcgtggtgg tggacgtgag ccaggaagac | 120 |
| cccgaggtcc agttcaactg gtacgtggat ggcgtggagg tgcataatgc caagacaaag | 180 |
| ccgcgggagg agcagttcaa cagcacgtac cgtgtggtca gcgtcctcac cgtcctgcac | 240 |

```
caggactggc tgaacggcaa ggagtacaag tgcaaggtct ccaacaaagg cctcccgtcc      300
tccatcgaga aaaccatctc caaagccaaa gggcagcccc gagagccaca ggtgtacacc      360
ctgcccccat cccaggagga gatgaccaag aaccaggtca gcctgacctg cctggtcaaa      420
ggcttctacc ccagcgacat cgccgtggag tgggagagca atgggcagcc ggagaacaac      480
tacaagacca cgcctcccgt gctggactcc gacggctcct tcttcctcta cagcaagctc      540
accgtggaca agagcaggtg gcaggagggg aacgtcttct catgctccgt gatgcatgag      600
gctctgcaca accactacac gcagaagagc ctctccctgt ctctgggtaa atga            654
```

<210> SEQ ID NO 84
<211> LENGTH: 329
<212> TYPE: PRT
<213> ORGANISM: Bos taurus

<400> SEQUENCE: 84

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Asp Pro Thr Cys Lys Pro Ser Pro Cys Asp Cys Cys Pro Pro Pro
            100                 105                 110

Glu Leu Pro Gly Gly Pro Ser Val Phe Ile Phe Pro Pro Lys Pro Lys
        115                 120                 125

Asp Thr Leu Thr Ile Ser Gly Thr Pro Glu Val Thr Cys Val Val Val
    130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
    210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Ser Ser Tyr Phe Leu
        275                 280                 285

Tyr Ser Lys Leu Arg Val Asp Arg Asn Ser Trp Gln Glu Gly Asp Thr
    290                 295                 300
```

Tyr Thr Cys Val Val Met His Glu Ala Leu His Asn His Tyr Thr Gln
305                 310                 315                 320

Lys Ser Thr Ser Lys Ser Ala Gly Lys
            325

<210> SEQ ID NO 85
<211> LENGTH: 329
<212> TYPE: PRT
<213> ORGANISM: Bos taurus

<400> SEQUENCE: 85

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Asp Pro Thr Cys Lys Pro Ser Pro Cys Asp Cys Cys Pro Pro Pro
            100                 105                 110

Glu Leu Pro Gly Gly Pro Ser Val Phe Ile Phe Pro Pro Lys Pro Lys
        115                 120                 125

Asp Thr Leu Thr Ile Ser Gly Thr Pro Glu Val Thr Cys Val Val Val
130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Ser Ser Tyr Phe Leu
        275                 280                 285

Tyr Ser Lys Leu Arg Val Asp Arg Asn Ser Trp Gln Glu Gly Asp Thr
290                 295                 300

Tyr Thr Cys Val Val Met His Glu Ala Leu His Asn His Tyr Thr Gln
305                 310                 315                 320

Lys Ser Thr Ser Lys Ser Ala Gly Lys
            325

<210> SEQ ID NO 86
<211> LENGTH: 329
<212> TYPE: PRT
<213> ORGANISM: Bos taurus

<400> SEQUENCE: 86

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Thr Gln Thr
65                  70                  75                  80

Phe Thr Cys Asn Val Ala His Pro Ala Ser Ser Thr Lys Val Asp Lys
                85                  90                  95

Ala Val Asp Pro Arg Cys Lys Thr Cys Asp Cys Cys Pro Pro
            100                 105                 110

Glu Leu Pro Gly Gly Pro Ser Val Phe Ile Phe Pro Pro Lys Pro Lys
            115                 120                 125

Asp Thr Leu Thr Ile Ser Gly Thr Pro Glu Val Thr Cys Val Val Val
            130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
    210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Gly Ser Tyr Phe Leu
        275                 280                 285

Tyr Ser Arg Leu Arg Val Asp Arg Asn Ser Trp Gln Glu Gly Asp Thr
    290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325
```

<210> SEQ ID NO 87
<211> LENGTH: 326
<212> TYPE: PRT
<213> ORGANISM: Bos taurus

<400> SEQUENCE: 87

```
Ala Ser Thr Thr Ala Pro Lys Val Tyr Pro Leu Ala Ser Ser Cys Gly
1               5                   10                  15

Asp Thr Ser Ser Ser Thr Val Thr Leu Gly Cys Leu Val Ser Ser Tyr
                20                  25                  30

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
        50                  55                  60

Leu Ser Ser Met Val Thr Val Pro Ala Ser Ser Gly Gln Thr Phe
65                  70                  75                  80

Thr Cys Asn Val Ala His Pro Ala Ser Ser Thr Lys Val Asp Lys Ala
                85                  90                  95

Val Gly Val Ser Ile Asp Cys Ser Lys Cys His Asn Gln Pro Cys Val
                100                 105                 110

Arg Glu Pro Ser Val Phe Ile Phe Pro Pro Lys Pro Lys Asp Thr Leu
            115                 120                 125

Met Ile Thr Gly Thr Pro Glu Val Thr Cys Val Val Val Asn Val Gly
        130                 135                 140

His Asp Asn Pro Glu Val Gln Phe Ser Trp Phe Val Asp Asp Val Glu
145                 150                 155                 160

Val His Thr Ala Arg Ser Lys Pro Arg Glu Glu Gln Phe Asn Ser Thr
                165                 170                 175

Tyr Arg Val Val Ser Ala Leu Pro Ile Gln His Gln Asp Trp Thr Gly
            180                 185                 190

Gly Lys Glu Phe Lys Cys Lys Val Asn Asn Lys Gly Leu Ser Ala Pro
        195                 200                 205

Ile Val Arg Ile Ile Ser Arg Ser Lys Gly Pro Ala Arg Glu Pro Gln
        210                 215                 220

Val Tyr Val Leu Asp Pro Pro Lys Glu Glu Leu Ser Lys Ser Thr Leu
225                 230                 235                 240

Ser Val Thr Cys Met Val Thr Gly Phe Tyr Pro Glu Asp Val Ala Val
                245                 250                 255

Glu Trp Gln Arg Asn Arg Gln Thr Glu Ser Glu Asp Lys Tyr Arg Thr
            260                 265                 270

Thr Pro Pro Gln Leu Asp Thr Asp Arg Ser Tyr Phe Leu Tyr Ser Lys
        275                 280                 285

Leu Arg Val Asp Arg Asn Ser Trp Gln Glu Gly Asp Ala Tyr Thr Cys
        290                 295                 300

Val Val Met His Glu Ala Leu His Asn His Tyr Met Gln Lys Ser Thr
305                 310                 315                 320

Ser Lys Ser Ala Gly Lys
                325
```

<210> SEQ ID NO 88
<211> LENGTH: 326
<212> TYPE: PRT
<213> ORGANISM: Bos taurus

<400> SEQUENCE: 88

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
                20                  25                  30
```

-continued

```
Met Pro Glu Pro Val Thr Val Thr Trp Asn Ser Gly Ala Leu Lys Ser
             35                  40                  45

Gly Val His Thr Phe Pro Ala Val Leu Gln Ser Ser Gly Leu Tyr Ser
 50                  55                  60

Leu Ser Ser Met Val Thr Val Pro Gly Ser Thr Ser Gly Gln Thr Phe
 65                  70                  75                  80

Thr Cys Asn Val Ala His Pro Ala Ser Ser Thr Lys Val Asp Lys Ala
                 85                  90                  95

Val Gly Val Ser Ser Asp Cys Ser Lys Pro Asn Asn Gln His Cys Val
                100                 105                 110

Arg Glu Pro Ser Val Phe Ile Phe Pro Pro Lys Pro Lys Asp Thr Leu
            115                 120                 125

Met Ile Thr Gly Thr Pro Glu Val Thr Cys Val Val Val Asn Val Gly
    130                 135                 140

His Asp Asn Pro Glu Val Gln Phe Ser Trp Phe Val Asp Asp Val Glu
145                 150                 155                 160

Val His Thr Ala Arg Thr Lys Pro Arg Glu Glu Gln Phe Asn Ser Thr
                165                 170                 175

Tyr Arg Val Val Ser Ala Leu Pro Ile Gln His Gln Asp Trp Thr Gly
            180                 185                 190

Gly Lys Glu Phe Lys Cys Lys Val Asn Ile Lys Gly Leu Ser Ala Ser
        195                 200                 205

Ile Val Arg Ile Ile Ser Arg Ser Lys Gly Pro Ala Arg Glu Pro Gln
    210                 215                 220

Val Tyr Val Leu Asp Pro Pro Lys Glu Glu Leu Ser Lys Ser Thr Val
225                 230                 235                 240

Ser Val Thr Cys Met Val Ile Gly Phe Tyr Pro Glu Asp Val Asp Val
                245                 250                 255

Glu Trp Gln Arg Asp Arg Gln Thr Glu Ser Glu Asp Lys Tyr Arg Thr
            260                 265                 270

Thr Pro Pro Gln Leu Asp Ala Asp Arg Ser Tyr Phe Leu Tyr Ser Lys
        275                 280                 285

Leu Arg Val Asp Arg Asn Ser Trp Gln Arg Gly Asp Thr Tyr Thr Cys
    290                 295                 300

Val Val Met His Glu Ala Leu His Asn His Tyr Met Gln Lys Ser Thr
305                 310                 315                 320

Ser Lys Ser Ala Gly Lys
                325

<210> SEQ ID NO 89
<211> LENGTH: 327
<212> TYPE: PRT
<213> ORGANISM: Bos taurus

<400> SEQUENCE: 89

Ala Ser Thr Thr Ala Pro Lys Val Tyr Pro Leu Ser Ser Cys Cys Gly
1               5                   10                  15

Asp Lys Ser Ser Ser Gly Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Ser Gly Thr Gln Thr
65                  70                  75                  80
```

Phe Thr Cys Asn Val Ala His Pro Ala Ser Ser Thr Lys Val Asp Lys
            85                  90                  95

Ala Val Gly Val Ser Ser Asp Cys Ser Lys Pro Asn Asn Gln His Cys
        100                 105                 110

Val Arg Glu Pro Ser Val Phe Ile Phe Pro Pro Lys Pro Lys Asp Thr
    115                 120                 125

Leu Met Ile Thr Gly Thr Pro Glu Val Thr Cys Val Val Val Asn Val
130                 135                 140

Gly His Asp Asn Pro Glu Val Gln Phe Ser Trp Phe Val Asp Asp Val
145                 150                 155                 160

Glu Val His Thr Ala Arg Thr Lys Pro Arg Glu Glu Gln Phe Asn Ser
                165                 170                 175

Thr Tyr Arg Val Val Ser Ala Leu Pro Ile Gln His Gln Asp Trp Thr
            180                 185                 190

Gly Gly Lys Glu Phe Lys Cys Lys Val Asn Ile Lys Gly Leu Ser Ala
        195                 200                 205

Ser Ile Val Arg Ile Ile Ser Arg Ser Lys Gly Pro Ala Arg Glu Pro
    210                 215                 220

Gln Val Tyr Val Leu Asp Pro Pro Lys Glu Glu Leu Ser Lys Ser Thr
225                 230                 235                 240

Val Ser Leu Thr Cys Met Val Ile Gly Phe Tyr Pro Glu Asp Val Asp
                245                 250                 255

Val Glu Trp Gln Arg Asp Arg Gln Thr Glu Ser Glu Asp Lys Tyr Arg
            260                 265                 270

Thr Thr Pro Pro Gln Leu Asp Ala Asp Arg Ser Tyr Phe Leu Tyr Ser
        275                 280                 285

Lys Leu Arg Val Asp Arg Asn Ser Trp Gln Arg Gly Asp Thr Tyr Thr
    290                 295                 300

Cys Val Val Met His Glu Ala Leu His Asn His Tyr Met Gln Lys Ser
305                 310                 315                 320

Thr Ser Lys Ser Ala Gly Lys
                325

<210> SEQ ID NO 90
<211> LENGTH: 352
<212> TYPE: PRT
<213> ORGANISM: Bos taurus

<400> SEQUENCE: 90

Ala Ser Thr Thr Ala Pro Lys Val Tyr Pro Leu Ala Ser Ser Cys Gly
1               5                   10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Arg Gln Ser Ser Gly Leu Tyr Ser
    50                  55                  60

Leu Ser Ser Met Val Thr Val Pro Ala Ser Ser Glu Thr Gln Thr
65                  70                  75                  80

Phe Thr Cys Asn Val Ala His Pro Ala Ser Ser Thr Lys Val Asp Lys
            85                  90                  95

Ala Val Thr Ala Arg Arg Pro Val Pro Thr Thr Pro Lys Thr Thr Ile
        100                 105                 110

Pro Pro Gly Lys Pro Thr Thr Pro Lys Ser Glu Val Glu Lys Thr Pro
    115                 120                 125

Cys Gln Cys Ser Lys Cys Pro Glu Pro Leu Gly Gly Leu Ser Val Phe
    130                 135                 140

Ile Phe Pro Pro Lys Pro Lys Asp Thr Leu Thr Ile Ser Gly Thr Pro
145                 150                 155                 160

Glu Val Thr Cys Val Val Val Asp Val Gly Gln Asp Asp Pro Glu Val
                165                 170                 175

Gln Phe Ser Trp Phe Val Asp Asp Val Glu Val His Thr Ala Arg Thr
            180                 185                 190

Lys Pro Arg Glu Glu Gln Phe Asn Ser Thr Tyr Arg Val Val Ser Ala
        195                 200                 205

Leu Arg Ile Gln His Gln Asp Trp Leu Gln Gly Lys Glu Phe Lys Cys
210                 215                 220

Lys Val Asn Asn Lys Gly Leu Pro Ala Pro Ile Val Arg Thr Ile Ser
225                 230                 235                 240

Arg Thr Lys Gly Gln Ala Arg Glu Pro Gln Val Tyr Val Leu Ala Pro
                245                 250                 255

Pro Arg Glu Glu Leu Ser Lys Ser Thr Leu Ser Leu Thr Cys Leu Ile
            260                 265                 270

Thr Gly Phe Tyr Pro Glu Glu Ile Asp Val Glu Trp Gln Arg Asn Gly
        275                 280                 285

Gln Pro Glu Ser Glu Asp Lys Tyr His Thr Thr Ala Pro Gln Leu Asp
    290                 295                 300

Ala Asp Gly Ser Tyr Phe Leu Tyr Ser Lys Leu Arg Val Asn Lys Ser
305                 310                 315                 320

Ser Trp Gln Glu Gly Asp His Tyr Thr Cys Ala Val Met His Glu Ala
                325                 330                 335

Leu Arg Asn His Tyr Lys Glu Lys Ser Ile Ser Arg Ser Pro Gly Lys
            340                 345                 350

<210> SEQ ID NO 91
<211> LENGTH: 352
<212> TYPE: PRT
<213> ORGANISM: Bos taurus

<400> SEQUENCE: 91

Ala Ser Thr Thr Ala Pro Lys Val Tyr Pro Leu Ala Ser Arg Cys Gly
1               5                   10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Glu Thr Gln Thr
65                  70                  75                  80

Phe Thr Cys Asn Val Ala His Pro Ala Ser Ser Thr Lys Val Asp Lys
                85                  90                  95

Ala Val Thr Ala Arg Arg Pro Val Pro Thr Pro Lys Thr Thr Ile
            100                 105                 110

Pro Pro Gly Lys Pro Thr Thr Gln Glu Ser Glu Val Glu Lys Thr Pro
        115                 120                 125

Cys Gln Cys Ser Lys Cys Pro Glu Pro Leu Gly Gly Leu Ser Val Phe
    130                 135                 140

Ile Phe Pro Pro Lys Pro Lys Asp Thr Leu Thr Ile Ser Gly Thr Pro
145                 150                 155                 160

```
Glu Val Thr Cys Val Val Asp Val Gly Gln Asp Pro Glu Val
            165                 170                 175
Gln Phe Ser Trp Phe Val Asp Asp Val Glu Val His Thr Ala Arg Thr
        180                 185                 190
Lys Pro Arg Glu Glu Gln Phe Asn Ser Thr Tyr Arg Val Val Ser Ala
        195                 200                 205
Leu Arg Ile Gln His Gln Asp Trp Leu Gln Gly Lys Glu Phe Lys Cys
    210                 215                 220
Lys Val Asn Asn Lys Gly Leu Pro Ala Pro Ile Val Arg Thr Ile Ser
225                 230                 235                 240
Arg Thr Lys Gly Gln Ala Arg Glu Pro Gln Val Tyr Val Leu Ala Pro
                245                 250                 255
Pro Arg Glu Glu Leu Ser Lys Ser Thr Leu Ser Leu Thr Cys Leu Ile
            260                 265                 270
Thr Gly Phe Tyr Pro Glu Glu Ile Asp Val Glu Trp Gln Arg Asn Gly
        275                 280                 285
Gln Pro Glu Ser Glu Asp Lys Tyr His Thr Thr Ala Pro Gln Leu Asp
    290                 295                 300
Ala Asp Gly Ser Tyr Phe Leu Tyr Ser Arg Leu Arg Val Asn Lys Ser
305                 310                 315                 320
Ser Trp Gln Glu Gly Asp His Tyr Thr Cys Ala Val Met His Glu Ala
                325                 330                 335
Leu Arg Asn His Tyr Lys Glu Lys Ser Ile Ser Arg Ser Pro Gly Lys
            340                 345                 350

<210> SEQ ID NO 92
<211> LENGTH: 990
<212> TYPE: DNA
<213> ORGANISM: Bos taurus

<400> SEQUENCE: 92
gcctccacca cagccccgaa agtctaccct ctgagttctt gctgcgggga caagtccagc      60
tccaccgtga ccctgggctg cctggtctcc agctacatgc ccgagccggt gaccgtgacc     120
tggaactcgg gtgccctgaa gagcggcgtg cacaccttcc cggctgtcct tcagtcctcc     180
gggctgtact ctctcagcag catggtgacc gtgcccggca gcacctcagg acagaccttc     240
acctgcaacg tagcccaccc ggccagcagc accaaggtgg acaaggctgt tgatcccaca     300
tgcaaaccat caccctgtga ctgttgccca cccctgagc tccccggagg accctctgtc      360
ttcatcttcc caccgaaacc caaggacacc ctcacaatct cgggaacgcc cgaggtcacg     420
tgtgtggtgg tggacgtggg ccacgatgac cccgaggtga agttctcctg gttcgtggac     480
gacgtggagg taaacacagc cacgacgaag ccgagagagg agcagttcaa cagcacctac     540
cgcgtggtca gcgccctgcg catccagcac caggactgga ctggaggaaa ggagttcaag     600
tgcaaggtcc acaacgaagg cctcccggcc ccatcgtga ggaccatctc caggaccaaa      660
gggccggccc gggagccgca ggtgtatgtc ctggccccac cccaggaaga gctcagcaaa     720
agcacggtca gctcacctg catggtcacc agcttctacc cagactacat cgccgtggag     780
tggcagagaa cgggcagcc tgagtcggag gacaagtacg gcacgacccc gccccagctg     840
gacgccgaca gctcctactt cctgtacagc aagctcaggg tggacaggaa cagctggcag     900
gaaggagaca cctacacgtg tgtggtgatg cacgaggccc tgcacaatca ctacacgcag     960
aagtccaccc taagtctgc gggtaaatga                                       990
```

<210> SEQ ID NO 93
<211> LENGTH: 990
<212> TYPE: DNA
<213> ORGANISM: Bos taurus

<400> SEQUENCE: 93

```
gcctccacca cagccccgaa agtctaccct ctgagttctt gctgcgggga caagtccagc      60
tccaccgtga ccctgggctg cctggtctcc agctacatgc ccgagccggt gaccgtgacc     120
tggaactcgg gtgccctgaa gagcggcgtg cacaccttcc cggccgtcct tcagtcctcc     180
gggctgtact ctctcagcag catggtgacc gtgcccggca gcacctcagg acagaccttc     240
acctgcaacg tagcccaccc ggccagcagc accaaggtgg acaaggctgt tgatcccaca     300
tgcaaaccat caccctgtga ctgttgccca cccctgagc tccccggagg accctctgtc      360
ttcatcttcc caccgaaacc caaggacacc ctcacaatct cgggaacgcc cgaggtcacg     420
tgtgtggtgg tggacgtggg ccacgatgac cccgaggtga agttctcctg gttcgtggac     480
gacgtggagg taaacacagc cacgacgaag ccgagagagg agcagttcaa cagcacctac     540
cgcgtggtca gcgccctgcg catccagcac caggactgga ctggaggaaa ggagttcaag     600
tgcaaggtcc acaacgaagg cctcccggcc ccatcgtga ggaccatctc caggaccaaa      660
gggccggccc gggagccgca ggtgtatgtc ctggcccac cccaggaaga gctcagcaaa      720
agcacggtca gcctcacctg catggtcacc agcttctacc cagactacat cgccgtggag     780
tggcagagaa acgggcagcc tgagtcggag acaagtacg gcacgacccc gccccagctg      840
gacgccgaca gctcctactt cctgtacagc aagctcaggg tggacaggaa cagctggcag     900
gaaggagaca cctacacgtg tgtggtgatg cacgaggccc tgcacaatca ctacacgcag     960
aagtccacct ctaagtctgc gggtaaatga                                      990
```

<210> SEQ ID NO 94
<211> LENGTH: 990
<212> TYPE: DNA
<213> ORGANISM: Bos taurus

<400> SEQUENCE: 94

```
gcctccacca cagccccgaa agtctaccct ctgagttctt gctgcgggga caagtccagc      60
tccaccgtga ccctgggctg cctggtctcc agctacatgc ccgagccggt gaccgtgacc     120
tggaactcgg gtgccctgaa gagcggcgtg cacaccttcc cggccgtcct tcagtcctcc     180
gggctctact ctctcagcag catggtgacc gtgcccggca gcacctcagg aacccagacc     240
ttcacctgca acgtagccca cccggccagc agcaccaagg tggacaaggc tgttgatccc     300
agatgcaaaa caacctgtga ctgttgccca ccgcctgagc tccctggagg accctctgtc     360
ttcatcttcc caccgaaacc caaggacacc ctcacaatct cgggaacgcc cgaggtcacg     420
tgtgtggtgg tggacgtggg ccacgatgac cccgaggtga agttctcctg gttcgtggac     480
gacgtggagg taaacacagc cacgacgaag ccgagagagg agcagttcaa cagcacctac     540
cgcgtggtca gcgccctgcg catccagcac caggactgga ctggaggaaa ggagttcaag     600
tgcaaggtcc acaacgaagg cctcccagcc ccatcgtga ggaccatctc caggaccaaa      660
gggccggccc gggagccgca ggtgtatgtc ctggcccac cccaggaaga gctcagcaaa      720
agcacggtca gcctcacctg catggtcacc agcttctacc cagactacat cgccgtggag     780
tggcagagaa atgggcagcc tgagtcagag acaagtacg gcacgacccc tccccagctg      840
gacgccgacg gctcctactt cctgtacagc aggctcaggg tggacaggaa cagctggcag     900
```

| | |
|---|---|
| gaaggagaca cctacacgtg tgtggtgatg cacgaggccc tgcacaatca ctacacgcag | 960 |
| aagtccacct ctaagtctgc gggtaaatga | 990 |

<210> SEQ ID NO 95
<211> LENGTH: 981
<212> TYPE: DNA
<213> ORGANISM: Bos taurus

<400> SEQUENCE: 95

| | |
|---|---|
| gcctccacca cagccccgaa agtctaccct ctggcatcca gctgcggaga cacatccagc | 60 |
| tccaccgtga ccctgggctg cctggtgtcc agctacatgc ccgagccggt gaccgtgacc | 120 |
| tggaactcgg gtgccctgaa gagcggcgtg cacaccttcc cggctgtcct tcagtcctcc | 180 |
| gggctctact ctctcagcag catggtgacc gtgcccgcca gcagctcagg acagaccttc | 240 |
| acctgcaacg tagcccaccc ggccagcagc accaaggtgg acaaggctgt tggggtctcc | 300 |
| attgactgct ccaagtgtca taaccagcct tgcgtgaggg aaccatctgt cttcatcttc | 360 |
| ccaccgaaac ccaaagacac cctgatgatc acaggaacgc ccgaggtcac gtgtgtggtg | 420 |
| gtgaacgtgg ccacgataa ccccgaggtg cagttctcct ggttcgtgga tgacgtggag | 480 |
| gtgcacacgc caggtcgaa gccaagagag gagcagttca acagcacgta ccgcgtggtc | 540 |
| agcgccctgc ccatccagca ccaggactgg actggaggaa aggagttcaa gtgcaaggtc | 600 |
| aacaacaaag gcctctcggc ccccatcgtg aggatcatct ccaggagcaa agggccggcc | 660 |
| cgggagccgc aggtgtatgt cctggaccca cccaaggaag agctcagcaa aagcacgctc | 720 |
| agcgtcacct gcatggtcac cggcttctac ccagaagatg tagccgtgga gtggcagaga | 780 |
| aaccggcaga ctgagtcgga ggacaagtac cgcacgaccc cgccccagct ggacaccgac | 840 |
| cgctcctact tcctgtacag caagctcagg gtggacagga acagctggca ggaaggagac | 900 |
| gcctacacgt gtgtggtgat gcacgaggcc ctgcacaatc actacatgca gaagtccacc | 960 |
| tctaagtctg cgggtaaatg a | 981 |

<210> SEQ ID NO 96
<211> LENGTH: 981
<212> TYPE: DNA
<213> ORGANISM: Bos taurus

<400> SEQUENCE: 96

| | |
|---|---|
| gcctccacca cagccccgaa agtctaccct ctgagttctt gctgcgggga caagtccagc | 60 |
| tccaccgtga ccctgggctg cctggtgtcc agctacatgc ccgagccggt gaccgtgacc | 120 |
| tggaactcgg gtgccctgaa gagcggcgtg cacaccttcc cggccgtcct tcagtcctcc | 180 |
| gggctctact ctctcagcag catggtgacc gtgcccggca gcacctcagg acagaccttc | 240 |
| acctgcaacg tagcccaccc ggccagcagc accaaggtgg acaaggctgt tggggtctcc | 300 |
| agtgactgct ccaagcctaa taaccagcat tgcgtgaggg aaccatctgt cttcatcttc | 360 |
| ccaccgaaac ccaaagacac cctgatgatc acaggaacgc ccgaggtcac gtgtgtggtg | 420 |
| gtgaacgtgg ccacgataa ccccgaggtg cagttctcct ggttcgtgga cgacgtggag | 480 |
| gtgcacacgg ccaggacgaa gccgagagag gagcagttca acagcacgta ccgcgtggtc | 540 |
| agcgccctgc ccatccagca ccaggactgg actggaggaa aggagttcaa gtgcaaggtc | 600 |
| aacatcaaag gcctctcggc ctccatcgtg aggatcatct ccaggagcaa agggccggcc | 660 |
| cgggagccgc aggtgtatgt cctggaccca cccaaggaag agctcagcaa aagcacggtc | 720 |
| agcgtcacct gcatggtcat cggcttctac ccagaagatg tagacgtgga gtggcagaga | 780 |

| | |
|---|---|
| gaccggcaga ctgagtcgga ggacaagtac cgcacgaccc cgccccagct ggacgccgac | 840 |
| cgctcctact tcctgtacag caagctcagg gtggacagga acagctggca gagaggagac | 900 |
| acctacacgt gtgtggtgat gcacgaggcc ctgcacaatc actacatgca gaagtccacc | 960 |
| tctaagtctg cgggtaaatg a | 981 |

<210> SEQ ID NO 97
<211> LENGTH: 984
<212> TYPE: DNA
<213> ORGANISM: Bos taurus

<400> SEQUENCE: 97

| | |
|---|---|
| gcctccacca cagccccgaa agtctaccct ctgagttctt gctgcgggga caagtccagc | 60 |
| tcggggtga ccctgggctg cctggtctcc agctacatgc ccgagccggt gaccgtgacc | 120 |
| tggaactcgg gtgccctgaa gagcggcgtg cacaccttcc cggccgtcct tcagtcctcc | 180 |
| gggctctact ctctcagcag catggtgacc gtgcccgcca gcagctcagg aacccagacc | 240 |
| ttcacctgca acgtagccca cccggccagc agcaccaagg tggacaaggc tgttgggtc | 300 |
| tccagtgact gctccaagcc taataaccag cattgcgtga gggaaccatc tgtcttcatc | 360 |
| ttcccaccga aacccaaaga caccctgatg atcacaggaa cgcccgaggt cacgtgtgtg | 420 |
| gtggtgaacg tgggccacga taaccccgag gtgcagttct cctggttcgt ggacgacgtg | 480 |
| gaggtgcaca cggccaggac gaagccgaga gaggagcagt tcaacagcac gtaccgcgtg | 540 |
| gtcagcgccc tgcccatcca gcaccaggac tggactggag gaaaggagtt caagtgcaag | 600 |
| gtcaacatca aaggcctctc ggcctccatc gtgaggatca tctccaggag caaagggccg | 660 |
| gccccgggag cgcaggtgta tgtcctggac ccacccaagg aagagctcag caaaagcacg | 720 |
| gtcagcctca cctgcatggt catcggcttc tacccagaag atgtagacgt ggagtggcag | 780 |
| agagaccggc agactgagtc ggaggacaag taccgcacga ccccgcccca gctggacgcc | 840 |
| gaccgctcct acttcctgta cagcaagctc agggtggaca ggaacagctg gcagagagga | 900 |
| gacacctaca cgtgtgtggt gatgcacgag gccctgcaca atcactacat gcagaagtcc | 960 |
| acctctaagt ctgcgggtaa atga | 984 |

<210> SEQ ID NO 98
<211> LENGTH: 1059
<212> TYPE: DNA
<213> ORGANISM: Bos taurus

<400> SEQUENCE: 98

| | |
|---|---|
| gcctccacca cagccccgaa agtctaccct ctggcatcca gctgcggaga cacatccagc | 60 |
| tccaccgtga ccctgggctg cctggtctcc agctacatgc ccgagccggt gaccgtgacc | 120 |
| tggaactcgg gtgccctgaa gagcggcgtg cacaccttcc cggccgtccg gcagtcctct | 180 |
| gggctgtact ctctcagcag catggtgact gtgcccgcca gcagctcaga aacccagacc | 240 |
| ttcacctgca acgtagccca cccggccagc agcaccaagg tggacaaggc tgtcactgca | 300 |
| aggcgtccag tcccgacgac gccaaagaca actatccctc ctggaaaacc cacaaccccca | 360 |
| aagtctgaag ttgaaaagac accctgccag tgttccaaat gcccagaacc tctgggagga | 420 |
| ctgtctgtct tcatcttccc accgaaaccc aaggacaccc tcacaatctc gggaacgccc | 480 |
| gaggtcacgt gtgtggtggt ggacgtgggc caggatgacc ccgaggtgca gttctcctgg | 540 |
| ttcgtggacg acgtggaggt gcacacggcc aggacgaagc cgagagagga gcagttcaac | 600 |
| agcacctacc gcgtggtcag cgccctgcgc atccagcacc aggactggct gcagggaaag | 660 |

```
gagttcaagt gcaaggtcaa caacaaaggc ctcccggccc ccattgtgag gaccatctcc    720
aggaccaaag gcaggcccg ggagccgcag gtgtatgtcc tggccccacc ccgggaagag    780
ctcagcaaaa gcacgctcag cctcacctgc ctgatcaccg gtttctaccc agaagagata    840
gacgtggagt ggcagagaaa tgggcagcct gagtcggagg acaagtacca cacgaccgca    900
ccccagctgg atgctgacgg ctcctacttc ctgtacagca agctcagggt gaacaagagc    960
agctggcagg aaggagacca ctacacgtgt gcagtgatgc acgaagcttt acggaatcac   1020
tacaaagaga agtccatctc gaggtctccg ggtaaatga                         1059
```

<210> SEQ ID NO 99
<211> LENGTH: 1059
<212> TYPE: DNA
<213> ORGANISM: Bos taurus

<400> SEQUENCE: 99

```
gcctccacca cagccccgaa agtctaccct ctggcatccc gctgcggaga cacatccagc     60
tccaccgtga ccctgggctg cctggtctcc agctacatgc ccgagccggt gaccgtgacc    120
tggaactcgg gtgccctgaa gagtggcgtg cacaccttcc cggccgtcct tcagtcctcc    180
gggctgtact ctctcagcag catggtgacc gtgcccgcca gcacctcaga aacccagacc    240
ttcacctgca acgtagccca cccggccagc agcaccaagg tggacaaggc tgtcactgca    300
aggcgtccag tcccgacgac gccaaagaca accatccctc ctggaaaacc cacaacccag    360
gagtctgaag ttgaaaagac accctgccag tgttccaaat gcccagaacc tctgggagga    420
ctgtctgtct tcatcttccc accgaaaccc aaggacaccc tcacaatctc gggaacgccc    480
gaggtcacgt gtgtggtggt ggacgtgggc caggatgacc ccgaggtgca gttctcctgg    540
ttcgtggacg acgtggaggt gcacacggcc aggacgaagc cgagagagga gcagttcaac    600
agcacctacc gcgtggtcag cgccctgcgc atccagcacc aggactggct gcagggaaag    660
gagttcaagt gcaaggtcaa caacaaaggc ctcccggccc ccattgtgag gaccatctcc    720
aggaccaaag gcaggcccg ggagccgcag gtgtatgtcc tggccccacc ccgggaagag    780
ctcagcaaaa gcacgctcag cctcacctgc ctgatcaccg gtttctaccc agaagagata    840
gacgtggagt ggcagagaaa tgggcagcct gagtcggagg acaagtacca cacgaccgca    900
ccccagctgg atgctgacgg ctcctacttc ctgtacagca ggctcagggt gaacaagagc    960
agctggcagg aaggagacca ctacacgtgt gcagtgatgc atgaagcttt acggaatcac   1020
tacaaagaga agtccatctc gaggtctccg ggtaaatga                         1059
```

<210> SEQ ID NO 100
<211> LENGTH: 105
<212> TYPE: PRT
<213> ORGANISM: Bos taurus

<400> SEQUENCE: 100

```
Gln Pro Lys Ser Pro Ser Val Thr Leu Phe Pro Pro Ser Thr Glu
 1               5                  10                  15

Glu Leu Asn Gly Asn Lys Ala Thr Leu Val Cys Leu Ile Ser Asp Phe
             20                  25                  30

Tyr Pro Gly Ser Val Thr Val Val Trp Lys Ala Asp Gly Ser Thr Ile
         35                  40                  45

Thr Arg Asn Val Glu Thr Thr Arg Ala Ser Lys Gln Ser Asn Ser Lys
     50                  55                  60
```

Tyr Ala Ala Ser Ser Tyr Leu Ser Leu Thr Ser Ser Asp Trp Lys Ser
65                  70                  75                  80

Lys Gly Ser Tyr Ser Cys Glu Val Thr His Glu Gly Ser Thr Val Thr
                85                  90                  95

Lys Thr Val Lys Pro Ser Glu Cys Ser
            100                 105

<210> SEQ ID NO 101
<211> LENGTH: 318
<212> TYPE: DNA
<213> ORGANISM: Bos taurus

<400> SEQUENCE: 101
cagcccaagt cccacccctc ggtcaccctg ttcccgccct ccacggagga gctcaacggc      60
aacaaggcca ccctggtgtg tctcatcagc gacttctacc cgggtagcgt gaccgtggtc     120
tggaaggcag acggcagcac catcacccgc aacgtggaga ccacccgggc ctccaaacag     180
agcaacagca gtacgcggc cagcagctac ctgagcctga cgagcagcga ctggaaatcg     240
aaaggcagtt acagctgcga ggtcacgcac gaggggagca ccgtgacgaa gacagtgaag     300
ccctcagagt gttcttag                                                   318

<210> SEQ ID NO 102
<211> LENGTH: 328
<212> TYPE: PRT
<213> ORGANISM: Bos taurus

<400> SEQUENCE: 102

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
                20                  25                  30

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
        50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Asp Pro Thr Cys Lys Pro Ser Pro Cys Asp Cys Cys Pro Pro Pro
            100                 105                 110

Pro Val Ala Gly Pro Ser Val Phe Ile Phe Pro Pro Lys Pro Lys Asp
        115                 120                 125

Thr Leu Thr Ile Ser Gly Thr Pro Glu Val Thr Cys Val Val Val Asp
    130                 135                 140

Val Gly His Asp Asp Pro Glu Val Lys Phe Ser Trp Phe Val Asp Asp
145                 150                 155                 160

Val Glu Val Asn Thr Ala Thr Thr Lys Pro Arg Glu Glu Gln Phe Asn
                165                 170                 175

Ser Thr Tyr Arg Val Val Ser Ala Leu Arg Ile Gln His Gln Asp Trp
            180                 185                 190

Thr Gly Gly Lys Glu Phe Lys Cys Lys Val His Asn Glu Gly Leu Pro
        195                 200                 205

Ser Ser Ile Val Arg Thr Ile Ser Arg Thr Lys Gly Pro Ala Arg Glu
    210                 215                 220

```
Pro Gln Val Tyr Val Leu Ala Pro Pro Gln Glu Leu Ser Lys Ser
225                 230                 235                 240

Thr Val Ser Leu Thr Cys Met Val Thr Ser Phe Tyr Pro Asp Tyr Ile
                245                 250                 255

Ala Val Glu Trp Gln Arg Asn Gly Gln Pro Glu Ser Glu Asp Lys Tyr
            260                 265                 270

Gly Thr Thr Pro Pro Gln Leu Asp Ala Asp Ser Ser Tyr Phe Leu Tyr
        275                 280                 285

Ser Lys Leu Arg Val Asp Arg Asn Ser Trp Gln Glu Gly Asp Thr Tyr
    290                 295                 300

Thr Cys Val Val Met His Glu Ala Leu His Asn His Tyr Thr Gln Lys
305                 310                 315                 320

Ser Thr Ser Lys Ser Ala Gly Lys
                325

<210> SEQ ID NO 103
<211> LENGTH: 987
<212> TYPE: DNA
<213> ORGANISM: Bos taurus

<400> SEQUENCE: 103
gctagcacaa ctgctcctaa ggtgtacccc ctgagctctt gctgcggcga caagtctagc      60
agcaccgtga ccctcggatg cctcgtcagc agctatatgc ctgagccagt tacagtgaca     120
tggaattctg gtgcccttaa gtccggcgtc cataccttcc ctgctgtgct gcagtcctct     180
ggcctgtaca gtttgtcctc tatggtgaca gtacccggtt ccacctccgg acagaccttt     240
acctgtaatg tggctcatcc cgcctcctcc acaaaggtgg ataaggctgt tgaccctacc     300
tgtaaaccca gtccatgcga ctgctgtccc cccctccag ttgccggacc ctcagtcttt      360
attttcccac ccaaacccaa agacaccctg acaatctctg gaacaccaga agtcacctgc     420
gtcgtcgtgg atgtgggcca cgacgatcct gaggtaaaat tctcatggtt cgtcgacgat     480
gtggaagtga atacagctac tacaaaacct cgcgaagagc agtttaactc tacctatcga     540
gtggtttctg ctttgcggat tcagcatcag gattggacag gcggcaaaga gtttaaatgt     600
aaagtccata cgaggggact tccttctagt atcgtgcgca ctatcagtag aactaaaggg     660
cctgctcggg aacctcaggt gtacgtcctg gcacctccac aggaagagct gagtaagtct     720
acagtttctc tgacttgtat ggtaacatct ttttatccag attacatcgc agttgaatgg     780
cagaggaacg ggcagccaga gagtgaggat aagtacggga ctactccacc acagctggac     840
gcagactcaa gttacttcct gtactcaaag ctgagggttg acagaaactc atggcaggag     900
ggggacactt acacttgcgt agttatgcac gaggcacttc acaaccacta cactcagaag     960
agtacttcaa agagtgcagg gaagtaa                                         987

<210> SEQ ID NO 104
<211> LENGTH: 318
<212> TYPE: DNA
<213> ORGANISM: Artificial Sequence
<220> FEATURE:
<223> OTHER INFORMATION: codon-optimized sequence

<400> SEQUENCE: 104
cagcctaaga gtcctccttc tgtaacactc tttccccccct ctaccgagga actcaacggc      60
aataaagcta ccttggtttg ccttatttct gatttctacc ccgggtctgt gaccgtggtg     120
tggaaagctg atgggtccac cattactcgg aatgtggaaa ccaccccggc ttctaagcag     180
```

```
tccaactcta aatacgcagc atcctcctat tgagtctta ctagtagtga ctggaagtca    240
aagggtagtt acagttgcga agtcacacat gaaggttcaa cagtgacaaa gacagtcaag    300
ccctcagagt gctcatag                                                   318
```

```
<210> SEQ ID NO 105
<211> LENGTH: 238
<212> TYPE: PRT
<213> ORGANISM: Artificial Sequence
<220> FEATURE:
<223> OTHER INFORMATION: chimeric L chain

<400> SEQUENCE: 105
```

Met Glu Ser Gln Thr His Val Leu Ile Ser Leu Leu Leu Ser Val Ser
1               5                   10                  15

Gly Thr Tyr Gly Asp Ile Ala Ile Thr Gln Ser Pro Ser Ser Val Ala
            20                  25                  30

Val Ser Val Gly Glu Thr Val Thr Leu Ser Cys Lys Ser Ser Gln Ser
        35                  40                  45

Leu Leu Tyr Ser Glu Asn Gln Lys Asp Tyr Leu Gly Trp Tyr Gln Gln
    50                  55                  60

Lys Pro Gly Gln Thr Pro Lys Pro Leu Ile Tyr Trp Ala Thr Asn Arg
65                  70                  75                  80

His Thr Gly Val Pro Asp Arg Phe Thr Gly Ser Gly Ser Gly Thr Asp
                85                  90                  95

Phe Thr Leu Ile Ile Ser Ser Val Gln Ala Glu Asp Leu Ala Asp Tyr
            100                 105                 110

Tyr Cys Gly Gln Tyr Leu Val Tyr Pro Phe Thr Phe Gly Pro Gly Thr
        115                 120                 125

Lys Leu Glu Leu Lys Gln Pro Lys Ser Pro Ser Val Thr Leu Phe
    130                 135                 140

Pro Pro Ser Thr Glu Glu Leu Asn Gly Asn Lys Ala Thr Leu Val Cys
145                 150                 155                 160

Leu Ile Ser Asp Phe Tyr Pro Gly Ser Val Thr Val Val Trp Lys Ala
                165                 170                 175

Asp Gly Ser Thr Ile Thr Arg Asn Val Glu Thr Thr Arg Ala Ser Lys
            180                 185                 190

Gln Ser Asn Ser Lys Tyr Ala Ala Ser Ser Tyr Leu Ser Leu Thr Ser
        195                 200                 205

Ser Asp Trp Lys Ser Lys Gly Ser Tyr Ser Cys Glu Val Thr His Glu
    210                 215                 220

Gly Ser Thr Val Thr Lys Thr Val Lys Pro Ser Glu Cys Ser
225                 230                 235

```
<210> SEQ ID NO 106
<211> LENGTH: 465
<212> TYPE: PRT
<213> ORGANISM: Artificial Sequence
<220> FEATURE:
<223> OTHER INFORMATION: chimeric H chain

<400> SEQUENCE: 106
```

Met Gly Trp Ser Gln Ile Ile Leu Phe Leu Val Ala Ala Ala Thr Cys
1               5                   10                  15

Val His Ser Gln Val Gln Leu Gln Gln Ser Gly Ala Glu Leu Val Lys
            20                  25                  30

Pro Gly Ser Ser Val Lys Ile Ser Cys Lys Ala Ser Gly Tyr Thr Phe
        35                  40                  45

```
Thr Ser Asn Phe Met His Trp Val Lys Gln Gln Pro Gly Asn Gly Leu
 50                  55                  60

Glu Trp Ile Gly Trp Ile Tyr Pro Glu Tyr Gly Asn Thr Lys Tyr Asn
 65                  70                  75                  80

Gln Lys Phe Asp Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
            100                 105                 110

Tyr Phe Cys Ala Ser Glu Glu Ala Val Ile Ser Leu Val Tyr Trp Gly
        115                 120                 125

Gln Gly Thr Leu Val Thr Val Ser Ser Ala Ser Thr Thr Ala Pro Lys
    130                 135                 140

Val Tyr Pro Leu Ser Ser Cys Cys Gly Asp Lys Ser Ser Ser Thr Val
145                 150                 155                 160

Thr Leu Gly Cys Leu Val Ser Ser Tyr Met Pro Glu Pro Val Thr Val
                165                 170                 175

Thr Trp Asn Ser Gly Ala Leu Lys Ser Gly Val His Thr Phe Pro Ala
            180                 185                 190

Val Leu Gln Ser Ser Gly Leu Tyr Ser Leu Ser Ser Met Val Thr Val
        195                 200                 205

Pro Gly Ser Thr Ser Gly Gln Thr Phe Thr Cys Asn Val Ala His Pro
    210                 215                 220

Ala Ser Ser Thr Lys Val Asp Lys Ala Val Asp Pro Thr Cys Lys Pro
225                 230                 235                 240

Ser Pro Cys Asp Cys Cys Pro Pro Pro Val Ala Gly Pro Ser Val
                245                 250                 255

Phe Ile Phe Pro Pro Lys Pro Lys Asp Thr Leu Thr Ile Ser Gly Thr
                260                 265                 270

Pro Glu Val Thr Cys Val Val Val Asp Val Gly His Asp Asp Pro Glu
            275                 280                 285

Val Lys Phe Ser Trp Phe Val Asp Asp Val Glu Val Asn Thr Ala Thr
        290                 295                 300

Thr Lys Pro Arg Glu Glu Gln Phe Asn Ser Thr Tyr Arg Val Val Ser
305                 310                 315                 320

Ala Leu Arg Ile Gln His Gln Asp Trp Thr Gly Gly Lys Glu Phe Lys
                325                 330                 335

Cys Lys Val His Asn Glu Gly Leu Pro Ser Ser Ile Val Arg Thr Ile
            340                 345                 350

Ser Arg Thr Lys Gly Pro Ala Arg Glu Pro Gln Val Tyr Val Leu Ala
        355                 360                 365

Pro Pro Gln Glu Glu Leu Ser Lys Ser Thr Val Ser Leu Thr Cys Met
    370                 375                 380

Val Thr Ser Phe Tyr Pro Asp Tyr Ile Ala Val Glu Trp Gln Arg Asn
385                 390                 395                 400

Gly Gln Pro Glu Ser Glu Asp Lys Tyr Gly Thr Thr Pro Pro Gln Leu
                405                 410                 415

Asp Ala Asp Ser Ser Tyr Phe Leu Tyr Ser Lys Leu Arg Val Asp Arg
            420                 425                 430

Asn Ser Trp Gln Glu Gly Asp Thr Tyr Thr Cys Val Val Met His Glu
        435                 440                 445
```

Ala Leu His Asn His Tyr Thr Gln Lys Ser Thr Ser Lys Ser Ala Gly
    450                 455                 460

Lys
465

<210> SEQ ID NO 107
<211> LENGTH: 717
<212> TYPE: DNA
<213> ORGANISM: Artificial Sequence
<220> FEATURE:
<223> OTHER INFORMATION: codon-optimized sequence

<400> SEQUENCE: 107

| | | | | | | |
|---|---|---|---|---|---|---|
| atggaatctc | aaactcatgt | tttgatttca | ttacttctga | gtgtttccgg | aacctacggt | 60 |
| gatatcgcta | tcactcaatc | tccctcctct | gttgctgtgt | ctgtgggcga | aaccgttacc | 120 |
| ctgtcctgca | agtccagtca | gtctcttctc | tactccgaga | atcaaaagga | ctacctgggc | 180 |
| tggtaccaac | agaagcccgg | ccagacccca | aagccactga | tatactgggc | aaccaacagg | 240 |
| cacaccggag | tgcccgacag | gttcacaggc | agtggatctg | gcaccgactt | taccttgatc | 300 |
| atttcaagcg | tgcaggctga | agatctggcc | gactactact | gtggtcagta | tctggtgtat | 360 |
| cctttcactt | tcgggccagg | gacaaaactc | gagctcaaac | agcctaagag | tcctccttct | 420 |
| gtaacactct | ttccccctc | taccgaggaa | ctcaacggca | taaagctac | cttggtttgc | 480 |
| cttatttctg | atttctaccc | cgggtctgtg | accgtggtgt | ggaaagctga | tgggtccacc | 540 |
| attactcgga | atgtggaaac | cacccgggct | tctaagcagt | ccaactctaa | atacgcagca | 600 |
| tcctcctatt | tgagtcttac | tagtagtgac | tggaagtcaa | agggtagtta | cagttgcgaa | 660 |
| gtcacacatg | aaggttcaac | agtgacaaag | acagtcaagc | cctcagagtg | ctcatag | 717 |

<210> SEQ ID NO 108
<211> LENGTH: 1398
<212> TYPE: DNA
<213> ORGANISM: Artificial Sequence
<220> FEATURE:
<223> OTHER INFORMATION: codon-optimized sequence

<400> SEQUENCE: 108

| | | | | | | |
|---|---|---|---|---|---|---|
| atggggtggt | cccagattat | attgttcctc | gtcgccgccg | ccacttgcgt | acacagccaa | 60 |
| gtgcaacttc | aacaaagcgg | tgcagaactg | gtaaagcccg | gtagctctgt | gaaaatatcc | 120 |
| tgtaaagcca | gtggctacac | atttaccagc | aactttatgc | actgggtgaa | gcaacagccc | 180 |
| ggaaatggct | tggagtggat | tggctggatc | tatcccgaat | atggtaacac | caagtataat | 240 |
| cagaagttcg | acggtaaggc | caccctcacc | gccgataagt | catcctccac | cgcctatatg | 300 |
| cagctcagca | gcctgaccag | cgaggattcc | gctgtgtact | tctgtgccag | cgaagaggct | 360 |
| gtgatctcat | tggtgtattg | gggacagggc | accctcgtca | ccgtgtccag | cgctagcaca | 420 |
| actgctccta | aggtgtaccc | cctgagctct | tgctgcggcg | acaagtctag | cagcaccgtg | 480 |
| accctcggat | gcctcgtcag | cagctatatg | cctgagccag | ttacagtgac | atggaattct | 540 |
| ggtgcccctta | agtccggcgt | ccataccttc | cctgctgtgc | tgcagtcctc | tggcctgtac | 600 |
| agtttgtcct | ctatggtgac | agtacccggt | tccacctccg | acagaccttt | acctgtaat | 660 |
| gtggctcatc | ccgcctcctc | cacaaaggtg | gataaggctg | ttgaccctac | ctgtaaaccc | 720 |
| agtccatgcg | actgctgtcc | cccccctcca | gttgccggac | cctcagtctt | tatttttccca | 780 |
| cccaaaccca | aagacaccct | gacaatctct | ggaacaccag | aagtcacctg | cgtcgtcgtg | 840 |
| gatgtgggcc | acgacgatcc | tgaggtaaaa | ttctcatggt | tcgtcgacga | tgtggaagtg | 900 |

| | |
|---|---|
| aatacagcta ctacaaaacc tcgcgaagag cagtttaact ctacctatcg agtggtttct | 960 |
| gctttgcgga ttcagcatca ggattggaca ggcggcaaag agtttaaatg taaagtccat | 1020 |
| aacgagggac ttccttctag tatcgtgcgc actatcagta gaactaaagg gcctgctcgg | 1080 |
| gaacctcagg tgtacgtcct ggcacctcca caggaagagc tgagtaagtc tacagtttct | 1140 |
| ctgacttgta tggtaacatc ttttatcca gattacatcg cagttgaatg gcagaggaac | 1200 |
| gggcagccag agagtgagga taagtacggg actactccac cacagctgga cgcagactca | 1260 |
| agttacttcc tgtactcaaa gctgagggtt gacagaaact catggcagga ggggacact | 1320 |
| tacacttgcg tagttatgca cgaggcactt cacaaccact acactcagaa gagtacttca | 1380 |
| aagagtgcag ggaagtaa | 1398 |

```
<210> SEQ ID NO 109
<211> LENGTH: 25
<212> TYPE: DNA
<213> ORGANISM: Artificial Sequence
<220> FEATURE:
<223> OTHER INFORMATION: primer

<400> SEQUENCE: 109
```

| | |
|---|---|
| atgaggatat atagtgtctt aacat | 25 |

```
<210> SEQ ID NO 110
<211> LENGTH: 20
<212> TYPE: DNA
<213> ORGANISM: Artificial Sequence
<220> FEATURE:
<223> OTHER INFORMATION: primer

<400> SEQUENCE: 110
```

| | |
|---|---|
| ttacgtctcc tcaaaatgtg | 20 |

```
<210> SEQ ID NO 111
<211> LENGTH: 25
<212> TYPE: DNA
<213> ORGANISM: Artificial Sequence
<220> FEATURE:
<223> OTHER INFORMATION: primer

<400> SEQUENCE: 111
```

| | |
|---|---|
| atgaggatat gtagtatctt tacat | 25 |

```
<210> SEQ ID NO 112
<211> LENGTH: 21
<212> TYPE: DNA
<213> ORGANISM: Artificial Sequence
<220> FEATURE:
<223> OTHER INFORMATION: primer

<400> SEQUENCE: 112
```

| | |
|---|---|
| ttacgtctcc tcaaattgtg t | 21 |

```
<210> SEQ ID NO 113
<211> LENGTH: 20
<212> TYPE: DNA
<213> ORGANISM: Artificial Sequence
<220> FEATURE:
<223> OTHER INFORMATION: primer

<400> SEQUENCE: 113
```

| | |
|---|---|
| atgaggatat atagtgtctt | 20 |

```
<210> SEQ ID NO 114
<211> LENGTH: 20
<212> TYPE: DNA
<213> ORGANISM: Artificial Sequence
<220> FEATURE:
<223> OTHER INFORMATION: primer

<400> SEQUENCE: 114
gccactcagg acttggtgat                                                 20

<210> SEQ ID NO 115
<211> LENGTH: 20
<212> TYPE: DNA
<213> ORGANISM: Artificial Sequence
<220> FEATURE:
<223> OTHER INFORMATION: primer

<400> SEQUENCE: 115
gggggtttac tgttgcttga                                                 20

<210> SEQ ID NO 116
<211> LENGTH: 19
<212> TYPE: DNA
<213> ORGANISM: Artificial Sequence
<220> FEATURE:
<223> OTHER INFORMATION: primer

<400> SEQUENCE: 116
ttacgtctcc tcaaattgt                                                  19

<210> SEQ ID NO 117
<211> LENGTH: 29
<212> TYPE: DNA
<213> ORGANISM: Artificial Sequence
<220> FEATURE:
<223> OTHER INFORMATION: primer

<400> SEQUENCE: 117
gaagatctat ggggaccccg cgggcgccg                                       29

<210> SEQ ID NO 118
<211> LENGTH: 29
<212> TYPE: DNA
<213> ORGANISM: Artificial Sequence
<220> FEATURE:
<223> OTHER INFORMATION: primer

<400> SEQUENCE: 118
gacccgggga ggggccagga gcagtgtcc                                       29

<210> SEQ ID NO 119
<211> LENGTH: 28
<212> TYPE: DNA
<213> ORGANISM: Artificial Sequence
<220> FEATURE:
<223> OTHER INFORMATION: primer

<400> SEQUENCE: 119
ccgctcgaga tgaggatata tagtgtct                                        28

<210> SEQ ID NO 120
<211> LENGTH: 28
<212> TYPE: DNA
<213> ORGANISM: Artificial Sequence
<220> FEATURE:
<223> OTHER INFORMATION: primer
```

<400> SEQUENCE: 120
atcccgggcg tctcctcaaa atgtgtag                                          28

<210> SEQ ID NO 121
<211> LENGTH: 25
<212> TYPE: DNA
<213> ORGANISM: Artificial Sequence
<220> FEATURE:
<223> OTHER INFORMATION: primer

<400> SEQUENCE: 121
actaagctta tggggacccc gcggg                                             25

<210> SEQ ID NO 122
<211> LENGTH: 26
<212> TYPE: DNA
<213> ORGANISM: Artificial Sequence
<220> FEATURE:
<223> OTHER INFORMATION: primer

<400> SEQUENCE: 122
actcccgggg aggggccaag agcagt                                            26

<210> SEQ ID NO 123
<211> LENGTH: 29
<212> TYPE: DNA
<213> ORGANISM: Artificial Sequence
<220> FEATURE:
<223> OTHER INFORMATION: primer

<400> SEQUENCE: 123
ccgctcgaga tgaggatatg tagtatctt                                         29

<210> SEQ ID NO 124
<211> LENGTH: 29
<212> TYPE: DNA
<213> ORGANISM: Artificial Sequence
<220> FEATURE:
<223> OTHER INFORMATION: primer

<400> SEQUENCE: 124
atcccgggcg tctcctcaaa ttgtgtatc                                         29

<210> SEQ ID NO 125
<211> LENGTH: 28
<212> TYPE: DNA
<213> ORGANISM: Artificial Sequence
<220> FEATURE:
<223> OTHER INFORMATION: primer

<400> SEQUENCE: 125
gacgctagca tgaggatata tagtgtct                                          28

<210> SEQ ID NO 126
<211> LENGTH: 28
<212> TYPE: DNA
<213> ORGANISM: Artificial Sequence
<220> FEATURE:
<223> OTHER INFORMATION: primer

<400> SEQUENCE: 126
gctctgatat ccctcgtttt tgctggat                                          28

```
<210> SEQ ID NO 127
<211> LENGTH: 29
<212> TYPE: DNA
<213> ORGANISM: Artificial Sequence
<220> FEATURE:
<223> OTHER INFORMATION: primer

<400> SEQUENCE: 127
gacgctagca tgaggatatg tagtatctt                                29

<210> SEQ ID NO 128
<211> LENGTH: 29
<212> TYPE: DNA
<213> ORGANISM: Artificial Sequence
<220> FEATURE:
<223> OTHER INFORMATION: primer

<400> SEQUENCE: 128
agcttgatat ccctctttct tgctggatc                                29

<210> SEQ ID NO 129
<211> LENGTH: 30
<212> TYPE: DNA
<213> ORGANISM: Artificial Sequence
<220> FEATURE:
<223> OTHER INFORMATION: primer

<400> SEQUENCE: 129
cgcggatatc atggattaca cagcgaagtg                               30

<210> SEQ ID NO 130
<211> LENGTH: 29
<212> TYPE: DNA
<213> ORGANISM: Artificial Sequence
<220> FEATURE:
<223> OTHER INFORMATION: primer

<400> SEQUENCE: 130
cggggtaccc cagagctgtt gctggttat                                29

<210> SEQ ID NO 131
<211> LENGTH: 30
<212> TYPE: DNA
<213> ORGANISM: Artificial Sequence
<220> FEATURE:
<223> OTHER INFORMATION: primer

<400> SEQUENCE: 131
cgcggctagc atgagaatgt ttagtgtctt                               30

<210> SEQ ID NO 132
<211> LENGTH: 49
<212> TYPE: DNA
<213> ORGANISM: Artificial Sequence
<220> FEATURE:
<223> OTHER INFORMATION: primer

<400> SEQUENCE: 132
cgcggatatc ttaatggtga tggtgatggt gagtcctctc acttgctgg          49

<210> SEQ ID NO 133
<211> LENGTH: 32
<212> TYPE: DNA
<213> ORGANISM: Artificial Sequence
<220> FEATURE:
<223> OTHER INFORMATION: primer
```

```
<400> SEQUENCE: 133
atatgcggcc gcatggggac cccgcgggcg ct                                32

<210> SEQ ID NO 134
<211> LENGTH: 30
<212> TYPE: DNA
<213> ORGANISM: Artificial Sequence
<220> FEATURE:
<223> OTHER INFORMATION: primer

<400> SEQUENCE: 134
gcgcaagctt tcagaggggc caggagcagt                                   30

<210> SEQ ID NO 135
<211> LENGTH: 35
<212> TYPE: DNA
<213> ORGANISM: Artificial Sequence
<220> FEATURE:
<223> OTHER INFORMATION: primer

<400> SEQUENCE: 135
ctagctagca ccatgaggat atatagtgtc ttaac                             35

<210> SEQ ID NO 136
<211> LENGTH: 31
<212> TYPE: DNA
<213> ORGANISM: Artificial Sequence
<220> FEATURE:
<223> OTHER INFORMATION: primer

<400> SEQUENCE: 136
caatctcgag ttacagacag aagatgactg c                                 31

<210> SEQ ID NO 137
<211> LENGTH: 29
<212> TYPE: DNA
<213> ORGANISM: Artificial Sequence
<220> FEATURE:
<223> OTHER INFORMATION: primer

<400> SEQUENCE: 137
gctagcatga ggatatatag tgtcttaac                                    29

<210> SEQ ID NO 138
<211> LENGTH: 26
<212> TYPE: DNA
<213> ORGANISM: Artificial Sequence
<220> FEATURE:
<223> OTHER INFORMATION: primer

<400> SEQUENCE: 138
gatatcattc ctcttttttg ctggat                                       26
```

ANTI-PD-L1 ANTIBODY

PRIORITY APPLICATIONS

This application is a U.S. National Stage Filing under 35 U.S.C. 371 from International Application No. PCT/JP2017/029055, filed on Aug. 10, 2017, and published as WO2018/034225 on Feb. 22, 2018, which claims the benefit of priority to Japanese Application No. 2017-110723, filed on Jun. 5, 2017 and to Japanese Application No. 2017-061454, filed on Mar. 27, 2017 and to Japanese Application No. 2016-159089, filed on Aug. 15, 2016 and to Japanese Application No. 2016-159088, filed on Aug. 15, 2016; the benefit of priority of each of which is hereby claimed herein, and which applications and publication are hereby incorporated herein by reference in their entirety.

TECHNICAL FIELD

The present invention relates to an anti-PD-L1 antibody. More specifically, the present invention relates to an anti-PD-L1 antibody comprising a variable region containing complementarity-determining regions (CDR) of a rat anti-bovine PD-L1 antibody and a constant region of an antibody of an animal other than rat.

BACKGROUND ART

Programmed cell death 1 (PD-1), an immunoinhibitory receptor, and its ligand programmed cell death ligand 1 (PD-L1) are molecules identified by Prof. Tasuku Honjo et al., Kyoto University, as factors which inhibit excessive immune response and are deeply involved in immunotolerance (Non-Patent Document No. 1: Ishida Y, Agata Y, Shibahara K, Honjo T The EMBO Journal. 1992 November; 11(1):3887-3895). Recently, it has been elucidated that these molecules are also involved in immunosuppression in tumors. In the field of human medical care, an antibody drug that inhibits the effect of PD-1 has been developed and put into practical use (Opdivo™, Ono Pharmaceutical Co., Ltd.)

To date, the present inventors have been developing an immunotherapy for animal refractory diseases targeting PD-1 or PD-L1, and have revealed that this novel immunotherapy is applicable to multiple-diseases and multiple-animals. (Non-Patent Document No. 2: Ikebuchi R, Konnai S, Okagawa T, Yokoyama K, Nakajima C, Suzuki Y, Murata S, Ohashi K. Immunology. 2014 August; 142(4):551-61; Non-Patent Document No. 3: Maekawa N, Konnai S, Ikebuchi R, Okagawa T, Adachi M. Takagi S, Kagawa Y, Nakjima C, Suzuki Y, Murata S, Ohashi K. PLoS One. 2014 Jun. 10; 9(6):e98415; Non-Patent Document No. 4: Mingala C N, Konnai S, Ikebuchi R, Ohashi K. Comp. Immunol. Microbiol. Infect. Dis. 2011 January; 34(1):55-63.)

However, the antibodies which the present inventors have prepared to date are rat antibodies, and therefore it is impossible to administer those antibodies repeatedly to animals other than rat.

PRIOR ART LITERATURE

Non-Patent Documents

Non-Patent Document No. 1: Ishida Y, Agata Y, Shibahara K, Honjo T The EMBO Journal. 1992 November; 11(11): 3887-3895.

Non-Patent Document No. 2: Ikebuchi R, Konnai S, Okagawa T, Yokoyama K, Nakajima C, Suzuki Y, Murata S, Ohashi K. Immunology. 2014 August; 142(4):551-61.

Non-Patent Document No. 3: Maekawa N, Konnai S, Ikebuchi R, Okagawa T, Adachi M, Takagi S, Kagawa Y, Nakjima C, Suzuki Y, Murata S, Ohashi K. PLoS One. 2014 Jun. 10; 9(6):e98415.

Non-Patent Document No. 4: Mingala C N, Konnai S, Ikebuchi R, Ohashi K. Comp. Immunol. Microbiol. Infect. Dis. 2011 January; 34(1):55-63.

DISCLOSURE OF THE INVENTION

Problem for Solution by the Invention

It is an object of the present invention to provide an anti-PD-L1 antibody capable of repeated administration even to animals other than rat.

Means to Solve the Problem

The present inventors have determined the variable regions of a rat anti-bovine PD-L1 monoclonal antibody (4G12) capable of inhibiting the binding of canine PD-1 to PD-L1, and then combined genes encoding the resultant variable regions with genes encoding the constant regions of a canine immunoglobulin (IgG-D equivalent to human IgG4) to thereby obtain a chimeric antibody gene, which was introduced into Chinese hamster ovary cells (CHO cells). By culturing/proliferating the resultant CHO cells, the present inventors have succeeded in preparing a rat-canine chimeric anti-PD-L1 antibody. Further, the present inventors have determined the CDRs of the variable region of the rat anti-bovine PD-L1 monoclonal antibody 4G12.

Furthermore, the present inventors have determined the variable regions of the rat anti-bovine PD-L1 monoclonal antibody 4G12 capable of inhibiting the binding of bovine PD-1 to PD-L1, and then combined genes encoding the resultant variable regions with genes encoding the constant regions of a bovine immunoglobulin (bovine IgG1, with mutations having been introduced into the putative binding sites of Fcγ receptors in CH2 domain in order to inhibit ADCC activity; see FIG. 19 for amino acid numbers and mutations: 250 E→P, 251 L→V, 252 P→A, 253 G→deletion, 347 A→S, 348 P→S; Ikebuchi R, Konnai S, Okagawa T, Yokoyama K, Nakajima C, Suzuki Y, Murata S, Ohashi K. Immunology 2014 August; 142(4):551-561) to thereby obtain a chimeric antibody gene. This gene was introduced into Chinese hamster ovary cells (CHO cells). By culturing/proliferating the resultant cells, the present inventors have succeeded in preparing a rat-bovine chimeric anti-PD-L1 antibody. The present invention has been achieved based on these findings.

A summary of the present invention is as described below.

(1) An anti-PD-L1 antibody comprising (a) a light chain comprising a light chain variable region containing CDR1 having the amino acid sequence of QSLLYSENQKDY (SEQ ID NO: 37), CDR2 having the amino acid sequence of WAT and CDR3 having the amino acid sequence of GQYLVYPFT (SEQ ID NO: 38) and the light chain constant region of an antibody of an animal other than rat; and (b) a heavy chain comprising a heavy chain variable region containing CDR1 having the amino acid sequence of GYTFTSNF (SEQ ID NO: 39), CDR2 having the amino acid sequence of IYPEYGNT (SEQ ID NO: 40) and CDR3 having the amino acid sequence of ASEE- AVISLVY (SEQ ID NO: 41) and the heavy chain constant region of an antibody of an animal other than rat.

(2) The antibody of (1) above, wherein the light chain variable region and the heavy chain variable region are derived from rat.

(3) The antibody of (2) above, wherein the light chain variable region is the light chain variable region of a rat anti-bovine PD-L1 antibody and the heavy chain variable region is the heavy chain variable region of a rat anti-bovine PD-L1 antibody.

(4) The antibody of (3) above, wherein the light chain variable region has the amino acid sequence as shown in SEQ ID NO. 1 and the heavy chain variable region has the amino acid sequence as shown in SEQ ID NO: 2.

(5) The antibody of any one of (1) to (4) above, wherein the light chain constant region of an antibody of an animal other than rat has the amino acid sequence of the constant region of lambda chain or kappa chain.

(6) The antibody of any one of (1) to (5) above, wherein the heavy chain constant region of an antibody of an animal other than rat has the amino acid sequence of like constant region of an immunoglobulin equivalent to human IgG4.

(7) The antibody of any one of (1) to (5) above, wherein the animal other than rat is bovine and the heavy chain constant region of the bovine antibody has mutations introduced thereinto that reduce ADCC activity and/or CDC activity.

(8) The antibody of (6) above, wherein the animal other than rat is canine; the light chain constant region of the canine antibody has the amino acid sequence of the constant region of lambda chain; and the heavy chain constant region of the canine antibody has the amino acid sequence of the constant region of an immunoglobulin equivalent to human IgG4.

(9) The antibody of (7) above, wherein the light chain constant region of the bovine antibody has the amino acid sequence of the constant region of lambda chain and the heavy chain constant region of the bovine antibody has mutations introduced thereinto that reduce ADCC activity and/or CDC activity.

(10) The antibody of (8) above, wherein the light chain constant region of the canine antibody has the amino acid sequence as shown in SEQ ID NO: 3 and the heavy chain constant region of the canine antibody has the amino acid sequence as show % n in SEQ ID NO: 4.

(11) The antibody of (9) above, wherein the light chain constant region of the bovine antibody has the amino acid sequence as shown in SEQ ID NO: 100 and the heavy chain constant region of the bovine antibody has the amino acid sequence as shown in SEQ ID NO: 102.

(12) The antibody of any one of (1) to (11) above which has a four-chain structure comprising two light chains and two heavy chains.

(13) A pharmaceutical composition comprising the antibody of any one of (1) to (12) above as an active ingredient.

(14) The composition of (13) above for prevention and/or treatment of cancers and/or inflammations.

(15) The composition of (14) above, wherein the cancers and/or inflammations are selected from the group consisting of neoplastic diseases, leukemia, Johne's disease, anaplasmosis, bacterial mastitis, mycotic mastitis, mycoplasma infections (such as mycoplasma mastitis, mycoplasma pneumonia or the like), tuberculosis, *Theileria orientalis* infection, cryptosporidiosis, coccidiosis, trypanosomiasis and leishmaniasis.

(16) An artificial genetic DNA comprising (a') a DNA encoding a light chain comprising a light chain variable region containing CDR1 having the amino acid sequence of QSLLYSENQKDY (SEQ ID NO: 37), CDR2 having the amino acid sequence of WAT and CDR3 having the amino acid sequence of GQYLVYPFT (SEQ ID NO: 38) and the light chain constant region of an antibody of an animal other than rat and (b) a DNA encoding a heavy chain comprising a heavy chain variable region containing CDR1 having the amino acid sequence of GYTFTSNF (SEQ ID NO: 39), CDR2 having the amino acid sequence of IYPEYGNT (SEQ ID NO: 40) and CDR3 having the amino acid sequence of ASEEAVISLVY (SEQ ID NO: 41) and the heavy chain constant region of an antibody of an animal other than rat.

(17) A vector comprising the artificial genetic DNA of (16) above.

(18) A host cell transformed with the vector of (17) above.

(19) A method of preparing an antibody, comprising culturing the host cell of (18) above and collecting an anti-PD-L1 antibody from the resultant culture.

(20) A DNA encoding a light chain comprising a light chain variable region containing CDR1 having the amino acid sequence of QSLLYSENQKDY (SEQ ID NO: 37), CDR2 having the amino acid sequence of WAT and CDR3 having the amino acid sequence of GQYLVYPFT (SEQ ID NO: 38) and the light chain constant region of an antibody of an animal other than rat.

(21) A DNA encoding a heavy chain comprising a heavy chain variable region containing CDR1 having the amino acid sequence of GYTFTSNF (SEQ ID NO: 39), CDR2 having the amino acid sequence of IYPEYGNT (SEQ ID NO: 40) and CDR3 having the amino acid sequence of ASEEAVISLVY (SEQ ID NO: 41) and the heavy chain constant region of an antibody of an animal other than rat.

The present specification encompasses the contents disclosed in the specifications and/or drawings of Japanese Patent Applications No. 2016-159088, No. 2016-159089, No. 2017-110723 and No. 2017-61454 based on which the present patent application claims priority.

Effect of the Invention

According to the present invention, a novel anti-PD-L1 antibody has been obtained. This antibody is applicable even to those animals other than rat.

BRIEF DESCRIPTION OF THE DRAWINGS

FIG. 15 CDR1, CDR2 and CDR3 regions in the light chain variable region and the heavy chain variable region of rat anti-bovine PD-L1 antibody 4G12 are illustrated.

FIG. 19 The amino acid sequence of rat-bovine chimeric anti-bovine PD-L1 antibody ch4G12. CDR1, CDR2 and CDR3 regions in the light chain variable region and the heavy chain variable region of rat anti-bovine PD-L1 antibody 4G12 are shown. Further, amino acids introduced as mutations to bovine IgG1 (CH2 domain) are also shown (amino acid numbers and mutations: 250 E→P, 251 L→V, 252 P→A, 253 G →deletion, 347 A→S, 348 P→S).

BEST MODES FOR CARRYING OUT THE INVENTION

Figure 1:
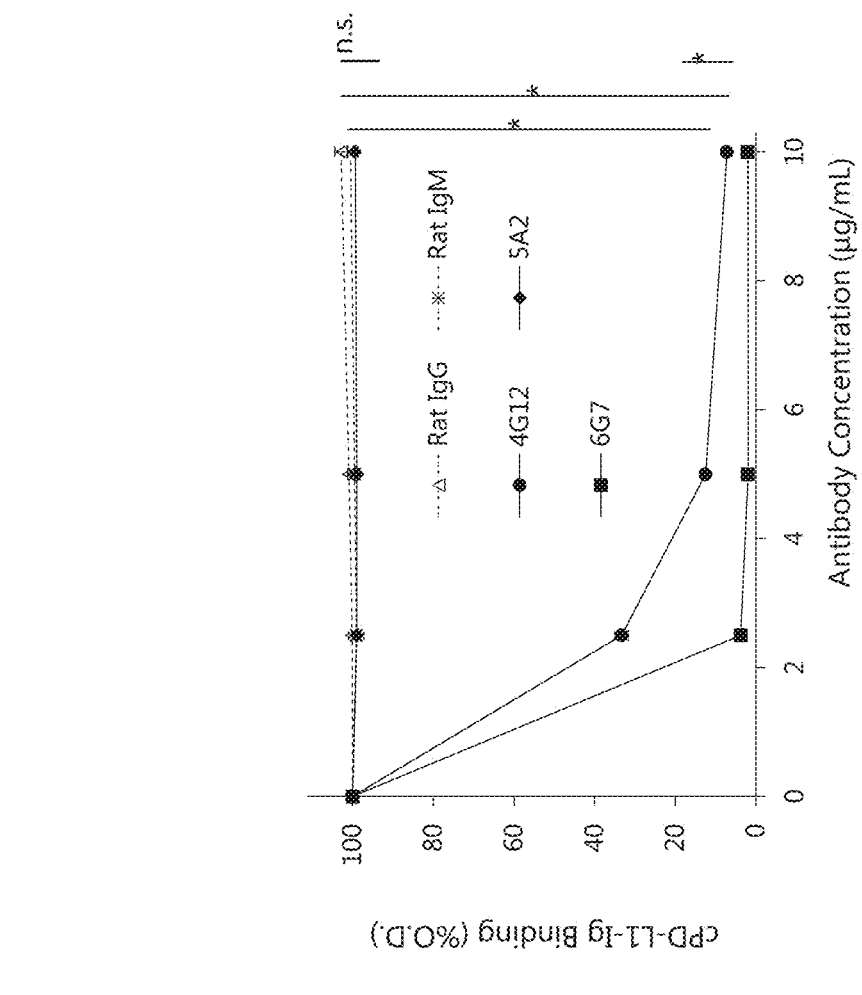
FIG. 1 Inhibition of the binding of recombinant canine PD-L1 to recombinant canine PD-1. The binding of canine PD-L1-Ig to canine PD-1-Ig was detected on ELISA plates. The optical density (O.D.) without addition of antibody was taken as 100%. O.D. at each antibody concentration was shown as relative value. Among rat anti-bovine PD-L1 monoclonal antibodies 4G12 (Rat IgG2a (κ)), 5A2 (Rat IgG1 (κ)) and 607 (Rat IgM (κ)) which showed cross-reaction with canine PD-L1, clones 4G12 and 6G7 exhibited a high binding inhibition capacity.

Hereinbelow, the present invention will be described in detail.

The present invention provides an anti-PD-L1 antibody comprising (a) a light chain comprising a light chain variable region containing CDR1 having the amino acid sequence of QSLLYSENQKDY (SEQ ID NO: 37), CDR2 having the amino acid sequence of WAT and CDR3 having the amino acid sequence of GQYLVYPFT (SEQ ID NO: 38) and a light chain constant region of an antibody of an animal other than rat; and (b) a heavy chain comprising a heavy chain variable region containing CDR1 having the amino acid sequence of GYTFTSNF (SEQ ID NO: 39), CDR2 having the amino acid sequence of IYPEYGNT (SEQ ID NO: 40) and CDR3 having the amino acid sequence of ASEEAVISLVY (SEQ ID NO: 41) and a heavy chain constant region of an antibody of an animal other than rat.

CDR1, CDR2 and CDR3 in the light chain variable region (VL) of rat anti-bovine PD-L1 antibody 4G12 are a region consisting of the amino acid sequence of QSLLYSENQKDY (SEQ ID NO: 37), a region consisting of the amino acid sequence of WAT and a region consisting of the amino acid sequence of GQYLVYPFT (SEQ ID NO: 38), respectively (see FIG. 15).

Further, CDR1, CDR2 and CDR3 in the heavy chain variable region (VH) of rat anti-bovine PD-L1 antibody 4G12 are a region consisting of the amino acid sequence of GYTFTSNF (SEQ ID NO: 39), a region consisting of the amino acid sequence of IYPEYGNT (SEQ ID NO: 40) and a region consisting of the amino acid sequence of ASEEAVISLVY (SEQ ID NO: 41), respectively (see FIG. 15).

In the amino acid sequences of QSLLYSENQKDY (SEQ ID NO: 37), WAT and GQYLVYPFT (SEQ ID NO: 38), as well as the amino acid sequences of GYTFTSNF (SEQ ID NO: 39), IYPEYGNT (SEQ ID NO: 40) and ASEEAVISLVY (SEQ ID NO: 41), one, two, three, four or five amino acids may be deleted, substituted or added.

As used herein, the term "antibody" is a concept encompassing not only full-length antibodies but also antibodies of smaller molecular sizes such as Fab, F(ab)'$_2$, ScFv, Diabody, $V_H$, $V_L$, Sc(Fv)$_2$, Bispecific sc(Fv)$_2$, Minibody, scFv-Fc monomer and scFv-Fc dimer.

In the anti-PD-L1 antibody of the present invention, VL and VH thereof may be derived from rat. For example, VL thereof may be the VL of a rat anti-bovine PD-L1 antibody, and VH thereof may be the VH of the rat anti-bovine PD-L1 antibody.

The amino acid sequence of the VL and the amino acid sequence of the VH of the rat anti-bovine PD-L1 antibody are shown in SEQ ID NOS: 1 and 2, respectively. The amino acid sequences as shown in SEQ ID NOS: 1 and 2 may have deletion(s), substitution(s) or addition(s) of one or several (e.g., up to five, about 10 at the most) amino acids. Even when such mutations have been introduced, the resulting amino acid sequences are capable of having the function as VL or VH of the PD-L1 antibody.

The VL and VH of an antibody of an animal other than rat may be derived from an animal which produces a PD-L1 that cross-reacts with rat anti-bovine PD-L1 antibody 4G12.

There are two types of immunoglobulin light chain, which are called Kappa chain (κ) and Lambda chain (λ). In the anti-PD-L1 antibody of the present invention, the light chain constant region (CL) of an antibody of an animal other than rat may have the amino acid sequence of the constant region of either Kappa chain or Lambda chain. However, the relative abundance of Lambda chain is higher in ovine, feline, canine, equine and bovine, and that of Kappa chain is higher in mouse, rat, human and porcine. Since a chain with a higher relative abundance is considered to be preferable, an ovine, feline, canine, equine or bovine antibody preferably has the amino acid sequence of the constant region of Lambda chain whereas a mouse, rat, human or porcine antibody preferably has the amino acid sequence of the constant region of Kappa chain.

The heavy chain constant region (CH) of an antibody of an animal other than rat may have the amino acid sequence of the constant region of an immunoglobulin equivalent to human IgG4. Immunoglobulin heavy chain is classified into γ chain, μ chain, α chain, δ chain and ε chain depending on the difference in constant region. According to the type of heavy chain present, five classes (isotypes) of immunoglobulin are formed; they are IgG, IgM, IgA, IgD and IgE.

Immunoglobulin G (IgG) accounts for 70-75% of human immunoglobulins and is the most abundantly found monomeric antibody in plasma. IgG has a four-chain structure consisting of two light chains and two heavy chains. Human IgG1, IgG2 and IgG4 have molecular weights of about 146,000, whereas human IgG3 has a long hinge region that connects Fab region and Fc region and has a larger molecular weight of 170,000. Human IgG1 accounts for about 65%, human IgG2 about 25%, human IgG3 about 7%, and human IgG4 about 3% of human IgG. They are uniformly distributed inside and outside of blood vessels. Having a strong affinity for Fc receptors and complement factors on effector cell surfaces, human IgG1 induces antibody-dependent cell cytotoxicity (ADCC) and also activates complements to induce complement-dependent cell cytotoxicity (CDC). Human IgG2 and IgG4 are low at ADCC and CDC activities because their affinity for Fc receptors and complement factors is low.

Immunoglobulin M (IgM), which accounts for about 10% of human immunoglobulins, is a pentameric antibody consisting of five basic four-chain structures joined together. It has a molecular weight of 970,000. Usually occurring only in blood, IgM is produced against infectious microorganisms and takes charge of early stage immunity.

Immunoglobulin A (IgA) accounts for 10-15% of human immunoglobulins. It has a molecular weight of 160,000. Secreted IgA is a dimeric antibody consisting of two IgA molecules joined together. IgA1 is found in serum, nasal discharge, saliva and breast milk. In intestinal juice, IgA2 is found abundantly.

Immunoglobulin D (IgD) is a monomeric antibody accounting for no more than 1% of human immunoglobulins. IgD is found on B cell surfaces and involved in induction of antibody production.

Immunoglobulin E (IgE) is a monomeric antibody that occurs in an extremely small amount, accounting for only 0.001% or less of human immunoglobulins. Immunoglobulin E is considered to be involved in immune response to parasites but in advanced countries where parasites are rare, IgE is largely involved in bronchial asthma and allergy among other things.

With respect to canine, sequences of IgG-A (equivalent to human IgG2), IgG-B (equivalent to human IgG1), IgG-C (equivalent to human IgG3) and IgG-D (equivalent to human IgG4) have been identified as the heavy chain of IgG. In the antibody of the present invention, an IgG's heavy chain constant region with neither ADCC activity nor CDC activity is preferable (IgG4 in human). In the case where the constant region of an immunoglobulin equivalent to human IgG4 has not been identified, one may use a constant region that has lost both ADCC activity and CDC activity as a result of introducing mutations into the relevant region of an immunoglobulin equivalent to human IgG4.

With respect to bovine, sequences of IgG1, IgG2 and IgG3 have been identified as the heavy chain of IgG. In the antibody of the present invention, an IgG's heavy chain constant region with neither ADCC activity nor CDC activity is preferable (IgG4 in human). Although the constant region of wild-type human IgG1 has ADCC activity and CDC activity, it is known that these activities can be reduced by introducing amino acid substitutions or deletions into specific sites. In bovine, the constant region of an immunoglobulin equivalent to human IgG4 has not been identified, so mutations may be added at the relevant region of an immunoglobulin equivalent to human IgG1 and the resultant constant region then used. As one example, the amino acid sequence of the CH of a bovine antibody (IgG1 chain, GenBank: X62916) having mutations introduced into CH2 domain and a nucleotide sequence for such amino acid sequence (after codon optimization) are shown in SEQ ID NOS: 102 and 102, respectively.

When an animal other than rat is canine, an anti-PD-L1 antibody is more preferable in which (i) the CL of a canine antibody has the amino acid sequence of the constant region of Lambda chain and (ii) the CH of the canine antibody has the amino acid sequence of the constant region of an immunoglobulin equivalent to human IgG4.

When an animal other than rat is bovine, an anti-PD-L1 antibody is more preferable in which (i) the CL of a bovine antibody has the amino acid sequence of the constant region of Lambda chain and (ii) the CH of the bovine antibody has mutations introduced thereinto that reduce ADCC activity and/or CDC activity.

The anti-PD-L1 antibody of the present invention encompasses rat-canine chimeric antibodies, caninized antibodies, complete canine-type antibodies, rat-bovine chimeric antibodies, bovinized antibodies and complete bovine-type antibodies. However, animals are not limited to canine and bovine and may be exemplified by human, porcine, simian, mouse, feline, equine, goat, sheep, water buffalo, rabbit, hamster, guinea pig and the like.

For example, the anti-PD-L1 antibody of the present invention may be an anti-PD-L1 antibody in which the CL of a canine antibody has the amino acid sequence as shown in SEQ ID NO: 3 and the CH of the canine antibody has the amino acid sequence as shown in SEQ ID NO: 4.

As a further example, the anti-PD-L1 antibody of the present invention may be an anti-PD-L1 antibody in which the CL of a bovine antibody has the amino acid sequence as shown in SEQ ID NO: 100 and the CH of the bovine antibody has the amino acid sequence as shown in SEQ ID NO: 102.

The amino acid sequences as shown in SEQ ID NOS: 3 and 4 as well as SEQ ID NOS: 100 and 102 may have deletion(s), substitution(s) or addition(s) of one or several (e.g., up to five, about 10 at the most) amino acids. Even when such mutations have been introduced, the resulting amino acid sequences are capable of having the function as CL or CH of the PD-L1 antibody.

The anti-PD-L1 antibody of the present invention may have a four-chain structure comprising two light chains and two heavy chains.

The anti-PD-L1 antibody of the present invention may be prepared as described below. Briefly, an artificial gene is synthesized which comprises (i) the identified variable region sequences of a rat anti-bovine PD-L1 antibody and (ii) the constant region sequences of an antibody of an animal other than rat (e.g., canine or bovine) (preferably, human IgG4 antibody; antibody equivalent to human IgG4 antibody; or an immunoglobulin equivalent to human IgG1, in which mutations have been introduced into the relevant region to reduce ADCC activity and/or CDC activity). The resultant gene is inserted into a vector (e.g., plasmid), which is then introduced into a host cell (e.g., mammal cell such as CHO cell). The host cell is cultured, and the antibody of interest is collected from the resultant culture.

The amino acid sequence and the nucleotide sequence of the VL of the rat anti-bovine PD-L1 antibody identified by the present inventors are shown in SEQ ID NOS: 1 and 5, respectively. Further, the nucleotide sequence after codon optimization is shown in SEQ ID NO: 15.

The amino acid sequence and the nucleotide sequence of the VH of the rat anti-bovine PD-L1 antibody identified by the present inventors are shown in SEQ ID NOS: 2 and 6, respectively. Further, the nucleotide sequence after codon optimization is shown in SEQ ID NO: 16.

The amino acid sequence and the nucleotide sequence of the CL (Lambda chain, GenBank: E02824.1) of a canine antibody are shown in SEQ ID NOS: 3 and 7, respectively. Further, the nucleotide sequence after codon optimization is shown in SEQ ID NO: 17.

The amino acid sequence and the nucleotide sequence of the CL (Lambda chain, GenBank: X62917) of a bovine antibody are shown in SEQ ID NOS: 100 and 101, respectively. Further, the nucleotide sequence after codon optimization is shown in SEQ ID NO: 104.

The amino acid sequence and the nucleotide sequence of the CH (IgG-D chain, GenBank: AF354267.1) of the canine antibody are shown in SEQ ID NOS: 4 and 8, respectively. Further, the nucleotide sequence after codon optimization is shown in SEQ ID NO: 18.

The amino acid sequence and the nucleotide sequence (after codon optimization) of the CH (IgG1 chain, modified from GenBank: X62916) of the bovine antibody are shown in SEQ ID NOS: 102 and 103, respectively.

Further, SEQ ID NO: 9 shows the amino acid sequence of a chimeric light chain consisting of the VL of the rat anti-bovine PD-L1 antibody and the CL (Lambda chain, GenBank: E02824.1) of the canine antibody. The nucleotide sequence (after codon optimization) of the chimeric light chain consisting of the VL of the rat anti-bovine PD-L1 antibody and the CL (Lambda chain, GenBank: E02824.1) of the canine antibody is shown in SEQ ID NO: 19.

Further, SEQ ID NO: 105 shows the amino acid sequence of a chimeric light chain consisting of the VL of the rat anti-bovine PD-L1 antibody and the CL (Lambda chain, GenBank: X62917) of the bovine antibody. The nucleotide sequence (after codon optimization) of the chimeric light chain consisting of the VL of the rat anti-bovine PD-L1 antibody and the CL (Lambda chain, GenBank: X62917) of the bovine antibody is shown in SEQ ID NO: 107.

SEQ ID NO: 10 shows the amino acid sequence of a chimeric heavy chain consisting of the VH of the rat anti-bovine PD-L1 antibody and the CH (IgG-D chain, GenBank: AF354267.1) of the canine antibody. The nucleotide sequence (after codon optimization) of the chimeric heavy chain consisting of the VH of the rat anti-bovine PD-L1 antibody and the CH (IgG-D chain, GenBank: AF354267.1) of the canine antibody is shown in SEQ ID NO: 20.

SEQ ID NO: 106 shows the amino acid sequence of a chimeric heavy chain consisting of the VH of the rat anti-bovine PD-L1 antibody and the CH (IgG1 chain, modified from GenBank: X62916) of the bovine antibody. The nucleotide sequence (after codon optimization) of the chimeric heavy chain consisting of the VH of the rat anti-bovine PD-L1 antibody and the CH (IgG1 chain, modified from GenBank: X62916) of the bovine antibody is shown in SEQ ID NO: 108.

Amino acid sequences and nucleotide sequences of CLs and CHs for various animals other than the above may be obtained from known databases for use in the present invention.

Amino acid sequences and nucleotide sequences of CLs and CHs for canine, ovine, porcine, water buffalo, human and bovine are summarized in the table below.

TABLE

| Species | Ig Domain | Nucleotide Sequences | Amino Acid Sequence | GenBank Accession No. | IMGT Database | Reference |
|---|---|---|---|---|---|---|
| Canine (Scientific Name: Canis lupus familiaris) | | GCCTCCACCACGGCCCCCTCG GTTTTCCCACTGGCCCCCAGC TGCGCCTTCCACTTCCGGCTCC ACGGTGGCCCTGGCCTGCCTG GTGTCAGGCTACTTCCCCGAG CCTGTAACTGTGTCCTGGAAT TCCGGCTCCTTGACCAGCGGT GTGCACACCTTCCCGTCCGTC CTGCAGTCCTCAGGGCTCTAC TCCCTCAGCAGCACGGTGAC AGTGCCCTCCAGCAGGTGGC CCAGCGAGACCTTCACCTGCA ACGTGGTCCACCCGGCCAGC AACACTAAAGTAGACAAGCC AGTGCCCAAAGAGTCCACCT GCAAGTGTATATCCCCATGCC CAGTCCCTGAATCACTGGGAG GGCCTTCGGTCTTCATCTTTCC CCCGAAACCCAAGGACATCCT CAGGATTACCCGAACACCCGA GATCACCTGTGTCTGTGTTAGA TCTGGGCCGTGAGGACCCTG AGGTGCAGATCAGCTGGTTCG TGGATGGTAAGGAGGTGCAC ACAGCCAAGACCTCAGCCTCG TGAGCAGCAGTTCAACAGCA CCTACCGTGTGGTCAGCGTCC TCCCCATTGAGCACCAGGACT GGCTCACCGGAAAGGAGTTC AAGTGCAGAGTCAACCACAT AGGCCTCCCGTCCCCCATCGA GAGGACTATCTCCAAAGCCAG AGGGCAAGCCCATCAGCCCA GTGTGTATGTCCTGCCACCAT CCCCAAAGGAGTTGTCATCCA GTGACACGGTCACCCTGACCT GCCTGATCAAAGACTTCTTCC CACCTGAGATTGATGTGGAGT GGCAGAGCAATGGACAGCCG GAGCCCGAGAGCAAGTACCA CACGACTGCGCCCCAGCTGG ACGAGGACGGGTCCTACTTCC TGTACAGCAAGCTCTCTGTGG ACAAGAGCCGCTGGCAGCAG GGAGACACCTTCACATGTGCG GTGATGCATGAAGCTCTACAG AACCACTACACAGATCTATCC CTCTCCCATTCTCCGGGTAAA TGA (SEQ ID NO: 8) | ASTTAPSVFPLAPSCGSTS GSTVALACLVSGYFPEPVT VSWNSGSLTSGVHTFPSV LQSSGLYSLSSTVTVPSSR WPSETFTCNVVHPASNTK VDKPVPKESTCKCISPCPV PESLGGPSVEEPPKPKDIL RITRTPEITCVVLDLGRED PEVQISWFVDGKEVHTAK TQPREQQFNSTYRVVSVL PIEHQDWLTGKEFKCRVN HIGLPSPIERTISKARGQAH QPSVYVLPPSPKELSSSDT VTLTCLIKDFFPPEIDVEW QSNGQPEPESKYHTTAPQ LDEDGSYFLYSKLSVDKS RWQQGDTFTCAVMHEAL QNHYTDLSLSHSPGK* (SEQ ID NO: 4) | AF354267 | http://www.imgt.org/IMGTrepertoire/index.php?section=LocusGenes&repertoire=genetable&species=dog&group=IGHC | Tang L. et al., Vet. Immunol. Immunopathol. 80 (3-4). 259-270 (2001). PMID: 11457479 |
| | Canine Ig lambda light chain constant region (CL) | CAGCCCAAGGCCTCCCCCT CGGTCACACTCTTCCCGCC CTCCTCTGAGGAGCTCGGC GCCAACAAGGCCACCCTG GTGCCTCATCAGCGACTTC TACCCCAGCGGCGTGACGG TGGCCTGGAAGGCAAGCGG CAGCCCCGTCACCCAGGGC GTGGAGACCACCAAGCCCT CCAAGCAGAGCAACAACAA GTACGCGGCCAGCAGCTAC CTGAGCCTGACGCCTGACA AGTGGAAATCTCACAGCAG CTTCAGCTGCCTGGTCACG CACGAGGGGAGCACCGTGG AGAAGAAGGTGGCCCCCGC AGAGTGCTCTTAG (SEQ ID NO: 7) | QPKASPSVTLFPPSSEE LGANKATLVCLISDFYP SGVTVAWKASGSPVFQ GVETTKPSKQSNNKYA ASSYLSLTPDKWKSHSS FSCLVTHEGSTVEKKVA PAECS* (SEQ ID NO: 3) | E02824 | Not registered | None |

TABLE-continued

| Species | Ig Domain | Nucleotide Sequences | Amino Acid Sequence | GenBank Accession No. | IMGT Database | Reference |
|---|---|---|---|---|---|---|
| Ovine (Scientific Name: Ovis aries) | Ovine heavy chain constant region (CH1-CH3) | GCCTCAACAACACCCCCGAA AGTCTACCCTCTGACTTCTTG CTGCGGGACACGTCCAGCT CCATCGTGACCCTGGGCTGCC TGGTCTCCAGCTATATGCCCG AGCCGGTGACCGTGACCTGG AACTCTGGTGCCCTGACCAGC GGCGTGCACACCTTCCGGCC ATCCTGCAGTCCTCCGGGCTC TACTCTCTCAGCAGCGTGGTG ACCGTGCCGGCCAGCACCTC AGGAGCCCAGACCTTCATCTG CAACGTAGCCCACCCGGCCA GCAGCACCAAGGTGGACAAG CGTGTTGAGCCCGGATGCCCG GACCCATGCAAACATTGCCGA TGCCCACCCCCTGAGCTCCC GGAGCACCGTCTGTCTTCATC TTCCCACCGAAACCCAAGGA CACCCTTACAATCTCTGGAAC GCCCGAGGTCACGTGTGTGGT GGTGGACGTGGGCCAGGATG ACCCCGAGGTGCAGTTCTCCT GGTTCGTGGACAACGTGGAG GTGCGCACGGCCAGGACAAA GCCGAGAGAGGAGCAGTTCA ACAGCACCTTCCGCGTGGTCA GCGCCCTGCCCATCCAGCACC AAGACTGGACTGGAGGAAAG GAGTTCAAGTGCAAGGTCCA CAACGAAGCCCTCCCGGCCC CCATCGTGAGGACCATCTCCA GGACCAAAGGGCAGGCCCGG GAGCCGCAGGTGTACGTCCTG GCCCCACCCCAGGAAGAGCT CAGCAAAAGCACGCTCAGCG TCACCTGCCTGGTCACCGGCT TCTACCCAGACTACATCGCCG TGGAGTGGCAGAAAAATGGG CAGCCTGAGTCGGAGGACAA GTACGGCACGACCACATCCA GCTGGACGCCGACGGCTCCTA CTTCCTGTACAGCAGGCTCAG GGTGGACAAGAACAGCTGGC AAGAAGGAGACACCTACGCG TGTGTGGTGATGCACGAGGCT CTGCACAACCACTACACACA GAAGTCGATCTCTAAGCCTCC GGGTAAATGA (SEQ ID NO: 43) | ASTTPPKVYPLTSCCGDTS SSIVTLGCLVSSYMPEPVT VTWNSGALTSGVHTFPAI LQSSGLYSLSSVVTVPAST SGAQTFICNVAHPASSTKV DKRVEPGCPDPCKHCRCP PPELPGGPSVFIFPPKPKDT LTISGTPEVTCVVVDVGQ DDPEVQFSWFVDNVEVRT ARTKPREEQFNSTFRVVSA LPIQHQDWTGGKEFKCKV HNEALPAPIVRTISRTKGQ AREPQVYVLAPPQEELSK STLSVTCLVTGFYPDYIAV EWQKNGQPESEDKYGTT TSQLDADGSYFLYSRLRV DKNSWQEGDTYACVVMH EALHNHYTQKSISKPPGK* (SEQ ID NO: 42) | X69797 | http://www.imgt.org/IMGTrepertoire/i ndex.php?section=LocusGenes&repertoire=genetable&species=sheep&group=IGHC | Dufour V. et al., J. Immunol., 156, 2163-2170 (1996). PMID: 8690905 |
| | IgG2 | GCCTCCACCACAGCCCCGAA AGTCTACCCTCTGACTTCTTG CTGCGGGGACACGTCCAGCT CCAGCTCCATCGTGACCCTGG GCTGCCTGGTCTCCAGCTATAT GCCCGAGCCGGTGACCGTGA CCTGGAACTCTCTGTGCCCTGA CCAGCGGCGTGCACACCTTCC CGGCCATCCTGCAGTCCTCCG GGCTCTACTCTCTCAGCAGCG TGGTGACCGTGCCGGCCAGC ACCTCAGGAGCCCAGACCTTC ATCTGCAACGTAGCCCACCCG GCCAGCAGCGCCAAGGTGGA CAAGCGTGTTGGGATCTCCAG TGACTACTCCAAGTGTCTAA ACCGCCTTGCGTGAGCCGACC GTCTGTCTTCATCTTCCCCCCG AAACCCAAGGACAGCCTCAT GATCACAGGAACGCCCGAGG TCACGTGTGTGGTGGTGGACG TGGGCCAGGGTGACCCCGAG GTGCAGTTCTCCTGGTTCGTG GACAACGTGGAGGTGCGCAC | ASTTAPKVYPLTSCCGDTS SSSSIVTLGCLVSSYMPEP VTVTWNSGALTSGVHTFP AILQSSGLYSLSSVVTVPA STSGAQTFICNVAHPASSA KVDKRVGISSDYSKCSKP PCVSRPSVFIFPPKPKDSL MITGTPEVTCVVVDVQG DPEVQFSWFVDNVEVRTA RTKPREEQFNSTERVVSAL PIQHDHWTGGKEFKCKV HSKGLPAPIVRTISRAKGQ AREPQVYVLAPPQEELSK STLSVTCLVTGFYPDYIAV EWQRARQPESEDKYGTTT SQLDADGSYFLYSRLRVD KSSWQRGDTYACVVMHE ALHNHYTQKSISKPPGK* (SEQ ID NO: 44) | X70983 | | Clarkson C.A. et al., Mol. Immunol., 30. 1195-1204 (1993). PMID: 8413324 |

TABLE-continued

| Species | Ig Domain | Nucleotide Sequences | Amino Acid Sequence | GenBank Accession No. | IMGT Database | Reference |
|---|---|---|---|---|---|---|
| | | GGCCAGGACAAAGCCGAGAG AGGAGCAGTTCAACAGCACC TTCCGCGTGGTCAGCGCCCTG CCCATCCAGCACGACCACTGG ACTGGAGGAAAGGAGTTCAA GTGCAAGGTCCACAGCAAAG GCCTCCCGGCCCCCATCGTGA GGACCATCTCCAGGGCCAAA GGGCAGGCCCGGGAGCCGCA GGTGTACGTCCTGGCCCCACC CCAGGAAGAGCTCAGCAAAA GCACGCTCAGCGTCACCTGCC TGGTCACCGGCTTCTACCCAG ACTACATCGCCGTGGAGTGGC AGAGAGCGCGGCAGCCTGAG TCGGAGGACAAGTACGGCAC GACCACATCCCAGCTGGACGC CGACGGCTCCTACTTCCTGTA CAGCAGGCTCAGGGTGGACA AGAGCAGCTGGCAAAGAGGA GACACCTACGCGTGTGTGGTG ATGCACGAGGCTCTGCACAAC CACTACACACAGAAGTCGATC TCTAAGCCTCCGGGTAAATGA (SEQ ID NO: 45) | | | | |
| | Ovine Ig light kappa chain (CK) constant region | CCATCCGTCTTCCTCTTCAAA CCATCTGAGGAACAGCTGAG GACCGGAACTGTCTCTGTCGT GTGCTTGGTGAATGATTTCTA CCCCAAAGATATCAATGTCAA GGTGAAAGTGGATGGGGTTA CCCAGAACAGCAACTTCCAG AACAGCTTCACAGACCAGGA CAGCAAGAAAAGCACCTACA GCCTCAGCAGCACCCTGACA CTGTCCAGCTCAGAGTACCAG AGCCATAACGCCTATGCGTGT GAGGTCAGCCACAAGAGCCT GCCCACCGCCCTCGTCAAGA GCTTCAATAAGAATGAATGTT AG (SEQ ID NO: 47) | PSVFLFKPSEEQLRTGTVS VVCLVNDFYPKDINVKVK VDGVTQNSNFQNSFTDQD SKKSTYSLSSTLTLSSSEY QSHNAYACEVSHKSLPTA LVKSFNKNEC* (SEQ ID NO: 46) | X54110 | Not registered | Jenne C.N. et al., Dev. Comp. Immunol. 30 (1-2), 165-174 (2006). PMID: 16083958 |
| | Ig lambda (CL) | GGTCAGCCCAAGTCCGCACC CTCGGTCACCCTGTTCCCGCC TTCCACGGAGGAGCTCAGTAC CAACAAGGCCACCGTGGTGT GTCTCATCAACGACTTCTACC CGGGTAGCGTGAACGTGGTCT GGAAGGCAGATGGCAGCACC ATCAATCAGAACGTGAAGACC ACCCAGGCCTCCAAACAGAG CAACAGCAAGTACGCGGCCA GCAGCTACCTGACCCTGACGG GCAGCGAGTGGAAGTCTAAG AGCAGTTACACCTGCGAGGTC ACGCACGAGGGGAGCACCGT GACGAAGACAGTGAAGCCCT CAGAGTGTTCTTAG (SEQ ID NO: 49) | GQPKSAPSVTLFPPSTEEL STNKATVVCLINDFYPGS VNVVWKADGSTINQNVK TTQASKQSNSKYAASSYL TLTGSEWKSKSSYTCEVT HEGSTVTKTVKPSECS* (SEQ ID NO: 48) | AY734681 | | |
| Porcine (Scientific Name: Sus scrofa) | Porcine Ig heavy chaine constant region (CH1-CH3) | IgG1ᵃ GCCCCCAAGACGGCCCCATCG GTCTACCCTCTGGCCCCCTGC GGCAGGGACACGTCTGGCCC TAACGTGGCCTTGGGCTGCCT GGCCTCAAGCTACTTCCCCGA GCCAGTGACCATGACCTGGA ACTCGGGCGCCCTGACCAGT GGCGTGCATACCTTCCCATCC GTCCTGCAGCCGTCAGGCCTC TACTCCCTCAGCAGCATGGTG ACCGTGCCGGCCAGCAGCCT GTCCAGCAAGAGCTACACCT GCAATGTCAACCACCCGGCCA CCACCACCAAGGTGGACAAG CGTGTTGGAACAAAGACCAA | APKTAPSVYPLAPCGRDT SGPNVALGCLASSYFPEPV TMTWNSGALTSGVHTFPS VLQPSGLYSLSSMVTVPAS SLSSKSYTCNVNHPATTTK VDKRVGTKTKPPCPICPGC EVAGPSVFIFPPKPKDTLM ISQTPEVTCVVVDVSKEH AEVQFSWYVDGVEVHTA ETRPKEEQFNSTYRVVSV LPIQHQDWLKGKEFKCKV NNVDLPAPITRTISKAIGQS REPQVYTLPPPAEELSRSK VTVTCLVIGFYPPDIHVEW KSNGQPEPEGNYRTTPPQ | U03781 | http://www.imgt.org/IMGTrepertoire/index.php?section=LocusGenes&repertoire=genetable&species=Pig&group=IGHC | Butler J.E. et al., Immunogenetics i61(3): 209-230 (2009). PMID: 19048248 Kacskovics I. et. al., J. Immunol. 153(8): 3565-3573 (1994). PMID: 7930579 |

TABLE-continued

| Species | Ig Domain | Nucleotide Sequences | Amino Acid Sequence | GenBank Accession No. | IMGT Database | Reference |
|---|---|---|---|---|---|---|
| | | ACCACCATGTCCCATATGCCC AGGCTGTGAAGTGGCCGGGC CCTCGGTCTTCATCTTCCCTCC AAAACCCAAGGACACCCTCA TGATCTCCCAGACCCCCGAGG TCACGTGCGTGGTGGTGGAC GTCAGCAAGGAGCACGCCGA GGTCCAGTTCTCCTGGTACGT GGACGGCGTAGAGGTGCACA CGGCCCGAGACGAGACCAAAG GAGGAGCAGTTCAACAGCAC CTACCGTGTGGTCAGCGTCCT GCCCATCCAGCACCAGGACTG GCTGAAGGGGAAGGAGTTCA AGTGCAAGGTCAACAACGTA GACCTCCCAGCCCCCATCACG AGGACCATCTCCAAGGCTATA GGGCAGAGCCGGGAGCCGCA GGTGTACACCCTGCCCCCACC CGCCGAGGAGCTGTCCAGGA GCAAAGTCACCGTAACCTGCC TGGTCATTGGCTTCTACCCAC CTGACATCCATGTTGAGTGGA AGAGCAACGGACAGCCGGAG CCAGAGGGCAATTACCGCACC ACCCCGCCCCAGCAGGACGT GGACGGGACCTTCTTCCTGTA CAGCAAGCTCGCGGTGGACA AGGCAAGATGGGACCATGGA GAAACATTTGAGTGTGCGGTG ATGCACGAGGCTCTCTCACAAC CACTACACCCAGAAGTCCATC TCCAAGACTCAGGGTAAATGA (SEQ ID NO: 51) | QDVDGTFFLYSKLAVDKA RWDHGETFECAVMHEAL HNHYTQKSISKTQGK* (SEQ ID NO: 50) | | | |
| | IgG1[b] | GCCCCCAAGACGGCCCCATCG GTCTACCCTCTGGCCCCCTGC GGCAGGGACGTGTCTGGCCCT AACGTGGCCTTGGGCTGCCTG GCCTCAAGCTACTTCCCCGAG CCAGTGACCGTGACCTGGAA CTCGGGCGCCCTGACCAGTG GCGTGCACACCTTCCCATCCG TCCTGCAGCCGTCAGGGCTCT ACTCCCTCAGCAGCATGGTGA CCGTGCCGGCCAGCAGCCTGT CCAGCAAGAGCTACACCTGC AATGTCAACCACCCGGCCACC ACCACCAAGGTGGACAGCG TGTTGGAATACACCAGCCGCA AACATGTCCCATATGCCCAGG CTGTGAAGTGGCCGGGCCCTC GGTCTTCATCTTCCCTCCAAA ACCCAAGGACACCCTCATGAT CTCCCAGACCCCCGAGGTCAC GTGCGTGGTGGTGGACGTCA GCAAGGAGCACGCCGAGGTC CAGTTCTCCTGGTACGTGGAC GGCGTAGAGGTGCACACGGC CGAGACGAGACCAAAGGAGG AGCAGTTCAACAGCACCTACC GTGTGGTCAGCGTCCTGCCCA TCCAGCACCAGGACTGGCTG AAGGGGAAGGAGTTCAAGTG CAAGGTCAACAACGTACACC TCCCAGCCCCCATCACGAGGA CCATCTCCAAGGCTATAGGGC AGAGCCGGGAGCCGCAGGTG TACACCCTGCCCCCACCCGCC GAGGAGCTGTCCAGGAGCAA AGTCACGCTAACCTGCCTGGT CATTGGCTTCTACCCACCTGA CATCCATGTTGAGTGGAAGAG CAACGGACAGCCGGAGCCAG AGAACACATACCGCACCACCC CGCCCCAGCAGGACGTGGAC | APKTAPSVYPLAPCGRDV SGPNVALGCLASSYFPEPV TVTWNSGALTSGVHTFPS VLQPSGLYSLSSMVTVPAS SLSSKSYTCNVNHPATTTK VDKRVGIHQPQTCPICPGC EVAGPSVFIFPPKPKDTLM ISQTPEVTCVVVDVSKEH AEVQFSWYVDGVENTHTA ETRPKEEQFNSTYRVVSV LPIQHQDWLKGKEFKCKV NNYDLPAPITRTISKAIGQS REPQVYTLPPPAEELSRSK VTLTCLVIGFYPPDIHVEW KSNGQPEPENTYRTTPPQ QDVDGTFFLYSKLAVDKA RWDHGDKFECAVMHEAL HNHYTQKSISKTQGK* (SEQ ID NO: 52) | U03778 | | |

TABLE-continued

| Species | Ig Domain | Nucleotide Sequences | Amino Acid Sequence | GenBank Accession No. | IMGT Database | Reference |
|---|---|---|---|---|---|---|
| | | GGGACCTTCTTCCTGTACAGC AAACTCGCGGTGGACAAGGC AAGATGGGACCATGGAGACA AATTTGAGTGTGCGGTGATGC ACGAGGCTCTGCACAACCACT ACACCCAGAAGTCCATCTCCA AGACTCAGGGTAAATGA (SEQ ID NO: 53) | | | | |
| | IgG2[a] | GCCCCCAAGACGGCCCCATCG GTCTACCCTCTGGCCCCTGC AGCAGGGACACGTCTGGCCC TAACGTGGCCTTGGGCTGCCT GGCCTCAAGCTACTTCCCCGA GCCAGTGACCGTGACCTGGA ACTCGGGCGCCCTGTCCAGTG GCGTGCATACCTTCCCATCCG TCCTGCAGCCGTCAGGGCTCT ACTCCCTCAGCAGCATGGTGA CCGTGCCGGCCAGCAGCCTGT CCAGCAAGAGCTACACCTGC AATGTCAACCACCCGGCCACC ACCACCAAGGTGGACAAGCG TGTTGGAACAAAGACCAAAC CACCATGTCCCATATGCCCAG CCTGTGAATCACCAGGGCCCT CGTCTTCATCTTCCCTCAA AACCCAAGGACACCCTCATGA TCTCCCGGACACCCCAGGTCA CGTGCGTGGTGGTTGATGTGA GCCAGGAGAACCCGGAGGTC CAGTTCTCCTGGTACGTGGAC GGCGTAGAGGTGCACACGGC CCAGACGAGGCCAAAGGAGG AGCAGTTCAACAGCACCTACC GCGTGGTCAGCGTCCTACCCA TCCAGCACCAGGACTGGCTG AACGGGAAGGAGTTCAAGTG CAAGGTCAACAACAAAGACC TCCCAGCCCCCATCACAAGGA TCATCTCCAAGGCCAAAGGGC AGACCCGGGAGCCGCAGGTG TACACCCTGCCCCCACACGCC GAGGAGCTGTCCAGGAGCAA AGTCAGCATAACCTGCCTGGT CATTGGCTTCTACCCACCTGA CATCGATGTCGAGTGGCAAAG AAACGGACAGCCGGAGCCAG AGGGCAATTACCGCACCACCC CGCCCCAGCAGGACGTGGAC GGGACCTACTTCCTGTACAGC AAGTTCTCGGTGGACAAGGC CAGCTGGCAGGGTGGAGGCA TATTCCAGTGTGCGGTGATGC ACGAGGCTCTGCACAACCACT ACACCCAGAAGTCTATCTCCA AGACTCCGGGTAAATGA (SEQ ID NO: 55) | APKTAPSVYPLAPCSRDTS GPNVALGCLASSYFPEPVT VTWNSGALSSGVHTFPSV LQPSGLYSLSSMVTVPASS LSSKSYTCNVNHPATTTK VDKRVGTKTKPPCPICPAC ESPGPSVFIFPPKPKDTLMI SRTPQVTCVVVDVSQENP EVQFSWYVDGVEVHTAQ TRPKEEQFNSTYRVVSVLP IQHQDWLNGKEFKCKVN NKDLPAPITRIISKAKGQT REPQVYTLPPHAEELSRSK VSITCLVIGFYPPDIDVEW QRNGQPEPEGNYRTTPPQ QDVDGTYFLYSKFSVDKA SWQGGGIFQCAVMHEAL HNHYTQKSISKTPGK* (SEQ ID NO: 54) | U03779 | | |
| | IgG2[b] | GCCCCCAAGACGGCCCCATTG GTCTACCCTCTGGCCCCTGC AGCAGGGACACGTCTGGCCC TAACGTGGCCTTGCGCTGCCT GGCCTCAAGCTACTTCCCCGA GCCAGTGACCGTGACCTGGA ACTCGGGCGCCCTGACCAGT GGCGTGCATACCTTCCCATCC GTCCTGCAGCCGTCAGGGCTC TACTCCCTCAGCAGCATGGTG ACCGTGCCGGCCAGCAGCCT GTCCAGCAAGAGCTACACCT GCAATGTCAACCACCCGGCCA CCACCACCAAGGTGGACAAG CGTGTTGGAACAAAGACCAA ACCACCATGTCCCATATGCCC | APKTAPLVYPLAPCGRDT SGPNVALGCLASSYFPEPV TVTWNSGALTSGVHTFPS VLQPSGLYSLSSMVTVPAS SLSSKSYTCNVNHPATTTK VDKRVGTKTKPPCPICPAC ESPGPSVFIFPPKPKDTLMI SRTPQVTCVVVDVSQENP EVQFSWYVDGVEVHTAQ TRPKEEQFNSTYRVVSVLP IQHQDWLNGKEFKCKVN NKDLPAPITRIISKAKGQT REPQVYTLPPHAEELSRSK VSITCLVIGFYPPDIDVEW QRNGQPEPEGNYRTTPPQ QDVDGTYFLYSKFSVDKA | U03780 | | |

TABLE-continued

| Species | Ig Domain | Nucleotide Sequences | Amino Acid Sequence | GenBank Accession No. | IMGT Database | Reference |
|---|---|---|---|---|---|---|
| | | AGCCTGTGAATCGCCAGGGCC CTCGGTCTTCATCTTCCCTCCA AAACCCAAGGACACCCTCAT GATCTCCCGGACACCCCAGGT CACGTGCGTGGTAGTTGATGT GAGCCAGGAGAACCCGGAGG TCCAGTTCTCCTGGTACGTGG ACGGCGTAGAGGTGCACACG GCCCAGACGAGGCCAAAGGA GGAGCAGTTCAACAGCACCT ACCGCGTGGTCAGCGTCCTGC CCATCCAGCACCAGGACTGGC TGAACGGGAAGGAGTTCAAG TGCAAGGTCAACAACAAAGA CCTCCCAGCCCCCATCACAAG GATCATCTCCAAGGCCAAAGG GCAGACCCGGGAGCCGCAGG TGTACACCCTGCCCCCACACG CCGAGGAGCTGTCCAGGAGC AAAGTCAGCATAACCTGCCTG GTCATTGCCTTCTACCCACCT GACATCGATGTCGAGTGGCAA AGAAACGGACAGCCGGAGCC AGAGGGCAATTACCGCACCA CCCCGCCCCAGCAGGACGTG GACGGGACCTACTTCCTGTAC AGCAAGTTCTCGGTGGACAA GGCCAGCTGGCAGGGTGGAG GCATATTCCAGTGTGCGGTGA TGCACGAGGCTCTGCACAAC CACTACACCCAGAAGTCTATC TCCAAGACTCCGGGTAAATGA (SEQ ID NO: 57) | SWQGGGIFQCAVMHEAL HNHYTQKSISKTPGK* (SEQ ID NO: 56) | | | |
| | IgG3 | GCCTACAACACAGCTCCATCG GTCTACCCTCTGGCCCCCTGT GGCAGGGACGTGTCTGATCAT AACGTGGCCTTGGGCTGCCTT GTCTCAAGCTACTTCCCCGAG CCAGTGACCGTGACCTGCAA CTCGGGTGCCCTGTCCAGAGT CGTGCATACCTTCCCATCCGT CCTGCAGCCGTCAGGGCTCTA CTCCCTCAGCAGCATGGTGAT CGTGGCGGCCAGCAGCCTGT CCACCCTGAGCTACACGTGCA ACGTCTACCACCCGGCCACCA ACACCAAGGTGGACAAGCGT GTTGACATCGAACCCCCCACA CCCATCTGTCCCGAAATTTGC TCATGCCCAGCTGCAGAGGTC CTGGGAGCACCGTCGGTCTTC CTCTTCCCTCCAAAACCCAAG GACATCCTCATGATCTCCCGG ACACCCAAGGTCACGTGCGT GGTGGTGGACGTGAGCCAGG AGGAGGCTGAAGTCCAGTTC TCCTGGTACGTGGACGGCGTA CAGTTGTACACGGCCCAGAC GAGGCCAATGGAGGAGCAGT TCAACAGCACCTACCGCGTGG TCAGCGTCCTGCCCATCCAGC ACCAGGACTGGCTGAAGGGG AAGGAGTTCAAGTGCAAGGT CAACAACAAAGACCTCCTTTC CCCCATCACGAGGACCATCTC CAAGGCTACAGGGCCGAGCC GGGTGCCGCAGGTGTACACC CTGCCCCCAGCCTGGGAAGA GCTGTCCAAGAGCAAAGTCA GCATAACCTGCCTGGTCACTG GCTTCTACCCACCTGACATCG ATGTCGAGTGGCAGAGCAAC GGACAACAAGAGCCAGAGGG CAATTACCGCACCACCCCGCC CCAGCAGGACGTGGATGGGA | AYNTAPSVYPLAPCGRDV SDHNVALGCLVSSYFPEPV TVTWNSGALSRVVHTFPS VLQPSGLYSLSSMVIVAAS SLSTLSYTCNVYHPATNTK VDKRVDIEPPTPICPEICSC PAAEVLGAPSVFLFPPKPK DILMISRTPKVTCVVVDVS QEEAEVQFSWYVDGVQL YTAQTRPMEEQFNSTYRV VSVLPIQHQDWLKGKEFK CKVNNKDLLSPITRTISKA TGPSRVPQVYTLPPAWEEL SKSKVSITCLVTGFYPPDI DVEWQSNGQQEPEGNYR TTPPQQDVDGTYFLYSKL AVDKVRWQRGDLFQCAV MHEALHNHYTQKSISKTQ GK (SEQ ID NO: 58) | EU372658 | | |

| Species | Ig Domain | Nucleotide Sequences | Amino Acid Sequence | GenBank Accession No. | IMGT Database | Reference |
|---|---|---|---|---|---|---|
| | | CCTACTTCCTGTACAGCAAGC TCGCGGTGGACAAGGTCAGG TGGCAGCGTGGAGACCTATTC CAGTGTGCGGTGATGCACGA GGCTCTGCACAACCACTACAC CCAGAAGTCCATCTCCAAGAC TCAGGGTAAATGA (SEQ ID NO: 59) | | | | |
| | IgG4[a] | ACCTTCCCATCCGTCCTGCAG CCGTCAGGGCTCTACTCCCTC AGCAGCATGGTGACCGTGCC GGCCAGCAGCCTGTCCAGCA AGAGCTACACCTGCAATGTCA ACCACCCGGCCACCACCACC AAGGTGGACAAGCGTGTTGG AACAAAGACCAAACCACCAT GTCCCATATGCCCAGCCTGTG AAGGGCCCGGGCCCTCGGCC TTCATCTTCCCTCCAAAACCC AAGGACACCCTCATGATCTCC CGGACCCCCAAGGTCACGTG CGTGGTGGTAGATGTGAGCCA GGAGAACCCGGAGGTCCAGT TCTCCTGGTACGTGGACGGCG TAGAGGTGCACACGGCCCAG ACGAGGCCAAAGGAGGAGCA GTTCAACAGCACCTACCGCGT GGTCAGCGTCCTGCCCATCCA GCACCAGGACTGGCTGAACG GGAAGGAGTTCAAGTGCAAG GTCAACAACAAAGACCTCCC AGCCCCCATCACAAGGATCAT CTCCAAGGCCAAAGGGCAGA CCCGGGAGCCGCAGGTGTAC ACCCTGCCCCCACCCACCGAG GAGCTGTCCAGGAGCAAAGT CACGCTAACCTGCCTGGTCAC TGGCTTCTACCCACCTGACAT CGATGTCGAGTGGCAAAGAA ACGGACAGCCGGAGCCAGAG GGCAATTACCGCACCACCCCG CCCCAGCAGACGTGGACGG GACCTACTTCCTGTACAGCAA GCTCGCGGTGGACAAGGCCA GCTGGCAGCGTGGAGACACA TTCCAGTGTGCGGTGATGCAC GAGGCTCTGCACAACCACTAC ACCCAGAAGTCCATCTTCAAG ACTCCGGGTAAATGA (SEQ ID NO: 61) | TFPSVLQPSGLYSLSSMVT VPASSLSSKSYTCNVNHPA TTTKVDKRVGTKTKPPCPI CPACEGPGPSAFIFPPKPK DTLMISRTPKVTCVVVDV SQENPEVQFSWYVDGVE VHTAQTRPKEEQFNSTYR VVSVLPIQHQDWLNGKEF KCKVNNKDLPAPITRIISK AKGQTREPQVYTLPPPTE ELSRSKVTLTCLVTGFYPP DIDVEWQRNGQPEPEGNY RTTPPQQDVDGTYFLYSK LAVDKASWQRGDTFQCA VMHEALHNHYTQKSIFKT PGK* (SEQ ID NO: 60) | U03782 | | |
| | IgG4[b] | GCCCCCAAGACGGCCCCATCG GTCTACCCTCTGGCCCCCTGC GGCAGGGACGTGTCTGGCCCT AACGTGGCCTTGGGCTGCCTG GCCTCAAGCTACTTCCCCGAG CCAGTGACCGTGACCTGGAA CTCGGGCGCCCTGACCAGTG GCGTGCACACCTTCCCATCCG TCCTGCAGCCGTCAGGGCTCT ACTCCCTCAGCAGCATGGTGA CCGTGCCGGCCAGCAGCCTGT CCAGCAAGAGCTACACCTGC AATGTCAACCACCCGGCCACC ACCACCAAGGTGGACAAGCG TGTTGGAATACACCAGCCGCA AACATGTCCCATATGCCCAGC CTGTGAAGGGCCCGGGCCCT CGGCCTTCATCTTCCCTCCAA AACCCAAGGACACCCTCATGA TCTCCCGGACCCCCAAGGTCA CGTGCGTGGTGGTTGATGTGA GCCAGGAGAACCCGGAGGTC CAGTTCTCCTGGTACGTGGAC GGCGTAGAGGTGCACACGGC | APKTAPSVYPLAPCGRDV SGPNVALGCLASSYFPEPV TVTWNSGALTSGVHTFPS VLQPSGLYSLSSMVTVPAS SLSSKSYTCNVNHPATTTK VDKRVGIHQPQTCPICPAC EGPGPSAFIFTPKPKDTLM ISRTPKVTCVVVDVSQEN PEVQFSWYVDGVEHTA QTRPKEEQFNSTYRVVSV LLIQHQDWLNGKEFKCK VNNKDLPAPITRIISKAKG QTREPQVYTLPPPTEELSR SKVTLTCLVTGFYPPDIDV EWQRNGQPEPEGNYRTTP PQQDVDGTYFLYSKLAVD KASWQRGDTFQCAVMHE ALHNHYT (SEQ ID NO: 62) | EU372654 | | |

TABLE-continued

| Species | Ig Domain | Nucleotide Sequences | Amino Acid Sequence | GenBank Accession No. | IMGT Database | Reference |
|---------|-----------|----------------------|---------------------|-----------------------|---------------|-----------|
| | | CCAGACGAGGCCAAAGGAGG AGCAGTTCAACAGCACCTACC GCGTGGTCAGCGTCCTGCTCA TCCAGCACCAGGACTGGCTG AACGGCAAGGAGTTCAAGTG CAAGGTCAACAACAAAGACC TCCCAGCCCCCATCACAAGGA TCATCTCCAAGGCCAAAGGGC AGACCCGGGAGCCGCAGGTG TACACCCTGCCCCCACCCACC GAGGAGCTGTCCAGGAGCAA AGTCACGCTAACCTGCCTGGT CACTGGCTTCTACCCACCTGA CATCGATGTCGAGTGGCAAAG AAACGGACAGCCGGAGCCAG AGGGCAATTACCGCACCACCC CGCCCCAGCAGGACGTGGAC GGGACCTACTTCCTGTACAGC AAGCTCGCGGTGGACAAGGC CAGCTGGCAGCGTGGAGACA CATTCCAGTGTGCGGTGATGC ACGAGGCTCTGCACAACCACT ACACCC (SEQ ID NO: 63) | | | | |
| | IgG5ᵃ | GCCCCCAAGACGGCCCCATCG GTCTACCCTCTGGCCCCCTGC AGCAGGGACACGTCTGGCCC TAACGTGGCCTTGGGTGCCT GGTCTCAAGCTACTTCCCCGA GCCAGTGACCGTGACCTGGA ACTCGGGCGCCCTGACCAGT GGCGTGCACACCTTCCCATCC GTCCTGCAGCCGTCAGGGCTC TACTCCCTCAGCAGCATGGTG ACCGTGCCGGCCCACAGCTTG TCCAGCAAGCGCTATACGTGC AATGTCAACCACCCAGCCACC AAAACCAAGGTGGACCTGTG TGTTGGACGACCATGTCCCAT ATGCCCAGGCTGTGAAGTGGC CGGGGCCCTCGGTCTTCATCTT CCCTCCAAAACCCAAGGACAT CCTCATGATCTCCCGGACCCC CGAGGTCACGTGCGTGGTGG TGGACGTCAGCAAGGAGCAC GCCGAGGTCCAGTTCTCCTGG TACGTGGACGCCGAAGAGGT GCACACGGCCGAGACGAGGC CAAAGGAGGAGCAGTTCAAC AGCACCTACCGCGTGGTCAGC GTCCGCCCATCCAGCACGAG GACTGGCTGAAGGGGAAGGA GTTCGAGTGCAAGGTCAACA ACGAAGACCTCCCAGGCCCC ATCACGAGGACCATCTCCAAG GCCAAAGGGGTGGTACGGAG CCCGGAGGTGTACACCCTGCC CCCACCCGCCGAGGAGCTGT CCAAGAGCATAGTCACGCTAA CCTGCCTGGTCAAAAGCATCT TCCCGNCTTCATCCATGTTG AGTCTGAAAATCAACCTGAAAA CCAGAGCCAGAGAACGCATAT CGCACCACCCCGCCTCAGGA GGACGAGGACACTGACCTACT TCCTGTACAGCAAGCTCGCGG TGGACAAGGCAAGATGGGAC CATGGAGAAACATTTGAGTGT GCGGTGATGCACGAGGCTCTG CACAACCACTACACCCAGAA GTCCATCTCCAAGACTCAGGG TAAATGA (SEQ ID NO: 65) | APKTAPSVYPLAPCSRDTS GPNVALGCLVSSYFPEPVT VTWNSGALTSGVHTFPSV LQPSGLYSLSSMVTVPAHS LSSKRYTCNVNHPATKTK VDLCVGRPCPICPGCEVA GPSVFIPPKPKDILMISRT PEVTCVVVDVSKEHAEV QFSWYVDGEEVHTAETRP KEEQFNSTYRVVSVLPIQH EDWLKGKEFECKVNNED LPGPITRTISKAKGVVRSP EVYTLPPPAEELSKSIVLT CLVKSIFP? FIHVEWKING KPEPENAYRTTPPQEDEDR TYFLYSKLAVDKARWDH GETFECAVMHEALHNHY TQKSISKTQGK* (SEQ ID NO: 64) | EU372657 | | |

TABLE-continued

| Species | Ig Domain | Nucleotide Sequences | Amino Acid Sequence | GenBank Accession No. | IMGT Database | Reference |
|---|---|---|---|---|---|---|
| | IgG5b | GCCTACAACACAGCTCCATCG GTCTACCCTCTGGCCCCTGT GGCAGGGACGTGTCTGATCAT AACGTGGCCTTGGGCTGCCTG GTCTCAAGCTACTTCCCCGAG CCAGTGACCGTGACCTGGAA CTGGCTGCGCCCAGACCAGTG GCGTGCACACCTTCCCATCCG TCCTGCAGCCGTCAGGGCTCT ACTCCCTCAGCAGCACGGTG ACCGTGCCGGCCCACAGCTTG TCCAGCAAGTCTCTTCACGTGC AATGTCAACCACCCGGCCACC ACCACCAAGGTGGACCTGTG TGTTGGAAAAAGACCAAGC CTCGATGTCCCATATGCCCAG GCTGTGAAGTGGCCGGGCCC TCGGTCTTCATCTTCCCTCCA AAACCCAAGGACATCCTCATG ATCTCCCGGACCCCGAGGTC ACGTGCGTCTGTGGTGGACGT CAGCAAGGAGCACCGCCGAGG TCCAGTTCTCCTGGTACGTGG ACGGCGAAGAGGTGCACACG GCCGAGACGAGACCAAAGGA GGAGCAGTTCAACAGCACTT ACCGCGTGGTCAGCGTCCTGC CCATCCAGCACGAGGACTGG CTGAAGGGGAAGGAGTTCGA GTGCAAGGTCAACAACGAAG ACCTCCCAGGCCCCATCACGA GGACCATCTCCAAGGCCAAA GGGGTGGTACGGAGCCCGGA GGTGTACACCCTGCCCCCACC CGCCGAGGAGCTGTCCAAGA GCATAGTCACGCTAACCTGCC TGGTCAAAAGCTTCTTCCCGC CTTTCATCCATGTTGAGTGGA AAATCAACGGAAAACCAGAG CCAGAGAACGCATACCGCAC CACCCCGCCCCAGGAGGACG AGGACGGGACCTACTTCCTGT ACAGCAAGTTCTCGGTGGAA AAGTTCAGGTGGCACAGTGG AGGCATCCACTGTGCGGTGAT GCACGAGGCTCTGCACAACC ACTACACCC (SEQ ID NO: 67) | AYNTAPSVYPLAPCGRDV SDHNVALGCLVSSYFPEPV TVTWNWGAQTSGVHTFP SVLQPSGLYSLSSTVTVPA HSLSSKCFTCNVNHPATTT KVDLCVGKKTKPRCPICP GCEVAGPSVFIFPPKPKDIL MISRTPEVTCVVVDVSKE HAEVQFSWYVDGEEVHT AETRPKEEQFNSTYRVVS VLPIQHEDWLKGKEFECK VNNEDLPGPITRTISKAKG VVRSPEVYTLPPPAEELSK SIVTLTCLVKSFFPPFIHVE WKINGKPEPENAYRTTPP QEDEDGTYFLYSKFSVEK FRWHSGGIHCAVMHEAL HNHYT (SEQ ID NO: 66) | EU372656 | | |
| | IgG6ᵃ | GCCCCCAAGACGGCCCCATCG GTCTACCCTCTGGCCCCCTGC GGCAGGGACACGTCTGGCCC TAACGTGGCCTTGGGCTGCCT GGCCTCAAGCTACTTCCCCGA GCCAGTGACCCTGACCTGGA ACTCGGGCGCCCTGACCAGT GGCGTGCATACCTTCCCATCC GTCCTGCAGCCGTCAGGGCTC TACTCCCTCAGCAGCATGCTG ACCGTGCCGGCCAGCAGCCT GTCCAGCAAGAGCTACACCT GCAATGTCAACCACCCGGCCA CCACCACCAAGGTGGACCTG TGTGTTGGACGACCATGTCCC ATATGCCCAGCCTGTGAAGGG CCCGGGGCCCTCGGTCTTCATC TTCCCTCCAAAACCCAAGGAC ACCCTCATGATCTCCCGGACA CCCAGGTCACGTGCGTGGTG GTAGATGTGAGCCAGGAAAA CCCGGAGGTCCAGTTCTCCTG GTATGTGGACGGTGTAGAGGT GCACACGGCCCAGACGAGGC CAAAGGAGGCGCAGTTCAAC AGCACCTACCGTGTGGTCAGC GTCCTGCCCATCCAGCACGAG | APKTAPSVYPLAPCGRDT SGPNVALGCLASSYFPEPV TLTWNSGALTSGVHTFPS VLQPSGLYSLSSMVTVPAS SLSSKSYTCNVNHPATTTK VDLCVGRPCPICPACEGPG PSVFIFPPKPKDTLMISRTP QVTCVVVDVSQENPEVQF SWYVDGVEVHTAQTRPK EAQFNSTYRVVSVLPIQHE DWLKGKEFECKVNNKDL PAPITRIISKAKGPSREPQV YTLSPSAEELSRSKVSITCL VTGFYPPDIDVEWKSNGQ PEPEGNYRTTPPQQDVDG TYFLYSKLAVDKASWQRG DPFQCAVMHEALHNHYT (SEQ ID NO: 68) | EU372655 | | |

| Species | Ig Domain | Nucleotide Sequences | Amino Acid Sequence | GenBank Accession No. | IMGT Database | Reference |
|---|---|---|---|---|---|---|
| | | GACTGGCTGAAGGGGAAGGA GTTCGAGTGCAAGGTCAACA ACAAAGACCTCCCAGCCCCA TCACAAGGATCATCTCCAAGG CCAAAGGGCCGAGCCGGGAG CCGCAGGTGTACACCCTGTCC CCATCCGCCGAGGAGCTGTCC AGGAGCAAAGTCAGCATAAC CTGCCTGGTCACTGGCTTCTA CCCACCTGACATCGATGTCGA GTGGAAGAGCAACGGACAGC CGGAGCCAGAGGGCAATTAC CGCACCACCCCGCCCCAGCA GGACGTGGACGGGACCTACT TCCTGTACAGCAAGCTCGCGG TGGACAAGGCCAGCTGGCAG CGTGGAGACCCATTCCAGTGT GCGGTGATGCACGAGGCTCTG CACAACCACTACACCC (SEQ ID NO: 69) | | | | |
| | IgG6[b] | GCCCCCAAGACGGCCCCATCG GTCTACCCTCTGGCCCCCTGC GGCAGGGACACGTCTGGCCC TAACGTGGCCTTGGGCTGCCT GGCCTCAAGCTACTTCCCCGA GCCAGTGACCGTGACCTGGA ACTCGGGCGCCCTGACCAGT GGCGTGCACACCTTCCCATCC GTCCTGCAGCCGTCAGGGCTC TACTCCCTCAGCAGCACGGTG ACCGTGCCGGCCAGGAGCTC GTCCAGAAAGTGCTTCACGTG CAATGTCAACCACCCGGCCAC CACCACCAAGGTGGACCTGT GTGTTGGACGACCATGTCCCA TATGCCCAGCCTGTGAAGGGA ACGGGCCCTCGGTCTTCATCT TCCCTCCAAAACCCAAGGAC ACCCTCATGATCTCCCGGACC CCCGAGGTCACGTGCGTGGT GGTAGATGTGAGCCAGGAAA ACCCGGAGGTCCAGTTCTCCT GGTACGTGGACGGCGAAGAG GTGCACACGGCCGAGACGAG GCCAAAGGAGGAGCAGTTCA ACAGCACCTACCGTGTGGTCA GCGTCCTGCCCATCCAGCACC AGGACTGGCTGAAGGGAAAG GAGTTCGAGTGCAAGGTCAA CAACAAAGACCTCCCAGCCC CCATCACAAGGATCATCTCCA AGGCCAAAGGGCCGAGCCGG GAGCCGCAGCTGTACACCCT GTCCCCATCCGCCGAGGAGCT GTCCAGGAGCAAAGTCAGCA TAACCTGCCTGGTCACTGGCT TCTACCCACCTGACATCGATG TCGAGTGGAAGAGCAACGGA CAGCCGGAGCCAGAGGGCAA TTACCGCTCCACCCCGCCCCA GGAGGACGAGGACGGGACCT ACTTCCTGTACAGCAAACTCG CGGTGGACAAGGCGAGGTTG CAGAGTGGAGGCATCCACTGT GCGGTGATGCACGAGGCTCTG CACAACCACTACACCCAGAA GTCCATCTCCAAGACT (SEQ ID NO: 71) | APKTAPSVYPLAPCGRDT SGPNVALGCLASSYFPEPV TVTWNSGALTSGVHTTFPS VLQPSGLYSLSSTVTVPAR SSSRKCFTCNVNHPATTTK VDLCVGRPCPICPACEGN GPSVFIFPPKPKDTLMISRT PEVTCVVVDVSQENPEVQ FSWYVDGEEVHTAETRPK EEQFNSTYRVVSVLPIQHQ DWLKGKEFECKVNNKDL PAPITRIISKAKGPSREPQV YTLSPSAEELSRSKVSITCL VTGFYPPDIDVEWKSNCQ PEPEGNYRSTPPQEDEDG TYFLYSKLAVDKARLQSG GIHCAVMHEALHNHYTQ KSISKT (SEQ ID NO: 70) | EU372653 | | |

TABLE-continued

| Species | Ig Domain | Nucleotide Sequences | Amino Acid Sequence | GenBank Accession No. | IMGT Database | Reference |
|---|---|---|---|---|---|---|
| | Porcine Ig light chain constant region | Ig kappa (CK) variant 1 | | | FP312898 | http://www.imgt.org/IMGTrepertoire/index.php?section=LocusGenes&repertoire=genetable&species=Pig&group=IGLC | Schwartz J.C. et al., Immunogenetics, i64, 303-311 (2012). PMID: 22109540 |
| | | Ig kappa (CK) variant 2 | | | CU694848 | | |
| | | Ig lambda (CL) variant 1 | | | CU467669 | http://www.imgt.org/IMGTrepertoire/index.php?section=LocusGenes&repertoire=genetable&species=Pig&group=IGKC | |
| | | Ig lambda (CK) variant 2 | | | CU467599 | | |
| Water buffalo (Scientific Name: Bubalus bubalis) | Water buffalo Ig heavy chain constant region (CH1-CH3) | IgG1? | GAGCGCCGTGCACACCTTCCCGGCCGTCCTTCAGTCCTCCGGGCTCTACTCTCTCAGCAGCACGGTGACCGCGCCCGCCAGCGCCACAAAAAGCCAGACCTTCACCTGCAACGTAGCCCACCCGGCCAGCAGCACCAAGGTGGACAAGGCTGTTGTTCCCCCATGCAGACCGAAACCCTGTGATTGCTGCCCACCCCCTGAGCTCCCCGGAGGACCCTCTGTCTTCATCTTCCCACCAAAACCCAAGCACACCCTCACAATCTCTGGAACTCCTGAGGTCACGTGTGTGGTGGTGGACGTGGGCCACGATGACCCCGAGGTGAAGTTCTCCTGGTTCGTGGACGATGTGGAGGTAAACACAGCCAGGACGAAGCCAAGAGAGGAGCAGTTCAACAGCACCTACCGCGTGGTCAGCGCCCTGCCCATCCAGCACAACGACTGGACTGGAGGAAAGGAGTTCAAGTGCAAGGTCTACAATGAAGGCCTCCCAGCCCCCATCGTGAGGACCATCTCCAGGACCAAAGGGCAGGCCCGGCAGCCGCAGGTGTACGTCCTGGCCCCACCCCAGGACGAGCTCAGCAAAAGCACGGTCAGCATCACTTGCATGGTCACTGCCTTCTACCCAGACTACATCGCCGTAGAGTGGCAGAAAGATGGGCAGCCTGAGTCAGAGGACAAATATGGCACGACCCCGCCCCAGCTGGACAGCGATGGCTCCTACTTCCTGTACAGCAGGCTCAGGCTGAACAAGAACAGCTGGCAAG | SGVHTFPAVLQSSGLYSLSSTVTAPASATKSQTFTCNVAHPASSTKVDKAVVPPCRPKPCDCCPPPELPGGPSVFIFPPKPKDTLTISGTPEVTCVVVDVGHDDPEVKFSWFVDDVEVNTARTKPREEQFNSTYRVVSALPIQHNDWTGGKEFKCKVYNEGLPAPIVRTISRTKGQAREPQVYVLAPPQDELSKSTVSITCMVTGFYPDYIAVEWQKDGQPESEDKYGTTPPQLDSDGSYFLYSRLRVNKNSWQEGGAYTCVVMHE (SEQ ID NO: 72) | NW_005690903 | Not registered | None |

TABLE-continued

| Species | Ig Domain | Nucleotide Sequences | Amino Acid Sequence | GenBank Accession No. | IMGT Database | Reference |
|---|---|---|---|---|---|---|
| | | AAGGAGGCGCCTACACGTGT GTAGTGATGCATGAGGC (SEQ ID NO: 73) | | | | |
| | IgG2? | GCCTCCATCACAGCCCCGAAA GTCTACCCTCTGACTTCTTGC CGCGGGGAAACGTCCAGCTC CACCGTGACCCTGGGCTGCCT GGTCTCCAGCTACATGCCCGA GCCGGTGACCGTGACCTGGA ACTCGGGTGCCCTGAAGAGC GGCGTGCACACCTTCCCGGCC GTCCTTCAGTCCTCTGGGCTC TACTCTCTCAGCAGCACGGTG ACCGCGCCCGCCAGCGCCAC AAAAAGCCAGACCTTCACCT GCAACGTAGCCCACCCGGCC AGCAGCACCAAGGTGGACAC GGCTGTTGGGTTCTCCAGTGA CTGCTGCAAGTTTCCTAAGCC TTGTGTGAGGGGACCATCTGT CTTCATCTTCCCGCCGAAACC CAAAGACACCCTGATGATCAC AGGAAATCCCGAGGTCACATG TGTGGTGGTGGACGTGGGCC GGGATAACCCCGAGGTGCAG TTCTCCTGGTTCGTGGGTGAT GTGGAGGTGCACACGCTGCAG GTCGAAGCCGAGAGAGGAGC AGTTCAACAGCACCTACCGCG TGGTCAGCACCCTGCCCATCC AGCACAATGACTGGACTGGA GGAAAGGAGTTCAAGTGCAA GGTCAACAACAAAGGCCTCC CAGCCCCCATCGTGAGGACCA TCTCCAGGACCAAAGGGCAG GCCCGGGAGCCGCAGGTGTA CGTCCTGGCCCCACCCCAGGA AGAGCTCAGCAAAAGCACGG TCAGCGTCACTTGCATGGTCA CTGGCTTCTACCCAGACTACA TCGCCGTAGAGTGGCATAGAG ACCGGCAGGCTGAGTCGGAG GACAAGTACCGCACGACCCC GCCCCAGCTGGACAGCGATG GCTCCTACTTCCTGTACAGCA GGCTCAAGGTGAACAAGAAC AGCTGGCAAGAAGGAGGCGC CTACACGTGTGTAGTGATGCA TGAGGC (SEQ ID NO: 75) | ASITAPKVYPLTSCRGETS SSTVTLGCLVSSYMPEPVT VTWNSGALKSGVHTFPAV LQSSGLYSLSSTVTAPASA TKSQTFTCNVAHPASSTK VDTAVGFSSDCCKFPKPC VRGPSVFIFPPKPKDTLMI TGNPEVTCVVVDVGRDN PEVQFSWFVGDVEVHTG RSKPREEQFNSTYRVVSTL PIQHNDWTGGKEFKCKV NNKGLPAPIVRTISRTKGQ AREPQVYVLAPPQEELSK STVSVTCMVTGFYPDYIA VEWHRDRQAESEDKYRT TPPQLDSDGSYFLYSRLKV NKNSWQEGGAYTCVVMH E (SEQ ID NO: 74) | NW_00576 6143 | | |
| | IgG3? | GCCTCCACCACAGCCCCGAA AGTCTACCCTCTGGCATCCAG CTGCGGGGACACGTCCAGCT CCACCGTGACCCTGGGCTGCC TGGTCTCCAGCTACATGCCCG AGCCGGTGACCGTGACCTGG AACTCGGGTGCCCTGAACTAA CGGCGTGCACACCTTCCCGGC CGTCCGGCAGTCCTCCGGGCT CTACTCTCTCAGCAGCATGGT GACCATGCCCACCAGCACCGC AGGAACCCAGACCTTCACCT GCAACGTAGCCCACCCGGCC AGCAGCACCAAGGTGGACAC GGCTGTCACTGCAAGGCATCC GGTCCCGAAGACACCAGAGA CACCTATCCATCCTGTAAAAC CCCCAACCCAGGAGCCCAGA GATGAAAAGACACCCTGCCA GTGTCCCAAATGCCCAGAACC TCTGGGAGGACTGTCTGTCTT CATCTTCCCACCGAAACCCAA GGACACCCTCACAATCTCTGG AACGCCCGAGGTCACGTGTG TGGTGGTGGACGTGCTGCCAG | ASTTAPKVYPLASSCGDTS SSTVTLGCLVSSYMPEPVT VTWNSGALKNGVHTFPA VRQSSGLYSLSSMVTMPT STAGTQTFTCNVAHPASST KVDTAVTARHPVPKTPET PIHPVKPPTQEPRDEKTPC QCPKCPEPLGGLSVFIFPP KPKDTLTISGTPEVTCVVV DVGQDDPEVQFSWFVDD VEVHTARMKPREEQFNST YRVVSALPIQHQDWLREK EFKCKVNNKGLPAPIVRTI SRTKGQAREPQVYVLAPP REELSKSTLSLTCLITGFYP EEVDVEWQRNGQPESED KYHTTPPQLDADGSYFLY SRLRVNRSSWQEGDHYTC AVMHEALRNHYKEKPISR SPGK* (SEQ ID NO: 76) | NW_00578 4206 | | |

TABLE-continued

| Species | Ig Domain | Nucleotide Sequences | Amino Acid Sequence | GenBank Accession No. | IMGT Database | Reference |
|---|---|---|---|---|---|---|
| | | GATGACCCCGAAGTGCAGTTC TCCTGGTTCGTGGATGACGTG GAGGTGCACACAGCCAGGAT GAAGCCAAGAGAGGAGCAGT TCAACAGCACCTACCGCGTGG TCAGCGCCCTGCCCATCCAGC ACCAGGACTGGCTGCGGGAA AAGGAGTTCAAGTGCAAGGT CAACAACAAAGGCCTCCCGG CCCCCATCGTGAGGACCATCT CCAGGACCAAAGGGCAGGCC CGGGAGCCACAGGTGTATGTC CTGGCCCCACCCCGGGAAGA GCTCAGCAAAAGCACGCTCA GCCTCACCTGCCTAATCACCG GCTTCTACCCAGAAGAGGTAG ACGTGGAGTGGCAGAGAAAT GGGCAGCCTGAGTCAGAGGA CAAGTACCACACGACCCCAC CCCAGCTGGACGCTGACGGC TCCTACTTCCTGTACAGCAGG CTCAGGGTGAACAGGAGCAG CTGGCAGGAAGGAGACCACT ACACGTGTGCAGTGATGCATG AAGCTTTACGGAATCACTACA AAGAGAAGCCCATCTCGAGG TCTCCGGGTAAATGA (SEQ ID NO: 77) | | | | |
| Water buf- falo Ig light chain con- stant region (CL) | Ig lambd a? | CAGCCCAAGTCCGCACCCTCA GTCACCCTGTTCCCACCCTCC ACGGAGGAGCTCAGCGCCAA CAAGGCCACCCTGGTGTGTCT CATCAGCGACTTCTACCCGGG TAGCATGACCGTGGCCAGGA AGGCAGACGGCAGCACCATC ACCCGGAACGTGGAGACCAC CCGGGCCTCCAAACAGAGCA ACAGCAAGTACGCGGCCAGC AGCTACCTGAGCCTGACGGG CAGCGAGTGGAAATCGAAAG GCAGTTACAGCTGCGAGGTC ACGCACGAGGGGAGCACCGT GACAAAGACAGTGAAGCCCT CAGAGTGTTCTTAG (SEQ ID NO: 79) | QPKSAPSVTLFPPSTEELS ANKATLVCLISDFYPGSMT VARKADGSTITRNVETTR ASKQSNSKYAASSYLSLT GSEWKSKGSYSCEVTHEG STVTKTVKPSECS* (SEQ ID NO: 78) | NW_00569 0786 | Not registered | None |
| Humna (Scien- tific Name: Homo sapiens) | Human Ig heavy chain con- stant region (CH1- CH3) | IgG4 var- iant 1 | GAGTCCAAATATGGTCCCCCA TGCCCATCATGCCCAGCACCT GAGTTCCTGCGGGGACCATCA GTCTTCCTGTTCCCCCCAAAA CCCAAGGACACTCTCATGATC TCCCGGACCCCTGAGGTCACG TGCGTGGTGGTGGACGTGAG CCAGGAAGACCCCGAGGTCC AGTTCAACTGGTACGTGGATG GCGTGGAGGTGCATAATGCCA AGACAAAGCCGCGGGAGGAG CAGTTCAACAGCACGTACCGT GTGGTCAGCGTCCTCACCGTC CTGCACCAGGACTGGCTGAA CGGCAAGGAGTACAAGTGCA AGGTCTCCAACAAAGGCCTC CCGTCCTCCATCGAGAAAACC ATCTCCAAAGCCAAAGGGCA GCCCCGAGAGCCACAGGTGT ACACCCTGCCCCCATCCCAGG AGGAGATGACCAAGAACCAG GTCAGCCTGACCTGCCTGGTC AAAGGCTTCTACCCCAGCGAC ATCGCCGTGGAGTGGGAGAG CAATGGGCAGCCGGAGAACA ACTACAAGACCACGCCTCCCG TGCTGGACTCCGACGGCTCCT TCTTCCTCTACAGCAGGCTAA CCGTGGACAAGAGCAGCTGG | ESKYGPPCPSCPAPEFLGG PSVFLFPPKPKDTLMISRT PEVTCVVVDVSQEDPEVQ FNWYVDGVEVHNAKTKP REEQFNSTYRVVSVLTVL HQDWLNGKEYKCKVSNK GLPSSIEKTISKAKGQPRE PQVYTLPPSQEEMTKNQV SLTCLVKGFYPSDIAVEWE SNGQPENNYKTTPPVLDS DGSFFLYSRLTVDKSRWQ EGNVFSCSVMHEALHNH YTQKSLSLSLGK* (SEQ ID NO: 12) | K01316 | http://ww w.imgt.or g/IMGTre pertoire/iP ndex.php ?section= LocusGe nes&repe rtoire=ge netable&s pecies=hu man&gro up=IGHC | Ellison J. et al., DNA, 1, 11-18 (1981). PMID: 6299662 |

TABLE-continued

| Species | Ig Domain | Nucleotide Sequences | Amino Acid Sequence | GenBank Accession No. | IMGT Database | Reference |
|---|---|---|---|---|---|---|
| | | CAGGAGGGGAATGTCTTCTCA TGCTCCGTGATCCATGAGGCT CTGCACAACCACTACACACA GAAGAGCCTCTCCCTGTCTCT GGGTAAATGA (SEQ ID NO: 14) | | | | |
| | IgG4 variant 2 | GAGTCCAAATATGGTCCCCCG TGCCCATCATGCCCAGCACCT GAGTTCCTGGGGGGACCATCA GTCTTCCTGTTCCCCCCAAAA CCCAAGGACACTCTCATGATC TCCCGGACCCCTGAGGTCACG TGCGTGGTGGTGGACGTGAGC CAGGAAGACCCCGAGGTCC AGTTCAACTGGTACGTGGATG GCGTGGAGGTGCATAATGCCA AGACAAAGCCGCGGGAGGAG CAGTTCAACAGCACGTACCGT GTGGTCAGCGTCCTCACCGTC GTGCACCAGGACTGGCTGAA CGGCAAGGAGTACAAGTGCA AGGTCTCCAACAAAGGCCTC CCGTCCTCCATCGAGAAAACC ATCTCCAAAGCCAAGGGCA GCCCCGAGAGCCACAGGTGT ACACCCTGCCCCCATCCCAGG AGGAGATGACCAAGAACCAG GTCAGCCTGACCTGCCTGGTC AAAGCCTTCTACCCCAGCGAC ATCGCCGTGGAGTGGGAGAG CAATGGGCAGCCGGAGAACA ACTACAAGACCACGCCTCCCG TGCTGGACTCCGACGGCTCCT TCTTCCTCTACAGCAGGCTAA CCGTGGACAAGAGCAGGTGG CAGGAGGGGAATGTCTTCTCA TGCTCCGTGATGCATGAGGCT CTGCACAACCACTACACGCA GAAGAGCCTCTCCCTGTCTCT GGGTAAATGA (SEQ ID NO: 81) | ESKYGPPCPSCPAPEFLGG PSVFLFPPKPKDTLMISRT PEVTCVVVDVSQEDPEVQ FNWYVDGVEVHNAKTKP REEQFNSTYRVVSVLTVV HQDWLNGKEYKCKVSNK GLPSSIEKTISKAKGQPRE PQVYTLPPSQEEMTKNQV SLTCLVKGFYPSDIAVEWE SNGQPENNYKTTPPVLDS DGSFFLYSRLTVDKSRWQ EGNVFSCSVMHEALHNH YTQKSLSLSLGK (SEQ ID NO: 80) | AJ001563 | | Brusco A. et al., Eur. J. Immunogenet., 25, 349-355 (1998). PMID: 9805657 |
| | IgG4 variant 3 | GCACCTGAGTTCCTGGGGGG ACCATCAGTCTTCCTGTTCCC CCCAAAACCCAAGGACACTC TCATGATCTCCCGGACCCCTG AGGTCACGTGCGTGGTGGTG GACGTGAGCCAGGAAGACCC CGAGGTCCAGTTCAACTGGTA CGTGGATGGCGTGGAGGTGCA TAATGCCAAGACAAAGCCGC GGGAGGAGCAGTTCAACAGC ACGTACCGTGTGGTCAGCGTC CTCACCGTCCTGCACCAGGAC TGGCTGAACGGCAAGGAGTA CAAGTGCAAGGTCTCCAACA AAGGCCTCCCGTCCTCCATCG AGAAAACCATCTCCAAAGCC AAAGGGCAGCCCCGAGAGCC ACAGGTGTACACCCTGCCCCC ATCCCAGGAGGAGATGACCA AGAACCAGGTCAGCCTGACC TGCCTGGTCAAAGGCTTCTAC CCCAGCGACATCGCCGTGGA GTGGGAGAGCAATGGGCAGC CGGAGAACAACTACAAGACC ACGCCTCCCGTGCTGGACTCC GACGGCTCCTTCTTCCTCTAC AGCAAGCTCACCGTGGACAA GAGCAGGTGGCAGGAGGGA ACGTCTTCTCATGCTCCGTGA TGCATGAGGCTCTGCACAACC ACTACACGCAGAAGAGCCTC TCCCTGTCTCTGGGTAAATGA (SEQ ID NO: 83) | APEFLGGPSVFLFPPKPKD TLMISRTPEVTCVVVDVS QEDPEVQFNWYVDGVEV HNAKTKPREEQFNSTYRV VSVLTVLHQDWLNGKEY KCKVSNKGLPSSIEKTISK AKGQPREPQVYTLPPSQE EMTKNQVSLTCLVKGFYP SDIAVEWESNGQPENNYK TTPPVLDSDGSFFLYSKLT VDKSRWQEGNVFSCSVM HEALHNHYTQKSLSLSLG K* (SEQ ID NO: 82) | AJ001564 | | |

| Species | Ig Domain | Nucleotide Sequences | Amino Acid Sequence | GenBank Accession No. | IMGT Database | Reference |
|---|---|---|---|---|---|---|
| | Human Ig light chain constant region | Ig kappa (CK) | ACTGTGGCTGCACCATCTGTC TTCATCTTCCCGCCATCTGATG AGCAGTTGAAATCTGGAACTG CCTCTGTTGTGTGCCTGCTGA ATAACTTCTATCCCAGAGAGG CCAAAGTACAGTGGAAGGTG GATAACGCCCTCCAATCGGGT AACTCCCAGGAGAGTGTCAC AGAGCAGGACAGCAAGGACA GCACCTACAGCCTCAGCAGC ACCCTGACGCTGAGCAAAGC AGACTACGAGAAACACAAAG TCTACGCCTGCGAAGTCACCC ATCAGGGCCTGAGCTCGCCCG TCACAAAGAGCTTCAACAGG GGAGAGTGTTAG (SEQ ID NO: 13) | TVAAPSVFIFPPSDEQLKS GTASVVCLLNNFYPREAK VQWKVDNALQSGNSQES VTEQDSKDSTYSLSSTLTL SKADYEKHKVYACEVTH QGLSSPVTKSFNRGEC* (SEQ ID NO: 11) | X96754 | http://ww w.imgt.or g/IMGTre pertoire/i ndex.php ?section= LocusGe nes&repe rtoire=ge netable&s pecies=hu man&gro up=IGKC | None |
| Bovine (Scientific Name: Bos taurus) | Bovine Ig heavy chain constant region (CH1-CH3) | IgG1 variant 1 | GCCTCCACCACAGCCCCGAA AGTCTACCCTCTGAGTTCTTG CTGCGGGGACAAGTCCAGCT CCACCGTGACCCTGGGCTGCC TGGTCTCCAGCTACATGCCCG AGCCGGTGACCGTGACCTGG AACTCGGGTGCCCTGAAGAG CGGCGTGCACACCTTCCCGGC TGTCCTTCAGTCCTCCGGGCT GTACTCTCTCAGCAGCATGGT GACCGTGCCCGGCACGCACCT CAGGACAGACCTTCACCTGC AACGTAGCCCACCCGGCCAG CAGCACCAAGGTGGACAAGG CTGTTGATCCCACATGCAAAC CATCACCCTGTGACTGTTGCC CACCCCCTGAGCTCCCCGGAG GACCCTCTGTCTTCATCTTCCC ACCGAAACCCAAGGACACCC TCACAATCTCGGGAACGCCCG AGGTCACGTGTGTGGTGGTG GACGTGGGCCACGATGACCC CGAGGTGAAGTTCTCCTGGTT CGTGGACGACGTGCAGGTAA ACACAGCCACGACGAAGCCG AGAGAGGAGCAGTTCAACAG CACCTACCGCGTGGTCAGCGC CCTGCGCATCCAGCACCAGGA CTGGACTGGAGGAAAGGAGT TCAAGTGCAAGGTCCACAAC GAAGGCCTCCCGGCCCCCATC GTGAGGACCATCTCCAGGACC AAAGGGCCGGCCCGGGAGCC GCAGGTGTATGTCCTGGCCCC ACCCCAGGAAGAGCTCAGCA AAAGCACGGTCAGCCTCACC TGCATGGTCACCAGCTTCTAC CCAGACTACATCGCCGTGGAG TGGCAGAGAAACGGGCAGCC TGAGTCGGAGGACAAGTACG GCACGACCCCGCCCCAGCTG GACGCCGACAGCTCCTACTTC CTGTACAGCAAGCTCAGGGT GGACAGGAACAGCTGGCAGG AAGGAGACACCTACACGTGT GTGCTGATGCACGAGGCCCTG CACAATCACTACACGCAGAA GTCCACCTCTAAGTCTGCGGG TAAATGA (SEQ ID NO: 92) | ASTTAPKVYPLSSCCGDK SSSTVTLGCLVSSYMPEPV TVTWNSGALKSGVHTFPA VLQSSGLYSLSSMVTVPG STSGQTFTCNVAHPASSTK VDKAVDPTCKPSPCDCCP PPELPGGPSVFIFPPKPKDT LTISGTPEVTCVVVDVGh DDPEVKFSWFVDDVEVNT ATTKPREEQFNSTYRVVS ALRIQHQDWTGGKEFKC KVHNEGLPAPIVRTISRTK GPAREPQVYVLAPPQEEL SKSTVSLTCMVTSFYPDYI AVEWQRNGQPESEDKYG TTPPQLDADSSYFLYSKLR VDRNSWQEGDTYTCVVM HEALHNHYTQKSTSKSAG K (SEQ ID NO: 84) | X62916 | http://ww w.imgt.or g/IMGTre pertoire/i ndex.php ?section= LocusGe nes&repe rtoire=ge netable&s pecies=bo vine&gro up=IGHC | Symons D.B. et al., J. Immunogenet., 14, 273-283 (1987). PMID: 3141517 Symons D.B. et al., Mol. Immuno., 26, 841-850 (1989). PMID: 2513487 Kacskovics I. and Butler J.E. Mol. Immunol., 33, 189-195 (1996). PMID: 8649440 Rabbani J. et al., Immunogenetics, 46. 326-331 (1997). PMID: 9218535 Saini S.S. et al., Scand. J. Immunol. 65, 32-8 (2007). PMID: 17212764 |
| | | IgG1 variant 2 | GCCTCCACCACAGCCCCGAA AGTCTACCCTCTGAGTTCTTG CTGCGGGGACAAGTCCAGCT CCACCGTGACCCTGGGCTGCC TGGTCTCCAGCTACATGCCCG AGCCGGTGACCGTGACCTGG AACTCGGGTGCCCTGAAGAG CGGCGTGCACACCTTCCCGGC | ASTTAPKVYPLSSCCGDK SSSTVTLGCLVSSYMPEPV TVTWNSGALKSGVHTFPA VLQSSGLYSLSSMVTVPG STSGQTFTCNVAHPASSTK VDKAVDPTCKPSPCDCCP PPELPGGPSVFIFPPKPKDT LTISGTPEVTCVVVDVGH | X16701 (M25278) | | |

| Species | Ig Domain | Nucleotide Sequences | Amino Acid Sequence | GenBank Accession No. | IMGT Database | Reference |
|---|---|---|---|---|---|---|
| | | CGTCCTTCAGTCCTCCGGGCT GTACTCTCTCAGCAGCATGGT GACCGTGCCCGGCAGCACCT CAGGACAGACCTTCACCTGC AACGTAGCCCACCCGGCCAG CAGCACCAAGGTGGACAAGG CTGTTGATCCCACATGCAAAC CATCACCCTGTGACTGTTGCC CACCCCCTGAGCTCCCCGGAG GACCCTCTGTCTTCATCTTCCC ACCGAAACCCAAGGACACCC TCACAATCTCGGCAACGCCCG AGGTCACGTGTGTGGTGGTG GACGTGGGCCACGATGACCC CGAGGTGAAGTTCTCCTGGTT CGTGGACGACGTGGAGGTAA ACACAGCCACGACGAAGCCG AGAGAGGAGCAGTTCAACAG CACCTACCGCGTGGTCAGCGC CCTGCGCATCCAGCACCAGGA CTGGACTGGAGGAAAGGAGT TCAAGTGCAAGGTCCACAAC GAAGGCCTCCCGGCCCCCATC GTGAGGACCATCTCCAGGACC AAAGGGCCGGCCCGGGAGCC GCAGGTGTATGTCCTGGCCCC ACCCCAGGAAGAGCTCAGCA AAAGCACGGTCAGCCTCACC TGCATGGTCACCAGCTTCTAC CCAGACTACATCGCCGTGGAG TGGCAGAGAAACGGGCAGCC TGAGTCGGAGGACAAGTACG GCACGACCCCGCCCCAGCTG GACGCCGACAGCTCCTACTTC CTGTACAGCAAGCTCAGGGT GGACAGGAACAGCTGGCAGG AAGGAGACACCTACACGTGT GTGCTGATGCACGAGGCCCTG CACAATCACTACACGCAGAA GTCCACCTCTAAGTCTGCGGG TAAATGA (SEQ ID NO: 93) | DDPEVKFSWFVDDVEVNT ATTKPREEQFNSTYRVVS ALRIQHQDWTGGKEFKC KVHNEGLPAPIVRTISRTK GPAREPQVYVLAPPQEEL SKSTVSLTCMVTSFYPDYI AVEWQRNGQPESEDKYG TTPPQLDADSSYFLYSKLR VDRNSWQEGDTYTCVVM HEALHNHYTQKSTSKSAG K* (SEQ ID NO: 85) | | | |
| | IgG1 variant 3 | GCCTCCACCACAGCCCCGAA AGTCTACCCTCTGAGTTCTTG CTGCGGGGACAAGTCCAGCT CCACCGTGACCCTGGGCTGCC TGGTCTCCAGCTACATGCCCG AGCCGGTGACCGTGACCTGG AACTCGGGTGCCCTGAAGAG CGGCGTGCACACCTTCCCGGC CGTCCTTCAGTCCTCCGGGCT CTACTCTCTCAGCAGCATGGT GACCGTGCCCGGCAGCACCT CAGGAACCCAGACCTTCACCT GCAACGTAGCCCACCCGGCC AGCAGCACCAAGGTGGACAA GGCTGTTGATCCCAGATGCAA AACAACCTGTGACTGTTGCCC ACCGCCTGAGCTCCCTGGAG GACCCTCTGTCTTCATCTTCCC ACCGAAACCCAAGGACACCC TCACAATCTCGGGAACGCCCG AGGTCACGTGTGTGGTGGTG GACGTGGGCCACGATGACCC CGAGGTGAAGTTCTCCTGGTT CGTGGACGACGTGGAGGTAA ACACAGCCACGACGAAGCCG AGAGAGGAGCAGTTCAACAG CACCTACCGCGTGGTCAGCGC CCTGCGCATCCAGCACCAGGA CTGGACTGGAGGAAAGGAGT TCAAGTGCAAGGTCCACAAC GAAGGCCTCCCAGCCCCCATC GTGAGGACCATCTCCAGGACC AAAGGGCCGGCCCGGGAGCC GCAGGTGTATGTCCTGGCCCC | ASTTAPKVYPLSSCCGDK SSSTVTLGCLVSSYMPEPV TVTWNSGALKSGVHTFPA VLQSSGLYSLSSMVTVPG STSGTQTFTCNVAHPASST KVDKAVDPRCKTTCDCCP PPELPGGPSVFIFPPKPKDT LTISGTPEVTCVVVDVGH DDPEVKFSWFVDDVEVNT ATTKPREEQFNSTYRVVS ALRIQHQDWIGGKEFKC KVHNEGLPAPIVRTISRTK GPAREPQVYVLAPPQEEL SKSTVSLTCMVTSFYPDYI AVEWQRNGQPESEDKYG TTPPQLDADGSYFLYSRLR VDRNSWQEGDTYTCVVM HEALHNHYTQKSTSKSAG K* (SEQ ID NO: 86) | S82409 | | |

TABLE-continued

| Species | Ig Domain | Nucleotide Sequences | Amino Acid Sequence | GenBank Accession No. | IMGT Database | Reference |
|---------|-----------|----------------------|---------------------|------------------------|---------------|-----------|
| | | ACCCCAGGAAGAGCTCAGCA AAAGCACGGTCACCCTCACC TGCATGGTCACCAGCTTCTAC CCAGACTACATCGCCGTGGAG TGGCAGAGAAATGGGCAGCC TGAGTCAGAGGACAAGTACG GCACGACCCCTCCCCAGCTGG ACGCCGACGGCTCCTACTTCC TGTACAGCAGGCTCAGGGTG GACAGGAACAGCTGGCAGGA AGGAGACACCTACACGTGTG TGGTGATGC ACGAGGCCCTGC ACAATACTACACGCAGAAGT CCACCTCTAAGTCTGCGGGIA AATGA (SEQ ID NO: 94) | | | | |
| | IgG2 variant 1 | GCCTCCACCACAGCCCCGAA AGTCTACCCTCTGGCATCCAG CTGCGGAGACACATCCAGCTC CACCGTGACCCTGGGCTGCCT GGTGTCCAGCTACATGCCCGA GCCGGTGACCGTGACCTGGA ACTCGGGTGCCCTGAAGAGC GGCGTGCACACCTTCCCGGCT GTCCTTCAGTCCTCCGGGCTC TACTCTCTCAGCAGCATGGTG ACCGTGCCCGCCAGCAGCTC AGGACAGACCTTCACCTGCA ACGTAGCCCACCCGGCCAGC AGCACCAAGGTGGACAAGGC TGTTGGGGTCTCCATTGACTG CTCCAAGTGTCATAACCAGCC TTGCGTGAGGGAACCATCTGT CTTCATCTTCCCACCGAAACC CAAAGACACCCTGATGATCAC AGGAACGCCCGAGGTCACGT GTGTGGTGGTGAACGTGGGC CACGATAACCCCGAGGTGCA GTTCTCCTGGTTCGTGGATGA CGTGGAGGTGCACACGGCCA GGTCGAAGCCAAGAGAGGAG CAGTTCAACAGCACGTACCGC GTGGTCAGCGCCCTGCCCATC CAGCACCAGGACTGGACTGG AGGAAAGGAGTTCAAGTGCA AGGTCAACAACAAAGGCCTC TCGGCCCCCATCGTGAGGATC ATCTCCAGGAGCAAAGGGCC GGCCCGGGAGCCGCAGGTGT ATGTCCTGGACCCACCCAAGG AAGAGCTCAGCAAAAGCACG CTCAGCGTCACCTGCATGGTC ACCGGCTTCTACCCAGAAGAT GTAGCCGTGGAGTGGCAGAG AAACCGGCAGACTGAGTCGG AGGACAAGTACCGCACGACC CCGCCCCAGCTGGACACCGA CCGCTCCTACTTCCTGTACAG CAAGCTCAGGGTGGACAGGA ACAGCTGGCACTGAAGGAGAC GCCTACACGTGTGTGGTGATG CACGAGGCCCTGCACAATCAC TACATGCAGAAGTCCACCTCT AAGTCTGCGGGTAAATGA (SEQ ID NO: 95) | ASTTAPKVYPLASSCGDTS SSTVTLGCLVSSYMPEPVT VTWNSGALKSGVHTFPAV LQSSGLYSLSSMVTVPASS SGQTFTCNVAHPASSTKV DKAVGVSIDCSKCHNQPC VREPSVFIFPPKPKDTLMI TGTPEVTCVVVNVGHDN PEVQFSWFVDDVEVHTAR SKPREEQFNSTYRVVSALP IQHQDWTGGKEFKCKVN NKGLSAPIVRIISRSKGPAR EPQVYVLDPPKEELSKSTL SVTCMVTGFYPEDVAVEW QRNRQTESEDKYRTTPPQ LDTDRSYFLYSKLRVDRN SWQEGDAYTCVVMHEAL HNHYMQKSTSKSAGK* (SEQ ID NO: 87) | S82407 | | |
| | IgG2 variant 2 | GCCTCCACCACAGCCCCGAA AGTCTACCCTCTGAGTTCTTG CTGCGGGGACAAGTCCAGCT CCACCGTGACCCTGGGCTGCC TGGTGTCCAGCTACATGCCCG AGCCGGTGACCGTGACCTGG AACTCGGGTGCCCTGAAGAG CGGCGTGCACACCTTCCCGGC CGTCCTTCAGTCCTCCGGGCT CTACTCTCTCAGCAGCATGGT | ASTTAPKVYPLSSCCGDK SSSTVTLGCLVSSYMPEPV TVTWNSGALKSGVHTFPA VLQSSGLYSLSSMVTVPG STSGQTFTCNVAHPASSTK VDKAVGVSSDCSKPNNQ HCVREPSVFIFPPKPKDTL MITGTPEVTCVVVNVGHD NPEVQFSWFVDDVEVHTA RTKPREEQFNSTYRVVSA | M36946 (X06703) | | |

TABLE-continued

| Species | Ig Domain | Nucleotide Sequences | Amino Acid Sequence | GenBank Accession No. | IMGT Database | Reference |
|---|---|---|---|---|---|---|
| | | GACCGTGCCCGGCAGCACCT CAGGACAGACCTTCACCTGC AACGTAGCCCACCCGGCCAG CAGCACCAAGGTGGACAAGG CTGTTGGTCTCCAGTGACT GCTCCAAGCCTAATAACCAGC ATTGCGTGAGGGAACCAtCTG TCTTCATCTTCCCACCGAAAC CCAAAGACACCCTGATGATCA CAGGAACGCCCGAGGTCACG TGTGTGGTGGTGAACGTGGG CCACGATAACCCCGAGGTGCA GTTCTCCTGGTTCGTGGACGA CGTGGAGGTGCACACGGCCA GGACGAAGCCGAGAGAGGAG CAGTTCAACAGCACGTACCGC GTGGTCAGCGCCCTGCCCATC CAGCACCAGGACTGGACTGG AGGAAAGGAGTTCAAGTGCA AGGTCAACATCAAAGGCCTCT CGGCCTCCATCGTGAGGATCA TCTCCAGGAGCAAAGGGCCG GCCCGGGAGCCGCAGGTGTAT GTCCTGGACCCACCCAAGGA AGAGCTCAGCAAAAGCACGG TCAGCGTCACCTGCATGGTCA TCGCCTTCTACCCAGAAGATG TAGACGTGGAGTGGCAGAGA GACCGGCAGACTGAGTCGGA GGACAAGTACCGCACGACCC CGCCCCAGCTGGACGCCGAC CGCTCCTACTTCCTGTACAGC AAGCTCAGGGTGGACAGGAA CAGCTGCCAGAGAGGAGACA CCTACACGTGTGTGGTGATGC ACGAGGCCCTGCACAATCACT ACATGCAGAAGTCCACCTCTA AGTCTGCGGGTAAATGA (SEQ ID NO: 96) | | | | |
| | IgG2 variant 3 | GCCTCCACCACAGCCCCGAA AGTCTACCCTCTGAGTTCTTG CTGCGGGGACAAGTCCAGCT CGGGGGTGACCCTGGCCTGC CTGGTCTCCAGCTACATGCCC GAGCCGGTGACCGTGACCTG GAACTCGGGTGCCCTGAAGA GCGGCGTGCACACCTTCCCGG CCGTCCTTCAGTCCTCCGGGC TCTACTCTCTCAGCACCATGCT TGACCGTGCCCGCCAGCAGCT CAGGAACCCAGACCTTCACCT GCAACGTAGCCCACCCGGCC AGCAGCACCAAGGTGGACAA GGCTGTTGGGGTCTCCAGTGA CTGCTCCAAGCCTAATAACCA GCATTGCGTGAGGGAACCATC TGTCTTCATCTTCCCACCGAA ACCCAAAGACACCCTGATGAT CACAGGAACGCCCGAGGTCA CGTGTGTGGTGGTGAACGTG GGCCACGATAACCCCGAGGT GCAGTTCTCCTGGTTCGTGGA CGACGTGCAGGTGCACACGG CCAGGACGAAGCCGAGAGAG GAGCAGTTCAACAGCACGTA CCGCGTGGTCAGCGCCCTGCC CATCCAGCACCAGGACTGGA CTGGAGGAAAGGAGTTCAAG TGCAAGGTCAACATCAAAGG CCTCTCGGCCTCCATCGTGAG GATCATCTCCAGGAGCAAAGG GCCGGCCCGGGAGCCGCAGG TGTATGTCCTGGACCCACCCA AGGAAGAGCTCAGCAAAAGC ACGGTCAGCCTCACCTGCATG | ASTTAPKVYPLSSCCGDK SSSGVTLGCLVSSYMPEPV TVTWNSGALKSGVHTFPA VLQSSGLYSLSSMVTVPAS SSGTQTFTCNVAHPASSTK VDKAVGVSSDCSKPNNQ HCVREPSVFIFPPKPKDTL MITGTPEVTCVVVNVGHD NPEVQFSWFVDDVQVHTA RTKPREEQFNSTYRVVSA LPIQHQDWTGGKEFKCKV NIKGLSASIVRIISRSKGPA REPQVYVLDPPKEELSKS TVSLTCMVIGFYPEDVDV EWQRDRQTESEDKYRTTP PQLDADRSYFLYSKLRVD RNSWQRGDTYTCVVMHE ALHNHYMQKSTSKSAGK* (SEQ ID NO: 89) | X16702 (M25279) | | |

| Species | Ig Domain | Nucleotide Sequences | Amino Acid Sequence | GenBank Accession No. | IMGT Database | Reference |
|---|---|---|---|---|---|---|
| | | GTCATCGGCTTCTACCCAGAA GATGTAGACGTGGAGTGGCA GAGAGACCGGCAGACTGAGT CGGACTGACAAGTACCGCACG ACCCCGCCCCAGCTGGACGC CGACCGCTCCTACTTCCTGTA CAGCAAGCTCAGGGTGGACA GGAACAGCTGGCAGAGAGGA GACACCTACACGTGTGTGGTG ATGCACGAGGCCCTGCACAAT CACTACATGCAGAAGTCCACC TCTAAGTCTGCGCTGTAAATGA (SEQ ID NO: 97) | | | | |
| | IgG3 variant 1 | GCCTCCACCACAGCCCCGAA AGTCTACCCTCTGGCATCCAG CTGCGGAGACACATCCAGCTC CACCGTGACCCTGGGCTGCCT GGTCTCCAGCTACATGCCCGA GCCGGTGACCGTGACCTGGA ACTCGGGTGCCCTGAAGAGC GGCGTGCACACCTTCCCGGCC GTCCGGCAGTCCTCTGGGCTG TACTCTCTCAGCAGCATGGTG ACTGTGCCCGCCAGCAGCTCA GAAACCCAGACCTTCACCTGC AACGTAGCCCACCCGGCCAG CAGCACCAAGGTGGACAAGG CTGTCACTGCAAGGCGTCCAG TCCCGACGACGCCAAAGACA ACTATCCCTCCTGGAAAACCC ACAACCCCAAAGTCTGAAGT TGAAAAGACACCCTGCCAGT GTTCCAAATGCCCAGAACCTC TGGGAGGACTGTCTGTCTTCA TCTTCCCACCGAAACCCAAGG ACACCCTCACAATCTCGGGAA CGCCCGAGGTCACGTGTGTG GTGGTGGACGTGGGCCAGGA TGACCCCGAGGTGCAGTTCTC CTGGTTCGTGGACGACGTGG AGGTGCACACGGCCAGGACG AAGCCGAGAGAGGAGCAGTT CAACAGCACCTACCGCGTGGT CAGCGCCCTGCGCATCCAGCA CCAGGACTGGCTGCAGGGAA AGGAGTTCAAGTGCAAGGTC AACAACAAAGGCCTCCCGGC CCCCATTGTGAGGACCATCTC CAGGACCAAAGGGCAGGCCC GGGAGCCGCAGGTGTATGTCC TGGCCCCACCCCGGGAAGAG CTCAGCAAAAGCACGCTCAG CCTCACCTGCCTGATCACCGG TTTCTACCCAGAAGAGATAGA CGTGGAGTGGCAGAGAAATG GGCAGCCTGAGTCGGAGGAC AAGTACCACACGACCGCACC CCAGCTGGATGCTGACGGCTC CTACTTCCTGTACAGCAAGCT CAGGCTGAACAAGAGCAGCT GGCAGGAAGGAGACCACTAC ACGTGTGCAGTGATGCACGA AGCTTTACGGAATCACTACAA AGAGAAGTCCATCTCGAGGTC TCCGGGTAAATGA (SEQ ID NO: 98) | ASTTAPKVYPLASSCGDTS SSTVTLGCLVSSYMPEPVT VTWNSGALKSGVHTFPAV RQSSGLYSLSSMVTVPASS SETQTFTCNVAHPASSTKV DKAVTARRPVPTTPKTTIP PGKPTTPKSEVEKTPCQCS KCPEPLGGLSVFIFPPKPK DTLTISGTPEVTCVVVDV GQPDPEVQYSWFVDDVE VHTARTKPREEQFNSTYR VVSALRIQHQDWLQGKEF KCKVNNKGLPAPIVRTISR TKGQAREPQVYVLAPPRE ELSKSTLSLTCLITGFYPEE IDVEWQRNGQPESEDKYH TTAPQLDADGSYFLYSKL RVNKSSWQEGDHYTCAV MHEALRNHYKEKSISRSP GK* (SEQ ID NO: 90) | U63638 | | |
| | IgG3 variant 2 | GCCTCCACCACAGCCCCGAA AGTCTACCCTCTGGCATCCCG CTGCGGAGACACATCCAGCTC CACCGTGACCCTGGGCTGCCT GGTCTCCAGCTACATGCCCGA GCCGGTGACCGTGACCTGGA ACTCGGGTGCCCTGAAGAGT GGCGTGCACACCTTCCCGGCC | ASTTAPKVYPLASRCGDT SSSTVTLGCLVSSYMPEPV TVTWNSGALKSGVHTFPA VLQSSGLYSLSSMVTVPAS TSETQTFTCNVAHPASSTK VDKAVTARRPVPTTPKTTI PPGKPTTQESEVEKTPCQC SKCPEPLGGLSVFIFPPKP | U63639 | | |

TABLE-continued

| Species | Ig Domain | Nucleotide Sequences | Amino Acid Sequence | GenBank Accession No. | IMGT Database | Reference |
|---|---|---|---|---|---|---|
| | | GTCCTTCAGTCCTCCGGGCTG TACTCTCTCAGCAGCATGGTG ACCGTGCCCGCCAGCACCTCA GAAACCCAGACCTTCACCTGC AACGTAGCCCACCCGGCCAG CAGCACCAAGGTGGACAAGG CTGTCACTGCAAGGCGTCCAG TCCCGACGACGCCAAAGACA ACCATCCCTCCTGGAAAACCC ACAACCCAGGAGTCTGAAGT TGAAAAGACACCCTGCCAGT GTTCCAAATGCCCAGAACCTC TGGGAGGACTGTCTGTCTTCA TCTTCCCACCGAAACCCAAGG ACACCCTCACAATCTCGGGAA CGCCCGAGGTCACGTGTGTG GTGGTGGACGTGGGCCAGGA TGACCCCGAGGTGCAGTTCTC CTGGTTCGTGGACGACGTGG AGGTGCACACGGCCAGGACG AAGCCGAGAGAGGAGCAGTT CAACAGCACCTACCGCGTGGT CAGCGCCCTGCGCATCCAGCA CCAGGACTGCCTGCAGGGAA AGGAGTTCAAGTGCAAGGTC AACAACAAAGGCCTCCCGGC CCCCATTGTGAGGACCATCTC CAGGACCAAAGGGCAGGCCC GGGAGCCGCAGGTGTATGTCC TGGCCCCACCCCGGGAAGAG CTCAGCAAAAGCACGCTCAG CCTCACCTGCCTGATCACCGG TTTCTACCCAGAAGAGATAGA CGTGGAGTGCCAGAGAAATG GGCAGCCTGAGTCGGAGGAC AAGTACCACACGACCGCACC CCAGCTGGATGCTGACGGCTC CTACTTCCTGTACAGCAGGCT CAGGGTGAACAAGAGCAGCT GGCAGGAAGGAGACCACTAC ACGTGTGCAGTGATGCATGAA GCTTTACGGAATCACTACAAA GAGAAGTCCATCTCGAGGTCT CCGGGTAAATGA (SEQ ID NO: 99) | KDTLTISGTPEVTCVVVD VGQDDPEVQFSWFVDDV EVHTARTKPREEQFNSTY RVVSALRIQHQDWLQGKE FKCKVNNKGLPAPIVRTIS RTKGQAREPQVYVLAPPR EELSKSTLSLTCLITGFYPE EIDVEWQRNGQPESEDKY HTTAPQLDADGSYFLYSR LRVNKSSWQEGDHYTCA VMHEALRNHYKEKSISRS PGK* (SEQ ID NO: 91) | | | |
| | Bovine Ig Ig lambda light chain constant region (CL) | CAGCCCAAGTCCCCACCCTCG GTCACCCTGTTCCCGCCCTCC ACGGAGGAGCTCAACGGCAA CAAGGCCACCCTGGTGTGTCT CATCAGCGACTTCTACCCGGG TAGCGTGACCGTGGTCTGGAA GGCAGACGCCAGCACCATCA CCCGCAACGTGGAGACCACC CGGGCCTCCAAACAGAGCAA CAGCAAGTACGCGGCCAGCA GCTACCTGAGCCTGACGAGC AGCGACTGGAAATCGAAAGG CAGTTACAGCTGCGAGGTCAC GCACGAGGGGAGCACCGTGA CGAAGACAGTGAAGCCCTCA GAGTGTTCTTAG (SEQ ID NO: 101) | QPKSPPSVTLFPPSTEELN GNKATLVCLISDFYPGSVT VVWKADGSTITRNVETTR ASKQSNSKYAASSYLSLTS SDWKSKGSYSCEVTHEGS TVTKTVKPSECS* (SEQ ID NO: 100) | X62917 | Not registered | Chen L. et al., Vet. Immunol. Immunopathol., 124. 284-294 (2008). PMID: 18538861 |

The amino acid sequences as shown in SEQ ID NOS: 4, 3, 42, 44, 46, 48, 50, 52, 54, 56, 58, 60, 62, 64, 66, 68, 70, 72, 74, 76, 78, 12, 80, 82, 84-91, 100, 102 and 11 may have deletion(s), substitution(s) or addition(s) of one or several (e.g., up to five, about 10 at the most) amino acids. Even when such mutations have been introduced, the resulting amino acid sequences are capable of having the function as the constant region of Ig heavy chain or light chain.

Although the constant region of wild-type human IgG1 has ADCC activity and CDC activity, it is known that these activities can be reduced by introducing amino acid substitutions and deletions into specific sites. In the case of animals other than human where the constant region of an immunoglobulin equivalent to human IgG4 has not been identified, mutations may be introduced into the relevant region of an immunoglobulin equivalent to human IgG1 so that the resultant constant region with reduced ADCC activity and CDC activity can be used.

The present invention provides an artificial genetic DNA comprising (a') a DNA encoding alight chain comprising a light chain variable region (VL) containing CDR1 having the amino acid sequence of QSLLYSENQKDY (SEQ ID NO: 37), CDR2 having the amino acid sequence of WAT and CDR3 having the amino acid sequence of GQYLVYPFT (SEQ ID NO: 38) and the light chain constant region (CL) of an antibody of an animal other than rat and (b') a DNA encoding a heavy chain comprising a heavy chain variable region (VH) containing CDR1 having the amino acid sequence of GYTFTSNF (SEQ ID NO: 39), CDR2 having the amino acid sequence of IYPEYGNT (SEQ ID NO: 40) and CDR3 having the amino acid sequence of ASEEAVISLVY (SEQ ID NO: 41) and the heavy chain constant region (CH) of an antibody of an animal other than rat. The present invention also provides a DNA encoding a light chain comprising a VL containing CDR1 having the amino acid sequence of QSLLYSENQKDY (SEQ ID NO: 37), CDR2 having the amino acid sequence of WAT and CDR3 having the amino acid sequence of GQYLVYPFT (SEQ ID NO: 38) and the CL of an antibody of an animal other than rat (i.e., the DNA of (a') above). Further, the present invention also provides a DNA encoding a heavy chain comprising a VH containing CDR1 having GYTFTSNF (SEQ ID NO: 39), CDR2 having the amino acid sequence of IYPEYGNT (SEQ ID NO: 40) and CDR3 having the amino acid sequence of ASEEAVISLVY (SEQ ID NO: 41) and the CH of an antibody of an animal other than rat (i.e., the DNA of (b') above).

For (a) a light chain comprising a light chain variable region containing CDR1 having the amino acid sequence of QSLLYSENQKDY (SEQ ID NO: 37), CDR2 having the amino acid sequence of WAT and CDR3 having the amino acid sequence of GQYLVYPFT (SEQ ID NO: 38) and the light chain constant region of an antibody of an animal other than rat; and (b) a heavy chain comprising a heavy chain variable region containing CDR1 having the amino acid sequence of GYTFTSNF (SEQ ID NO: 39), CDR2 having the amino acid sequence of IYPEYGNT (SEQ ID NO. 40) and CDR3 having the amino acid sequence of ASEEAVISLVY (SEQ ID NO: 41) and the heavy chain constant region of an antibody of an animal other than rat, reference should be had to the foregoing description. The DNA of (a') is a DNA (gene) encoding the light chain of (a); and the DNA of (b') is a DNA (gene) encoding the heavy chain of (b). An artificial genetic DNA comprising the DNA of (a') and the DNA of ('b) may be synthesized on commercial synthesizer. Restriction enzyme recognition sites, KOZAK sequences, poly-A addition signal sequences, promoter sequences, intron sequences or the like may be added to the artificial genetic DNA.

The present invention also provides a vector comprising the above-mentioned artificial genetic DNA.

As the vector, *Escherichia coli*-derived plasmids (e.g., pBR322, pBR325, pUC12 or pUC13); *Bacillus subtilis*-derived plasmids (e.g., pUB110, pTP5 or pC194), yeast-derived plasmids (e.g., pSH19 or pSH15); bacteriophages such as λ phage; animal viruses such as retrovirus or vaccinia virus; or insect pathogen viruses such as baculovirus may be used. In the Examples described later, pDC6 (Japanese Patent No. 5704753, U.S. Pat. No. 9,096,878, EU Patent 2385115, Hong Kong (China) patent HK1163739 and Australia Patent 2009331326) was used.

The vector may also comprise promoters, enhancers, splicing signals, poly-A addition signals, intron sequences, selection markers, SV40 replication origins, and so forth.

The present invention also provides a host cell transformed by the above vector. It is possible to prepare the anti-PD-L1 antibody of the invention by culturing the host cell and collecting the antibody of interest from the resultant culture. Therefore, the present invention also provides a method of preparing an antibody, comprising culturing the above-described host cell and collecting the anti-PD-L1 antibody of the invention from the culture. In the method of the present invention for preparing an antibody, a vector incorporating an artificial genetic DNA comprising a DNA encoding the light chain and a DNA encoding the heavy chain may be transfected into a host cell. Alternatively, a vector incorporating a DNA encoding the light chain and a vector incorporating a DNA encoding the heavy chain may be co-transfected into a host cell.

Examples of the host cell include, but are not limited to, bacterial cells (such as *Escherichia* bacteria, *Bacillus* bacteria or *Bacillus subtilis*), fungal cells (such as yeast or *Aspergillus*), insect cells (such as S2 cells or Sf cells), animal cells (such as CHO cells, COS cells, HeLa cells, C127 cells, 3T3 cells, BHK cells or HEK 293 cells) and plant cells. Among these, CHO-DG44 cell (CHO-DG44 (dfhr$^{-/-}$)) which is a dihydrofolate reductase deficient cell is preferable.

Introduction of a recombinant vector into a host cell may be performed by the methods disclosed in Molecular Cloning 2nd Edition, J. Sambrook et al., Cold Spring Harbor Lab. Press, 1989 (e.g., the calcium phosphate method, the DEAE-dextran method, transfection, microinjection, lipofection, electroporation, transduction, scrape loading, the shotgun method, etc.) or by infection.

The resultant transformant may be cultured in a medium, followed by collection of the anti-PD-L1 antibody of the present invention from the culture. When the antibody is secreted into the medium, the medium may be recovered, followed by isolation and purification of the antibody from the medium. When the antibody is produced within the transformed cells, the cells may be lysed, followed by isolation and purification of the antibody from the cell lysate.

Examples of the medium include, but are not limited to, OptiCHO medium, Dynamis medium, CD CHO medium, ActiCHO medium, FortiCHO medium, Ex-Cell CD CHO medium, BalanCD CHO medium, ProCHO 5 medium and Cellvento CHO-100 medium.

The pH of the medium varies depending on the cell to be cultured. Generally, a pH range from 6.8 to 7.6 is used; mostly, a pH range from 7.0 to 7.4 is appropriate.

When the cell to be cultured is CHO cells, culture may be performed by methods known to those skilled in the art. For example, it is usually possible to perform culturing in a gas-phase atmosphere having a $CO_2$ concentration of 0-40%, preferably 2-10%, at 30-39° C., preferably around 37° C.

The appropriate period of culture is usually from one day to three months, preferably from one day to three weeks.

Isolation and purification of the antibody may be performed by known methods. Known isolation/purification methods which may be used in the present invention include, but are not limited to, methods using difference in solubility (such as salting-out or solvent precipitation); methods using difference in molecular weight (such as dialysis, ultrafiltration, gel filtration or SDS-polyacrylamide gel electrophoresis); methods using difference in electric charge (such as ion exchange chromatography); methods using specific affinity (such as affinity chromatography); methods using difference in hydrophobicity (such as reversed phase high performance liquid chromatography); and methods using difference in isoelectric point (such as isoelectric focusing).

The anti-PD-L1 antibody of the present invention may be used as an antibody drug for animals or human. Therefore, the present invention provides a pharmaceutical composition comprising the above-described anti-PD-L1 antibody as an active ingredient.

The pharmaceutical composition of the present invention may be used for prevention and/or treatment of cancers and/or infections. Examples of cancers and/or infections include, but are not limited to, neoplastic diseases (e.g., malignant melanoma, lung cancer, gastric cancer, renal cancer, breast cancer, bladder cancer, esophageal cancer, ovarian cancer and the like), leukemia, Johne's disease, anaplasmosis, bacterial mastitis, mycotic mastitis, mycoplasma infections (such as mycoplasma mastitis, mycoplasma pneumonia or the like), tuberculosis, *Theileria orientalis* infection, cryptosporidiosis, coccidiosis, trypanosomiasis and leishmaniasis.

The anti-PD-L1 antibody of the present invention may be dissolved in buffers such as PBS, physiological saline or sterile water, optionally filter-sterilized with a filter or the like, and then administered to animal subjects (including human) by injection. To the solution of this antibody, additives (such as coloring agents, emulsifiers, suspending agents, surfactants, solubilizers, stabilizers, preservatives, antioxidants, buffers, isotonizing agents, pH adjusters and the like) may be added. As routes of administration, intravenous, intramuscular, intraperitoneal, subcutaneous or intradermal administration and the like may be selected. Transnasal or oral administration may also be used.

The dose and the number of times and frequency of administration of the anti-PD-L1 antibody of the present invention may vary depending on the symptoms, age and body weight of the animal subject, the method of administration, the dosage form and so on. For example, 0.1-100 mg/kg body weight, preferably 1-10 mg/kg body weight, per adult animal may usually be administered at least once, at such a frequency that enables confirmation of the desired effect.

While the pharmaceutical composition of the present invention may be used alone, it may be used in combination with surgical operations, radiation therapies, other immunotherapies such as cancer vaccine, or molecular target drugs. Synergistic effect can be expected from such combinations.

EXAMPLES

Hereinbelow, the present invention will be described in more detail with reference to the following Examples. However, the present invention is not limited to these Examples.

[Example 1] Rat-Canine Chimeric Anti-PD-L1 Antibody

1. Introduction

Programmed cell death 1 (PD-1), an immunoinhibitory receptor, and its ligand programmed cell death ligand 1 (PD-L1) are molecules identified by Prof. Tasuku Honjo et al., Kyoto University, as factors which inhibit excessive immune response and are deeply involved in immunotolerance. Recently, it has been elucidated that these molecules are also involved in immunosuppression in tumors. In the subject Example, for the purpose of establishing a novel therapy for canine neoplastic diseases, a chimeric antibody gene was prepared in which a variable region gene of a rat anti-bovine PD-L1 monoclonal antibody (4G12) capable of inhibiting the binding of canine PD-1 to PD-L1 was linked to a constant region gene of a canine immunoglobulin (IgG4). The resultant chimeric antibody gene was introduced into Chinese hamster ovary cells (CHO cells), which were cultured to produce a rat-canine chimeric anti-PD-L1 antibody c4G12. The effect of this chimeric antibody was confirmed in vitro and in vivo.

2. Materials and Methods 2.1 Bovine PD-L1 Monoclonal Antibody Producing Cells

The nucleotide sequence of bovine PD-L1 was identified (Ikebuchi R, Konnai S, Shirai T, Sunden Y, Murata S, Onuma M, Ohashi K. Vet Res. 2011 Sep. 26; 42:103). Based on the sequence information, a recombinant bovine PD-L1 was prepared. Rat was immunized with this recombinant protein to prepare a rat anti-bovine PD-L1 antibody (Ikebuchi R, Konnai S, Okagawa T, Yokoyama K. Nakajima C, Suzuki Y, Murata S, Ohashi K. Immunology. 2014 August; 142(4):551-61; Clone 4G12 which would later serve as the variable region of the canine chimeric antibody of interest is described in this article.)

2.2 Identification of Full-Length Canine PD-1 and PD-L1 Genes

To determine the full lengths of canine PD-1 and PD-L1 cDNAs, PCR primers were first designed based on the putative nucleotide sequences of canine PD-1 and PD-L1 already registered at The National Center for Biotechnology Information (NCBI) (GenBank accession number; XM_543338 and XM_541302). Briefly, primers to amplify the inner sequence of the open reading frame (ORF) of each gene were designed (cPD-1 inner F and R, cPD-L1 inner F and R), and PCR was performed. For the amplified products, nucleotide sequences were determined with a capillary sequencer according to conventional methods. Further, to determine the nucleotide sequences of full-length PD-1 and PD-L1 cDNA, primers (cPD-1 5' GSP and 3' GSP; cPD-L1 5' GSP and 3'GSP) were designed based on the canine PD-1 and PD-L1 cDNA sequences determined above. 5'-RACE and 3'-RACE were then performed using the 5'-RACE system for rapid amplification of cDNA ends and 3'-RACE system for rapid amplification of cDNA ends (Invitrogen), respectively. The resultant gene fragments of interest were sequenced as described (Maekawa N, Konnai S, Ikebuchi R. Okagawa T, Adachi M, Takagi S, Kagawa Y, Nakajima C, Suzuki Y, Murata S, Ohashi K. PLoS One. 2014 Jun. 10; 9(6):e98415).

Primer (cPD-1 inner F): AGGATGGCTCCTAGACTCCC (SEQ ID NO: 21)

Primer (cPD-1 inner R): AGACGATGGTGGCATACTCG (SEQ ID NO: 22)

Primer (cPD-L1 inner F): ATGAGAATGTTTAGTGTCTT (SEQ ID NO: 23)

Primer (cPD-L1 inner R): TTATGTCTCTTCAAAT-TGTATATC (SEQ ID NO: 24)

Primer (cPD-1 5'GSP): GTTGATCTGTGTGTTG (SEQ ID NO: 25)

Primer (cPD-1 3'GSP): CGGGACTTCCACATGAGCAT (SEQ ID NO: 26)

Primer (cPD-L1 5'GSP): TTTTAGACAGAAAGTGA (SEQ ID NO: 27)

Primer (cPD-L1 3'GSP): GACCAGCTCTTCTTGGGGAA (SEQ ID NO: 28)

2.3 Construction of Canine PD-1 and PD-L1 Expressing COS-7 Cells

For preparing canine PD-1-EGFP and PD-L1-EGFP expression plasmids, PCR was performed using a synthesized beagle PBMC-derived cDNA as a template and primers designed by adding XhoI and BamHI recognition sites (PD-1) and BglII and EcoRI recognition sites (PD-L1) on the 5' side (cPD-1-EGFP F and R; cPD-L1-EGFP F and R). The resultant PCR products were digested with XhoI (Takara) and BamHI (Takara) (PD-1) and with BglII (New England Biolabs) and EcoRI (Takara) (PD-L1), and then purified with FastGene Gel/PCR Extraction Kit (NIPPON Genetics), followed by cloning into pEGFP-N2 vector (Clontech) treated with restriction enzymes in the same manner. The resultant expression plasmids of interest were extracted with QIAGEN Plasmid Midi kit (Qiagen) and stored at −30° C. until use in experiments. Hereinafter, the thus prepared expression plasmids are designated as pEGFP-N2-cPD-1 and pEGFP-N2-cPD-L1.

Primer (cPD-1-EGFP F): CCGCTCGAGATGGGGAGCCGGCGGGGGCC (SEQ ID NO: 29)
Primer (cPD-1-EGFP R): CGCGGATCCTGAGGGGCCACAGGCCGGGTC (SEQ ID NO: 30)
Primer (cPD-L1-EGFP F): GAAGATCTATGAGAATGTTTAGTGTC (SEQ ID NO: 31)
Primer (cPD-L1-EGFP R): GGAATTCTGTCTCTTCAAATTGTATATC (SEQ ID NO: 32)

COS-7 cells were subcultured at a density of $5\times10^4$ cells/cm$^2$ in 6-well plates, and then cultured overnight in RPMI 1640 medium containing 10% inactivated fetal bovine serum and 0.01% L-glutamine at 37° C. in the presence of 5% CO$_2$. The pEGFP-N2-cPD-1, pEGFP-N2-cPD-L1 or pEGFP-N2 (negative control) was introduced into COS-7 cells at 0.4 μg/cm$^2$ using Lipofectamine 2000 (Invitrogen). The cells were cultured for 48 hours (cPD-1-EGFP expressing cell and cPD-L1-EGFP expressing cell). In order to confirm the expression of canine PD-1 and PD-L1 in the thus prepared expressing cells, intracellular localization of enhanced green fluorescent protein (EGFP) was visualized with an inverted confocal laser microscope LSM700 (ZEISS) (Maekawa N, Konnai S, Ikebuchi R. Okagawa T, Adachi M, Takagi S, Kagawa Y. Nakajima C, Suzuki Y, Murata S, Ohashi K. PLoS One. 2014 Jun. 10; 9(6):e98415).

2.4 Construction of Recombinant Canine PD-1, PD-L1 and CD80

In order to amplify the extracellular regions of canine PD-1, PD-L1 and CD80 estimated from their putative amino acid sequences, primers were designed. Briefly, primers having an NheI or EcoRV recognition sequence (PD-1 and PD-L1) added on the 5' side (cPD-1-Ig F and R; cPD-L1-Ig F and R) or having an EcoRV or KpnI (CD80) recognition sequence added on the 5' side (cCD80-Ig F and R) were designed. PCR was performed using a synthesized beagle PBMC-derived cDNA as a template. The PCR products were digested with NheI (Takara) and EcRV (Takara) or with EcoRV (Takara) and KpnT (New England Biolabs) and purified with FastGene GeV/PCR Extraction Kit (NIPPON Genetics). The thus purified DNAs were individually cloned into pCXN2.1-Rabbit IgG Fc vector (Niwa et al., 1991; Zettimeissl et al., 1990; kindly provided by Dr. T Yokomizo, Juntendo University Graduate School of Medicine, and modified in the inventors' laboratory) treated with restriction enzymes in the same manner. The expression plasmids were purified with QIAGEN Plasmid Midi kit (Qiagen) and stored at −30° C. until use in experiments. Hereinafter, the thus prepared expression plasmids are designated as pCXN2.1-cPD-1-Ig, pCXN2.1-cPD-L1-Ig and pCXN2.1-cCD80-Ig, respectively.

```
Primer (cPD-1-Ig F):
                                (SEQ ID NO: 33)
CGCGGCTAGCArGGGGAGCCGGCGGGGGCC Primer (cPD-1-Ig R):
                                (SEQ ID NO: 34)
CGCGGATATCCAGCCCCTGCAACTGGCCGC Primer (cPD-L1-Ig F):
                                (SEQ ID NO: 35)
CGCGGCTAGCATGAGAATGTTTAGTGTCTT Primer (cPD-L1-Ig R):
                                (SEQ ID NO: 36)
CGCGGATATCAGTCCTCTCACTTGCTGGAA Primer (eCD804g F):
                                (SEQ ID NO: 129)
CGCGGATATCATGGATTACACAGCGAAGTG Primer (cCD80-Ig R):
                                (SEQ ID NO: 130)
CGGGGTACCCCAGAGCTGTTGCTGGTTAT
```

These expression vectors were individually transfected into Expi293F cells (Life Technologies) to obtain a culture supernatant containing a recombinant Ig fusion protein. The recombinant protein produced was purified from the supernatant with Ab Capcher Extra (Protein A mutant; ProteNova). After buffer exchange with phosphate-buffered physiological saline (PBS; pH 7.4) using PD-MidiTrap G-25 (GE Healthcare), each recombinant protein was stored at −30° C. until use in experiments (cPD-1-Ig, cPD-L1-Ig and cCD80-Ig). The concentration of each protein was measured with Pierce BCA Protein Assay Kit (Thermo Fisher Scientific) before use in subsequent experiments.

2.5 Identification of Rat Anti-Bovine PD-L1 Monoclonal Antibody Showing Cross-Reactivity with Canine PD-L1

In order to identify rat anti-bovine PD-L1 monoclonal antibody showing cross-reactivity with canine PD-L1, flow cytometry was performed using the anti-bovine PD-L1 antibody prepared in 2.1 above. The anti-bovine PD-L1 antibody (10 μg/ml) was reacted with $2\times10^5$-$1\times10^6$ cells at room temperature for 30 min. After washing, the anti-bovine PD-L1 antibody was detected with allophycocyanine-labeled anti-rat Ig goat antibody (Beckman Coulter). FACS Verse (Becton, Dickinson and Company) was used for analysis. As negative controls, rat IgG2a (κ) isotype control (BD Biosciences), rat IgG1 (κ) isotype control (BD Biosciences) and rat IgM (κ) isotype control (BD Biosciences) were used. For every washing operation and dilution of antibodies, 10% inactivated goat serum-supplemented PBS was used (Maekawa N, Konnai S, Ikebuchi R. Okagawa T, Adachi M, Takagi S, Kagawa Y, Nakajima C, Suzuki Y, Murata S, Ohashi K. PLoS One. 2014 Jun. 10; 9(6):e98415 which is an article describing the use of three bovine PD-L1 monoclonal antibodies: 4G12 (Rat IgG2a (κ)), 5A2 (Rat IgG1 (κ)) and 6G7 (Rat IgM (κ)).

2.6 Selection Test of Variable Region for Establishment of Rat-Canine Chimeric Anti-PD-L1 Antibody Out of 10 clones of rat anti-bovine PD-L1 monoclonal antibody which showed cross-reactivity with canine PD-L1, 4G12 (Rat IgG2a (κ)), 5A2 (Rat IgG1 (κ)) and 607 (Rat IgM (κ)) were selected and check was made to see whether these antibodies would inhibit canine PD-1/PD-L1 binding. Briefly, canine PD-1-Ig (prepared in 2.4 above) was immobilized on flat bottomed 96-well plates and blocked with 1%

BSA and 0.05% Tween 20-containing PBS. Canine PD-L1-Ig (prepared in 2.4 above) was biotinylated using Lightning-Link Biotin Conjugation Kit (Innova Bioscience) and reacted with various concentrations (0, 2.5, 5 and 10 µg/ml) of rat anti-bovine PD-L1 antibodies 4G12, 5A2 and 6G7 at 37° C. for 30 min, followed by addition to the 96-well plates. The binding of cPD-L1-Ig to cPD-1-Ig was measured by color reaction using Neutravidin-HRP (Thermo Fisher Scientific) and TMB one component substrate (Bethyl Laboratories). As a result, rat anti-bovine PD-L1 monoclonal antibodies 4G12 and 6G7 showed a good inhibitory activity against canine PD-1/PD-L1 binding, whereas 5A2 showed no binding inhibitory activity (FIG. 1).

Figure 2:
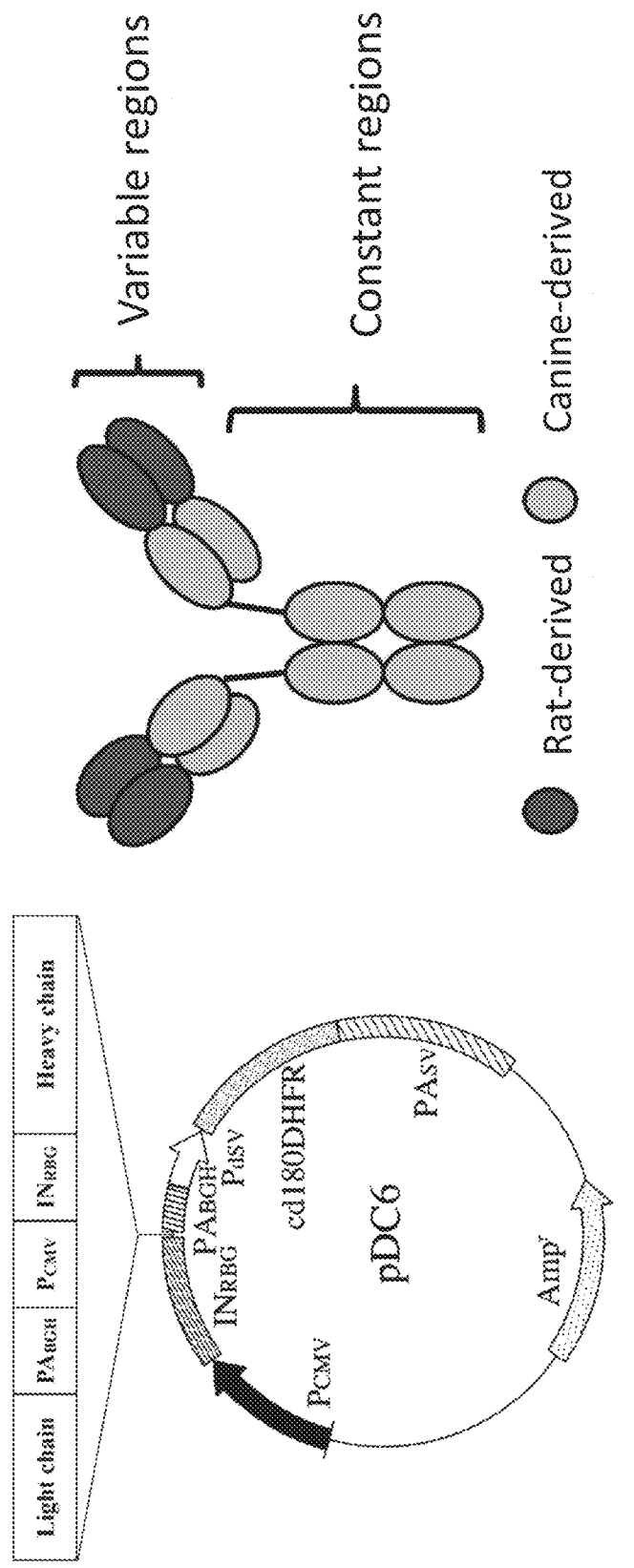
FIG. 2 Schematic drawings of pDC6 vector and a rat-canine chimeric anti-PD-L1 antibody.

2.7 Preparation of Rat-Canine Chimeric Anti-PD-L1 Antibody Expressing Vector (FIG. 2)

Using rat anti-bovine PD-L1 monoclonal antibodies 4G12 and 6G7 which showed a good inhibitory activity against canine PD-1/PD-L1 binding (FIG. 1) as the variable region, two types of rat-canine chimeric anti-PD-L1 antibodies were established.

Figure 3:
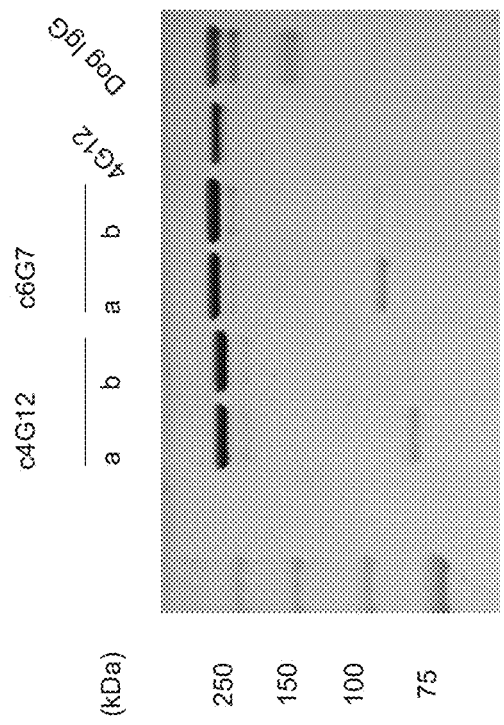
FIG. 3 Expression and purification of rat-canine chimeric anti-PD-L1 antibodies c4G12 and c6G7. SDS-PAGE was performed under non-reducing conditions, followed by visualization of bands by CBB staining. a: purification with protein A alone. b: a + gel filtration chromatography.
Figure 4:
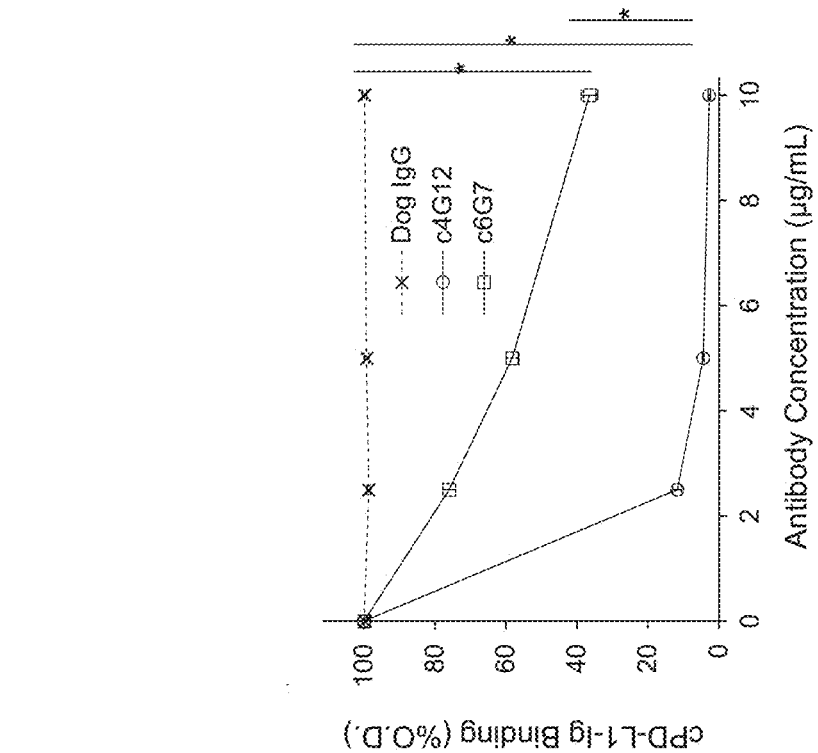
FIG. 4 PD-1/PD-L1 binding inhibition activities of rat-canine chimeric anti-PD-L1 antibodies c4G12 and c6G7.

Briefly, heavy chain and light chain variable region genes were identified from hybridomas producing rat anti-bovine PD-L1 monoclonal antibodies 4G12 and 6G7. Further, the heavy chain and light chain variable region genes of the above rat antibodies were linked to the constant region of heavy chain IgG4 and the constant region of light chain Lambda of a known canine antibody, respectively, to prepare nucleotide sequences, followed by codon optimization (SEQ ID NOS: 9 and 10 (amino acid sequences), SEQ ID NOS: 19 and 20 (nucleotide sequences after codon optimization). Then, synthesis of genes was performed so that NotI restriction enzyme recognition site. KOZAK sequence, chimeric antibody's light chain sequence, poly-A addition signal sequence (PABGH), promoter sequence (PCMV), SacI restriction enzyme recognition site, intron sequence (IN-RBG), KOZAK sequence, chimeric antibody's heavy chain sequence and XbaI restriction enzyme recognition site would be located in this order. The synthesized gene strands were individually incorporated into the cloning site (NotI and XbaI restriction enzyme recognition sequences downstream of PCMV and between INRBG and PABGH) of expression vector pDC6 (kindly provided by Prof. S. Suzuki, Hokkaido University Research Center for Zoonosis Control) using restriction enzyme recognition sequences so that the above-listed sequences would be located in the above-mentioned order (FIG. 2). Thus, rat-canine chimeric anti-PD-L1 antibody expressing vectors were constructed. Each of the expression vectors was transfected into Expi293F cells (Life Technologies) to obtain a culture supernatant containing a chimeric antibody. The chimeric antibody was purified from the supernatant with Ab Capcher Extra (Protein A mutant; ProteNova) and further purified by gel filtration chromatography. SDS-PAGE was performed under non-reducing conditions using 10% acrylamide gel. Bands were stained with Quick-CBB kit (Wako Pure Chemical) and decolorized in distilled water. Although contaminant proteins were observed after protein A purification alone, a highly purified antibody could be obtained by performing gel filtration chromatography (FIG. 3). It was confirmed by flow cytometry that the resultant purified antibodies specifically bound to canine PD-L1 expressing cells (data not shown). When the inhibitory activity of the two chimeric antibodies against canine PD-1/PD-L1 binding was examined by the method described in 2.6 above, rat-canine chimeric anti-PD-L1 antibody c4G12 showed a binding inhibitory activity similar to that of its original rat anti-bovine PD-L1 monoclonal antibody 4G12, whereas binding inhibition capacity was clearly attenuated in rat-canine chimeric anti-PD-L1 antibody c6G7 (FIG. 4) Therefore, rat-canine chimeric anti-PD-L1 antibody c4012 was selected as a therapeutic antibody, which incorporated the variable region sequences of rat anti-bovine PD-L1 monoclonal antibody 4G12 (SEQ ID NOS: 2 and 1 (amino acid sequences) and SEQ ID NOS: 16 and 15 (nucleotide sequences after codon optimization)). The amino acid sequence and the nucleotide sequence (after codon optimization) of the light chain of c4G12 are shown in SEQ ID NOS: 9 and 19, and the amino acid sequence and the nucleotide sequence (after codon optimization) of the heavy chain of c4G12 are shown in SEQ ID NOS: 10 and 20.

2.8 Expression of Rat-Canine Chimeric Anti-PD-L1 Antibody c4G12

Figure 5:
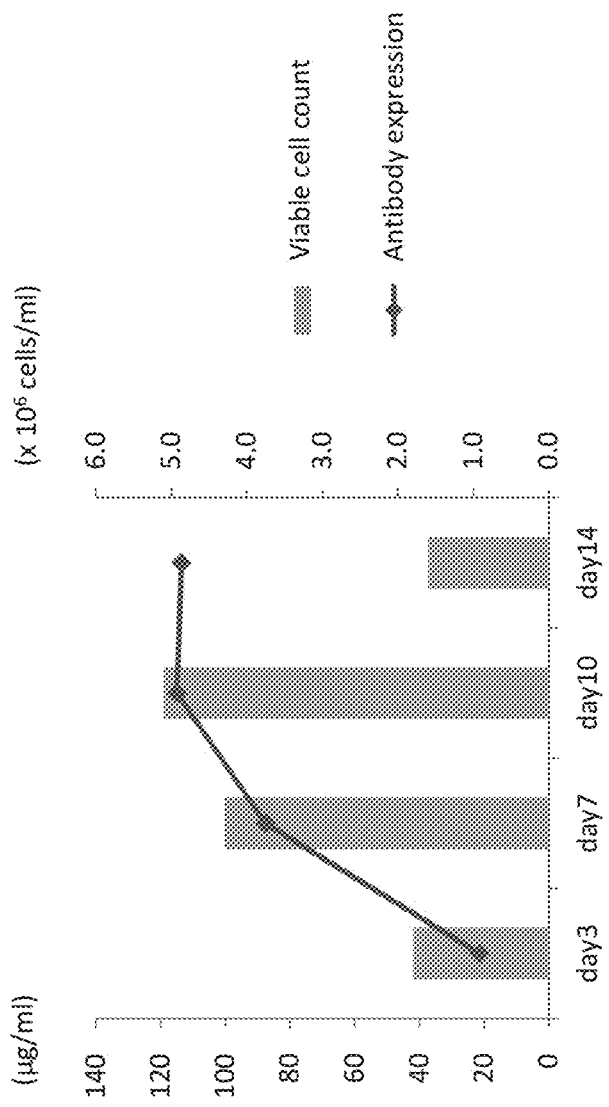
FIG. 5 Establishment of cell clones capable of high expression of rat-canine chimeric anti-PD-L1 antibody c4G12.

Rat-canine chimeric anti-PD-L1 antibody c4G12 expressing vector pDC6 as used in 2.7 above was transfected into CHO-DG44 cells (CHO-DG44(dfhr$^{-/-}$)) which were dihydrofolate reductase deficient cells and high expression clones were selected by dot blotting. Further, gene amplification treatment was performed by adding load on cells in a medium containing 60 nM methotrexate (Mtx). Cells stably expressing rat-canine chimeric anti-PD-L1 antibody c4G12 (clone name: 4.3F1) after gene amplification were transferred to Mtx-free Opti-CHO medium and cultured under shaking for 14 days (125 rpm, 37° C., 5% $CO_2$). Cell survival rate was calculated by trypan blue staining (FIG. 5). Chimeric antibody production in the culture supernatant was measured by ELISA (FIG. 5). The culture supernatant at day 14 was centrifuged at 10,000 g for 10 min to remove cells, then passed through a 0.22 µm filter before the process proceeded to purification steps for the antibody.

It should be noted that by exchanging the medium with Dynamis medium and doing appropriate feeding, antibody production was improved about two-fold compared to the conventional production (data not shown).

2.9 Purification of Rat-Canine Chimeric Anti-PD-L1 Antibody c4G12

The culture supernatant provided as described above was purified with Ab Capcher Extra (ProteNova). An open column method was used for binding to resin; PBS pH 7.4 was used as equilibration buffer and wash buffer. As elution buffer. IgG Elution Buffer (Thermo Scientific) was used. As neutralization buffer, 1 M Tris was used. The purified antibody was concentrated and buffer-exchanged with PBS by ultrafiltration using Amicon Ultra-15 (50 kDa, Millipore). The resultant antibody was passed through a 0.22 µm filter for use in respective experiments.

Figure 6:
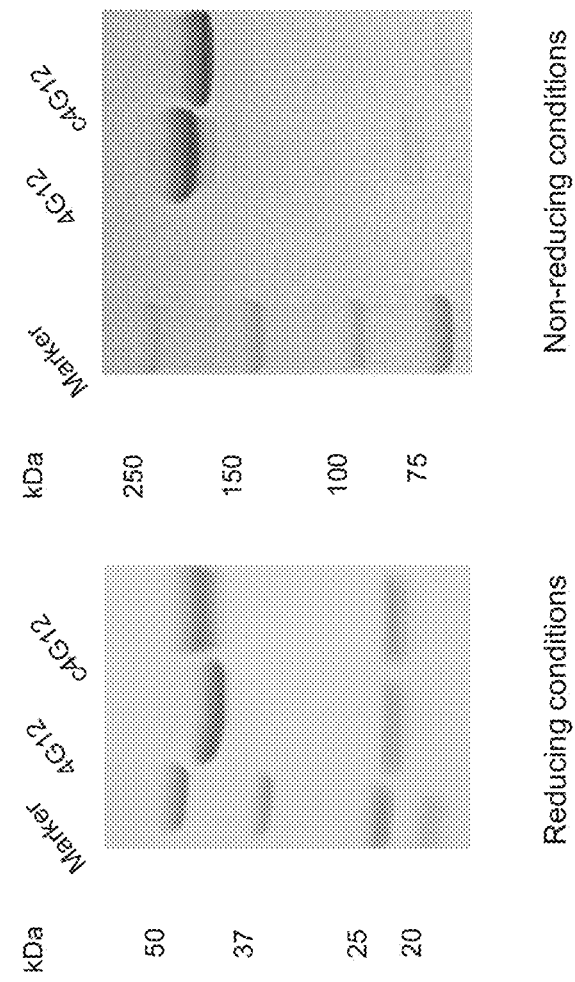
FIG. 6 SDS-PAGE images of rat-canine chimeric anti-PD-L1 antibody c4G12. Rat anti-bovine PD-L1 antibody 4G12 and rat-canine chimeric anti-PD-L1 antibody c4G12 were electrophoresed under reducing conditions and non-reducing conditions, followed by visualization of bands by CBB staining. Under reducing conditions, a band of antibody's heavy chain was detected at around 50 kDa and a band of antibody's light chain at around 25 kDa. No bands other than the bands of interest were detected.

2.10 Confirmation of Purification of Rat-Canine Chimeric Anti-PD-L1 Antibody c4G12 (FIG. 6)

In order to confirm the purity of the purified antibody, antibody proteins were detected by SDS-PAGE and CBB staining. Using SuperSep Ace 5-20% (Wako) gradient gel, rat anti-bovine PD-L1 monoclonal antibody 4G12 and rat-canine chimeric anti-PD-L1 antibody c4G12 were electrophoresed under reducing conditions and non-reducing conditions. Bands were stained with Quick-CBB kit (Wako) and decolored in distilled water. Bands were observed at positions of molecular weights corresponding to antibodies. No bands of contaminant proteins were recognized visually.

2.11 Measurement of Binding Avidities to cPD-L1-his of Rat Anti-Bovine PD-L1 Monoclonal Antibody 4G12 and Rat-Canine Chimeric Anti-PD-L1 Antibody c4G12

In order to amplify the extracellular region of canine PD-L1 estimated from its putative amino acid sequence, primers were designed. Briefly, a primer having an NheI recognition sequence added on the 5' side (cPD-L1-His F)

and a primer having an EcoRV recognition sequence and 6×His tag sequence added on the 5' side (cPD-L1-His R) were designed. PCR was performed using a synthesized beagle PBMC-derived cDNA as a template. The PCR products were digested with NheI (Takara) and EcoRV (Takara) and purified with FastGene Gel/PCR Extraction Kit (NIPPON Genetics). The thus purified DNA was cloned into pCXN2.1 vector (Niwa et al., 1991; kindly provided by Dr. T. Yokomizo, Juntendo University Graduate School of Medicine) treated with restriction enzymes in the same manner. The expression plasmids were purified with QIAGEN Plasmid Midi kit (Qiagen) and stored at −30° C. until use in experiments. Hereinafter, the thus prepared mid is designated as pCXN2.1-cPD-L1-His.

```
Primer (cPD-L1-His F):
                                           (SEQ ID NO: 131)
CGCGGCTAGCATGAGAATGTTTAGTGTCTT Primer (cPD-L1-His R):
                                           (SEQ ID NO: 132)
CGCGGATATCTTAATGGTGATGGTGATGGTGAGTCCTCTCACTTGCTGG
```

The expression vector was transfected into Expi293F cells (Life Technologies) to obtain a culture supernatant containing a recombinant protein. The recombinant protein produced was purified from the supernatant using TALON Metal Affinity Resin (Clontech), and the buffer was exchanged with PBS using Amicon Ultra-4 Ultracel-3 (Merck Millipore). The thus obtained recombinant protein was stored at 4° C. until use in experiments (cPD-L1-His). The protein concentration was measured with Pierce BCA Protein Assay Kit (Thermo Fisher Scientific) for use in subsequent experiments.

Using a biomolecular interaction analyzer (Biacore X100), the binding avidities to cPD-L1-His of rat anti-bovine PD-L1 monoclonal antibody 4G12 and rat-canine chimeric anti-PD-L1 antibody c4G12 were assessed. Briefly, anti-histidine antibody was fixed on CMS censor chip, followed by capturing of cPD-L1-His. Subsequently, monoclonal antibodies were added as analyte to observe specific binding. Both antibodies exhibited specific binding and their avidities were almost comparable (Table 1). Further, the binding avidities of canine PD-1-Ig and CD80-Ig to cPD-L1-His were measured in the same manner and found to be clearly lower than that of rat-canine chimeric anti-PD-L1 antibody c4G12 (Table 1).

TABLE 1

Binding Avidity of Each Antibody and Recombinant Protein to Canine PD-L1-His

| | ka (×10$^6$/Ms) | kd (×10$^{-3}$/s) | KD (nM) |
|---|---|---|---|
| 4G12 | 2.42 ± 0.10 | 4.54 ± 0.19 | 1.88 ± 0.06 |
| c4G12 | 3.14 ± 0.19 | 7.19 ± 0.26 | 2.30 ± 0.07 |
| cPD-1 | | | 25.4 ± 4.89 |
| cCD80 | | | 24.3 ± 0.89 |

Figure 7:
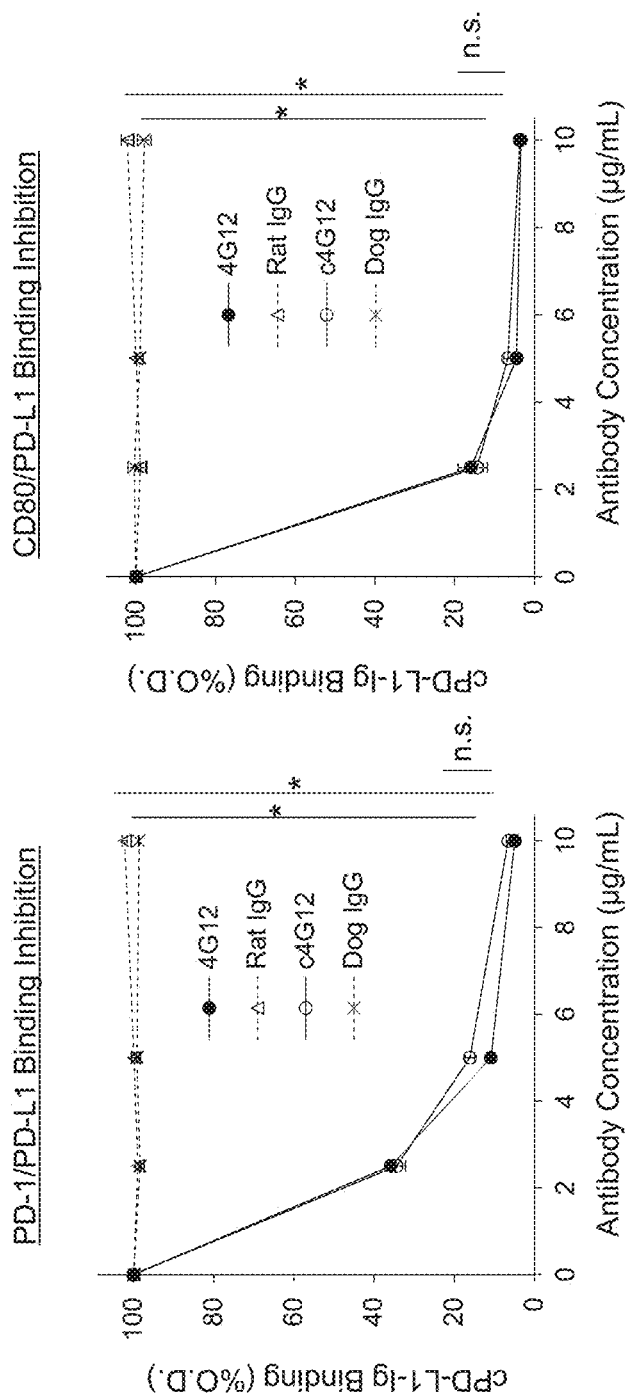
FIG. 7 Inhibitory activities of rat anti-bovine PD-L1 antibody 4G12 and rat-canine chimeric anti-PD-L1 antibody c4G12 against canine PD-1/PD-L1 binding and CD80/PD-L1 binding. Rat anti-bovine PD-L1 monoclonal antibody 4G12 and rat-canine chimeric anti-PD-L1 antibody c4G12 reduced the amounts of binding of PD-L1-Ig to canine PD-1-Ig and CD80-Ig. No change due to chimerization of the antibody was observed in binding inhibition activity FIG. 8 Canine immune cell activation effect by rat-canine chimeric anti-PD-L1 antibody c4G12. Canine PBMCs were cultured under stimulation for 3 days, followed by determination of IL-2 and IFN-γ concentrations in the supernatant by ELISA. Further, nucleic acid analogue EdU was added to the culture medium at day 2 of the culture under stimulation, followed by determination of the EdU uptake by flow cytometry. Rat-canine chimeric anti-PD-L1 antibody c4G12 increased the production of IL-2 and IFN-γ from canine PBMCs and enhanced proliferation of CD4+ and CD8+ lymphocytes.

2.12 Inhibitory Activity of Rat-Canine Chimeric Anti-PD-L1 Antibody c4012 Against Canine PD-1/PD-L1 Binding and CD80/PD-L1 Binding (FIG. 7)

Using the canine PD-1-Ig, PD-L1-Ig and CD80-Ig (described above), anti-PD-L1 antibody was tested for its ability to inhibit canine PD-1/PD-L1 binding and CD80/PD-L1 binding. Briefly, canine PD-1-Ig or CD80-Ig was immobilized on flat-bottom 96-well plates. Canine PD-L1-Ig was reacted with various concentrations (0, 2.5, 5 and 10 μg/ml) of rat anti-bovine PD-L1 antibody 4G12 or rat-canine chimeric anti-PD-L1 antibody c4G12 according to the same procedures as described in 2.6 above, and the binding of canine PD-L1-Ig was assessed. No change in binding inhibition activity was observed due to the chimerization of antibody.

Figure 8:
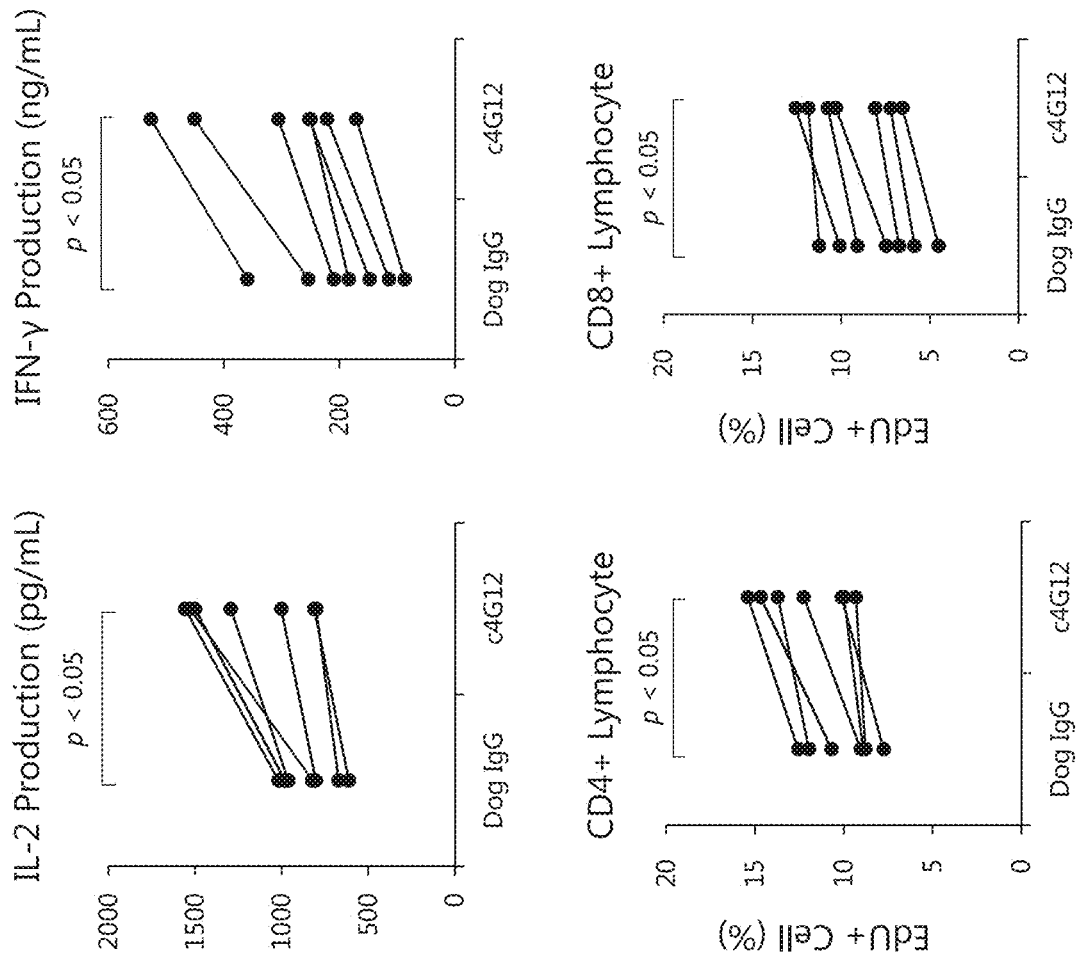

2.13. Canine Immune Cell Activating Effect of Rat-Canine Chimeric Anti-PD-L1 Antibody c4G12 (FIG. 8)

Canine PBMCs were cultured under stimulation with a super-antigen Staphylococcal Enterotoxin B (SEB) for three days, and changes in cytokine production by addition of rat-canine chimeric anti-PD-L1 antibody c4G12 were measured by ELISA using Duoset ELISA canine IL-2 or IFN-γ (R&D systems). Rat-canine chimeric anti-PD-L1 antibody c4G12 increased the production of IL-2 and IFN-γ from canine PBMCs. Further, nucleic acid analogue EdU was added to the culture medium at day 2 of the culture under SEB stimulation. Two hours later, uptake of EdU was measured by flow cytometry using Click-iT Plus EdU flow cytometry assay kit (Life Technologies). As a result, EdU uptake in canine CD4$^+$ and CD8$^+$ lymphocytes was enhanced by addition of rat-canine chimeric anti-PD-L1 antibody c4G12, indicating an elevated cell proliferation capacity.

2.14 Selection of Tumor-Affected Dogs to be Used in Canine Inoculation Test

Since the subject treatment is expected to manifest a higher efficacy when PD-L1 is being expressed in tumors, PD-L1 expression analysis at the tumor site of dogs was performed by immunohistochemical staining. Briefly, tumor tissue samples fixed with formaldehyde and embedded in paraffin were sliced into 4 μm thick sections with a microtome, attached to and dried on silane-coated slide glass (Matsunami Glass) and deparaffinized with xylene/alcohol. While the resultant sections were soaked in citrate buffer [citric acid (Wako Pure Chemical) 0.37 g, trisodium citrate dihydrate (Kishida Chemical) 2.4 g, distilled water 1000 ml], antigen retrieval treatment was performed for 10 min with microwave, followed by staining using a Nichirei automatic immuno-staining device. As pretreatment, sample sections were soaked in 0.3% hydrogen peroxide-containing methanol solution at room temperature for 15 min and washed with PBS. Then, anti-bovine PD-L1 monoclonal antibody was added and reaction was conducted at room temperature for 30 min. After washing with PBS, histofine simple stain MAX-PO (Rat) (Nichirei Bioscience) was added and reaction was carried at room temperature for 30 min, followed by coloring with 3,3'-diaminobenzidine tetrahydrocholride and observation with a light microscope. Dogs with oral melanoma or undifferentiated sarcoma in which tumor cells were PD-L1 positive were used in the following inoculation test (clinical trial). Anti-bovine PD-L1 monoclonal antibody was established from a rat anti-bovine PD-L1 monoclonal antibody producing hybridoma (Ikebuchi R, Konnai S, Okagawa T, Yokoyama K, Nakajima C, Suzuki Y, Murata S, Ohashi K. Immunology. 2014 August; 142(4):551-61).

2.15 Inoculation Test on Dogs

With respect to the rat-canine chimeric anti-PD-L1 antibody c4G12 to be inoculated into dogs in the clinical trial, the culture supernatant obtained by the procedures described in 2.8 above was purified by affinity chromatography using MabSelect SuRe LX (GE Healthcare) and then by hydroxyapatite chromatography using BioScale CHT20-I prepacked column (Bio-Rad) in order to remove contaminants and polymeric proteins. Aggregate-containing fractions were further purified by anion exchange chromatography using HiScreen Q-Sepharose HP prepacked column (GE Healthcare).

Figure 9:
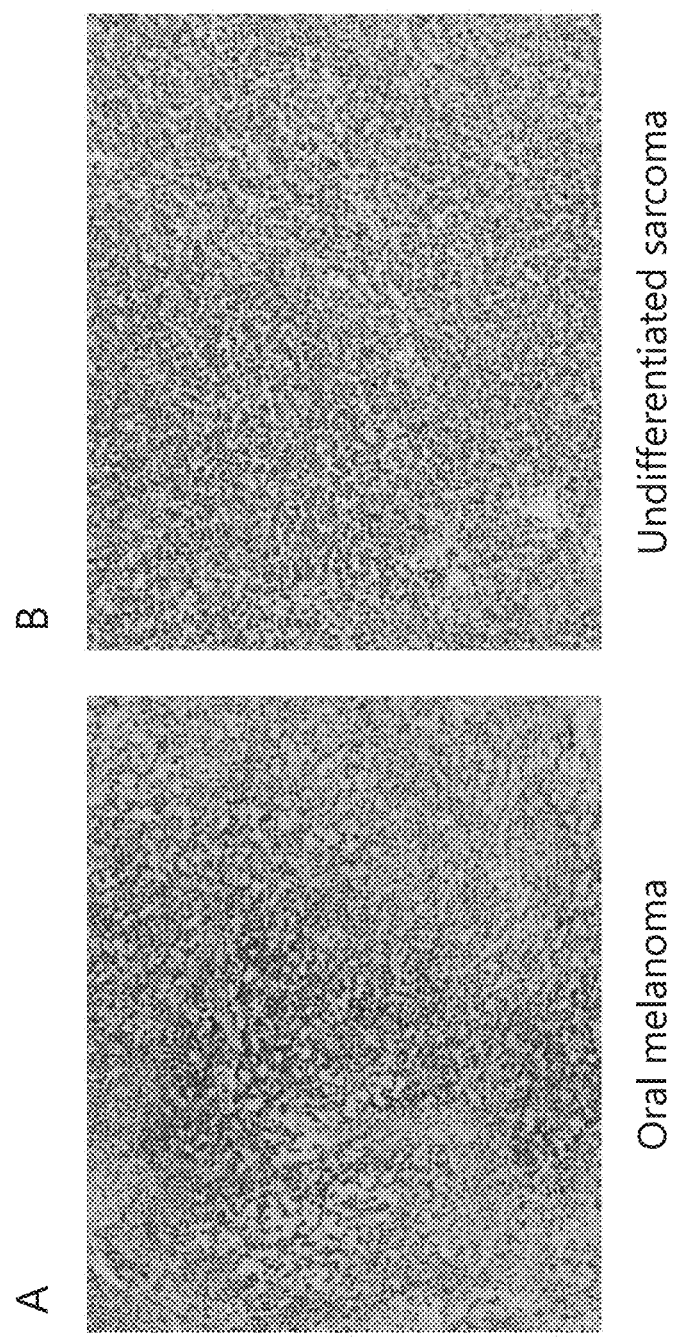
FIG. 9 Expression of PD-L1 in oral melanoma (A) and undifferentiated sarcoma (B)
Figure 10:
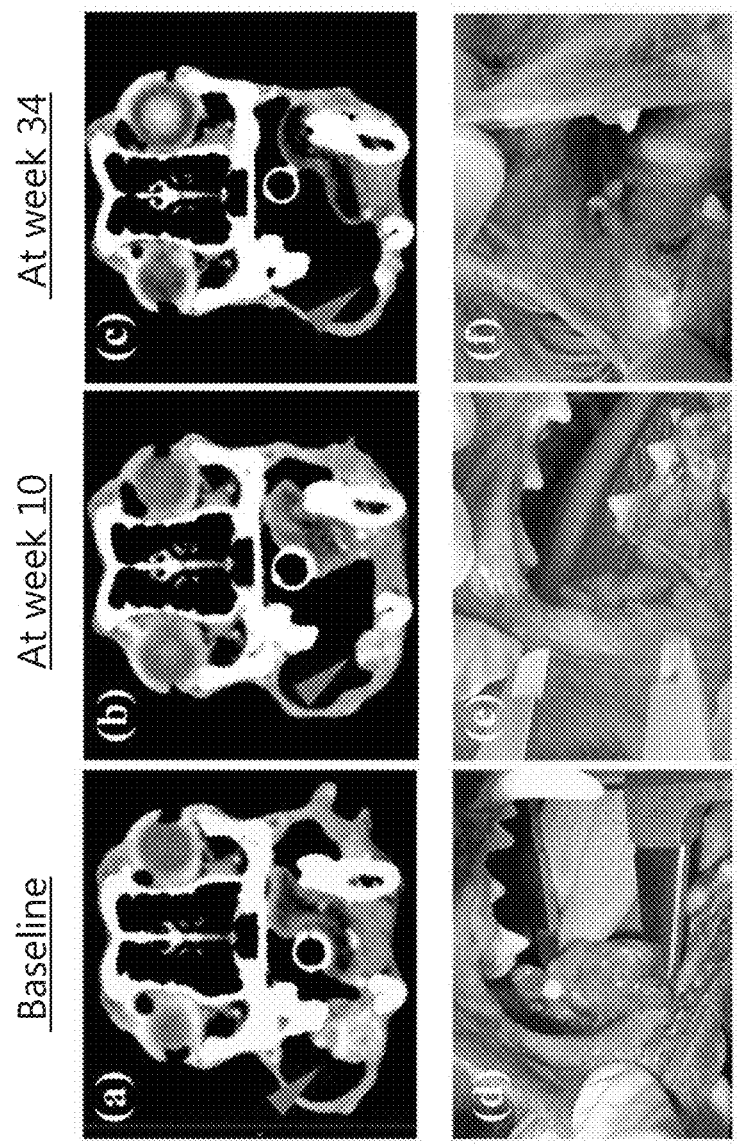
FIG. 10 CT images and appearances of tumor in a test of treatment by administering rat-canine chimeric anti-PD-L1 antibody c4G12 to a dog with oral melanoma. (a,d) Before the start of the treatment. (b,e) at week 10 of the treatment, and (c,f) at week 34 of the treatment. A remarkable anti-tumor effect was recognized upon five administrations of the antibody (at week 10 from the start of the treatment). At week 34, a further reduction of tumor was confirmed.
Figure 11:
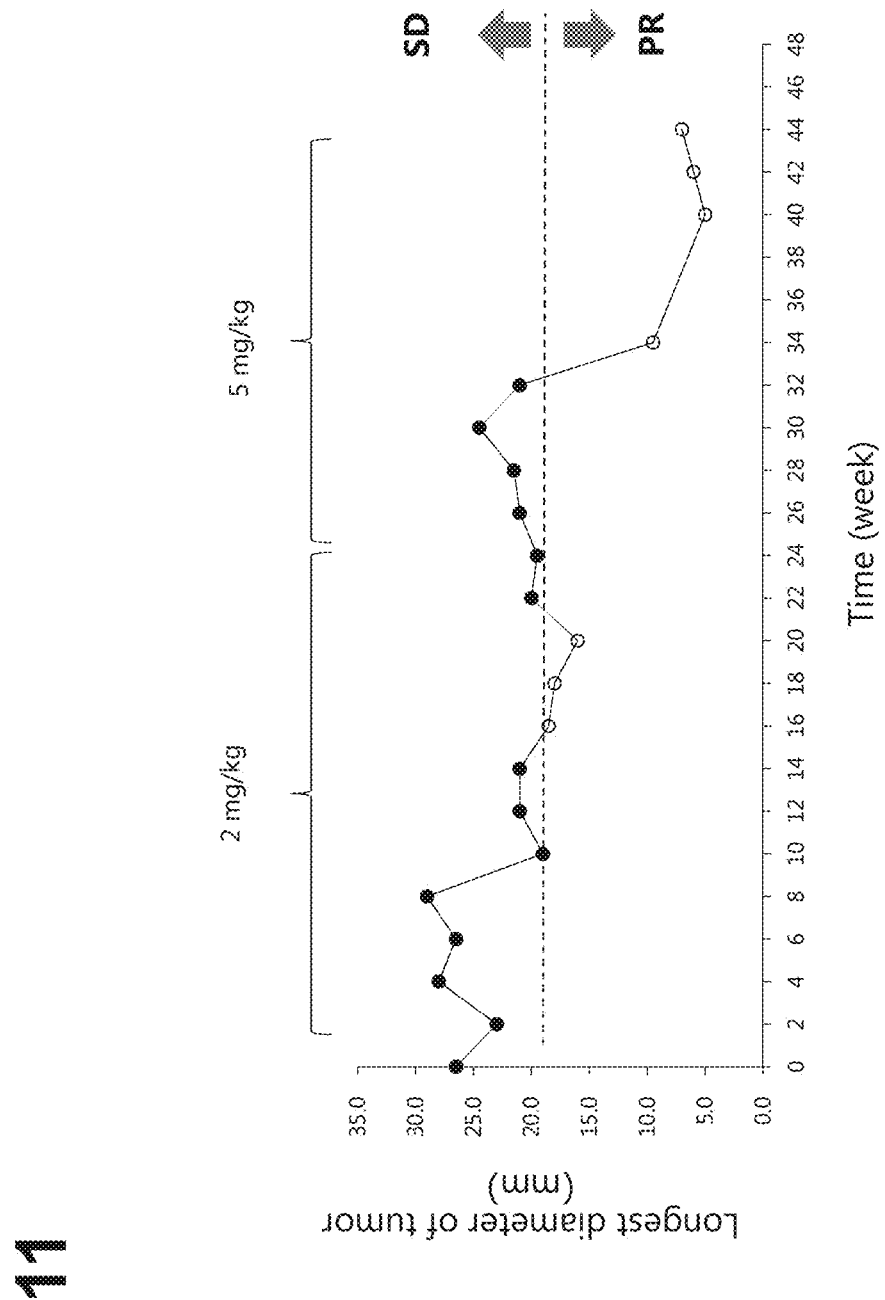
FIG. 11 Time-dependent changes in the longest diameter of the tumor in the dog with oral melanoma shown in FIG. 10. Reduction by 30% or more compared to the baseline longest diameter was regarded as partial response (PR).

(1) Safety Test: The established rat-canine chimeric anti-PD-L1 antibody c4G12 was administered intravenously into a dog (beagle, spayed female, 13-year-old, about 10 kg in body weight) at 2 mg/kg, every 2 weeks, 3 times in total. There was observed no anaphylaxis or other adverse effects that would cause any trouble in clinical trials. (2) Clinical Trial 1: The established rat-canine chimeric anti-PD-L1 antibody c4G12 was administered intravenously into a PD-L1 positive dog with relapsed oral melanoma (FIG. 9A) (miniature dachshund, male, 11-year-old, about 7.5 kg in body weight) at 2 mg/kg or 5 mg/kg, every 2 weeks, 22 times in total. At week 10 after the start of treatment, a remarkable reduction in tumor size was recognized. At week 34 after the start of treatment, a still further reduction was confirmed (FIG. 10). During the observation period of 44 weeks, no metastases to lymph nodes or the lung were observed. When 30% or more reduction in the longest diameter of tumor compared to that at the baseline is defined as PR (partial response), the criterion of PR was satisfied at weeks 16-20 and at week 34 and thereafter (FIG. 11).

Figure 12:
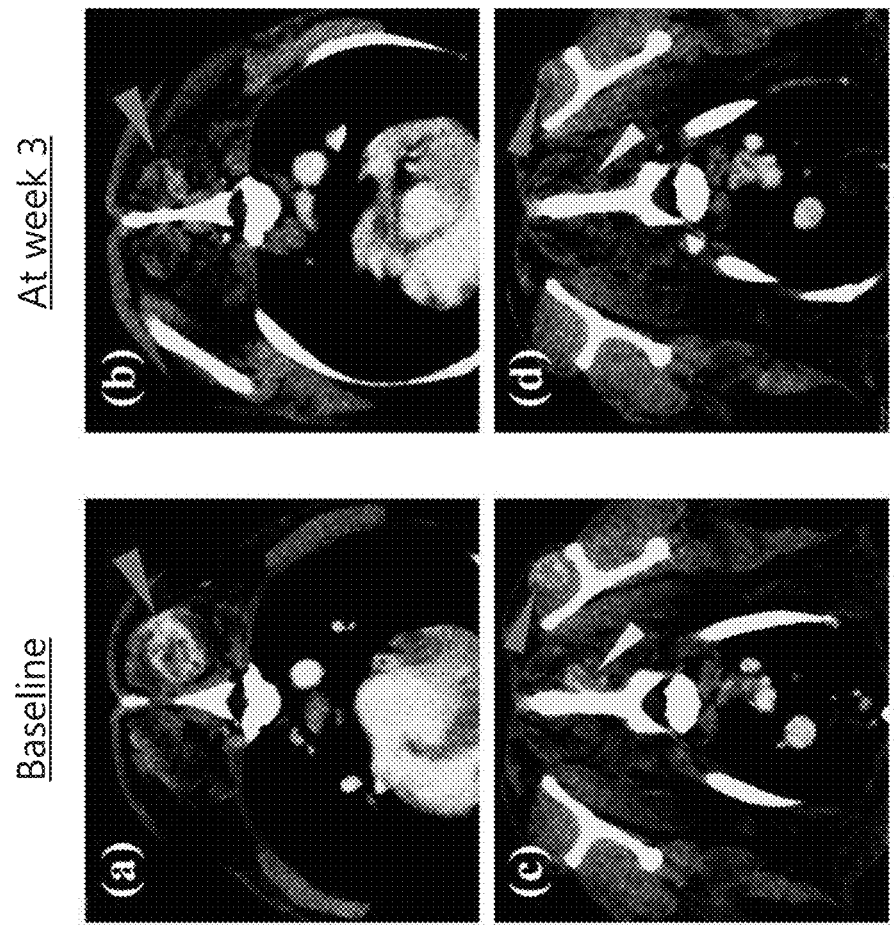
FIG. 12 CT images in a test of treatment by administering rat-canine chimeric anti-PD-L1 antibody c4G12 to a dog with undifferentiated sarcoma. (a,c) Before the start of the treatment, (b,d) at week 3 of the treatment. A remarkable reduction of tumor was recognized upon two administrations of the antibody.

(3) Clinical Trial 2: Rat-canine chimeric anti-PD-L1 antibody c4G12 was administered intravenously into a dog with undifferentiated sarcoma whose primary lesion was PD-L1 positive (FIG. 9B) and who had a plurality of metastatic lesions in muscles throughout the body (west highland white terrier, castrated male, 12-year-old, about 8 kg in body weight) at 5 mg/kg, every 2 weeks, 2 times in total. At week 3 from the start of treatment, a clear regression of tumor was recognized (FIG. 12).

Figure 13:
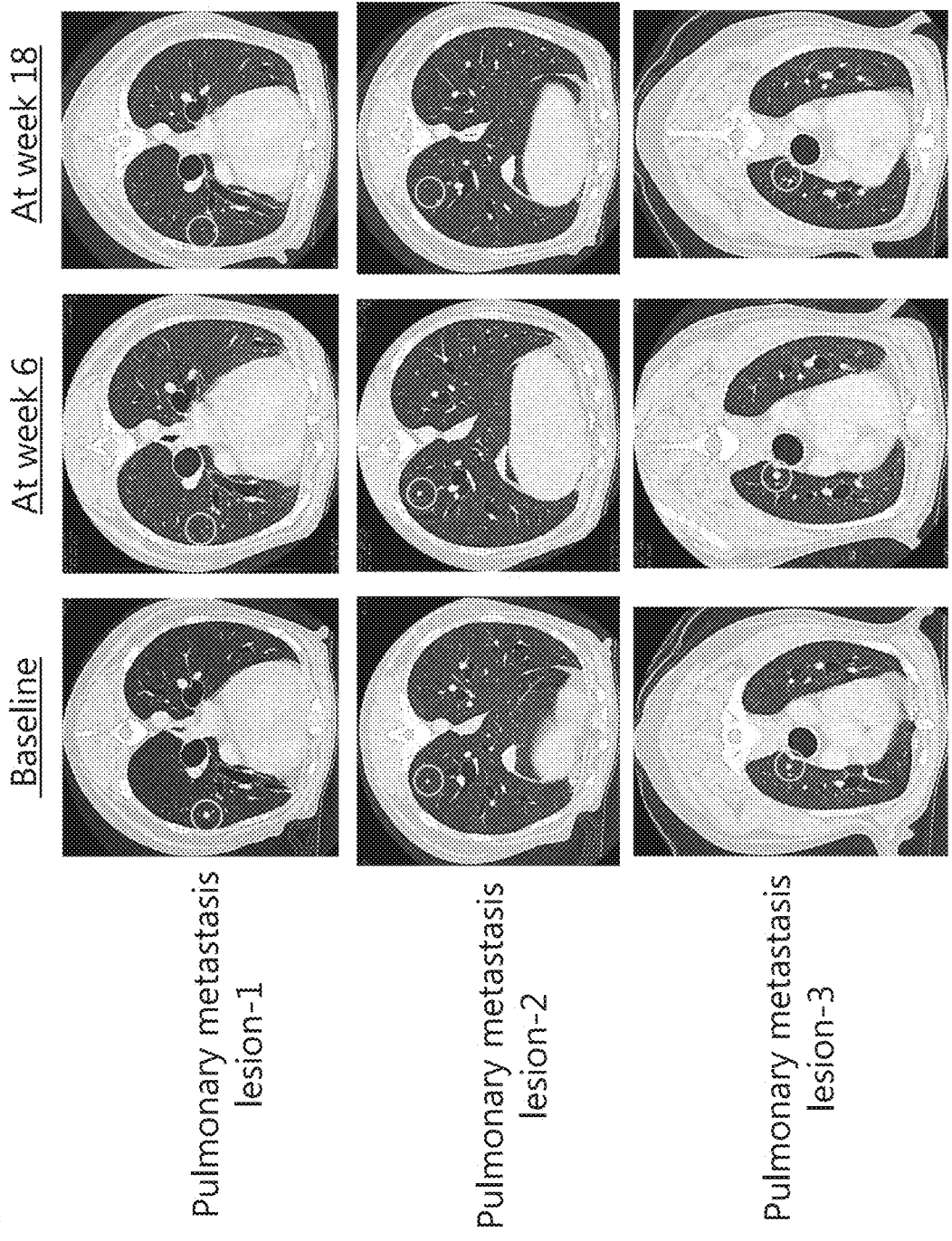
FIG. 13 CT images in a test of treatment by administering rat-canine chimeric anti-PD-L1 antibody c4G12 to dogs with oral melanoma (pulmonary metastatic cases). (a,d,g) Before the start of the treatment, (b,e,h) at week 6 of the treatment, and (c,f,i) at week 18 of the treatment. A plurality of pulmonary metastatic lesions disappeared upon nine administrations of the antibody.
Figure 14:
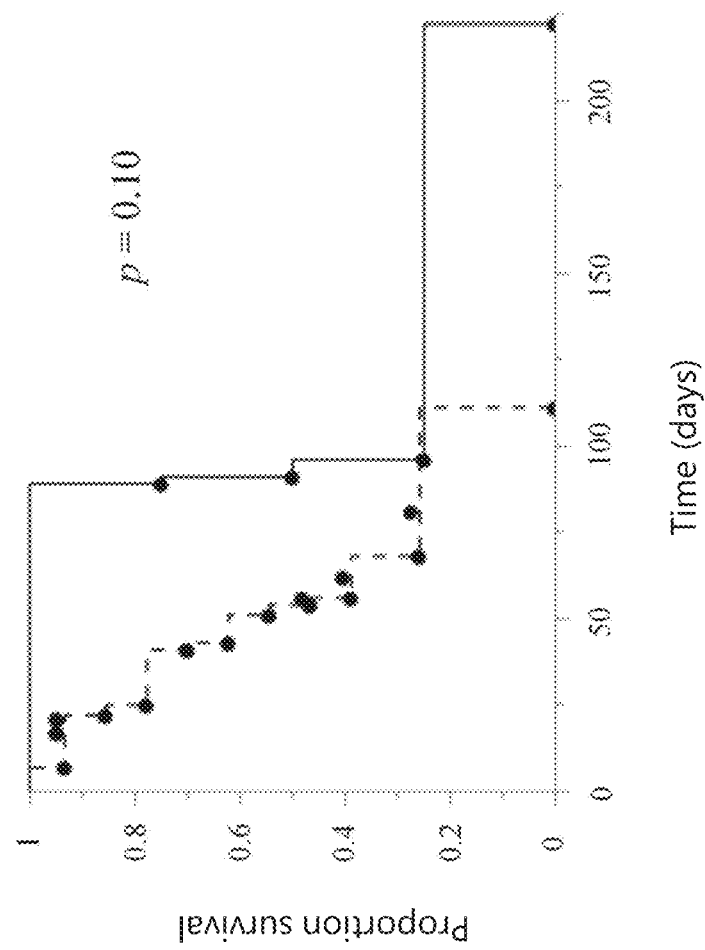
FIG. 14 Time-dependent changes in the proportion survival of dogs with oral melanoma after the occurrence of pulmonary metastasis. In the antibody administration group, the survival duration may have been prolonged compared to the control group.

(4) Clinical Trial 3: Rat-canine chimeric anti-PD-L1 antibody c4G12 was administered intravenously into a dog with oral melanoma whose primary lesion had been removed by surgery (beagle, spayed female, 11-year-old, about 10 kg in body weight) at 2 mg/kg or 5 mg/kg, every 2 weeks, 9 times in total. At week 18 after the start of treatment, a plurality of pulmonary metastatic lesions disappeared (FIG. 13), (5) Clinical Trial 4: Rat-canine chimeric anti-PD-L1 antibody c4G12 was administered intravenously into 4 dogs with oral melanoma with pulmonary metastasis at 2 mg/kg or 5 mg/kg, every 2 weeks. Although no clear reduction in tumor size was observed during the observation period, the duration of the treated dogs' survival after confirmation of pulmonary metastasis tended to be longer than that of a control group (antibody not administered, historical control group: n=15) (FIG. 14). Therefore, the survival duration may have been extended by antibody administration.

2.16 CDR Analysis of Anti-PD-L1 Antibody

The complementarity-determining regions (CDRs) of rat anti-bovine PD-L1 antibody 4G12 were determined using NCBI IGBLAST (http://www.ncbi.nlm.nih.gov/igblast/). The results are shown in FIG. 15.

[Example 2] Application of Anti-PD-L1 Antibody to Other Animal Species 1.1 Identification of Ovine, Porcine and Water Buffalo PD-L1 Genes In order to determine the full-lengths of the coding sequences (CDSs) of ovine, porcine and water buffalo PD-L1 cDNAs, primers for amplifying the full lengths of CDSs from the nucleotide sequences of ovine, porcine and water buffalo PD-L1 genes (GenBank accession number, XM_004004362, NM_001025221 and XM_613366) were first designed (ovPD-L1 CDS F and R; poPD-L1 CDS F and R; buPD-L1 CDS F1, R1, F2 and R2), and then PCR was performed. For the resultant amplified products, nucleotide sequences were determined with a capillary sequencer according to conventional methods (Mingala C N, Konnai S, Ikebuchi R, Ohashi K. Comp. Immunol. Microbiol. Infect. Dis. 2011 January; 34(1):55-63; Water buffalo PD-L1 gene was identified in this article).

```
Primer (ovTPD-L I CDS F):
                                    (SEQ ID NO: 109)
ATGAGGATATATTAGTGTCTTAACAT Primer (ovPD-L1 CDS R):
                                    (SEQ ID NO: 110)
TIACGTCTCCTCAAAATGTG Primer (poPD-L1 CDS F):
                                    (SEQ ID NO: 111)
ATGAGGATATGTAGTATCTTTACAT Primer (poPD-L1 CDS R):
                                    (SEQ ID NO: 112)
TTACGTCTCCTCAAATTGTGT Primer (buPD-L1 CDS F1):
                                    (SEQ ID NO: 113)
ATGAGGATATATAGTGTCTT Primer (buPD-L1 CDS R1):
                                    (SEQ ID NO: 114)
GCCACTCAGGACTTGGTGAT Primer (buPD-L1 CDS F2):
                                    (SEQ ID NO: 115)
GGGGGTTTACTGTTGCTTGA Primer (buPD-L1 CDS R2):
                                    (SEQ ID NO: 116)
TTACGTCTCCTCAAAFFGT
```

1.2 Construction of Ovine PD-1, Ovine PD-L1, Porcine PD-1 and Porcine PD-L1 Expressing COS-7 Cells In order to prepare ovine PD-1, ovine PD-L1, porcine PD-1 and porcine PD-L1 expressing plasmids, PCR was performed using a synthesized ovine or porcine PBMC-derived cDNA as a template and primers designed by adding BglII and SmaI (ovine PD-1), HindIII and SmaI (porcine PD-1), or XhoI and SmaI (ovine and porcine PD-L1) recognition sites on the 5' side (ovPD-1-EGFP F and R; ovPD-L1-EGFP F and R; poPD-1-EGFP F and R; or poPD-L1-EGFP F and R). The resultant PCR products were digested with BglII (Takara) and SmaI (Takara) (ovine PD-1), HindIII (Takara) and SmaI (Takara) (porcine PD-1), and XhoI (Takara) and SmaI (Takara) (ovine and porcine PD-L1), then purified with FastGene Gel/PCR Extraction Kit (NIPPON Genetics) and cloned into pEGFP-N2 vector (Clontech) treated with restriction enzymes in the same manner. Expression plasmids were extracted using FastGene Xpress Plasmid PLUS Kit (NIPPON Genetics) and stored at −30° C. until use in experiments. Hereinafter, the thus prepared plasmid is designated as pEGFP-N2-ovPD-1, pEGFP-N2-ovPD-L1, pEGFP-N2-poPD-1 or pEGFP-N2-poPD-L1.

```
Primer (ovPD-1-EGFP F):
                                    (SEQ ID NO: 117)
GAAGATCTATGGGACCCCGCGGGCGCCG Primer (ovPD-1-EGFP R):
                                    (SEQ ID NO: 118)
GACCCGGGGAGGGGCCAGGAGCAGTGTCC
```

```
Primer (ovPD-L1-EGFP F):
                                        (SEQ ID NO: 119)
CCGCTCGAGATGAGGATATATAGTGTCT Primer (ovPD-L1-EGFP R):
                                        (SEQ ID NO: 120)
ATCCCGGGCGTCTCCTCAAAATGTGTAG Primer (poPD-1-EGFP F):
                                        (SEQ ID NO: 121)
ACTAAGCTTATGGGGACCCCGCGGG Primer (poPD-1-EGFP R):
                                        (SEQ ID NO: 122)
ACTCCCGGGGAGGGGCCAAGAGCAGT Primer (poPD-L1-EGFP F):
                                        (SEQ ID NO: 123)
CCGCTCGAGATGAGGATATGTAGTATCTT Primer (poPD-L1-EGPR):
                                        (SEQ ID NO: 124)
ATCCCGGGCGTCTCCTCAAATTGTGTATC
```

COS-7 cells were subcultured at a density of 5×10$^4$ cells/cm$^2$ in 6-well plates, and then cultured overnight in RPMI 1640 medium containing 10% inactivated fetal bovine serum and 0.01% L-glutamine at 37° C. in the presence of 5% CO$_2$. The pEGFP-N2-ovPD-1, pEGFP-N2-ovPD-L1, pEGFP-N2-poPD-1, pEGFP-N2-poPD-L1 or pEGFP-N2 (negative control) was introduced into COS-7 cells at 0.4 µg/cm$^2$ using Lipofectamine 2000 (Invitrogen). The cells were cultured for 48 hours (ovPD-1-EGFP expressing cell, ovPD-L1-EGFP expressing cell, poPD-1-EGFP expressing cell, and poPD-L1-EGFP expressing cell). In order to confirm the expression of ovine PD-1, ovine PD-L1, porcine PD-1 and porcine PD-L1 in the thus prepared expressing cells, intracellular localization of EGFP was visualized with an inverted confocal laser microscope LSM700 (ZEISS) or an all-in-one fluorescence microscope BZ-9000 (KEYENCE).

1.3 Construction of Recombinant Ovine PD-L1 and Porcine PD-L1

In order to amplify the extracellular regions of ovine PD-L1 or porcine PD-L1 estimated from their putative amino acid sequences, primers were designed. Briefly, primers having an NheI or EcoRV recognition sequence added on the 5' side (ovPD-L1-Ig F and R, or poPD-L1-Ig F and R) were designed. PCR was performed using a synthesized ovine or porcine PBMC-derived cDNA as a template. The PCR products were digested with NheI (Takara) and EcoRV (Takara) and purified with FastGene Gel/PCR Extraction Kit (NIPPON Genetics). The thus purified DNAs were individually cloned into pCXN2.1-Rabbit IgG Fc vector (Niwa et al., 1991; Zettlmeissi et al., 1990; kindly provided by Dr. T Yokomizo, Juntendo University Graduate School of Medicine, and modified in the inventors' laboratory) treated with restriction enzymes in the same manner. The expression plasmids were purified with FastGene Xpress Plasmid PLUS Kit (NIPPON Genetics) and stored at −30° C. until use in experiments. Hereinafter, the thus prepared expression plasmids are designated as pCXN2.1-ovPD-L1-Ig and pCXN2.1-poPD-L1-Ig, respectively.

```
Primer (ovPD-L1-Ig F):
                                        (SEQ ID NO: 125)
GACGCTAGCATGAGGATATATAGTGTCT Primer (ovPD-L1-Ig R):
                                        (SEQ ID NO: 126)
GCTCTGATATCCCTCGTTTTTGCTGGAT Primer (poPD-L1-Ig F):
                                        (SEQ ID NO: 127)
GACGCTAGCATGAGGATATGTAGTATCTT Primer (poPD-L1-Ig R):
                                        (SEQ ID NO: 128)
AGCTTGATATCCCTCTTTCTTGCTGGATC
```

Thirty micrograms of pCXN2.1-ovPD-L1-Ig or pCXN2.1-poPD-L1-Ig was introduced into 7.5×10$^7$ Expi293F cells (Life Technologies) using Expifectamin (Life Technologies). After 6-day shaking culture, a culture supernatant was collected. The culture supernatant contained an Fc fusion recombinant protein. The produced Fc recombinant protein was purified from the supernatant using Ab-Capcher Extra (ProteNova). After purification, the buffer was exchanged with PBS (pH 7.4) using PD-10 Desalting Column (GE Healthcare). The resultant recombinant protein was stored at −30° C. until use in Experiment (ovine PD-L1-Ig). Concentrations of purified ovine PD-L1-Ig and porcine PD-L1-Ig were measured with Rabbit IgG ELISA Quantitation Set (BETHYL). For each washing operation in ELISA, Auto Palte Washer BIO WASHER 50 (DS Pharma Biomedical) was used. Absorbance was measured with Microplate Reader MTP-650FA (Corona Electric).

1.4 Reactivity of Rat Anti-Bovine PD-L1 Antibody 4G12 with Ovine and Porcine PD-L1

It was confirmed by flow cytometry that rat anti-bovine PD-L1 monoclonal antibody cross-reacts with ovine and porcine PD-LL. Ovine or Porcine PD-L1-EGFP expressing COS-7 cells were blocked with 10% inactivated goat serum supplemented PBS at room temperature for 15 min and reacted with 10 µg/ml of rat anti-bovine PD-L1 antibody 4G12 at room temperature for 30 min. After washing, the cells were reacted with allophycocyanine-labeled anti-rat Ig goat antibody (Beckman Coulter) at room temperature for 30 min. For analysis, FACS Verse (BD Bioscience) was used. As a negative control antibody, rat IgG2a (κ) isotype control (BD Bioscience) was used. For every washing operation and dilution of antibodies, 1% bovine serum albumin supplemented PBS was used.

Figure 16:
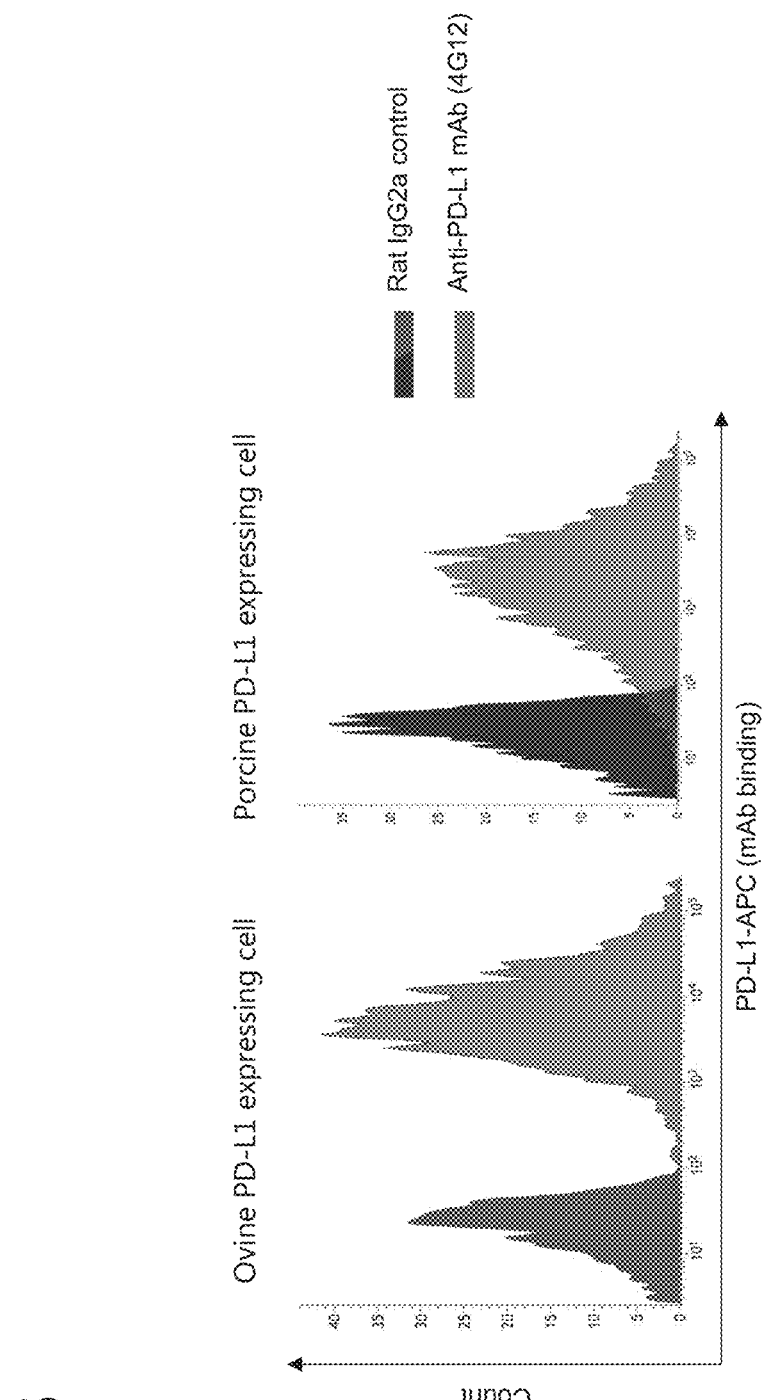
FIG. 16 Cross-reactivity of rat anti-bovine PD-L1 antibody 4G12. It was confirmed that rat anti-bovine PD-L1 antibody 4G12 binds to ovine PD-L1 and porcine PD-L1.

Experimental results are shown in FIG. 16. It was confirmed that rat anti-bovine PD-L1 antibody 4G12 binds to ovine and porcine PD-L1.

1.5 Reactivity of Rat Anti-Bovine PD-L1 Antibody 4G12 with Water Buffalo Leukocytes Peripheral blood of water buffalo (Bubalus bubalis; Asian water buffalo) was hemolyzed with ACK buffer to isolate leukocytes. After blocking with 10% inactivated goat serum supplemented PBS at room temperature for 15 min, reaction with rat anti-bovine PD-L1 antibody 4G12, peridinin-chlorophyll-protein complex/cyanin 5.5-labeled anti-bovine CD14 antibody (mouse IgG1, CAM36A, VMRD) and anti-bovine CD11b antibody (mouse IgG2b, CC126, AbD Serotec) was conducted at room temperature for 30 min. After washing, reaction with allophycocyanine-labelled anti-rat Ig goat antibody (Beckman Coulter) and fluorescein isothiocyanate-labeled anti-mouse IgG2 goat antibody (Beckman Coulter) was conducted at room temperature for 30 min. For analysis, FACS Calibur (BD Biosciences) was used. As a negative control antibody, rat IgG2a (κ) isotype control (BD Biosciences) was used. For every washing operation and dilution of antibodies, 10% inactivated goat serum supplemented PBS was used.

Figure 17:
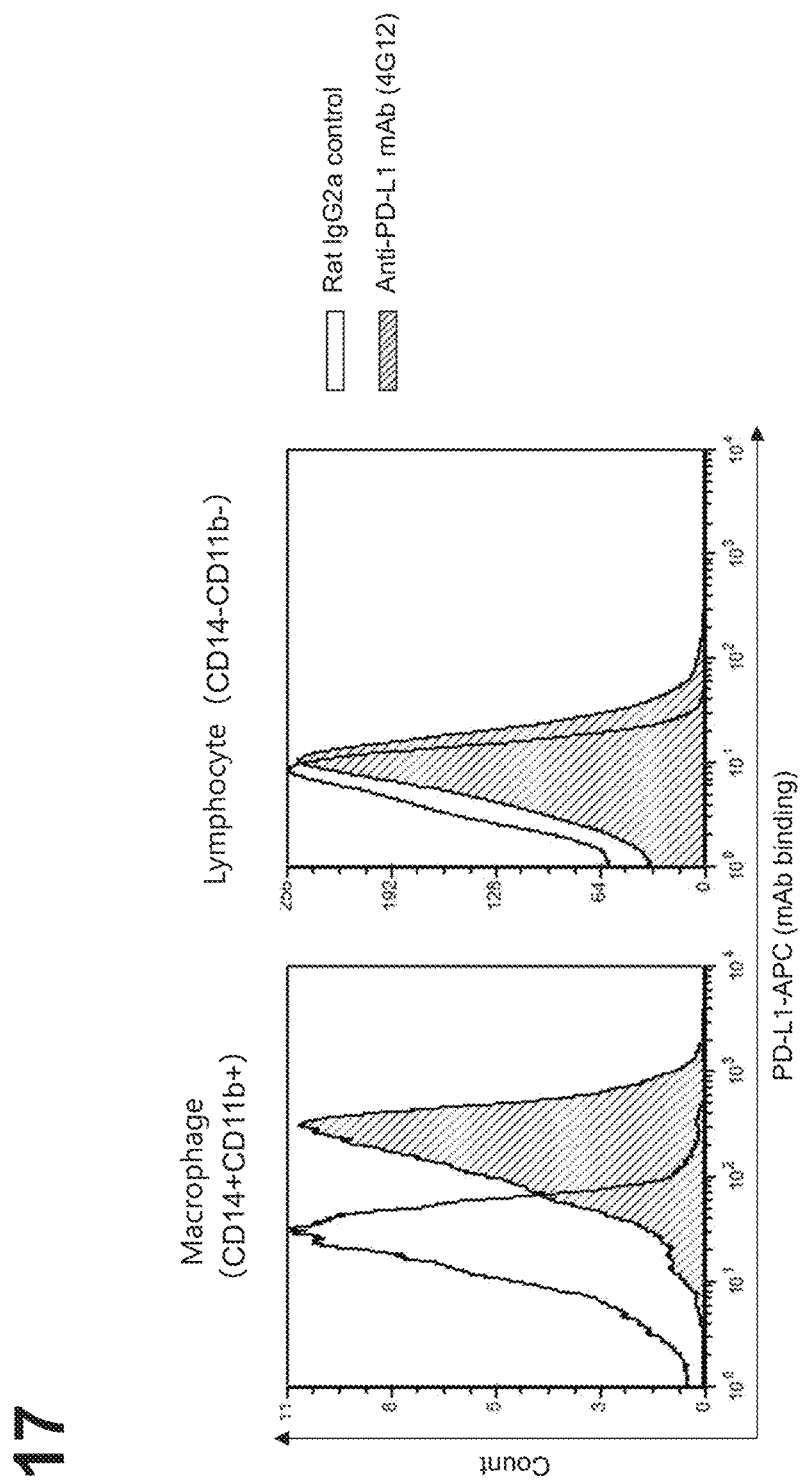
FIG. 17 Reactivity of rat anti-bovine PD-L1 antibody 4G12 with water buffalo leukocytes. Rat anti-bovine PD-L1 antibody 4G12 strongly bound to blood macrophages (CD14+ CD11b+ cells) of water buffalo, whereas rat anti-bovine PD-L1 antibody 4G12 bound weakly to lymphocytes (CD14−CD11b− cells) of water buffalo. It is believed that this difference in binding reflects the expression levels of PD-L1 in macrophages and lymphocytes.

Experimental results are shown in FIG. 17. Rat anti-bovine PD-L1 antibody 4G12 strongly bound to blood macrophages (CD14$^+$ CD11b$^+$ cells) of water buffalo. On the other hand, rat anti-bovine PD-L1 antibody 4G12 weakly bound to lymphocytes (CD14⁻ CD11b⁻ cells) of water buffalo. This difference in binding property is believed to reflect the expression levels of PD-L1 in macrophages and lymphocytes.

1.6 Inhibition Test on Ovine or Porcine PD-1/PD-L1 Binding with Rat Anti-Bovine PD-L1 Antibody 4G12

Using ovine PD-1-EGFP expressing COS-7 cells and ovine PD-L1-Ig recombinant protein, or porcine PD-1-EGFP expressing COS-7 cells and porcine PD-L1-Ig recombinant protein, inhibition of ovine or porcine PD-1/PD-L1 binding by rat anti-bovine PD-L1 antibody (4012) was tested. Briefly, rat anti-bovine PD-L1 antibody 4G12 of various concentrations (0, 1, 5, 10, 20, 50 µg/ml) was reacted in advance with ovine PD-L1-Ig (final concentration 1 µg/ml) or porcine PD-L1-Ig (final concentration 5 µg/ml) at 37° C. for 30 min. Subsequently, the antibody 4G12 was reacted with $2\times10^5$ ovine PD-1-EGFP expressing COS-7 cells or porcine PD-1-EGFP expressing COS-7 cells at 37° C. for 30 min. After washing, ovine PD-L1-Ig or porcine PD-L1-Ig bound to cell surfaces was detected with Alexa Fluor 647-labeled anti-rabbit IgG (H+L) goat F(ab')2 (Life Technologies). For analysis, FACS Verse (BD Biosciences) was used. As a negative control antibody, rat IgG2a (κ) isotype control (BD Biosciences) was used. Taking the proportion of PD-L1-Ig bound cells without antibody addition as 100%, the proportion of PD-L1-Ig bound cells at each antibody concentration was shown as relative value.

Figure 18:
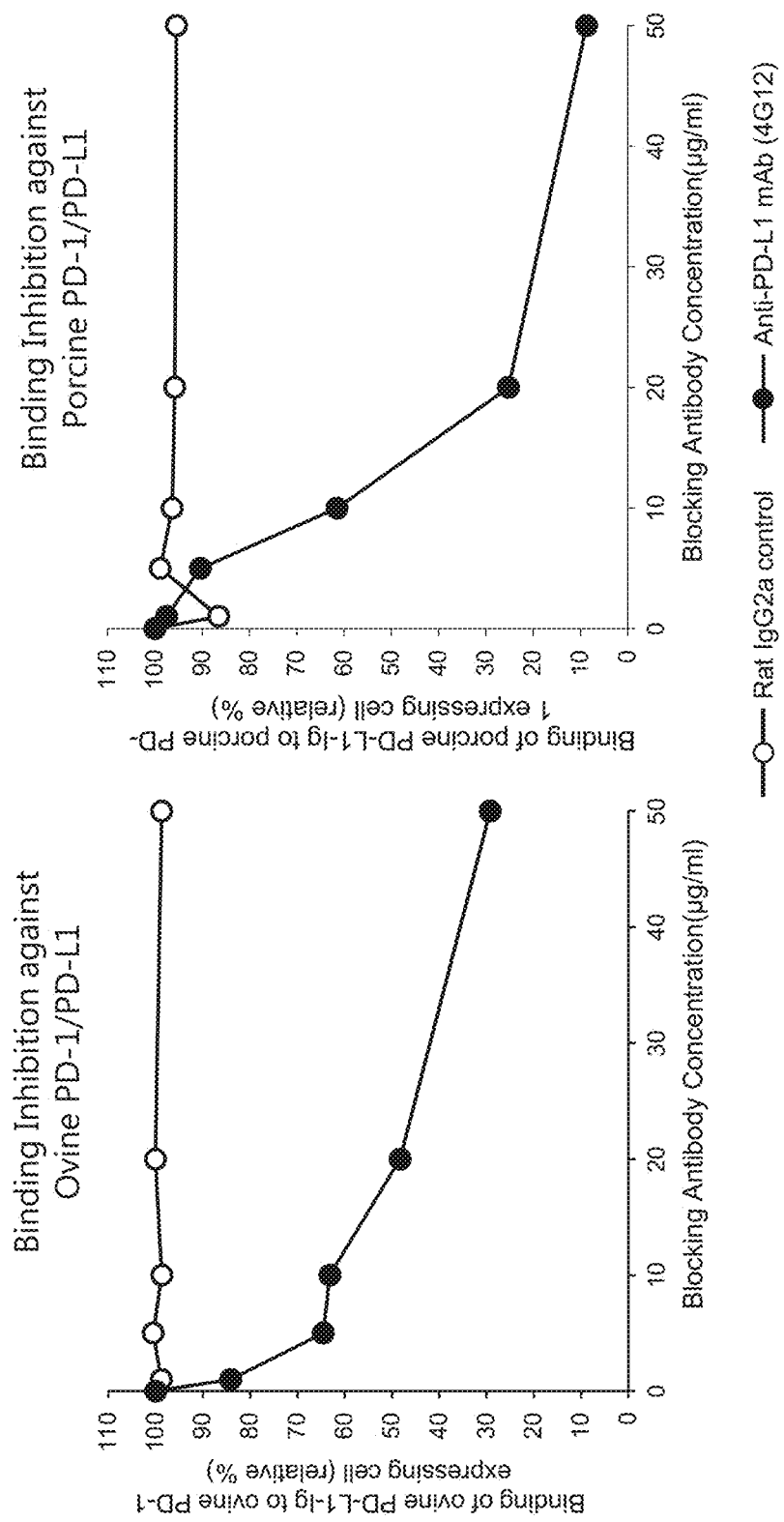
FIG. 18 Inhibition test on rat anti-bovine PD-L1 antibody 4G12 against ovine or porcine PD-1/PD-L1 binding. It was demonstrated that rat anti-bovine PD-L1 antibody 4G12 is capable of inhibiting ovine and porcine PD-1/PD-L1 binding in a concentration dependent manner.

The results revealed that rat anti-bovine PD-L1 antibody 4G12 is capable of inhibiting ovine PD-1/PD-L1 and porcine PD-1/PD-L1 binding in a concentration dependent manner (FIG. 18).

Example 3

1. Introduction

Programmed cell death 1 (PD-1), an immunoinhibitory receptor, and its ligand programmed cell death ligand 1 (PD-L1) are molecules identified by Prof. Tasuku Honjo et al., Kyoto University, as factors which inhibit excessive immune response and are deeply involved in immunotolerance. Recently, it has been elucidated that these molecules are also involved in immunosuppression in tumors. In the subject Example, for the purpose of establishing a novel therapy for bovine infections, the present inventors have prepared a chimeric antibody gene by linking the variable region gene of rat anti-bovine PD-L1 monoclonal antibody (4G12) capable of inhibiting the binding of bovine PD-1 and PD-L1 to the constant region gene of a bovine immunoglobulin (IgG1 with mutations having been introduced into the putative binding sites for Fcγ receptors in CH2 domain to inhibit ADCC activity; see FIG. 19 for amino acid numbers and mutations: 250 E→P, 251 L→V, 252 P→A, 253 G→deletion, 347 A→S, 348 P→S; Ikebuchi R, Konnai S, Okagawa T, Yokoyama K, Nakajima C, Suzuki Y. Murata S, Ohashi K. Immunology 2014 August; 142(4):551-561). This chimeric antibody gene was introduced into Chinese hamster ovary cells (CHO cells). By culturing/proliferating the resultant cells, the present inventors have obtained a rat-bovine chimeric anti-bovine PD-L1 antibody (ch4G12) and confirmed its effect in vitro and in vivo.

2. Materials and Methods

Construction of Bovine PD-1 and PD-L1 Expressing Cells

The nucleotide sequences of the full length cDNAs of bovine PD-1 gene (GenBank accession number AB510901; Ikebuchi R, Konnai S, Sunden Y, Onuma M, Ohashi K. Microbiol. Immunol. 2010 May; 54(5):291-298) and bovine PD-L1 gene (GenBank accession number AB510902; Ikebuchi R, Konnai S, Shirai T, Sunden Y, Murata S, Onuma M, Ohashi K. Vet. Res. 2011 Sep. 26; 42:103) were determined. Based on the resultant genetic information, bovine PD-1 and bovine PD-L1 membrane expressing cells were prepared. First, for preparing bovine PD-1 or PD-L1 expressing plasmid, PCR was performed using a synthesized bovine PBMC-derived cDNA as a template and designed primers having NotI and HindIII (bovine PD-1) recognition sites and NheI and XhoI (bovine PD-L1) recognition sites on the 5' side (boPD-L1-myc F and R; boPD-L1-EGFP F and R). The PCR products were digested with NotI (Takara) and HindIII (Takara; bovine PD-1), NheI (Takara) and XhoI (Takara; bovine PD-L1), purified with FastGene Gel/PCR Extraction Kit (NIPPON Genetics) and cloned into pCMV-Tag1 vector (Agilent Technologies; bovine PD-1) or pEGFP-N2 vector (Clontech; bovine PD-L1) treated with restriction enzymes in the same manner. The resultant expression plasmid of interest was extracted with QIAGEN Plasmid Midi kit (Qiagen) and stored at −30° C. until use in experiments. Hereinafter, the thus prepared expression plasmid is designated as pCMV-Tag1-boPD-1.

```
Primer (boPD-1-myc F):
                              (SEQ ID NO: 133)
ATAIGCGGCCGCATGGGGACCCCGCGGGCGCT Primer (boPD-1-myc R):
                              (SEQ ID NO: 134)
GCGCAAGCTTTCAGAGGGCCAGGAGCAGT Primer (boPD-L1-EGFP F):
                              (SEQ ID NO: 135)
CTAGCTAGCACCATGAGGATATAGTGTCTTAAC Primer (boPD-L1-EGFP R):
                              (SEQ ID NO: 136)
CAATCTCGAGTTACAGACAGAAGATGACTGC
```

Bovine PD-1 membrane expressing cells were prepared by the procedures described below. First, 2.5 µg of pCMV-Tag1-boPD-1 was introduced into $4\times10^6$ CHO-DG44 cells using Lipofectamine LTX (Invitrogen). Forty-eight hours later, the medium was exchanged with CD DG44 medium (Life Technologies) containing 800 µg/ml G418 (Enzo Life Science), 20 ml/L GlutaMAX supplement (Life Technologies), and 18 ml/L 10% Pluronic F-68 (Life Technologies), followed by selection. The resultant expression cells were reacted with rat anti-bovine PD-1 antibody 5D2 at room temperature. After washing, the cells were further reacted with anti-rat IgG microbeads-labeled antibody (Miltenyi Biotec) at room temperature. Cells expressing bovine PD-1 at high levels were isolated with Auto MACS (Miltenyi Biotec). Subsequently, re-isolation was performed in the same manner to obtain still higher purity. The resultant expression cells were subjected to cloning by limiting dilution to thereby obtain a CHO DG44 cell clone expressing bovine PD-1 at high level (bovine PD-1 expressing cells).

Bovine PD-L1 membrane expressing cells were prepared by the procedures described below. First, 2.5 µg of pEGFP-N2-boPD-L1 or pEGFP-N2 (negative control) was introduced into $4\times10^6$ CHO-DG44 cells using Lipofectamine LTX (Invitrogen). Forty-eight hours later, the medium was exchanged with CD DG44 medium (Life Technologies) containing G418 (Enzo Life Science) 800 µg/ml, GlutaMAX supplement (Life Technologies) 20 ml/L, and 10% Pluronic F-68 (Life Technologies) 18 ml/L, followed by selection and cloning by limiting dilution (bovine PD-L1 expressing cell clone). In order to confirm the expression of bovine PD-L1 in the thus prepared expressing cell clone, intracellular localization of EGFP was visualized with an inverted confocal laser microscope LSM700 (ZEISS).

Construction of Soluble Bovine PD-1 and PD-L1

Bovine PD-1-Ig expressing plasmid was constructed by the procedures described below. Briefly, the signal peptide and the extracellular region of bovine PD-1 (GenBank accession number AB510901) were linked to the Fc domain of the constant region of a known bovine IgG1 (GenBank accession number X62916) to prepare a gene sequence. After codons were optimized for CHO cells, gene synthesis was performed in such a manner that NoII recognition sequence, KOZAK sequence, bovine PD-1 signal peptide sequence, bovine PD-1 gene extracellular region sequence, bovine IgG1 Fc region sequence, and XbaI recognition sequence would be located in the gene in this order. It should be noted here that bovine IgG1 was mutated to inhibit ADCC activity; more specifically, mutations were introduced into the putative binding sites for Fcγ receptors of CH2 domain (sites of mutation: 185 E→P, 186 L→V, 187 P→A, 189 G→deletion, 281 A→S, 282 P→S; Ikebuchi R, Konnai S, Okagawa T, Yokoyama K, Nakajima C, Suzuki Y, Murata S, Ohashi K. Immunology 2014 August; 142(4):551-561; the amino acid sequence of PD-1-Ig and the sites of mutation are disclosed in FIG. 2 of this article). The synthesized gene strand was digested with NotI (Takara) and XbaI (Takara), purified with FastGene Gel/PCR Extraction Kit (NIPPON Genetics), and incorporated into the cloning site (NotI and XbaI restriction enzyme recognition sequences downstream of PCMV and between INRBG and PABGH) of expression vector pDN11 (kindly provided by Prof. S. Suzuki, Hokkaido University Research Center for Zoonosis Control) treated with restriction enzymes in the same manner, whereby bovine PD-1-Ig expressing vector was constructed. The expression plasmid was purified with QIAGEN Plasmid Midi kit (Qiagen) and stored at −30° C. until use in experiments. Hereinafter, the thus prepared expression plasmid is designated as pDN11-boPD-1-Ig.

Bovine PD-L1-Ig expressing plasmid was constructed by the procedures described below. In order to amplify the signal peptide and the extracellular region of bovine PD-L1 (GenBank accession number AB510902), primers were designed that had NheI and EcoRV recognition sites added on the 5' side (boPD-L1-Ig F and R). PCR was performed using a synthesized bovine PBMC-derived cDNA as a template. The PCR products were digested with NheI (Takara) and EcoRV (Takara), purified with FastGene Gel/PCR Extraction Kit (NIPPON Genetics) and cloned into pCXN2.1-Rabbit IgG1 Fc vector (Niwa et al., 1991; Zettdmeissl et al., 1990; kindly provided by Dr. T. Yokomizo, Juntendo University Graduate School of Medicine, and modified in the inventors' laboratory) treated with restriction enzymes in the same manner. The expression plasmid was purified with QIAGEN Plasmid Midi kit (Qiagen) or FastGene Xpress Plasmid PLUS Kit (NIPPON Genetics) and stored at −30° C. until use in experiments. Hereinafter, the thus prepared expression plasmid is designated as pCXN2.1-boPD-L1-Ig.

```
Primer (hoPD-L1-Ig F):
                           (SEQ ID NO: 137)
GCTAGCATGAGGATATATAGTGTCTTAAC Primer (boPD-L1-Ig R):
                           (SEQ ID NO: 138)
GATATCATTCCTCTTTTTGCTGGAT
```

Soluble bovine PD-1-Ig expressing cells were prepared by the procedures described below. Briefly, 2.5 μg of pDN11-boPD-1-Ig was introduced into 4×10⁶ CHO-DG44 cells using Lipofectamine LTX (Invitrogen). Forty-eight hours later, the medium was exchanged with OptiCHO AGT medium (Life Technologies) containing 800 μg/ml G418 (Enzo Life Science) and 20 ml/L GlutaMAX supplement (Life Technologies). After cultured for 3 weeks, the cells were subjected to selection. Briefly, the concentrations of the Fc fusion recombinant protein in the culture supernatants of the resultant cell clones were measured by ELISA using anti-bovine IgG F(c) rabbit polyclonal antibody (Rockland) to thereby select those cell clones that express the Fc fusion recombinant protein at high levels. The resultant highly expressing cell clone was transferred to a G418-free medium and cultured under shaking for 14 days, followed by collection of a culture supernatant. The culture supernatant containing the Fc fusion recombinants protein was ultrafiltered with Centricon Plus-70 (Millipore). Then, the Fc fusion recombinant protein was purified with Ab-Capcher Extra (ProteNova). After purification, the buffer was exchanged with phosphate-buffered physiological saline (PBS; pH 7.4) using PD-10 Desalting Column (GE Healthcare). The resultant protein was stored at −30° C. until use in experiments (bovine PD-1-Ig). The concentration of the purified bovine PD-1-Ig was measured by ELISA using IgG F(c) rabbit polyclonal antibody (Rockland). For each washing operation in ELISA, Auto Plate Washer BIO WASHER 50 (DS Pharma Biomedical) was used. Absorbance was measured with Microplate Reader MTP-650FA (Corona Electric).

Soluble bovine PD-L1-Ig expressing cells were prepared by the procedures described below. Briefly, 30 μg of pCXN2.1-boPD-L1-Ig was introduced into 7.5×10⁷ Expi293F cells (Life Technologies) using Expifectamine (Life Technologies). After 7-day culture under shaking, the culture supernatant was collected. The recombinant protein was purified from the supernatant using Ab-Capcher Extra (ProteNova; bovine PD-L1-Ig). After purification, the buffer was exchanged with PBS (pH 7.4) using PD MiniTrap G-25 (GE Healthcare). The resultant protein was stored at −30° C. until use in experiments (bovine PD-L1-Ig). The concentration of the purified bovine PD-L1-Ig was measured using Rabbit IgG ELISA Quantitation Set (Bethyl). For each washing operation in ELISA, Auto Plate Washer BIO WASHER 50 (DS Pharma Biomedical) was used. Absorbance was measured with Microplate Reader MTP-650FA (Corona Electric).

Preparation of Rat Anti-Bovine PD-L1 Monoclonal Antibody Producing Cells Rat was immunized in the footpad with bovine PD-L1-Ig (Ikebuchi R, Konnai S, Okagawa T, Yokoyama K. Nakajima C, Suzuki Y, Murata S, Ohashi K. Immunology 2014 August; 142(4):551-561; bovine PD-L1-Ig was prepared by the method disclosed in this article and used for immunization). Hybridomas were established by the iliac lymph node method to thereby obtain rat anti-bovine PD-L1 monoclonal antibody producing hybridoma 4G12. With respect to the method of establishment of rat anti-bovine PD-L1 monoclonal antibody, details are disclosed in the following non-patent document (Ikebuchi R, Konnai S, Okagawa T. Yokoyama K, Nakajima C, Suzuki Y, Murata S, Ohashi K. Vet. Res. 2013 Jul. 22; 44:59; Ikebuchi R, Konnai S, Okagawa T, Yokoyama K. Nakajima C, Suzuki Y, Murata S, Ohashi K. Immunology 2014 August; 142(4): 551-561).

Preparation of Rat-Bovine Chimeric Anti-Bovine PD-L1 Antibody Expressing Vector Rat-bovine chimeric anti-bovine PD-L1 antibody ch4G12 was established by fusing the antibody constant regions of bovine IgG1 and Igλ with rat anti-bovine PD-L1 antibody 4012 being used as an antibody variable region.

Figure 20:
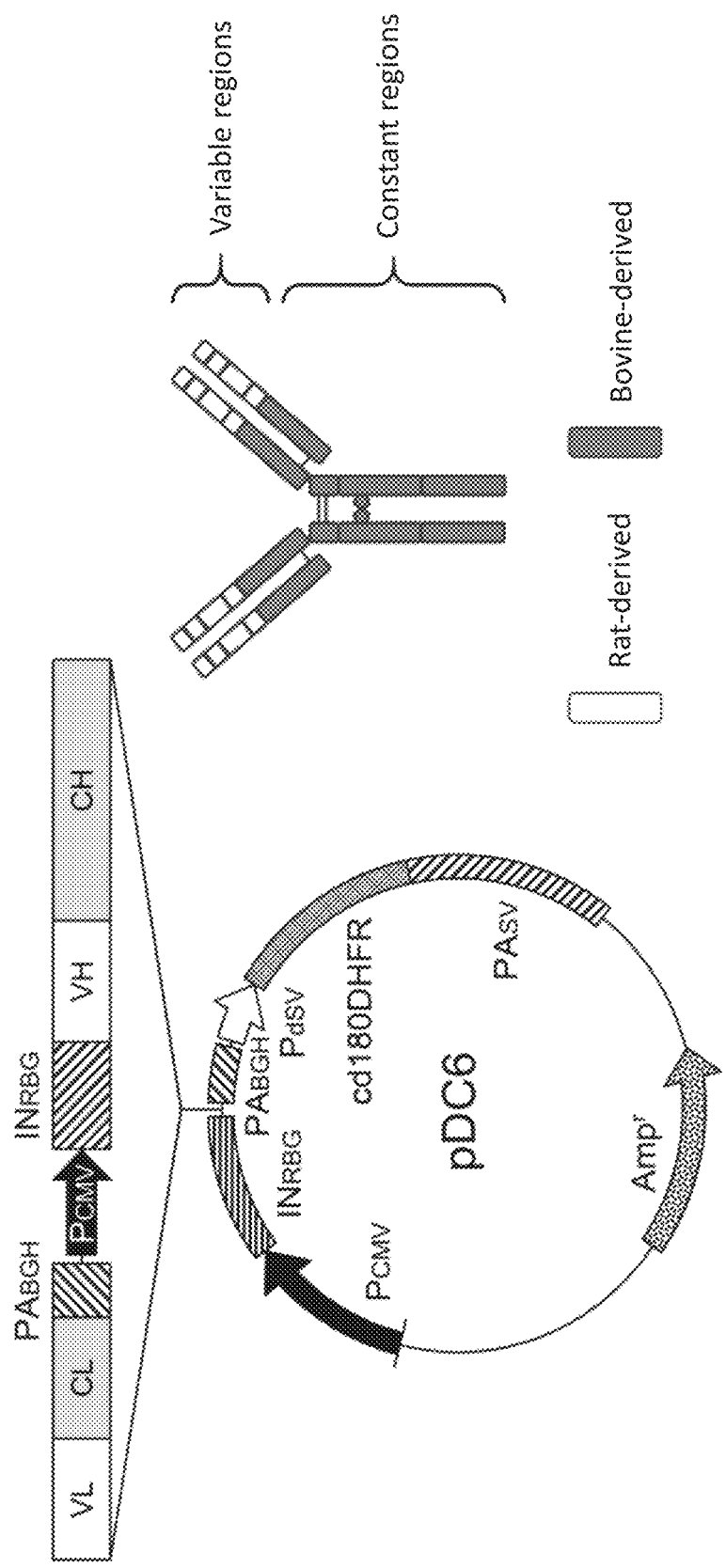
FIG. 20 Schematic drawings of pDC6 vector and rat-bovine chimeric anti-bovine PD-L1 antibody ch4G12.

First, the genes of heavy chain and light chain variable regions were identified from a hybridoma that would produce rat anti-bovine PD-L1 antibody 4G12. Subsequently, a gene sequence was prepared in which the heavy chain and the light chain variable regions of the antibody 4G12 were linked to known constant regions of bovine IgG1 (heavy chain; modified from GenBank Accession number X62916) and bovine Igλ (light chain; GenBank Accession number X62917), respectively, and codon optimization was carried out [rat-bovine chimeric anti-bovine PD-L1 antibody ch4G12: SEQ ID NOS: 105 and 106 (amino acid sequences), SEQ ID NOS: 107 and 108 (nucleotide sequences after codon optimization)]. It should be noted that in order to suppress the ADCC activity of bovine IgG1, mutations were added to the putative binding sites of Fcγ receptors in CH2 domain (See FIG. 19 for amino acid numbers and mutations: 250 E→P, 251 L→V, 252 P→A, 253 G→deletion, 347 A→S, 348 P→S; Ikebuchi R, Konnai S, Okagawa T, Yokoyama K, Nakajima C, Suzuki Y, Murata S, Ohashi K. Immunology 2014 August; 142(4):551-561). Then, the gene was artificially synthesized in such a manner that NotI recognition sequence, KOZAK sequence, chimeric antibody light chain sequence, poly-A addition signal sequence (PABGH), promoter sequence (PCMV), SacI recognition sequence, intron sequence (INRBG), KOZAK sequence, chimeric antibody heavy chain sequence and XbaI recognition sequence would be located in this order. The synthesized gene strand was digested with NotI (Takara) and XbaI (Takara), purified with FastGene Gel/PCR Extraction Kit (NIPPON Genetics) and cloned into the cloning site (NoII and XbaI restriction enzyme recognition sequences downstream of PCMV and between INRBG and PABGH) of expression plasmid pDC6 (kindly provided by Prof. S. Suzuki, Hokkaido University Research Center for Zoonosis Control) treated with restriction enzymes in the same manner (FIG. 20). The resultant plasmid was extracted with QIAGEN Plasmid Midi kit (Qiagen) and stored at −30° C. until use in experiments. Hereinafter, the thus prepared expression plasmid is designated as pDC6-boPD-L1ch4G12.

Expression of Rat-Bovine Chimeric Anti-Bovine PD-L1 Antibody The pDC6-boPD-L1ch4G12 was transfected into CHO-DG44 cells (CHO-DG44 (dfhr$^{-/-}$)) which were a dihydrofolate reductase deficient cell. Forty-eight hours later, the medium was exchanged with OptiCHO AGT medium (Life Technologies) containing 20 ml/L GlutaMAX supplement (Life Technologies). After cultured for 3 weeks, the cells were subjected to selection and cloning by limiting dilution. Subsequently, the concentrations of the chimeric antibody in the culture supernatants were measured by dot blotting and ELISA using anti-bovine IgG F(c) rabbit polyclonal antibody (Rockland) to thereby select high expression clones. Further, the selected clones expressing rat-bovine chimeric anti-bovine PD-L1 antibody at high levels were subjected to gene amplification treatment by adding a load with 60 nM methotrexate (Mtx)-containing medium. The thus established cell clone stably expressing rat-bovine chimeric anti-bovine PD-L1 antibody was transferred into Mtx-free Opti-CHO AGT medium and cultured under shaking for 14 days (125 rpm, 37° C., 5% CO$_2$). Chimeric antibody production in the culture supernatant was measured by ELISA using anti-bovine IgG F(c) rabbit polyclonal antibody (Rockland). For each washing operation in ELISA, Auto Plate Washer BIO WASHER 50 (DS Pharma Biomedical) was used. Absorbance was measured with Microplate Reader MTP-650FA (Corona Electric). The culture supernatant at day 14 was centrifuged at 10,000 g for 10 min to remove cells, and the centrifugal supernatant was passed through a Steritop-GP 0.22 μm filter (Millipore) for sterilization and then stored at 4° C. until it was subjected to purification.

Purification of Rat-Bovine Chimeric Anti-Bovine PD-L1 Antibody

From the culture supernatant prepared as described above, each chimeric antibody was purified using Ab Capcher Extra (ProteNova). An open column method was used for binding to resin; PBS pH 7.4 was used as an equilibration buffer and a wash buffer. As an elution buffer, IgG Elution Buffer (Thermo Fisher Scientific) was used. As a neutralization buffer, IM Tris (pH 9.0) was used. The purified antibody was subjected to buffer exchange with PBS (pH 7.4) using PD-10 Desalting Column (GE Healthcare) and concentrated using Amicon Ultra-15 (50 kDa, Millipore). The thus purified chimeric antibody was passed through a 0.22 μm syringe filter (Millipore) for sterilization and stored at 4° C. until use in experiments.

Figure 21:
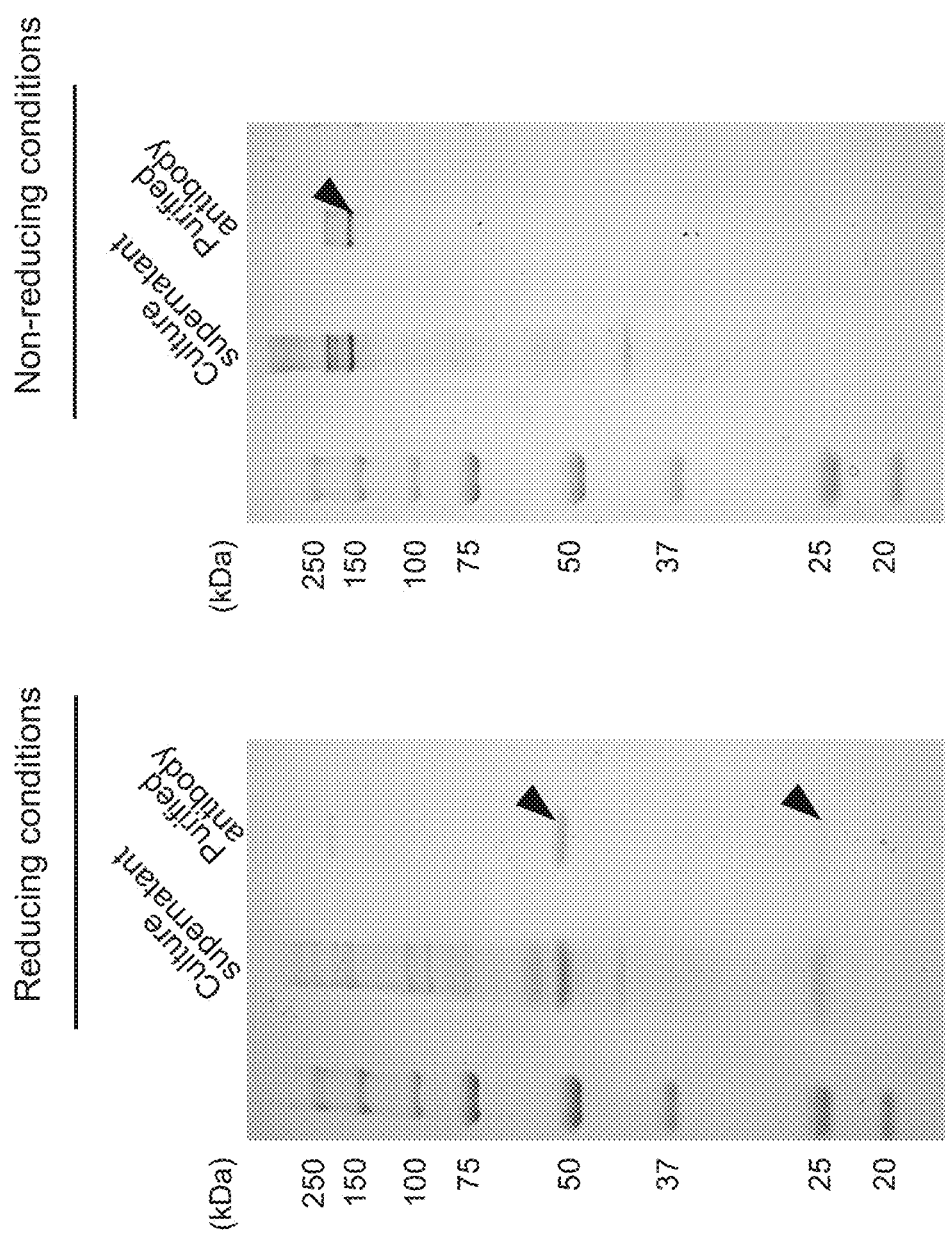
FIG. 21 Confirmation of the purity of purified rat-bovine chimeric anti-bovine PD-L1 antibody ch4G12.

Confirmation of the Purity of Purified Rat-Bovine Chimeric Anti-Bovine PD-L1 Antibody (FIG. 21)

In order to confirm the purity of purified rat-bovine chimeric anti-bovine PD-L1 antibody, antibody proteins were detected by SDS-PAGE and CBB staining. Using 10% acrylamide gel, the purified rat-bovine chimeric antibody was electrophoresed under reducing conditions (reduction with 2-mercaptoethanol from Sigma-Aldrich) and non-reducing conditions. Bands were stained with Quick-CBB kit (Wako) and decolored in distilled water. The results are shown in FIG. 21. Bands were observed at predicted positions, that is, at 25 kDa and 50 kDa under reducing conditions and at 150 kDa under non-reducing conditions.

Figure 22:
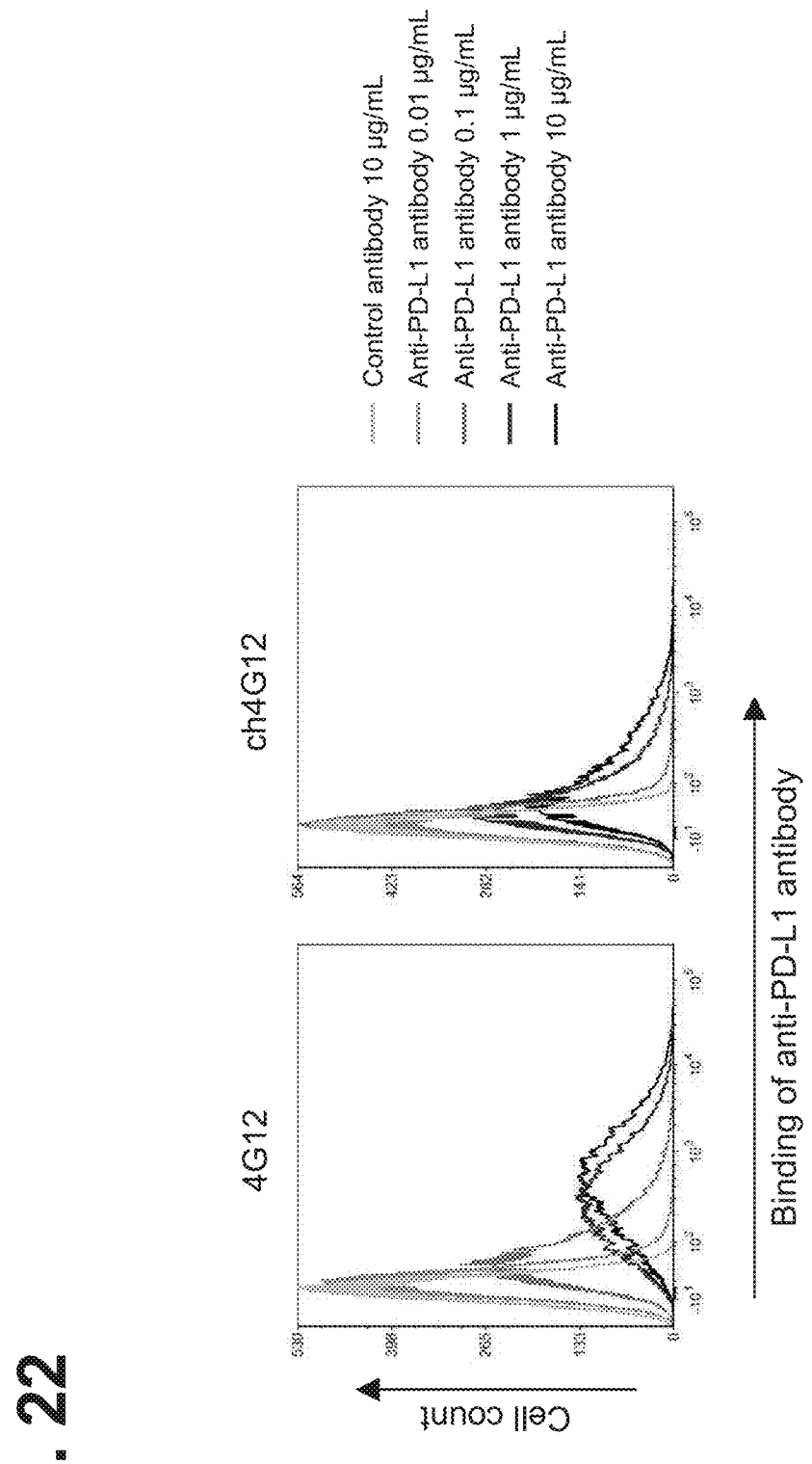
FIG. 22 Binding specificity of rat-bovine chimeric anti-bovine PD-L1 antibody ch4G12.

Binding Specificity of Rat-Bovine Chimeric Anti-Bovine PD-L1 Antibody (FIG. 22)

It was confirmed by flow cytometry that the rat-bovine chimeric anti-bovine PD-L1 antibody specifically binds to the bovine PD-L1 expressing cells (described above). First, rat anti-bovine PD-L1 antibody 4G12 or rat-bovine chimeric anti-bovine PD-L1 antibody ch4G12 was reacted with bovine PD-L1 expressing cells at room temperature for 30 min. After washing, APC-labeled anti-rat Ig goat antibody (Southern Biotech) or Alexa Fluor 647-labeled anti-bovine IgG (H+L) goat F(ab')2 (Jackson ImmunoResearch) was reacted at room temperature for 30 min. As negative control antibody, rat IgG2a (k) isotype control (BD Biosciences) or bovine IgG1 antibody (Bethyl) was used. After washing, each rat antibody or rat-bovine chimeric antibody bound to cell surfaces was detected by FACS Verse (BD Biosciences). For every washing operation and dilution of antibody, PBS supplemented with 1% bovine serum albumin (Sigma-Aldrich) was used.

The experimental results are shown in FIG. 22. It was revealed that rat-bovine chimeric anti-bovine PD-L1 antibody ch4G12 binds to bovine PD-L1 expressing cells in the same manner as rat anti-bovine PD-L1 antibody 4G12.

Figure 23:
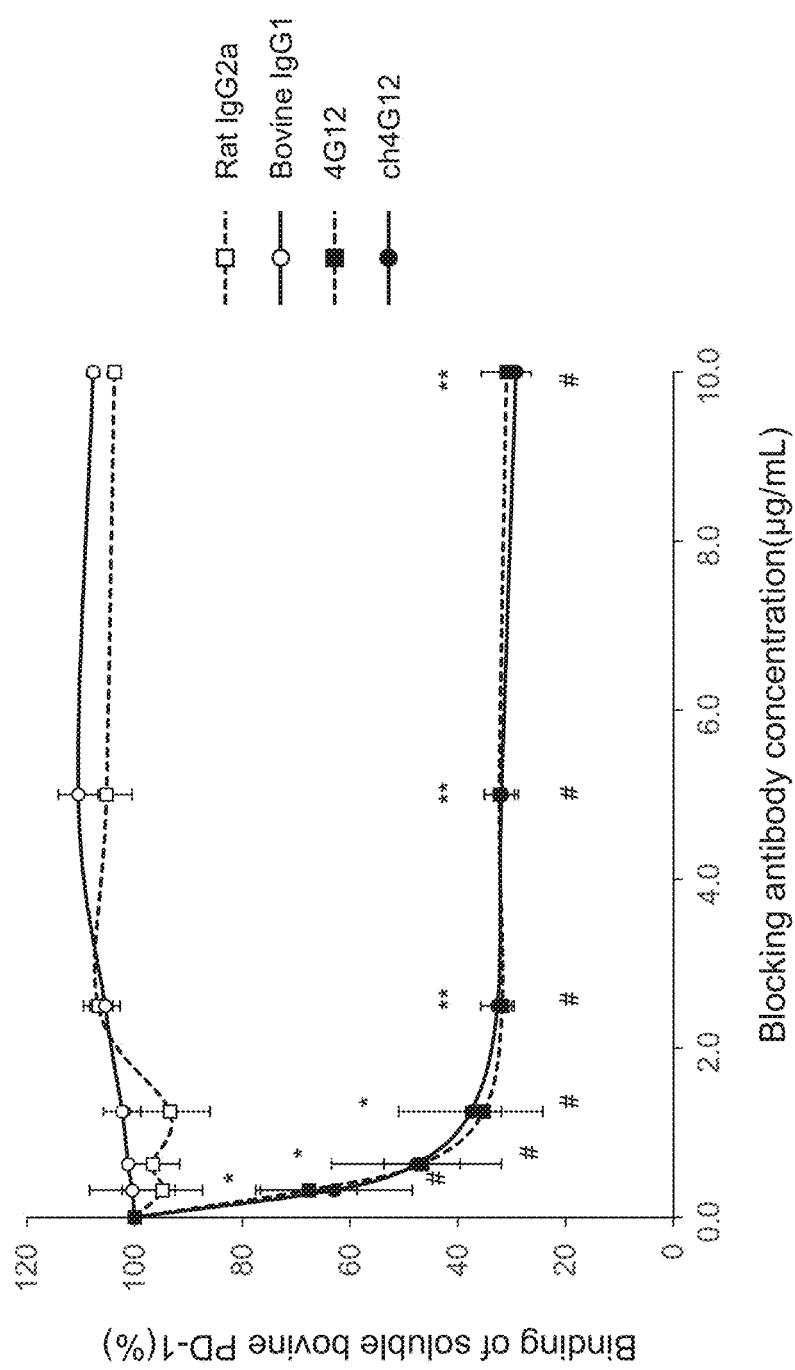
FIG. 23 Inhibitory activity of rat-bovine chimeric anti-bovine PD-L1 antibody ch4G12 against bovine PD-1/PD-L1 binding (the test results of inhibition against binding of bovine PD-L1 expressing cells and soluble bovine PD-1).

Inhibitory Activity of Rat-Bovine Chimeric Anti-PD-L1 Antibody against Bovine PD-1/PD-L1 Binding (1) Binding Inhibition Test on Bovine PD-L1 Expressing Cells and Soluble Bovine PD-1 (FIG. 23)

Using bovine PD-L1 expressing cells (described above) and bovine PD-1-Ig (described above), bovine PD-1/PD-L1 binding inhibition by anti-bovine PD-L1 antibody was tested. First, $2\times10^5$ bovine PD-L1 expressing cells were reacted with various concentrations (0, 0.32, 0.63, 1.25, 2.5, 5 or 10 µg/ml) of rat anti-bovine PD-L1 antibody 4G12 or rat-bovine chimeric anti-bovine PD-L1 antibody ch4G12 at room temperature for 30 min. As negative control antibody, rat IgG2a (w) isotype control (BD Biosciences) or bovine IgG1 antibody (Bethyl) was used. After washing, bovine PD-1-Ig labeled with biotin using Lightning-Link Type A Biotin Labeling Kit (Innova Bioscience) was added to a final concentration of 2 µg/ml, followed by reaction for another 30 min at room temperature. Subsequently, after washing, bovine PD-1-Ig bound to cell surfaces was detected with APC-labeled streptavidin (BioLegend). For analysis, FACS Verse (BD Biosciences) was used. For every washing operation and dilution of antibody. PBS supplemented with 1% bovine serum albumin (Sigma-Aldrich) was used. Taking the proportion of PD-1-Ig bound cells without antibody addition as 100%, the proportion of PD-1-Ig bound cells at each antibody concentration was shown as relative value.

The experimental results are shown in FIG. 23. It was revealed that like rat anti-bovine PD-L1 antibody 4G12, rat-bovine chimeric anti-bovine PD-L1 antibody ch4G12 is capable of inhibiting bovine PD-1/PD-L1 binding in a concentration dependent manner.

Figure 24:
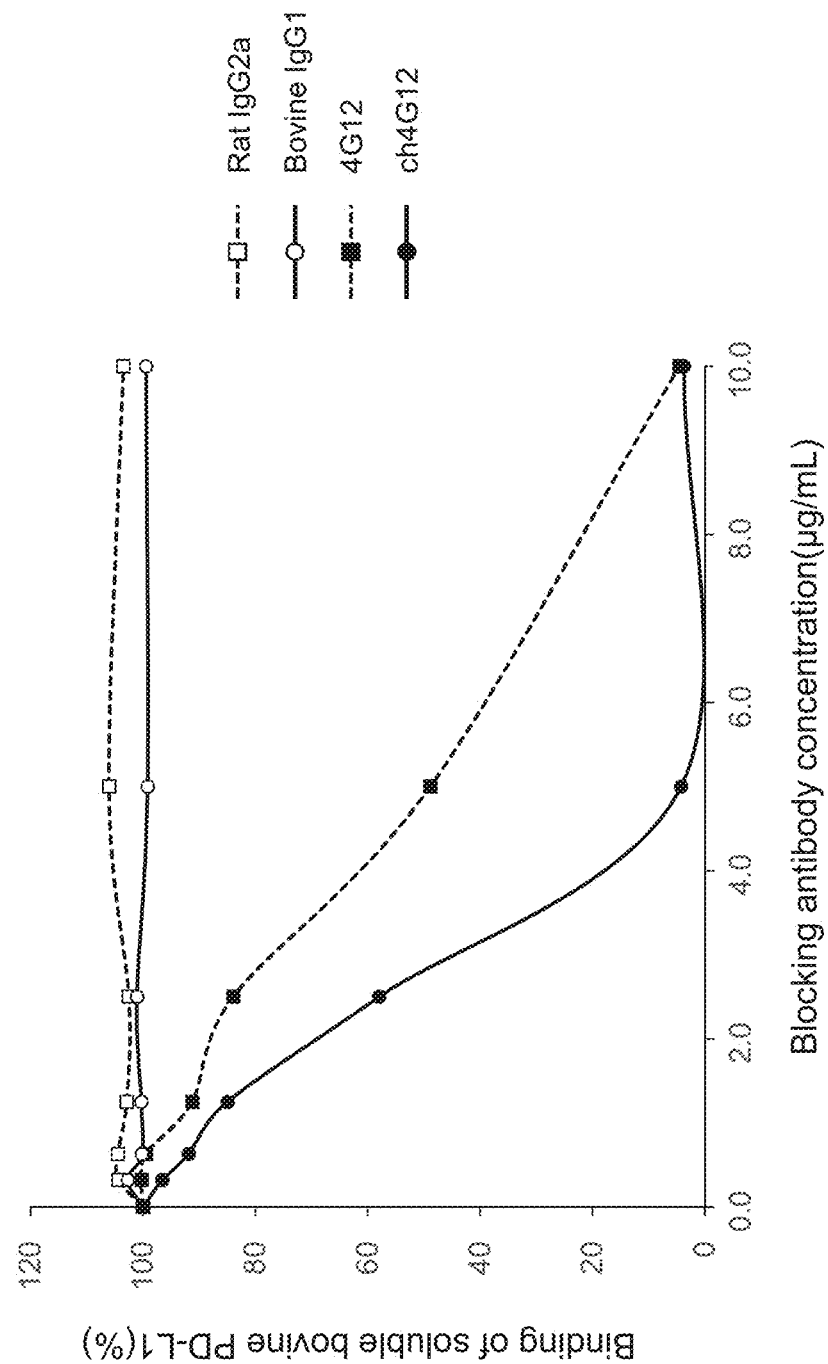
FIG. 24 Inhibitory activity of rat-bovine chimeric anti-bovine PD-L1 antibody ch4G12 against bovine PD-1/PD-L1 binding (the test results of inhibition against binding of bovine PD-1 expressing cells and soluble bovine PD-L1).

(2) Binding Inhibition Test on Bovine PD-1 Expressing Cells and Soluble Bovine PD-L1 (FIG. 24)

Using bovine PD-1 expressing cells (described above) and bovine PD-L1-Ig (described above), bovine pD-1/PD-L1 binding inhibition by anti-bovine PD-L1 antibody was tested. First, rat anti-bovine PD-L1 antibody 4G12 or rat-bovine chimeric anti-bovine PD-L1 antibody ch4G12 at a final concentration of 0, 0.32, 0.63, 1.25, 2.5, 5 or 10 µg/ml and bovine PD-L1-Ig at a final concentration of 1 µg/ml were placed in 96-well plates, where they were reacted at room temperature for 30 min. The resultant mixture was reacted with $2\times10^5$ bovine PD-1 expressing cells at room temperature for 30 min. As negative control antibody, rat IgG2a (κ) isotype control (BD Biosciences) or bovine IgG1 antibody (Bethyl) was used. After washing, Alexa Fluor 647-labeled anti-rabbit IgG (H+L) goat F(ab')2 (Life Technologies) was reacted at room temperature for 30 min to thereby detect bovine PD-L1-Ig bound to cell surfaces. For analysis, FACS Verse (BD Biosciences) was used. For every washing operation and dilution of antibody. PBS supplemented with 1% bovine serum albumin (Sigma-Aldrich) was used. Taking the proportion of PD-L1-Ig bound cells without antibody addition as 100%, the proportion of PD-L1-Ig bound cells at each antibody concentration was shown as relative value.

The experimental results are shown in FIG. 24. It was revealed that like rat anti-bovine PD-L1 antibody 4G12, rat-bovine chimeric anti-bovine PD-L1 antibody ch4G12 is capable of inhibiting bovine PD-1/PD-L1 binding in a concentration dependent manner.

Figure 25:
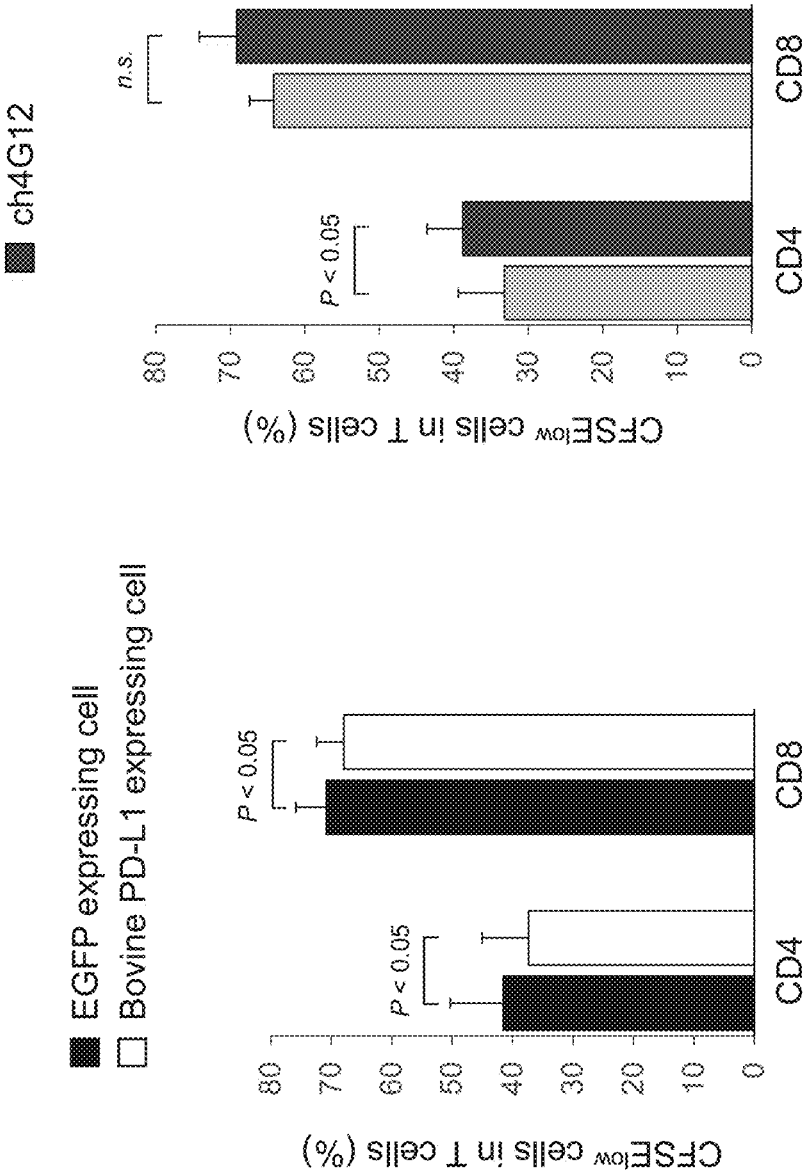
FIG. 25 Activation effect of rat-bovine chimeric anti-bovine PD-L1 antibody ch4G12 on bovine lymphocyte response (in terms of cell proliferation).

Biological Activity Test Using Rat-Bovine Chimeric Anti-Bovine PD-L1 Antibody (1) Effect on Cell Proliferation (FIG. 25)

In order to confirm that bovine PD-1/PD-L1 binding inhibition by rat-bovine chimeric anti-PD-L1 antibody activates lymphocytes, a biological activity test was performed using cell proliferation as an indicator. Briefly, bovine PBMCs isolated from peripheral blood of healthy cattle were suspended in PBS to give a concentration of $10\times10^6$ cells/ml, and reacted with carboxyfluorescein succinimidyl ester (CFSE) at room temperature for 20 min. After washing twice with RPMI 1640 medium (Sigma-Aldrich) containing 10% inactivated fetal bovine serum (Cell Culture Technologies), antibiotics (streptomycin 200 µg/ml, penicillin 200 U/ml) (Life Technologies) and 0.01% L-glutamine (Life Technologies), the PBMCs were reacted with anti-bovine CD3 mouse antibody (WSU Monoclonal Antibody Center) at 4° C. for 30 min. After washing, the PBMCs were reacted with anti-mouse IgG1 microbeads (Miltenyi Biotec) at 4° C. for 15 min, followed by isolation of CD3-positive T cells using autoMACS™ Pro(Miltenyi Biotec). To the isolated CD3-positive T cells, anti-bovine CD3 mouse antibody (WSU Monoclonal Antibody Center) and anti-bovine CD28 mouse antibody (Bio-Rad) were added. Then, the cells were co-cultured with bovine PD-L1 expressing cells (CD3-positive T cells:bovine PD-L1 expressing cells=10:1) in the presence or absence of µg/ml of rat-bovine chimeric anti-bovine PD-L1 antibody ch4G12. As a control for antibodies, serum-derived bovine IgG (Sigma-Aldrich) was used; as a control for PD-L1 expressing cells. EGFP expressing cells transfected with pEGFP-N2 were used. After a 6-day coculture, cells were harvested and reacted with anti-bovine CD4 mouse antibody and anti-bovine CD8 mouse antibody (Bio-Rad) at room temperature for 30 min. For the labeling of antibodies, Zenon Mouse IgG1 Labeling Kits (Life Technologies) or Lightning-Link Kit (Innova Biosciences) was used. For analysis, FACS Verse (BD Biosciences) was used. For washing operation after culturing and dilution of antibody, PBS supplemented with 1% bovine serum albumin (Sigma-Aldrich) was used.

The experimental results are shown in FIG. 25. Proliferation of CD4-positive and CD8-positive T cells was significantly suppressed by co-culture with bovine PD-L1 expressing cells. It was revealed that rat-bovine chimeric anti-bovine PD-L1 antibody ch4G12 inhibits this suppression in CD4-positive T cells.

Figure 26:
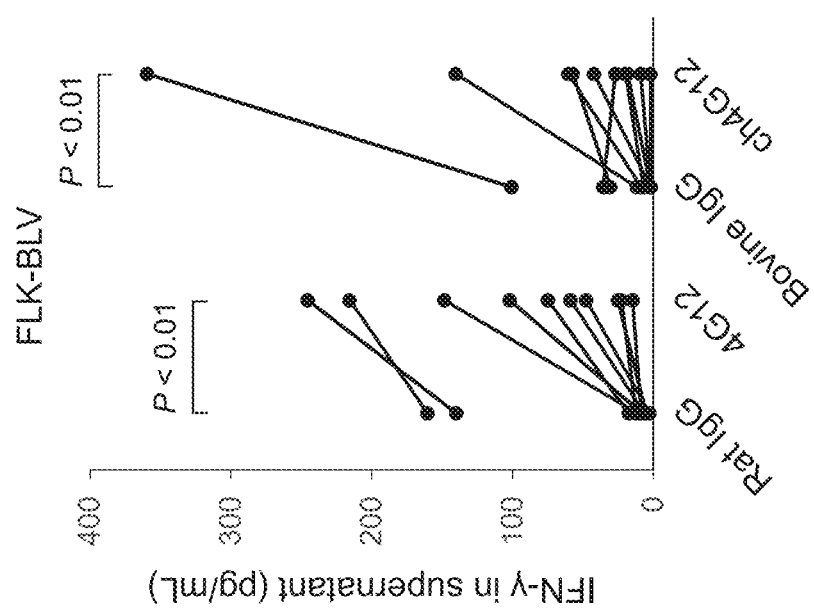
FIG. 26 Activation effect of rat-bovine chimeric anti-bovine PD-L1 antibody ch4G12 on bovine lymphocyte response to BLV antigen (in terms of IFN-γ production).

(2) Effect on IFN-γ Production (FIG. 26)

In order to confirm that bovine PD-1/PD-L1 binding inhibition by rat-bovine chimeric anti-PD-L1 antibody activates lymphocytes, a biological activity test was performed using IFN-γ production as an indicator. Briefly, PBMCs isolated from peripheral blood of BLV-infected cattle were suspended in RPMI medium (Sigma-Aldrich) containing 10% inactivated fetal bovine serum (Cell Culture Technologies), antibiotics (streptomycin 200 µg/ml, penicillin 200 U/ml) (Life Technologies) and 0.01% L-glutamine (Life Technologies) to give a concentration of $4\times10^6$ cells/ml. To the PBMCs, 10 µg/ml of rat anti-bovine PD-L1 antibody 4G12 or rat-bovine chimeric anti-bovine PD-L1 antibody ch4G12, and 2% BLV-infected fetal lamp kidney cell (FLK-BLV) culture supernatant were added; culturing was then performed at 37° C. under 5% $CO_2$ for 6 days. As control antibodies, serum-derived rat IgG (Sigma-Aldrich) and serum-derived bovine IgG (Sigma-Aldrich) were used. After a 6-day culture, a culture supernatant was collected, and IFN-γ production was measured with Bovine IFN-γ ELISA Kit (BETYL). For each washing operation in ELISA, Auto Plate Washer BIO WASHER 50 (DS Pharma Biomedical) was used. Absorbance was measured with Microplate Reader MTP-650FA (Corona Electric).

The experimental results are shown in FIG. 26. It was revealed that rat-bovine chimeric anti-bovine PD-L1 antibody ch4G12 increases bovine PBMCs' IFN-γ response to BLV antigen in the same manner as rat anti-bovine PD-L1 antibody 4G12 (n=10).

CDR Analysis of Rat Anti-Bovine PD-L1 Antibody

The complementarity-determining regions (CDRs) of rat anti-bovine PD-L1 antibody 4012 were determined using NCBI IGBLAST (http://www.ncbi.nlm.nih.gov/igblast/). The results are shown in FIG. 19.

Inoculation Test on Cattle

Established rat-bovine chimeric anti-bovine PD-L1 antibody ch4G12 (about 260 mg; 1 mg/kg) was intravenously administered into experimentally BLV-infected calf (Holstein, male, 7 months old, 267 kg). Blood samples were collected chronologically from the infected calf, followed by isolation of PBMCs by density gradient centrifugation.

Figure 27:
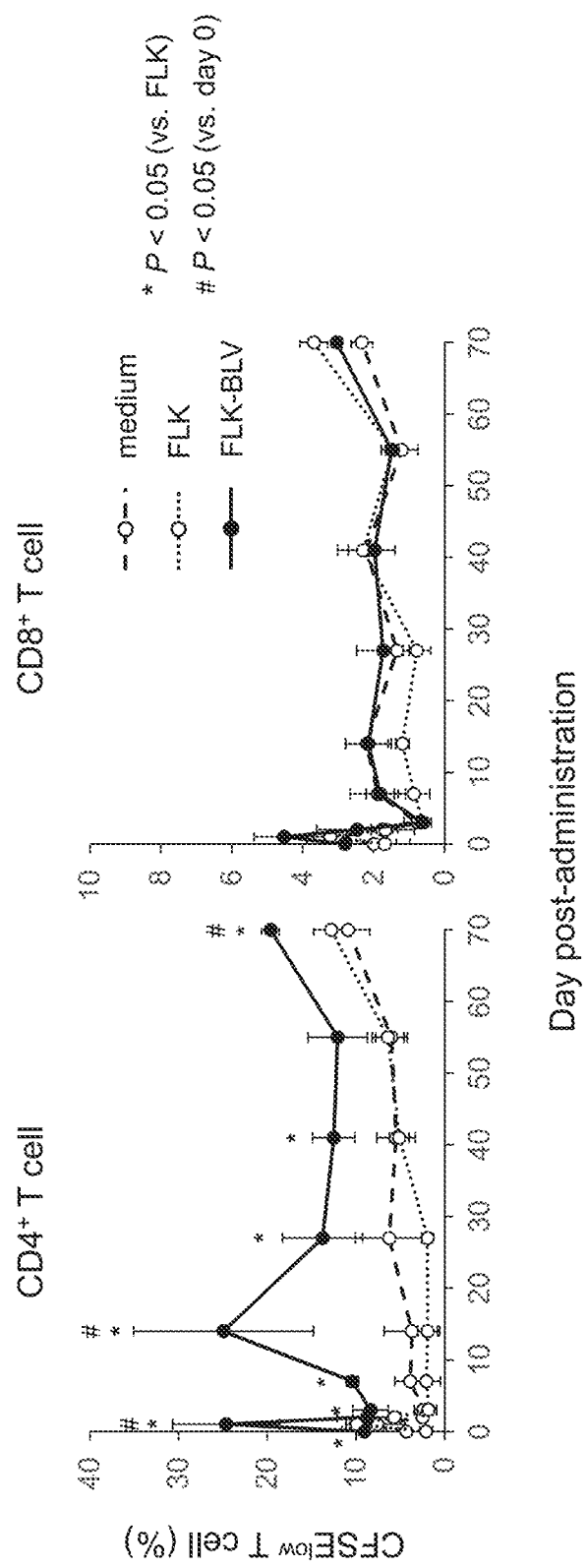
FIG. 27 The proliferation response of T cells against BLV antigen in a calf experimentally infected with BLV through administration of rat-bovine chimeric anti-bovine PD-L1 antibody ch4G12.

(1) Cell Proliferation Response of T Cells to BLV Antigen (FIG. 27)

Bovine PBMCs were suspended in PBS and reacted with CFSE at room temperature for 20 min. After washing twice with RPMI 1640 medium (Sigma-Aldrich) containing 10% inactivated fetal bovine serum (Cell Culture Technologies), antibiotics (streptomycin 200 μg/ml, penicillin 200 U/ml) (Life Technologies) and 0.01% L-glutamine (Life Technologies), the cell concentration was adjusted to $4 \times 10^6$ cells/ml using the same medium. Culture supernatant of 2% BLV-infected fetal lamp kidney cells (FLK-BLV) was added to the PBMCs, which were then cultured at 37° C. under 5% $CO_2$ for 6 days. As a control, culture supernatant of 2% BLV-not-infected fetal lamp kidney cells (FLK) was used. After a 6-day culture, PBMCs were collected and reacted with anti-bovine CD4 mouse antibody, anti-bovine CD8 mouse antibody and anti-bovine IgM mouse antibody (Bio-Rad) at 4° C. for 20 min. For the labeling of antibodies. Zenon Mouse IgG1 Labeling Kits (Life Technologies) or Lightning-Link Kit (Innova Biosciences) was used. For analysis, FACS Verse (BD Biosciences) was used. For every washing operation and dilution of antibody, PBS supplemented with 1% bovine serum albumin (Sigma-Aldrich) was used.

The experimental results are shown in FIG. 27. As a result of antibody administration, BLV-specific cell proliferation response of CD4-positive T cells increased compared to the response before administration.

Figure 28:
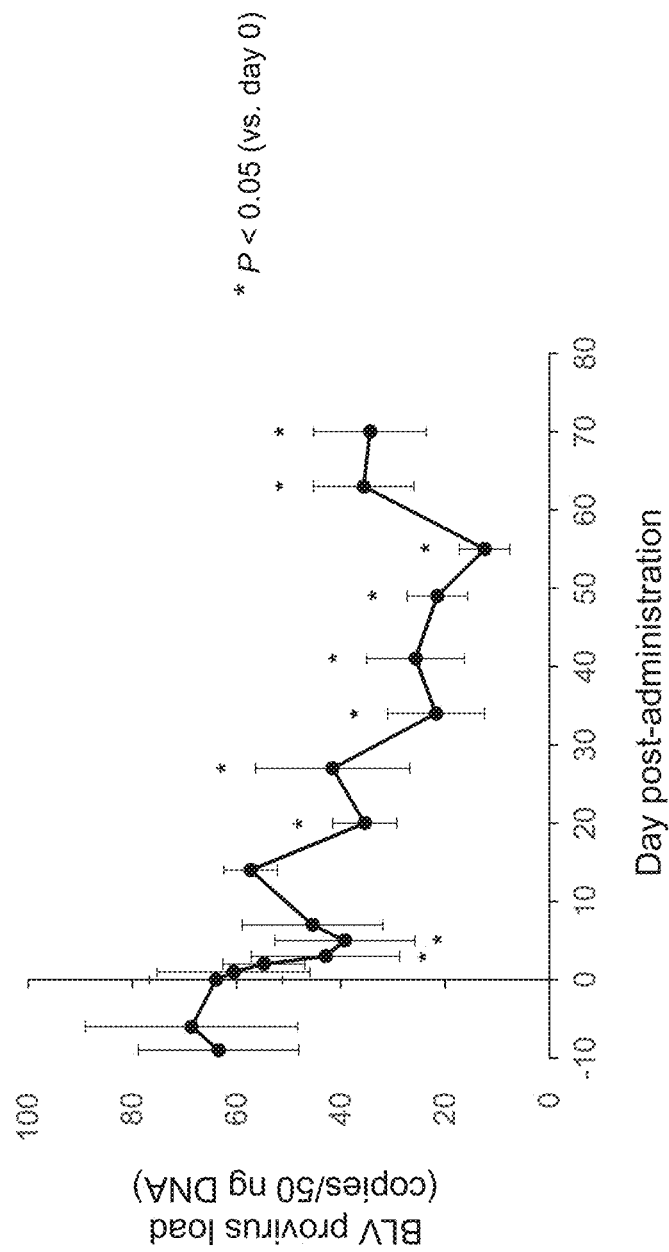
FIG. 28 Changes in BLV provirus loads in the calf experimentally infected with BLV through administration of rat-bovine chimeric anti-bovine PD-L1 antibody ch4G12.

(2) Changes in the BLV Provirus Load (FIG. 28)

DNA was extracted from isolated bovine PBMCs using Wizard DNA Purification kit (Promega). The concentration of the extracted DNA was quantitatively determined, taking the absorbance (260 nm) measured with Nanodrop 8000 Spectrophotometer (Thermo Fisher Scientific) as a reference. In order to measure the BLV provirus load in PBMCs, real time PCR was performed using Cycleave PCR Reaction Mix SP (TaKaRa) and Probe/Primer/Positive control for bovine leukemia virus detection (TaKaRa). Light Cycler 480 System II (Roche Diagnosis) was used for measurement.

The experimental results are shown in FIG. 28. The BLV provirus load significantly decreased until the end of test period compared to the load before administration.

All publications, patents and patent applications cited herein are incorporated herein by reference in their entirety.

INDUSTRIAL APPLICABILITY

The anti-PD-L1 antibody of the present invention is applicable to prevention and/or treatment of cancers and infections in animals.

The invention claimed is:

1. An anti-PD-L1 antibody comprising (a) a light chain comprising a light chain variable region containing CDR1 having the amino acid sequence of QSLLYSENQKDY (SEQ ID NO: 37), CDR2 having the amino acid sequence of WAT and CDR3 having the amino acid sequence of GQYLVYPFT (SEQ ID NO: 38) and the light chain constant region of an antibody of bovine; and (b) a heavy chain comprising a heavy chain variable region containing CDR1 having the amino acid sequence of GYTFTSNF (SEQ ID NO: 39), CDR2 having the amino acid sequence of IYPEYGNT (SEQ ID NO: 40) and CDR3 having the amino acid sequence of ASEEAVISLVY (SEQ ID NO: 41) and the heavy chain constant region of an antibody of bovine, wherein the light chain constant region of the bovine antibody has the amino acid sequence as shown in SEQ ID NO: 100 and the heavy chain constant region of the bovine antibody has the amino acid sequence as shown in SEQ ID NO: 102.

2. The antibody of claim 1, wherein the light chain variable region and the heavy chain variable region are derived from rat.

3. The antibody of claim 2, wherein the light chain variable region is the light chain variable region of a rat anti-bovine PD-L1 antibody and the heavy chain variable region is the heavy chain variable region of a rat anti-bovine PD-L1 antibody.

4. The antibody of claim 3, wherein the light chain variable region has the amino acid sequence as shown in SEQ ID NO. 1 and the heavy chain variable region has the amino acid sequence as shown in SEQ ID NO: 2.

5. The antibody of claim 1 which has a four-chain structure comprising two light chains and two heavy chains.

6. A pharmaceutical composition comprising the antibody of claim 1 as an active ingredient.

7. The pharmaceutical composition of claim 6 for treatment of cancers and/or infections.

8. The pharmaceutical composition of claim 7, wherein the cancers and/or infections are selected from the group consisting of neoplastic diseases, leukemia, Johne's disease, anaplasmosis, bacterial mastitis, mycotic mastitis, mycoplasma infections, tuberculosis, *Theileria orientalis* infection, cryptosporidiosis, coccidiosis, trypanosomiasis and leishmaniasis.

9. An artificial genetic DNA encoding the antibody of claim 1.

10. A vector comprising the artificial genetic DNA of claim 9.

11. A host cell transformed with the vector of claim 10.

12. A method of preparing an antibody, comprising culturing the host cell of claim 11 and collecting an anti-PD-L1 antibody from the resultant culture.

13. A DNA encoding a heavy chain comprising a heavy chain variable region containing CDR1 having the amino acid sequence of GYTFTSNF (SEQ ID NO: 39), CDR2 having the amino acid sequence of IYPEYGNT (SEQ ID NO: 40) and CDR3 having the amino acid sequence of ASEEAVISLVY (SEQ ID NO: 41) and the heavy chain constant region of an antibody of bovine an animal other than rat, wherein the heavy chain constant region of the bovine antibody has the amino acid sequence as shown in SEQ ID NO: 102.

* * * * *